US007884189B2

(12) United States Patent
Tong et al.

(10) Patent No.: US 7,884,189 B2
(45) Date of Patent: Feb. 8, 2011

(54) CARBOXYLTRANSFERASE DOMAIN OF ACETYL-COA CARBOXYLASE

(75) Inventors: Liang Tong, Scarsdale, NY (US); Hailong Zhang, New York, NY (US); Zhiru Yang, Pasadena, CA (US)

(73) Assignee: The Trustees of Columbia University in the City of new York, New York, NY (US)

( * ) Notice: Subject to any disclaimer, the term of this patent is extended or adjusted under 35 U.S.C. 154(b) by 1254 days.

(21) Appl. No.: 10/754,687

(22) Filed: Jan. 9, 2004

(65) Prior Publication Data

US 2005/0009163 A1 Jan. 13, 2005

Related U.S. Application Data

(60) Provisional application No. 60/439,383, filed on Jan. 10, 2003, provisional application No. 60/459,464, filed on Mar. 31, 2003, provisional application No. 60/491,640, filed on Jul. 31, 2003, provisional application No. 60/514,636, filed on Oct. 27, 2003.

(51) Int. Cl.
*C07K 14/00* (2006.01)
*C08H 1/00* (2006.01)
*A61K 38/43* (2006.01)

(52) U.S. Cl. ..................................... 530/350
(58) Field of Classification Search ....................... None
See application file for complete search history.

(56) References Cited

U.S. PATENT DOCUMENTS

| 6,255,559 | B1 | 7/2001 | Chea |
|---|---|---|---|
| 2002/0104111 | A1 | 8/2002 | Wakiil et al. |
| 2002/0112253 | A1 | 8/2002 | Wakil et al. |
| 2003/0028912 | A1 | 2/2003 | Matzuk et al. |
| 2003/0148297 | A1 | 8/2003 | Siegal |
| 2003/0187254 | A1 | 10/2003 | Perry et al. |
| 2009/0215627 | A1 | 8/2009 | Shen et al. |

OTHER PUBLICATIONS

Al-Feel et al., Cloning of the yeast FAS3 gene and primary structure of yeast acetyl-CoA carboxylase., Proc Natl Acad Sci U S A. May 15, 1992;89(10):4534-8.*
Giege et al., Crystallogenesis of Biological Macromolecule: Facts and Perspectives, (1994) Acta Cryst., vol. D50, pp. 339-350.*
Branden et al (1999) Introduction to Protein Structure, Second Edition, Garland Publishing Inc., New York, pp. 374-375 and 382.*
Drenth, Principles of Protein X-ray Crystallography (1995) Springer, New York, p. 1.*
Kierzek et al., Models of protein crystal growth, (2001) Biophys Chem, 91:1-20.*
Wiencek, New Strategies for Protein Crystal Growth, (1999) Ann Rev Biomed Eng., 1 :505-534.*
Harwood, Recent advances in the biosynthesis of plant fatty acids, Biochimica et Biophysica Acta, 1996, vol. 1301, pp. 7-56.*
Definition of domain (last viewed on Dec. 10, 2009).*

Thampy, K.G. et al., "Purification, characterization, and ontogeny of acetyl-CoA carboxylase isozyme of chick embryo brain," Journal of Lipid Research, vol. 32, 1991, 1667-1673.
Invitation to Pay Additional Fees and, Where Applicable, Protest Fee issued for International Patent Application No. PCT/US04/00585.
Abu-Elheiga et al., Continuous fatty acid oxidation and reduced fat storage in mice lacking acetyl-CoA carboxylase 2. Science. Mar. 30, 2001;291(5513):2613-6.
Alberts and Vagelos, 1972, The Enzymes, Boyer, ed., New York, NY, 6:37-82.
Benning et al. New reactions in the crotonase superfamily: structure of methylmalonyl CoA decarboxylase from *Escherichia coli*. Biochemistry. Apr. 25, 2000;39(16):4630-9.
Brunger et al. Crystallography & NMR system: A new software suite for macromolecular structure determination. Acta Crystallogr D Biol Crystallogr. Sep. 1, 1998;54 ( Pt 5):905-21.
Carson et al., 1987, J. Mol. Graphics 5:103-6.
Chothia and Lesk, The relation between the divergence of sequence and structure in proteins.EMBO J. Apr. 1986;5(4):823-6.
Chua et al. , 1989, Science 244:174-181.
Cronan and Waldrop, Multi-subunit acetyl-CoA carboxylases.Prog Lipid Res. Sep. 2002;41(5):407-35. Review.
Cwirla et al. Peptides on phage: a vast library of peptides for identifying ligands.Proc Natl Acad Sci U S A. Aug. 1990;87(16):6378-82.
Delye et al., 2003, An isoleucine residue within the carboxyltransferase domain of multidomain acetyl-coenzyme A carboxylase is a major determinant of sensitivity to aryloxyphenoxypropionate but not to cyclohexanedione inhibitors. Plant Physiol. Jul. 2003;132(3):1716-23.
Devine and Shukla, 2000, Crop Protection, 19:1881-9.
Devlin et al. Random peptide libraries: a source of specific protein binding molecules. Science. Jul. 27, 1990;249(4967):404-6.
Dunbrack et al., 1997, Folding and Design, 2:27-42.
Engel et al. Crystal structure of enoyl-coenzyme A (CoA) hydratase at 2.5 angstroms resolution: a spiral fold defines the CoA-binding pocket. EMBO J. Oct. 1, 1996;15(19):5135-45.
Evans et al., 1993, J. Mol. Graphics 11:134-8.
Gronwald, 1991, Weed Science 39:435-449.

(Continued)

*Primary Examiner*—David J Steadman
*Assistant Examiner*—Alexander D Kim
(74) *Attorney, Agent, or Firm*—Wilmer Cutler Pickering Hale and Dorr LLP

(57) ABSTRACT

The present invention provides compositions and crystals of the carboxyltransferase (CT) domain (the C-terminal ~90 kDa fragment) of various acetyl-CoA carboxylase (ACC) proteins, including yeast, mouse and human ACCs. Further, the present invention provides methods for identifying and designing compounds that can modulate ACC activity. These methods are based, in part, on the X-ray crystallographic structures of the CT domain of yeast ACC, either alone or bound to acetyl-CoA or a CT inhibitor, such as haloxyfop or diclofop or CP-640186. Thus, the present invention relates to the crystal structures of the carboxyltransferase ("CT") domain of acetyl-CoA carboxylase ("ACC"), and to the use of these structures in the design of anti-obesity compounds, anti-diabetes compounds, antibiotic compounds, herbicide compounds, and in the design of herbicide resistant plants.

23 Claims, 53 Drawing Sheets
(13 of 53 Drawing Sheet(s) Filed in Color)

OTHER PUBLICATIONS

Guchait et al., Acetyl coenzyme A carboxylase system of *Escherichia coli*. Purification and properties of the biotin carboxylase, carboxyltransferase, and carboxyl carrier protein components.J Biol Chem. Oct. 25, 1974;249(20):6633-45.

Harwood et al., 2003, Isozyme-nonselective N-substituted bipiperidylcarboxamide acetyl-CoA carboxylase inhibitors reduce tissue malonyl-CoA concentrations, inhibit fatty acid synthesis, and increase fatty acid oxidation in cultured cells and in experimental animals.J Biol Chem. Sep. 26, 2003;278(39):37099-111.

Hendrickson et al., Determination of macromolecular structures from anomalous diffraction of synchrotron radiation. Science. Oct. 4, 1991;254(5028):51-8.

Janssen and Gardner, 1989, Plant Molecular Biology, 14:61-72.

Jogl et al. COMO: a program for combined molecular replacement. Acta Crystallogr D Biol Crystallogr. Aug. 2001;57(Pt 8):1127-34.

Jones et al., Improved methods for building protein models in electron density maps and the location of errors in these models. Acta Crystallogr A. Mar. 1, 1991;47 ( Pt 2):110-9.

Jones T.A., 1978, A Graphics Model Building and Refinement System for Macromolecules, J. Appl. Cryst. 11:268-72.

Lenhard and Gottschalk, Preclinical developments in type 2 diabetes. Adv Drug Deliv Rev. Nov. 5, 2002;54(9):1199-212.

McGarry and Brown, The mitochondrial carnitine palmitoyltransferase system. From concept to molecular analysis. Eur J Biochem. Feb. 15, 1997;244(1):1-14.

Mursula et al., The crystal structure of delta(3)-delta(2)-enoyl-CoA isomerase. J Mol Biol. Jun. 15, 2001;309(4):845-53.

Nicholls et al., 1991, Proteins, 11:281-296.

Otwinowski and Minor, 1997, Methods Enzymolg. 276:307-326.

Pellecchia et al., 2002, Nature Reviews Drug Discovery 1:211-219.

Phillips et al. Multiple sequence alignment in phylogenetic analysis .Mol Phylogenet Evol. Sep. 2000;16(3):317-30.

Ramsay et al., Molecular enzymology of carnitine transfer and transport. Biochim Biophys Acta. Mar. 9, 2001;1546(1):21-43.

Rendina et al., 1990, Inhibition of acetyl-coenzyme A carboxylase by two classes of grass-selective herbicides, J. Agric. Food Chem., 1282-1287.

Scott and Smith, Searching for peptide ligands with an epitope library. Science. Jul. 27, 1990;249(4967):386-90.

Sheldrick et al., 1990, Acta Crystal A46:467-73.

Tatusova et al., BLAST 2 Sequences, a new tool for comparing protein and nucleotide sequences. FEMS Microbiol Lett. May 15, 1999;174(2):247-50. Erratum in: FEMS Microbiol Lett Aug. 1, 1999;177(1):187-8.

Terwilliger and Berendzen, Automated MAD and MIR structure solution. Acta Crystallogr D Biol Crystallogr. Apr. 1999;55 ( Pt 4):849-61.

Wakil et al. Fatty acid synthesis and its regulation. Annu Rev Biochem. 1983;52:537-79.

Weaver et al. Competing protein:protein interactions are proposed to control the biological switch of the E coli biotin repressor. Protein Sci. Dec. 2001;10(12):2618-22.

Weeks and Miller, 1999, J. Appl. Cryst. 32:120-4.

Weeks and Miller, Optimizing Shake-and-Bake for proteins. Acta Crystallogr D Biol Crystallogr. Feb. 1999;55 ( Pt 2):492-500.

Zagnitko et al., 2001 An isoleucine/leucine residue in the carboxyltransferase domain of acetyl-CoA carboxylase is critical for interaction with aryloxyphenoxypropionate and cyclohexanedione inhibitors. Proc Natl Acad Sci U S A. Jun. 5, 2001;98(12):6617-22. Epub May 29, 2001.

Zagnitko et al., 2001, An isoleucine/leucine residue in the carboxyltransferase domain of acetyl-CoA carboxylase is critical for interaction with aryloxyphenoxypropionate and cyclohexanedione inhibitors.Proc Natl Acad Sci U S A. Jun. 5, 2001;98(12):6617-22. Epub May 29, 2001.

Zhang et al., 2003, Crystal structure of the carboxyltransferase domain of acetyl-coenzyme A carboxylase. Science. Mar. 28, 2003;299(5615):2064-7.

International Search Report and Written Opinion issued for International Patent Application No. PCT/US2004/000585.

Waldrop, G. L. et al., "Three-Dimensional Structure of Biotin Carboxylase Subunit of Acetyl-CoA Carboxylase," Biochemistry 1994, 33, 10249-10256.

Zhang, H. et al., "Crystal Structure of the Carboxyltransferase Domain of Acetyl-Coenzyme A Carboxylase in Complex with CP-640186," Structure, vol. 12, 1683-1691, Sep. 2004.

Beaty, N.M. and Lane, M.D., "Acetyl Coenzyme A Carboxylase. Rapid Purification of the Chick Liver Enzyme and Steady State Kinetic Analysis of the Carboxylase-Catalyzed Reaction," J. Biol. Chem. 257,924-929 (1982).

Brun, T., Roche, E., Assimacopoulos-Jeannet, F., Corkey, B.E., Kim, K.H., and Prentki, M., "Evidence for an anaplerotic/Malonyl-CoA Pathway in Pancreatic β-Cell Nutrient Signaling," Diabetes 45, 190-198 (1996).

Chen, S., Ogawa, A., Ohneda, M., Unger, R.H., Foster, D.W., and J.D. McGarry, "More Direct Evidence for a Malonyl-CoA-Carnitine Palmitoyltransferase I Interaction as a Key Event in Pancreatic β-Cell Signaling," Diabetes 43,878-883 (1994).

Fukuda, N. and Ontko, J.A., "Interactions between fatty acid synthesis, oxidation, and esterification in the production of triglyceride-rich lipoproteins by the liver," J. Lipid Res. 25,831-842 (1984).

Ha, J., Lee, J.K., Jim, K.S., Witters, L.A., and Kim, K.H., "Cloning of human acetyl CoA carboxylase-II and its unique features," Proc. Nat'l. Acad. Sci. USA 93,11466-11470 (1996).

Haffner, S.M., Valdez, R.A., Hazuda, H.P., Mitchell, B.D., Morales, P.A., and Stren, M.P."Prospective Analysis of the Insulin-Resistance Syndrome (Syndrome X)," Diabetes 41,715-722 (1992).

Harwood, H.J. Jr., Barbacci-Tobin, E.G., Petras, S.F., Lindsey, S., and Pellarin L.D., "3-(4-Chlorophenyl)-2-(4-diethylaminoethoxyphenyl)A-pentenonitrile Monohydrogen Citrate and Related Analogs. Reversible, Competitive, First Half-Reaction Squalene Synthetase Inhibitors," Biochem. Pharmacol. 53,839-864 (1997).

Hashimoto, T and Numa, S., "Kinetic Studies on the Reaction Mechanism and the Citrate Activation of Liver Acetyl Coenzyme A Carboxylase," Eur. J. Biochem. 18,319-331 (1971).

McCune, S.A. and Harris, R.A., "Mechanism Responsible for 5-(Tetradecyloxy)-2-furoic Acid Inhibition of Hepatic Lipogenesis," J. Biol. Chem. 254, 10095-10101 (1979).

McGarry, J.D., Stark, M.J., and Foster, D.W., "Hepatic Malonyl-CoA Levels of Fed, Fasted and Diabetic Rats as Measured Using a Simple Radioisotopic Assay," J. Biol. Chem. 253, 8291-8293 (1978).

McGarry, J.D. and Foster, D.W., "Regulation of Hepatic Fatty Acid Oxidation and Ketone Body Production," Annu. Rev. Biochem. 49,395-420. (1980).

McGarry, J.D., Woeltje, K.F., Kuwajima, M., and Foster, D.W. , "Regulation of Ketogenesis and the Renaissance of Carnitine Palmitoyltransferase," Diabetes/Metabol. Revs. 5, 271-284 (1989).

Ogiwara, T., Tanabe, T., Nikawa, J.I., and Numa, S., "Inhibition of Rat-Liver Acetyl-Coenzyme-A Carboxylase by Palmitoyl-Coenzyme A," Eur. J. Biochem. 89,33-41 (1978).

Parker, R.A., Kariya, T., Grisar, J.M., and Petrow, V., 5-(Tetradecyloxy)-2-furancarboxylic Acid and Related Hypolipidemic Fatty Acid-Like Alkyloxyarylcarboxylic Acids J. Med. Chem. 20,781-791 (1977).

Polakis et al., "Acetyl coenzyme A carboxylase system of *Escherichia coli*. Studies on the mechanisms of the biotin carboxylase-and carboxyltransferase-catalyzed reactions," J. Biol. Chem, vol. 249, pp. 6657-6667 (1974).

Reaven, GM.,"Role of Insulin Resistance in Human Disease," Diabetes 37, pp. 1595-1607 (1988).

Tanabe, T., Nakanishi, S., Hashimoto, T., Ogiwara, H., Nikawa, J.I., Numa, S., "[1] Acetyl-CoA Carboxylase from Rat Liver EC 6.4.1.2 Acetyl-CoA : carbon-dioxide ligase (ADP-forming)," Meth. Enzymol. 71, 5-16 (1981).

Widmer, J., Fassihi, K.S., Schlichter, S.C., Wheeler, K.S., Crute, B.E., King, N., Nutile-McMenemy, Noll, W.W., Daniel, S, Ha, J., Kim, K.H., and Witters, L.A., "Identification of a second human acetyl-CoA carboxylase gene," Biochem. J. 316, 915-922. (1996).

Abu-Elheiga, L., Almarza-Ortega, D.B., Baldini, A., and Wakil, S.J., "Human Acetyl-CoA Carboxylase 2 Molecular Cloning, Characterization, Chromosomal Mapping, and Evidence for Two Isoforms," J. Biol. Chem.272, 10669-10677 (1997).

Alberti et al., Diabet Med., "Definition, Diagnosis and Classification of Diabetes Mellitus and its Complications. Part 1: Diagnosis and Classification of Diabetes Mellitus Provisional Report of a WHO Consultation," vol. 15, pp. 539-553 (1998).

Arbeeny, C.M., Meyers, D.S., Bergquist, K.E., and Gregg, R.E., "Inhibition of fatty acid synthesis decreases very low density lipoprotein secretion in the hamster," J. Lipid Res. 33,843-851 (1992).

Bai, Y., Zhang, S., Jim, K.S., Lee, J.K., and Kim, K.H., "Obese Gene Expression Alters the Ability of 30A5 Preadipocytes to Respond to Lipogenic Hormones," J. Biol. Chem. 271,13939-13942 (1996).

Benning et al., "Structure of 4-chlorobenzoyl coenzyme A dehalogenase determined to 1.8 A resolution: an enzyme catalyst generated via adaptive mutation," Biochem, vol. 35, pp. 8103-8109 (1996).

Bianchi, A., Evans, J.L., Iverson, A.J., Nordlund, A.C., Watts, T.D., and Witters, L.A., "Identification of an Isozymic Form of Acetyl-CoA Carboxylase," J. Biol. Chem. 265, 1502-1509 (1990).

Bjorntorp, P., "Fatty acids, hyperinsulinemia, and insulin resistance: which comes first?," Curr. Opin. Lipidology 5, 166-174 (1994).

Blanchard et al., "Overexpression and kinetic characterization of the carboxyltransferase component of acetyl-CoA carboxylase," J. Biol Chem, vol. 273, pp. 19140-19145 (1998).

Buckley, M.G. and Rath, E.A., "Regulation of fatty acid synthesis and malonyl-CoA content in mouse brown adipose tissue in response to cold-exposure,starvation or re-feeding," Biochem J. 243, 437-442 (1987).

Burton et al., "Kinetics of inhibition of acetyl-coenzyme A carboxylase by sethoxydim and haloxyfop," Pest Biochem. Physiol, vol. 39, pp. 100-109 (1991).

Campbell et al., "Bacterial fatty acid biosynthesis: Target for antibacterial drug discovery," Ann Rev. Microbiol, vol. 55, pp. 305-332 (2001).

Chien, D., Dean, D., Saha, A.K., Flatt, J.P., and Ruderman, N. B., "Malonyl-CoA content and fatty acid oxidation in rat muscle and liver in vivo," Am. J. Physiol. (Endocrinol. Metab.) 279, E259-E265 (2000).

Crepaldi et al., "Plurimetabolic Symdrome or Symdrome X: an overview," Antherosclerosis X. Elsevier Science B.V. New York, N.Y. pp. 511-515 (1995).

Despres, J.P. and Marette, A., "Relation of components of insulin resistance syndrome to coronary disease risk," Curr. Opin. Lipidology 5,274-289 (1994).

Ferrannini, E.,"The Theoretical Bases of Indirect Calorimetry: A Review," Metabolism 37,287-301 (1988).

Ford et al., "Prevalence of the Metabolic Syndrome Among US Adults Findings From the Third National Health and Nutrition Examination Survey," J. Am Med. Assn, vol. 287, pp. 356-359 (2002).

Grundy, S.M.,"Hypertriglyceridemia, Insulin Resistance, and the Metabolic Syndrome," Am J. Cardiol, vol. 83, pp. 25F-29F (1999).

Haghpassand, M. and Moberly. J.B., "9-cis-Retinoic acid increases apolipoprotein A1 secretion and mRNA expression in HepG2 cells," Atherosclerosis 117,199-207 (1995).

Haghpassand, M., Wilder, D.E., and Moberly, J.B., "Inhibition of apolipoprotein B and triglyceride secretion in human hepatoma cells (HepG2)," J. Lipid. Res. 37,1468-1480 (1996).

Harwood H.J. Jr, Silva, M., Chandler, C.E., Mikolay, L., Pellarin, L.D., Barbacci-Tobin, E., Wint, L.T., and McCarthy, P.A., "Efficacy, Tissue Distribution and Biliary Excretion of Methyl (3R,5S)-(E)-3,5-Dihydroxy-9,9Diphenyl-6,8-Nonadienoate (CP-83101), a Hepatoselective Inhibitor of HMG-CoA Reductase Activity in the Rat," Biochem. Pharmacol. 40, 1281-1293 (1990).

Howard, B.V. et al., Antherosclerosis X, Proceedings of the 10 International Symposium on Antherosclerosis, Montreal, Eslevier Science B.V. New York, NY. pp. 516-519 (1995).

Isomaa, B., Almgren, P., Tuomi, T., Forsen, B., Lahti, K., Nissen, M., Taskinen, M.R., and Groop, L.,"Cardiovascular Morbidity and Mortality Associated With the Metabolic Syndrome," Diabetes Care 24,683-689 (2001).

Iverson, A.J., Bianchi, A., Nordlund, A.C., and Witters, L.A., "Immunological analysis of acetyl-CoA carboxylase mass, tissue distribution and subunit composition," Biochem J. 269,365-371 (1990).

Jelenska et al., The carboxyltransferase activity of the apicoplast acetyl-Co caboxylase of *Toxoplasma gondii* is the Target of aryloxyphenoxypropionate inhibitors, J. Biol Chem, vol. 277, pp. 23208-23215 (2002).

Kemal et al., "Coenzyme A esters of 2-aryloxyphenoxypropionate herbicides and 2-arylpropionate antiinflammatory drugs are potent and stereoselective inhibitors of rat liver acetyl-CoA carboxylase," Life Sci, vol. 50, pp. 533-540 (1992).

Kempen, H.J., Imbach, A.P., Giller, T., Neumann, W.J., Hennes, U., and Nakada, N, "Secretion of apolipoproteins A4 and B by HepG2 cells: regulation by substrates and metabolic inhibitors," J.Lipid Res. 36, 1796-1806 (1995).

Kim, K.H., "Regulation of Mammalian Acetyl-Coenzyme A Carboxylase," Annu. Rev. Nutr. 17,77-99 (1997).

Knowles et al., "The Mechanism of biotin-dependent enzymes," Ann. Rev. Biochem, vol. 58, pp. 195-221 (1989).

Konishi et al., "Compartmentalization of two forms of acetyl-CoA carboxylase in plants and the origin of their tolerance toward herbicides," Proc. Natl. Acad. Sci. USA, vol. 91, pp. 3598-3601 (1994).

Kudo, N., Barr, A.J., Barr, R.L., Desai, S., and Lopaschuk, G.D., "High Rates of Fatty Acid Oxidation during Reperfusion of Ischemic Hearts Are Associated with a Decrease in Malonyl-CoA Levels Due to an Increase in 5'-AMP-activated Protein Kinase Inhibition of Acetyl-CoA Carboxylase," J. Biol. Chem. 270, 17513-17520 (1995).

Li et al., "The genes encoding the two carboxyltransferase subunits of *Escherichia coli* acetyl-CoA carboxylase," J. Biol Chem, vol. 267, pp. 16841-16847 (1992).

McGarry, J.D., "What If Minkowski Had Been Ageusic? An Alternative Angle on Diabetes," Science 258,766-770 (1992).

Minokoshi, Y., Kim, Y.B., Peroni, O.D., Fryer, L.G.D., Muller, C., Carling, D., and Kahn, B.B., "Leptin stimulates fatty-acid oxidation by activating AMP-activated protein kinase," Nature 415,339-343 (2002).

Moller, D.E., "New drug targets for type 2 diabetes and the metabolic syndrome," Nature, vol. 414, pp. 821-827 (2001).

Munday, M.R. and Hemingway, C.J."The Regulation of Acetyl-CoA Carboxylase—A Potential Target for the Action of Hypolipidemic Agents," Adv. Enzyme Reg. 39,205-234 (1999).

National Cholesterol Education Program Expert panel, "Executive Summary of the Third Report of the National Cholesterol Education Program (NCEP) Expert Panel on Detection, Evaluation, and Treatment of High Blood Cholesterol in Adults (Adult Treatment Panel III)," J. Am. Med. Assn, vol. 285, pp. 2486-2497 (2001).

Petras, S.F., Lindsey, S. and Harwood, H.J. Jr., "HMG-CoA reductase regulation: use of structurally diverse first half-reaction squalene synthetase inhibitors to characterize the site of mevalonate-derived nonsterol regulator production in cultured IM-9 cells," J. Lipid Res .40,24-38 (1999).

Rasmussen, B.B., Holmback, U.C., Volpi, E., Morio-Liondore, B., Paddon-Jones, D., and Wolfe, R.R., "Malonyl coenzyme A and the regulation of functional carnitine palmitoyltransferase-1 activity and fat oxidation in human skeletal muscle," J. Clin. Invest. 110, 1687-1693 (2002).

Redina et al., "Kinetic characterization, stereoselectivity, and species selectivity of the inhibition of plant acetyl-Co A carboxylase by the aryxyphenoxypropionic acid grass herbicides," Arch Biochem Biophys., vol. 265, pp. 219-225 (1988).

Saha, A.K., Kurowski, T.G., and Rudennan, N.B., "A malonyl-CoA fuel-sensing mechanism in muscle: effects of insulin, glucose, and denervation," Am. J. Physiol. (Endocrinol. Metab.) 269, E283-E289 (1995).

Taylor et al., "Inhibition of acetyl-coenzyme A carboxylase by coenzyme A conjugates of grass-selective herbicides," Pestic. Sci., vol. 43, pp. 177-180 (1995).

Thampy, K.G. and Wakil, S.J., "Activation of Acetyl-coA Carboxylase Purification and Properties of a Mn2+-Dependent Phosphatase," J. Biol. Chem. 260,6318-6323 (1985).

Trevisan, M., Liu, J., Bahsas, F.B., and Menotti, A., "Syndrome X and Mortality: A Population-based Study," Am. J. Epidemiol. 148,958-966 (1998).

Triscari, J. and Sullivan, A.C., "Anti-Obesity Activity of a Novel Lipid Synthesis inhibitor," Int. J. Obesity 8 (Suppl. 1), 227-239. (1984).

Trumble, G.E., Smith, M.A., and Winder, W.W., "Purification and characterization of rat skeletal muscle acetyl-CoA carboxylase," Eur. J. Biochem. 231, 192-198. (1995).

Wang et al, The Structure of ClpP at 2.3 A° Resolution Suggests a Model for ATP-Dependent Proteolysis, Cell 91, pp. 447-456 (1997).

Whittington, M., Esner, M., Pratt, J., Riddell, D., and Ashton, M.J., "Effect of Sodium 2-n-Pentadecyl-Benzimidazole-5-carboxylate (M & B 35347B), an Inhibitor of Acetyl-CoA Carboxylase, on Lipogenesis and fat deposition in obese Hyperglycaemic (OB/OB) and lean mice," *Int. J. Obesity* 11, 619-629 (1987).

Winder, W.W., Arogyasami, J., Elayan, I.M., and Cartmill, D., "Time course of exercise-induced decline in malonyl-CoA in different muscle types," Am. J. Physiol.(Endocrinol. Metab.) 259, E266-E271 (1990).

Levert et al., "A Biotin Analog Inhibits Acetyl-CoA Carboxylase Activity and Adipogenesis," Journal of Biological Chemistry, vol. 277, No. 19, pp. 16347-16350 (2002).

Abu-Elheiga et al., "Human acetyl-CoA carboxylase: Characterization, molecular cloning, and evidence for two isoforms," PNAS, vol. 92,, pp. 4011-4015 (1995).

Ha et al., "Cloning of Human acetyl-CoA carboxylase cDNA," Eur J. Biochem, vol. 219, pp. 297-306 (1994).

* cited by examiner

FIG. 1B

```
Score =  694 bits (1792), Expect = 0.0
Identities = 367/715 (51%), Positives = 472/715 (65%), Gaps = 17/715 (2%)

Query = SEQ ID NO:2
Sbjct = SEQ ID NO:6

Query:  46  KPGSMHLRPIATPYPVKEWLQPKRYKAHLMGTTYVYDFPELFRQASSSQWKNFSADVKLT  105
            K GS+H    I TPY K+ LQ KR++A  +GTTYVYDFPE+FRQA     W    +  K
Sbjct:   1  KQGSLHGMLINTPYVTKDLLQAKRFQAQSLGTTYVYDFPEMFRQALFKLW---GSPEKYP   57

Query: 106  DDFFISNELIEDENGELTEVEREPGANAIGMVAFKITVKTPEYPRGRQFVVVANDITFKI  165
            D       EL+ D  G+L E+ R PG N +GMVAFK+  KTPEYP GR  VV+ NDITF+I
Sbjct:  58  KDILTYTELVLDSQGQLVEMNRLPGCNEVGMVAFKMRFKTPEYPEGRDAVVIGNDITFQI  117

Query: 166  GSFGPQEDEFFNKVTEYARKRGIPRIYLAANSGARIGMAEEIVPLFQVAWNDAANPDKGF  225
            GSFG  ED + + +E AR  GIP+IYLAANSGAR+G+AEEI +FQVAW D  +P KGF
Sbjct: 118  GSFGIGEDFLYLRASEMARTEGIPQIYLAANSGARMGLAEEIKQIFQVAWVDPEDPHKGF  177

Query: 226  QYLYLTSEGMETLKKFDKENSVLTERTVINGEERFVIKTIIGSEDGLGVECLRGSGLIAG  285
            +YLYLT +    +  +NSV +     GE R+VI  +IG +  LGVE LRGSG+IAG
Sbjct: 178  RYLYLTPQDYTQISS---QNSVHCKHIEDEGESRYVIVDVIGKDANLGVENLRGSGMIAG  234

Query: 286  ATSRAYHDIFTITLVTCRSVGIGAYLVRLGQRAIQVEGQPIILTGAPAINKMLGREVYTS  345
                 S AY    TI++VTCR++GIGAYLVRLGQR IQVE    IILTGA A+NK+LGREVYTS
Sbjct: 235  EASLAYEKTVTISMVTCRALGIGAYLVRLGQRVIQVENSHIILTGAGALNKVLGREVYTS  294

Query: 346  NLQLGGTQIMYNNGVSHLTAVDDLAGVEKIVEWMSYVPAKRNMPVPILETKDTWDRPVDF  405
            N QLGG QIM+ NGVSH+T  DD  GV I+EW+S++P      PVPI    D DR ++F
Sbjct: 295  NNQLGGVQIMHTNGVSHVTVPDDFEGVCTILEWLSFIPKDNRSPVPITTPSDPIDREIEF  354

Query: 406  TPTNDETYDVRWMIEGRE---TESGFEYGLFDKGSFFETLSGWAKGVVVGRARLGGIPLG  462
            TPT   YD RWM+ GR      +  G FD GSF E ++ WA+ VV GRARLGGIP+G
Sbjct: 355  TPTK-APYDPRWMLAGRPHPTLKGTWQSGFFDHGSFKEIMAPWAQTVVTGRARLGGIPVG  413
```

FIG. 4A

```
Query: 463  VIGVETRTVENLIPADPANPNSAETLIQEPGQVWHPNSAFKTAQAINDFNNGEQLPMMIL 522
            VI VETRTVE +PADPAN +S  +IQ+ GQVW P+SA+KTAQ I DFN  E+LP+MI
Sbjct: 414  VIAVETRTVEVAVPADPANLDSEAKIIQQAGQVWFPDSAYKTAQVIRDFNK-ERLPLMIF 472

Query: 523  ANWRGFSGGQRDMFNEVLKYGSFIVDALVDYKQPIIIYIPPTGELRGGSWVVVDPTINAD 582
            ANWRGFSGG +DM+ ++LK+G++IVD L  Y+QPI+IYIPP  ELRGGSWVV+D TIN
Sbjct: 473  ANWRGFSGGMKDMYEQMLKFGAYIVDGLRLYEQPILIYIPPCAELRGGSWVVLDSTINPL 532

Query: 583  QMEMYADVNARAGVLEPQGMVGIKFRREKLLDTMNRLDDKYRELRSQLSNKSLAPEVHQQ 642
            +EMYAD +R GVLEP+G V IKFR++ L+ T+ R+D  ++L QL   L  +  ++
Sbjct: 533  CIEMYADKESRGGVLEPEGTVEIKFRKKDLVKTIRRIDPVCKKLVGQLGKAQLPDKDRKE 592

Query: 643  ISKQLADRERELLPIYGQISLQFADLHDRSSRMVAKGVISKELEWTEAXXXXXXXXXXXX 702
            +  QL  RE  LLPIY Q+++QFADLHD    M+  KG+IS. LEW  A
Sbjct: 593  LEGQLKAREELLLLPIYHQVAVQFADLHDTPGHMLEKGIISDVLEWKTARTFFYWRLRRLL 652

Query: 703  NEEYLIKRLSHQVGEASRLEKIARIRSWYPASVD------HEDDRQVATWIEENY 751
            E  + +    E +   + +R W+ +      + ++ V  W+E+++
Sbjct: 653  LEAQVKQEILRASPELNHEHTQSMLRRWFVETEGAVKAYLWDSNQVVVQWLEQHW 707
```

FIG. 4B

Score = 700 bits (1807), Expect = 0.0
Identities = 367/725 (50%), Positives = 487/725 (66%), Gaps = 20/725 (2%)

Query = SEQ ID NO:2
SBJCT = SEQ ID NO:8

```
Query:  40  VFKSLG-KPGSMHLRPIATPYPVKEWLQPKRYKAHLMGTTYVYDFPELFRQASSSQWKNF  98
            +F++  G K G +H    I TPY K+ LQ KR++A +GTTY+YD PE+FRQ+    W++
Sbjct:  10  MFQAYGDKQGPLHGMLINTPYVTKDLLQSKRFQAQSLGTTYIYDIPEMFRQSLIKLWESM  69

Query:  99  SADV-----KLTDDFFISNELIEDENGELTEVEREPGANAIGMVAFKITVKTPEYPRGRQ  153
            S        L D    EL+ D+ G+L  + R PG N IGMVA+K+T K+PEYP GR
Sbjct:  70  STQAFLPSPPLPSDMLTYTELVLDDQGQLVHMNRLPGGNEIGMVAWKMTFKSPEYPEGRD  129

Query: 154  FVVVANDITFKIGSFGPQEDEFFNKVTEYARKRGIPRIYLAANSGARIGMAEEIVPLFQV  213
            +V+ NDIT++IGSFGPQED  F + +E AR  GIPRIY++ANSGARIG+AEEI  +F V
Sbjct: 130  IIVIGNDITYRIGSFGPQEDLLFLRASELARAEGIPRIYVSANSGARIGLAEEIRHMFHV  189

Query: 214  AWNDAANPDKGFQYLYLTSEGMETLKKFDKENSVLTERTVINGEERFVIKTIIGSEDGLG  273
            AW D +P KG++YLYLT +      K+   NSV  E   GE R+ I  IIG E+G+G
Sbjct: 190  AWVDPEDPYKGYRYLYLTPQDY---KRVSALNSVHCEHVEDEGESRYKITDIIGKEEGIG  246

Query: 274  VECLRGSGLIAGATSRAYHDIFTITLVTCRSVGIGAYLVRLGQRAIQVEGQPIILTGAPA  333
            E LRGSG+IAG +S AY++I TI+LVTCR++GIGAYLVRLGQR IQVE  +ILTGA A
Sbjct: 247  PENLRGSGMIAGESSLAYNEIITISLVTCRAIGIGAYLVRLGQRTIQVENSHLILTGAGA  306
```

FIG. 4C

```
Query: 334  INKMLGREVYTSNLQLGGTQIMYNNGVSHLTAVDDLAGVEKIVEWMSYVPAKRNMPVPIL 393
            +NK+LGREVYTSN QLGG QIM+NNGV+H T  DD  GV  ++ W+SY+P   +  VP+L
Sbjct: 307  LNKVLGREVYTSNNQLGGIQIMHNNGVTHCTVCDDFEGVFTVLHWLSYMPKSVHSSVPLL 366

Query: 394  ETKDTWDRPVDFTPTNDETYDVRWMIEGRE-TESG-FEYGLFDKGSFFETLSGWAKGVV 450
            +KD  DR  ++F PT      YD RWM+ GR   T+ G    G FD GSF E  + WA+ VV
Sbjct: 367  NSKDPIDRIIEFVPTKTP-YDPRWMLAGRPHPTQKGQWLSGFFDYGSFSEIMQPWAQTVV 425

Query: 451  VGRARLGGIPLGVIGVETRTVENLIPADPANPNSAETLIQEPGQVWHPNSAFKTAQAIND 510
            VGRARLGGIP+GV+ VETRTVE   IPADPAN +S  +IQ+ GQVW P+SAFKT QAI D
Sbjct: 426  VGRARLGGIPVGVVAVETRTVELSIPADPANLDSEAKIIQQAGQVWFPDSAFKTYQAIKD 485

Query: 511  FNNGEQLPMMILANWRGFSGGQRDMFNEVLKYGSFIVDALVDYKQPIIIYIPPTGELRGG 570
            FN  E LP+M+ ANWRGFSGG +DM+++VLK+G++IVD L +  QP+++YIPP  ELRGG
Sbjct: 486  FNR-EGLPLMVFANWRGFSGGMKDMYDQVLKFGAYIVDGLRECCQPVLVYIPPQAELRGG 544

Query: 571  SWVVVDPTINADQMEMYADVNARAGVLEPQGMVGIKFRREKLLDTMNRLDDKYRELRSQL 630
            SWVV+D +IN    MEMYAD +R   VLEP+G V IKFRR+ L+ TM R+D  Y  L +L
Sbjct: 545  SWVVIDSSINPRHMEMYADRESRGSVLEPEGTVEIKFRRKDLVKTMRRVDPVYIHLAERL 604

Query: 631  SNKSLAPEVHQQISKQLADRERELLPIYGQISLQFADLHDRSSRMVAKGVISKELEWTEA 690
              L+    +++   +L +RE  L+PIY Q+++QFADLHD   RM  KGVIS  L+W  +
Sbjct: 605  GTPELSTAERKELENKLKEREEFLIPIYHQVAVQFADLHDTPGRMQEKGVISDILDWKTS 664

Query: 691  XXXXXXXXXXXXNEEYLIKRLSHQVGEASRLEKIARIRSWY------PASVDHEDDRQVA 744
                        +E+ + K++ + +   E +  + A +R W+    +    ++++ +A
Sbjct: 665  RTFFYWRLRRLLLEDLVKKKIHNANPELTDGQIQAMLRRWFVEVEGTVKAYVWDNNKDLA 724

Query: 745  TWIEE 749
             W+E+
Sbjct: 725  EWLEK 729
```

FIG. 4D

```
Score =  739 bits (1907),  Expect = 0.0
Identities = 390/762 (51%), Positives = 506/762 (66%), Gaps = 19/762 (2%)

Query = SEQ ID NO:2
Sbjct = SEQ ID NO:10

Query:   1   IKDPQTGAPVPLRALINNVSGYVIKTEMYTEVKNAK-GEWVFKSLG-KPGSMHLRPIATP  58
             I+   TG+ VP+R  I N SGY +   +Y EV +++ G +F S G K G    H   I TP
Sbjct:  11   IRQTTTGSAVPIRLFITNESGYYLDISLYKEVTDSRSGNIMFHSFGNKQGPQHGMLINTP  70

Query:  59   YPVKEWLQPKRYKAHLMGTTYVYDFPELFRQASSSQWKNFSADVKLTDDFFISNELIEDE 118
             Y K+ LQ KR++A  +GTTY+YDFPE+FRQA     W  + K  D      EL+ D
Sbjct:  71   YVTKDLLQAKRFQAQTLGTTYIYDFPEMFRQALFKLW---GSPDKYPKDILTYTELVLDS 127

Query: 119   NGELTEVEREPGANAIGMVAFKITVKTPEYPRGRQFVVVANDITFKIGSFGPQEDEFFNK 178
              G+L E+ R PG N +GMVAFK+  KT EYP GR  +V+ NDITF+IGSFGP ED + +
Sbjct: 128   QGQLVEMNRLPGGNEVGMVAFKMRFKTQEYPEGRDVIVIGNDITFRIGSFGPGEDLLYLR 187

Query: 179   VTEYARKRGIPRIYLAANSGARIGMAEEIVPLFQVAWNDAANPDKGFQYLYLTSEGMETL 238
             +E AR   IP+IY+AANSGARIGMAEEI  +F VAW D  +P KGF+YLYLT +      +
Sbjct: 188   ASEMARAEAIPKIYVAANSGARIGMAEEIKHMFHVAWVDPEDPHKGFKYLYLTPQDYTRI 247

Query: 239   KKFDKENSVLTERTVINGEERFVIKTIIGSEDGLGVECLRGSGLIAGATSRAYHDIFTIT 298
                       NSV +      GE R++I  IIG +DGLGVE LRGSG+IAG +S AY +I TI+
Sbjct: 248   SSL---NSVHCKHIEEGGESRYMITDIIGKDDGLGVENLRGSGMIAGESSLAYEEIVTIS 304

Query: 299   LVTCRSVGIGAYLVRLGQRAIQVEGQPIILTGAPAINKMLGREVYTSNLQLGGTQIMYNN 358
             LVTCR++GIGAYLVRLGQR IQVE    IILTGA A+NK+LGREVYTSN QLGG QIM+ N
Sbjct: 305   LVTCRAIGIGAYLVRLGQRVIQVENSHIILTGASALNKVLGREVYTSNNQLGGVQIMHYN 364

Query: 359   GVSHLTAVDDLAGVEKIVEWMSYVPAKRNMPVPILETKDTWDRPVDFTPTNDETYDVRWM 418
             GVSH+T  DD  GV  I+EW+SY+P +  + PVPI+   D  DR ++F P+    YD RWM
Sbjct: 365   GVSHITVPDDFEGVYTILEWLSYMPKDNHSPVPIITPTDPIDREIEFLPSR-APYDPRWM 423
```

FIG. 4E

```
Query:  419  IEGRE---TESGFEYGLFDKGSFFETLSGWAKGVVVGRARLGGIPLGVIGVETRTVENLI  475
             + GR       + ++ G FD GSF E ++ WA+ VV GRARLGGIP+GVI VETRTVE  +
Sbjct:  424  LAGRPHPTLKGTWQSGFFDHGSFKEIMAPWAQTVVTGRARLGGIPVGVIAVETRTVEVAV  483

Query:  476  PADPANPNSAETLIQEPGQVWHPNSAFKTAQAINDFNNGEQLPMMILANWRGFSGGQRDM  535
             PADPAN +S   +IQ+ GQVW P+SA+KTAQAI DFN  E+LP+MI ANWRGFSGG +DM
Sbjct:  484  PADPANLDSEAKIIQQAGQVWFPDSAYKTAQAIKDFNR-EKLPLMIFANWRGFSGGMKDM  542

Query:  536  FNEVLKYGSFIVDALVDYKQPIIIYIPPTGELRGGSWVVVDPTINADQMEMYADVNARAG  595
             +++VLK+G++IVD L  YKQPI+IYI P  ELRGGSWVV+D TIN   +EMYAD +R G
Sbjct:  543  YDQVLKFGAYIVDGLRQYKQPILIYIRPMRELRGGSWVVIDATINPLCIEMYADKESRGG  602

Query:  596  VLEPQGMVGIKFRREKLLDTMNRLDDKYRELRSQLSNKSLAPEVHQQISKQLADRERELL  655
             VLEP+G V IKFR+E L+ +M R+D Y++L  QL   L+ +  +   +L RE  LL
Sbjct:  603  VLEPEGTVEIKFRKEDLIKSMRRIDPAYKKLMEQLGEPDLSDKDRKDLEGRLKAREDLLL  662

Query:  656  PIYGQISLQFADLHDRSSRMVAKGVISKELEWTEAXXXXXXXXXXXXXNEEYLIKRLSHQV  715
             PIY Q+++QFAD HD   RM+ KGVIS  LEW  A              E+ + + + +
Sbjct:  663  PIYHQVAVQFADFHDTPGRMLEKGVISDILEWKTARTFLYWRLRRLLLEDQVKQEILQAS  722

Query:  716  GEASRLEKIARIRSWYPASVD------HEDDRQVATWIEENY  751
             GE S +   + +R W+  +          ++++ V  W+E+++
Sbjct:  723  GELSHVHIQSMLRRWFVETEGAVKAYLWDNNQVVVQWLEQHW  764
```

FIG. 4F

Score = 716 bits (1847), Expect = 0.0 Identities = 372/726 (51%), Positives
= 492/726 (67%), Gaps = 15/726 (2%)

Query = SEQ ID NO:2

Sbjct = SEQ ID NO:14

```
Query:  16   INNVSGYVIKTEMYTEVKNAK-GEWVFKSLG-KPGSMHLRPIATPYPVKEWLQPKRYKAH  73
             + N SGY +   +Y EV +++   + +F++ G K G +H   I TPY K+ LQ KR++A
Sbjct:   3   LTNESGYYLDISLYKEVTDSRTAQIMFQAYGDKQGPLHGMLINTPYVTKDLLQSKRFQAQ  62

Query:  74   LMGTTYVYDFPELFRQASSSQWKNFSADV-----KLTDDFFISNELIEDENGELTEVERE  128
             +GTTY+YD PE+FRQ+    W++ S          L  D    EL+ D+ G+L  + R
Sbjct:  63   SLGTTYIYDIPEMFRQSLIKLWESMSTQAFLPSPPLPSDILTYTELVLDDQGQLVHMNRL  122

Query: 129   PGANAIGMVAFKITVKTPEYPRGRQFVVVANDITFKIGSFGPQEDEFFNKVTEYARKRGI  188
             PG N IGMVA+K+++K+PEYP GR  +V+ NDIT++IGSFGPQED  F + +E AR  GI
Sbjct: 123   PGGNEIGMVAWKMSLKSPEYPDGRDIIVIGNDITYRIGSFGPQEDLLFLRASELARAEGI  182

Query: 189   PRIYLAANSGARIGMAEEIVPLFQVAWNDAANPDKGFQYLYLTSEGMETLKKFDKENSVL  248
             PRIY+AANSGARIG+AEEI  +F VAW D +P KG++YLYLT +      K+    NSV
Sbjct: 183   PRIYVAANSGARIGLAEEIRHMFHVAWVDPEDPYKGYKYLYLTPQDY---KRVSALNSVH  239

Query: 249   TERTVINGEERFVIKTIIGSEDGLGVECLRGSGLIAGATSRAYHDIFTITLVTCRSVGIG  308
              E     GE R+ I  IIG E+GLG E LRGSG+IAG +S AY ++  TI+LVTCR++GIG
Sbjct: 240   CEHVEDEGESRYKITDIIGKEEGLGAENLRGSGMIAGESSLAYDEVITISLVTCRAIGIG  299

Query: 309   AYLVRLGQRAIQVEGQPIILTGAPAINKMLGREVYTSNLQLGGTQIMYNNGVSHLTAVDD  368
             AYLVRLGQR IQVE    +ILTGA A+NK+LGREVYTSN QLGG QIM+NNGV H T  DD
Sbjct: 300   AYLVRLGQRTIQVENSHLILTGAGALNKVLGREVYTSNNQLGGIQIMHNNGVTHSTVCDD  359

Query: 369   LAGVEKIVEWMSYVPAKRNMPVPILETKDTWDRPVDFTPTNDETYDVRWMIEGRE-TES  426
                GV ++  W+SY+P  +  VP+L +KD  DR ++F PT   YD RWM+ GR    T+
Sbjct: 360   FEGVFTVLHWLSYMPKSVHSSVPLLNSKDPIDRIIEFVPTK-APYDPRWMLAGRPHPTQK  418
```

FIG. 4G

```
Query:  427 G-FEYGLFDKGSFFETLSGWAKGVVVGRARLGGIPLGVIGVETRTVENLIPADPANPNSA 485
             G +   G FD GSF E +   WA+ VVVGRARLGGIP+GV+ VETRTVE  IPADPAN +S
Sbjct:  419 GQWLSGFFDYGSFSEIMQPWAQTVVVGRARLGGIPVGVVAVETRTVELSIPADPANLDSE 478

Query:  486 ETLIQEPGQVWHPNSAFKTAQAINDFNNGEQLPMMILANWRGFSGGQRDMFNEVLKYGSF 545
             +IQ+ GQVW P+SAFKT QAI DFN  E LP+M+ ANWRGFSGG +DM+++VLK+G++
Sbjct:  479 AKIIQQAGQVWFPDSAFKTYQAIKDFNR-EGLPLMVFANWRGFSGGMKDMYDQVLKFGAY 537

Query:  546 IVDALVDYKQPIIIYIPPTGELRGGSWVVVDPTINADQMEMYADVNARAGVLEPQGMVGI 605
             IVD L +  QP+++YIPP  ELRGGSWVV+DPTIN    MEMYAD  +R  VLEP+G V I
Sbjct:  538 IVDGLRECSQPVMVYIPPQAELRGGSWVVIDPTINPRHMEMYADRESRGSVLEPEGTVEI 597

Query:  606 KFRREKLLDTMNRLDDKYRELRSQLSNKSLAPEVHQQISKQLADRERELLPIYGQISLQF 665
             KFR++ L+ TM R+D  Y  L  +L    L+P    +++  +L +RE  L+PIY Q++QF
Sbjct:  598 KFRKKDLVKTMRRVDPVYIRLAERLGTPELSPTERKELESKLKEREEFLIPIYHQVAVQF 657

Query:  666 ADLHDRSSRMVAKGVISKELEWTEAXXXXXXXXXXXXXNEEYLIKRLSHQVGEASRLEKIA 725
             ADLHD   RM  KGVI+  L+W +            E+ + K++ +   E +  + A
Sbjct:  658 ADLHDTPGRMQEKGVINDILDWKTSRTFFYWRLRRLLLEDLVKKKIHNANPELTDGQIQA 717

Query:  726 RIRSWY 731
             +R W+
Sbjct:  718 MLRRWF 723
```

FIG. 4H

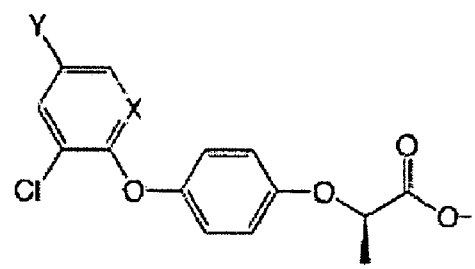
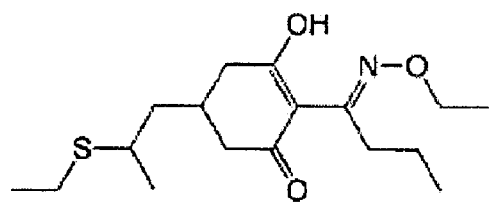
FIG. 5A
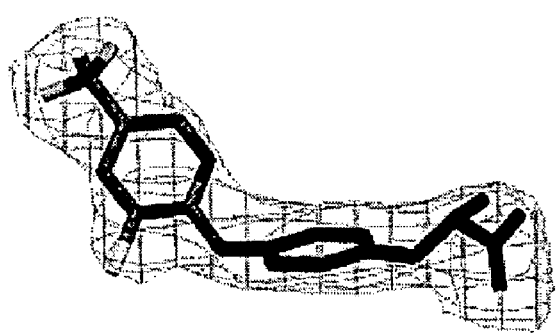
FIG. 5B

```
N Domain         1625 1630        1701    5 1710      5
S.S.                    β7              |------α4------
Yeast ACC        NSGARIGM         LGVECLRGSGLIAGAT
Human ACC1       ======-=L        I-=P=N-=-=-M==-ES
Human ACC2       ======-=-        -=--N-=-=-M==-ES
Wheat ACC        ======-=I        -=--NIH==AA==S-Y
T. gondii ACC    ======-=L        I=-=N--=--T==-E-

1730       5 1740    5 1750         5
S.S.                  β9   |--α5---|  |β10|     β11
Yeast ACC        CRSVGIGAYLVRLGQRAIQVEGQPIILTG
Human ACC1       S=AI=====-==---=T==--NSHL-===
Human ACC2       -=AI=====-==---=V==--NSH----=
Wheat ACC        G=T------=A=--I=C==RTD-----=
T. gondii ACC    G=--======I-==A-=T==MVRG-LL==

C Domain              5 1930      5
S.S.                β5 |-----α3-----
Yeast ACC        QVWHPNSAFKTAQAI
Human ACC1       ===P=D---==Y=---
Human ACC2       ===P=D--Y==----
Wheat ACC        ===P=D--T==---M
T. gondii ACC    ===P=D--Y==-=--

5 1960      5 1970    5 1980
S.S.                     β7B |-α4A-| |------α4------|
Yeast ACC        NWRGFSGGQRDMFNEVLKYGSFIVDALVD
Human ACC1       =========MK=-YHQ-=-F=AY==-G=RE
Human ACC2       =========MK==-YDQ-=-F=AY==-G=RQ
Wheat ACC        =========---L-EGI-QA--T==EN=RT
T. gondii ACC    =========T-=--E-I-==F-Q==-A=RT 5 2000       2020      5
S.S.                    |β9| |-α5-|      β11
Yeast ACC        GELROGSWVVD           ARAGVLE
Human ACC1       A=====-===I=          S-GS===
Human ACC2       R=====-===I=          S-G-===
Wheat ACC        A=====A===I=          -KGN===
T. gondii ACC    G=====-==-V=          --G-===
```

FIG. 7D

```
   1 mseeslfess pqkmeyeitn yserhtelpg hfiglntvdk leesplrdfv kshgghtvis
  61 kilianngia avkeirsvrk wayetfgddr tvqfvamatp edleanaeyi rmadqyievp
 121 ggtnnnnyan vdlivdiaer advdavwagw ghasenpllp eklsqskrkv ifigppgnam
 181 rslgdkisst ivaqsakvpc ipwsgtgvdt vhvdektglv svdddiyqkg cctspedglq
 241 kakrigfpvm ikaseggggk girqvereed fialyhqaan eipgspifim klagrarhle
 301 vqlladqygt nislfgrdcs vqrrhqkiie eapvtiakae tfhemekaav rlgklvgyvs
 361 agtveylysh ddgkfyflel nprlqvehpt temvsgvnlp aaqlqiamgi pmhrisdirt
 421 lygmnphsas eidfefktqd atkkqrrpip kghctacrit sedpndgfkp sggtlhelnf
 481 rsssnvwgyf svgnngnihs fsdsqfghif afgenrqasr khmvvalkel sirgdfrttv
 541 eylikllete dfedntittg wlddlithkm taekpdptla vicgaatkaf laseearhky
 601 ieslqkgqvl skdllqtmfp vdfihegkry kftvaksgnd rytlfingsk cdiilrqlsd
 661 gglliaiggk shtiywkeev aatrlsvdsm ttllevendp tqlrtpspgk lvkflvenge
 721 hiikgqpyae ievmkmqmpl vsqengivql lkqpgstiva gdimaimtld dpskvkhalp
 781 fegmlpdfgs pviegtkpay kfkslvstle nilkgydnqv imnaslqqli evlrnpklpy
 841 sewklhisal hsrlpaklde qmeelvarsl rrgavfparq lsklidmavk npeynpdkll
 901 gavvepladi ahkysnglea hehsifvhfl eeyyeveklf ngpnvreeni ilklrdenpk
 961 dldkvaltvl shskvsaknn lilailkhyq plcklsskvs aifstplqhi veleskatak
1021 valqareili qgalpsvker teqiehilks svvkvaygss npkrsepdln ilkdlidsny
1081 vvfdvllqfl thqdpvvtaa aaqvyirray raytigdirv hegvtvpive wkfqlpsaaf
1141 stfptvkskm gmnravsvsd lsyvansqss plregilmav dhlddvdeil sqsleviprh
1201 qsssngpapd rsgssaslsn vanvcvaste gfeseeeilv rlreildlnk qelinasirr
```

FIG. 9A

```
1261 itfmfgfkdg sypkyytfng pnynenetir hiepalafql elgrlsnfni kpiftdnrni
1321 hvyeavskts pldkrfftrg iirtghirdd isiqeyltse anrlmsdild nlevtdtsns
1381 dlnhifinfi avfdispedv eaafggfler fgkrllrlrv ssaeiriiik dpqtgapvpl
1441 ralinnvsgy viktemytev knakgewvfk slgkpgsmhl rpiatpypvk ewlqpkryka
1501 hlmgttyvyd fpelfrqass sqwknfsadv kltddffisn eliedengel teverepgan
1561 aigmvafkit vktpeyprgr qfvvvandit fkigsfgpqe deffnkvtey arkrgipriy
1621 laansgarig maeeivplfq vawndaanpd kgfqylylts egmetlkkfd kensvltert
1681 vingeerfvi ktiigsedgl gveclrgsgl iagatsrayh diftitlvtc rsvgigaylv
1741 rlgqraiqve gqpiiltgap ainkmlgrev ytsnlqlggt qimynngvsh ltavddlagv
1801 ekivewmsyv pakrnmpvpi letkdtwdrp vdftptndet ydvrwmiegr etesgfeygl
1861 fdkgsffetl sgwakgvvvg rarlggiplg vigvetrtve nlipadpanp nsaetliqep
1921 gqvwhpnsaf ktaqaindfn ngeqlpmmil anwrgfsggq rdmfnevlky gsfivdalvd
1981 ykqpiiiyip ptgelrggsw vvvdptinad qmemyadvna ragvlepqgm vgikfrrekl
2041 ldtmnrlddk yrelrsqlsn kslapevhqq iskqladrer ellpiygqis lqfadlhdrs
2101 srmvakgvis kelewtearr fffwlrrrl neeylikrls hqvgeasrle kiarirswyp
2161 asvdheddrq vatwieenyk tlddklkglk lesfaqdlak kirsdhdnai dglsevikml
2221 stddkekllk tlk (SEQ ID NO:1)
```

FIG. 9B

```
  1    ikdpqtgapv plralinnvs gyviktemyt evknakgewv fkslgkpgsm hlrpiatpyp
 61    vkewlqpkry kahlmgttyv ydfpelfrqa sssqwknfsa dvkltddffi sneliedeng
121    elteverepg anaigmvafk itvktpeypr grqfvvvand itfkigsfgp qedeffnkvt
181    eyarkrgipr iylaansgar igmaeeivpl fqvawndaan pdkgfqylyl tsegmetlkk
241    fdkensvlte rtvingeerf viktiigsed glgveclrgs gliagatsra yhdiftitlv
301    tcrsvgigay lvrlgqraiq vegqpiiltg apainkmlgr evytsnlqlg gtqimynngv
361    shltavddla gvekivewms yvpakrnmpv piletkdtwd rpvdftptnd etydvrwmie
421    gretesgfey glfdkgsffe tlsgwakgvv vgrarlggip lgvigvetrt venlipadpa
481    npnsaetliq epgqvwhpns afktaqaind fnngeqlpmm ilanwrgfsg gqrdmfnevl
541    kygsfivdal vdykqpiiiy ipptgelrgg swvvvdptin adqmemyadv naragvlepq
601    gmvgikfrre klldtmnrld dkyrelrsql snkslapevh qqiskqladr erellpiygq
661    islqfadlhd rssrmvakgv iskelewtea rrfffwrlrr rlneeylikr lshqvgeasr
721    lekiarirsw ypasvdhedd rqvatwieen yktlddklkg lklesfaqdl akkirsdhdn
781    aidglsevik mlstddkekl lktlk (SEQ ID NO:2)
```

FIG. 10

```
  1    gsmhlrpiat pypvkewlqp krykahlmgt tyvydfpelf rqasssqwkn fsadvkltdd
 61    ffisnelied engeltever epganaigmv afkitvktpe yprgrqfvvv anditfkigs
121    fgpqedeffn kvteyarkrg ipriylaans garigmaeei vplfqvawnd aanpdkgfqy
181    lyltsegmet lkkfdkensv ltertvinge erfviktiig sedglgvecl rgsgliagat
241    srayhdifti tlvtcrsvgi gaylvrlgqr aiqvegqpii ltgapainkm lgrevytsnl
301    qlggtqimyn ngvshltavd dlagvekive wmsyvpakrn mpvpiletkd twdrpvdftp
361    tndetydvrw miegretesg feyglfdkgs ffetlsgwak gvvvgrarlg giplgvigve
421    trtvenlipa dpanpnsaet liqepgqvwh pnsafktaqa indfnngeql pmmilanwrg
481    fsggqrdmfn evlkygsfiv dalvdykqpi iiyipptgel rggswvvvdp tinadqmemy
541    advnaragvl epqgmvgikf rreklldtmn rlddkyrelr sqlsnkslap evhqqiskql
601    adrerellpi ygqislqfad lhdrssrmva kgviskelew tearrfffwr lrrrlneeyl
661    ikrlshqvge asrlekiari rswypasvdh eddrqvatwi eenyktlddk lkglklesfa
721    qdlakkirsd hdnaidglse vikmlstddk ekllktlk (SEQ ID NO:3)
```

FIG. 11

```
  1   gsmhlrpiat pypvkewlqp krykahlmgt tyvydfpelf rqasssqwkn fsadvkltdd
 61   ffisnelied engeltever epganaigmv afkitvktpe yprgrqfvvv anditfkigs
121   fgpqedeffn kvteyarkrg ipriylaans garigmaeei vplfqvawnd aanpdkgfqy
181   lyltsegmet lkkfdkensv ltertvinge erfviktiig sedglgveci rgsgliagat
241   srayhdifti tlvtcrsvgi gaylvrlgqr aiqvegqpii ltgapainkm lgrevytsnl
301   qlggtqimyn ngvshltavd dlagvekive wmsyvpakrn mpvpiletkd twdrpvdftp
361   tndetydvrw miegretesg feyglfdkgs ffetlsgwak gvvvgrarlg giplgvigve
421   trtvenlipa dpanpnsaet liqepgqvwh pnsafktaqa indfnngeql pmmilanwrg
481   fsggqrdmfn eilkygsfiv dalvdykqpi iiyipptgel rggswvvvdp tinadqmemy
541   advnaragvl epqgmvgikf rreklldtmn rlddkyrelr sqlsnkslap evhqqiskql
601   adrerellpi ygqislqfad lhdrssrmva kgviskelew tearrfffwr lrrrlneeyl
661   ikrlshqvge asrlekiari rswypasvdh eddrqvatwi eenyktlddk lkglklesfa
721   qdlakkirsd hdnaidglse vikmlstddk ekllktlk (SEQ ID NO:4)
```

FIG. 12

```
  1    lfitnesgyy ldislyrevt dsrsgnimfh sfgnkqgslh gmlintpyvt kdllqakrfq
 61    aqslgttyvy dfpemfrqal fklwgspeky pkdiltytel vldsqgqlve mnrlpgcnev
121    gmvafkmrfk tpeypegrda vvignditfq igsfgigedf lylrasemar tegipqiyla
181    ansgarmgla eeikqifqva wvdpedphkg frylyltpqd ytqissqnsv hckhiedege
241    sryvivdvig kdanlgvenl rgsgmiagea slayektvti smvtcralgi gaylvrlgqr
301    viqvenshii ltgagalnkv lgrevytsnn qlggvqimht ngvshvtvpd dfegvctile
361    wlsfipkdnr spvpittpsd pidreieftp tkapydprwm lagrphptlk gtwqsgffdh
421    gsfkeimapw aqtvvtgrar lggipvgvia vetrtvevav padpanldse akiiqqagqv
481    wfpdsaykta qvirdfnker lplmifanwr gfsggmkdmy eqmlkfgayi vdglrlyeqp
541    iliyippcae lrggswvvld stinplciem yadkesrggv lepegtveik frkkdlvkti
601    rridpvckkl vgqlgkaqlp dkdrkelegq lkareelllp iyhqvavqfa dlhdtpghml
661    ekgiisdvle wktartffyw rlrrllleaq vkqeilrasp elnhehtqsm lrrwfveteg
721    avkaylwdsn qvvvqwleqh wsakdglrsn ireninylkr dsvlktiqsl vqehpevimd
781    cvaylsqhlt paeriqvaql lsttespass (SEQ ID NO:5)
```

FIG. 13

```
  1    kqgslhgmli ntpyvtkdll qakrfqaqsl gttyvydfpe mfrqalfklw gspekypkdi
 61    ltytelvlds qgqlvemnrl pgcnevgmva fkmrfktpey pegrdavvig nditfqigsf
121    gigedflylr asemartegi pqiylaansg armglaeeik qifqvawvdp edphkgfryl
181    yltpqdytqi ssqnsvhckh iedegesryv ivdvigkdan lgvenlrgsg miageaslay
241    ektvtismvt cralgigayl vrlgqrviqv enshiiltga galnkvlgre vytsnnqlgg
301    vqimhtngvs hvtvpddfeg vctilewlsf ipkdnrspvp ittpsdpidr eieftptkap
361    ydprwmlagr phptlkgtwq sgffdhgsfk eimapwaqtv vtgrarlggi pvgviavetr
421    tvevavpadp anldseakii qqagqvwfpd sayktaqvir dfnkerlplm ifanwrgfsg
481    gmkdmyeqml kfgayivdgl rlyeqpiliy ippcaelrgg swvvldstin plciemyadk
541    esrggvlepe gtveikfrkk dlvktirrid pvckklvgql gkaqlpdkdr kelegqlkar
601    eelllpiyhq vavqfadlhd tpghmlekgi isdvlewkta rtffywrlrr llleaqvkqe
661    ilraspelnh ehtqsmlrrw fvetegavka ylwdsnqvvv qwleqhwsak dglrsniren
721    inylkrdsvl kti (SEQ ID NO:6)
```

FIG. 14

```
   1 mdepsplaqp lelnqhsrfi igsvsedense deisnlvkld lleekegsls pasvgsdtls
  61 dlgisslqdg lalhirssms glhlvkqgrd rkkidsqrdf tvaspaefvt rfggnkviek
 121 vlianngiaa vkcmrsirrw syemfrnera irfvvmvtpe dlkanaeyik madhyvpvpg
 181 gpnnnnyanv elildiakri pvqavwagwg hasenpklpe lllkngiafm gppsqamwal
 241 gdkiassiva qtagiptlpw sgsglrvdwq endfskriln vpqelyekgy vkdvddglqa
 301 aeevgypvmi kaseggggkg irkvnnaddf pnlfrqvqae vpgspifvmr lakqsrhlev
 361 qilvdqygna islfgrdcsv qrrhqkiiee apatiatpav fehmeqcavk lakmvgyvsa
 421 gtveylysqd gsfyflelnp rlqvehpcte mvadvnlpaa qlqiamgipl yrikdirmmy
 481 gvspwgdspi dfedsahvpc prghviaari tsenpdegfk pssgtvqeln frsnknvwgy
 541 fsvaaagglh efadsqfghc fswgenreea isnmvvalke lsirgdfrtt veylikllet
 601 esfqmnridt gwldrliaek vqaerpdtml gvvcgalhva dvslrnsvsn flhslergqv
 661 lpahtllntv dveliyegvk yvlkvtrqsp nsyvvimngs cvevdvhrls dgglllsydg
 721 ssyttymkee vdryritign ktcvfekend psvmrspsag kliqyivedg ghvfagqcya
 781 eievmkmvmt ltavesgcih yvkrpgaald pgcilakmql dnpskvqqae lhtgslpriq
 841 stalrgeklh rvfhyvldnl vnvmngyclp dpffsskvkd wverlmktlr dpslpllelq
 901 dimtsvsgri ppnveksikk emaqyasnit svlcqfpsqq ianildshaa tlnrkserev
 961 ffmntqsivq lvqryrsgir ghmkavvmdl lrqylrvetq fqnghydkcv falreenksd
1021 mntvlnyifs haqvtkknll vtmlidqlcg rdptltdell nilteltqls kttnakvalr
1081 arqvliashl psyelrhnqv esiflsaidm yghqfcienl qklilsetsi fdvlpnffyh
1141 snqvvrmaal evyvrrayia yelnsvqhrq lkdntcvvef qfmlptshpn rgniptlnrm
1201 sfssnlnhyg mthvasvsdv lldnsftppc qrmggmvsfr tfedfvrifd evmgcfsdsp
1261 pqsptfpeag htslydedkv prdepihiln vaiktdcdie ddrlaamfre ftqqnkatlv
```

FIG. 15A

```
1321 dhgirrltfl vaqkdfrkqv nyevdrrfhr efpkfftfra rdkfeedriy rhlepalafq
1381 lelnrmrnfd ltaipcanhk mhlylgaakv evgtevtdyr ffvraiirhs dlvtkeasfe
1441 ylqnegerll leamdeleva fnntnvrtdc nhiflnfvpt vimdpskiee svrsmvmryg
1501 srlwklrvlq aelkinirlt ptgkaipirl fltnesgyyl dislykevtd srtaqimfqa
1561 ygdkqgplhg mlintpyvtk dllqskrfqa qslgttyiyd ipemfrqsli klwesmstqa
1621 flpspplpsd mltytelvld dqgqlvhmnr lpggneigmv awkmtfkspe ypegrdiivi
1681 gndityrigs fgpqedllfl raselaraeg ipriyvsans gariglaeei rhmfhvawvd
1741 pedpykgyry lyltpqdykr vsalnsvhce hvedegesry kitdiigkee gigpenlrgs
1801 gmiagessla yneiitislv tcraigigay lvrlgqrtiq venshliltg agalnkvlgr
1861 evytsnnqlg giqimhnngv thctvcddfe gvftvlhwls ympksvhssv pllnskdpid
1921 riiefvptkt pydprwmlag rphptqkgqw lsgffdygsf seimqpwaqt vvvgrarlgg
1981 ipvgvvavet rtvelsipad panldseaki iqqagqvwfp dsafktyqai kdfnreglpl
2041 mvfanwrgfs ggmkdmydqv lkfgayivdg lreccqpvlv yippqaelrg gswvvidssi
2101 nprhmemyad resrgsvlep egtveikfrr kdlvktmrrv dpvyihlaer lgtpelstae
2161 rkelenklke reeflipiyh qvavqfadlh dtpgrmqekg visdildwkt srtffywrlr
2221 rllledlvkk kihnanpelt dgqiqamlrr wfvevegtvk ayvwdnnkdl aewlekqlte
2281 edgvhsviee nikcisrdyv lkqirslvqa npevamdsii rmtqhisptq raevirilst
2341 mdspst (SEQ ID NO:7)
```

FIG. 15B

| | | | | | |
|---|---|---|---|---|---|
| 1 | vtdsrtaqim | fqaygdkqgp | lhgmlintpy | vtkdllqskr | fqaqslgtty | iydipemfrq |
| 61 | sliklwesms | tqaflpsppl | psdmltytel | vlddqgqlvh | mnrlpggnei | gmvawkmtfk |
| 121 | speypegrdi | ivignditvr | igsfgpqedl | lflraselar | aegipriyvs | ansgarigla |
| 181 | eeirhmfhva | wvdpedpykg | yrylyltpqd | ykrvsalnsv | hcehvedege | srykitdiig |
| 241 | keegigpenl | rgsgmiages | slayneiiti | slvtcraigi | gaylvrlgqr | tiqvenshli |
| 301 | ltgagalnkv | lgrevytsnn | qlggiqimhn | ngvthctvcd | dfegvftvlh | wlsympksvh |
| 361 | ssvpllnskd | pidriiefvp | tktpydprwm | lagrphptqk | gqwlsgffdy | gsfseimqpw |
| 421 | aqtvvvgrar | lggipvgvva | vetrtvelsi | padpanldse | akiiqqagqv | wfpdsafkty |
| 481 | qaikdfnreg | lplmvfanwr | gfsggmkdmy | dqvlkfgayi | vdglreccqp | vlvyippqae |
| 541 | lrggswvvid | ssinprhmem | yadresrgsv | lepegtveik | frrkdlvktm | rrvdpvyihl |
| 601 | aerlgtpels | taerkelenk | lkereeflip | iyhqvavqfa | dlhdtpgrmq | ekgvisdild |
| 661 | wktsrtffyw | rlrrllledl | vkkkihnanp | eltdgqiqam | lrrwfveveg | tvkayvwdnn |
| 721 | kdlaewlekq | lteedgvhsv | ieenikcisr | dyvlkqirsl | vqanpevamd | siirmtqhis |
| 781 | ptqraeviri | lstmdspst | (SEQ ID NO:8) | | | |

FIG. 16

```
   1 mvlllclscl ifscltfswl kiwekmtdsk pitksksean lipsqepfpa sdnsgetpqr
  61 ngeghtlhkd tqpgraqppt kaqrsgrrrn slppsrqkpp rnplsssdaa pspelqangt
 121 gtqgleatdt nglsssarpq gsklvpsked kkqanikrql mtnfilgsfd dyssdedsva
 181 gssrestrkg sraslgalsl eaylttgeae trvptmrpsm sglhlvkrgr ehkkldlhrd
 241 ftvaspaefv trfggdrvie kvlianngia avkcmrsirr wayemfrner airfvrmvtp
 301 edlkanaeyi kmadhygpap ggpnnnnyan velivdiakr iplqavwagw ghalenpklp
 361 ellckngvaf lgpprlrpmv glgdkiastv vaqtlqvptl prsgsaltve wteddlqqgk
 421 risvpedvyd kgcvkdvdeg leaaerigfp lmikaseggg gkgiretesa edfpilfrqv
 481 qseipgspif lmklaqharh levqiladqy gnavslfgrd csiqrrhqki veeapatiap
 541 laifefmeqc airlaktvgy vsagtveyly sqdgsfhfle lnprlqvehp ctemiadvnl
 601 paaqlqiamg aplhrlkdir llygespwgd spisfensah lpcprghvia tritsenpde
 661 gfkpssgtvq elnfrssknv wgyftvaatg glhefaisqf ghcfswgenr keaisnmvva
 721 lkelslrgdf rttveylinl letesfqnny idtgwldyli aekvqkkpni mlgvvcgale
 781 rgdamfrtcm tdflhslerg qvlpadslln lvdveliyeg vkyilkvtrq sltmfvlimn
 841 gchieidahr lndgglllsy ngnsyttymk eevdsyrtig nktcvfeken dptvlrspsa
 901 gkltqitved gghveagrry aemevmkmim tlnvqergrv kyikrpgavl eagcvvarle
 961 lddpskvhpa epftgelpaq qntadlgkkl hrvfhsvlgs ltnvmsgfcl pepffsiklk
1021 ewvqklmmtl rhpsllldvq eimtsragri pppveksvrk vmaqyasnit svlcqfpsqq
1081 iatildchaa tlqrkadrev ffintqsmvq lvqryrsgir ghmktvvidl lrrylrveti
1141 fgkardadan ssgmvggvrs lsftsvwvvl sppahydkcv inlreqfkpd msqvldcifs
1201 haqvtkknql vimlidelcg pdpslsdeli silneltqls ksehckvalr arqiliasps
```

FIG. 17A

```
1261 yelrhnqves iflsaidmyg hqfcpenlqk lilsettifd vlntffyhan kvvcmaslev
1321 yvggayiayv lnslqhrqlp dgtcvvefqf mlpsshpnrm tvpisitnpd llrhttelfm
1381 dsgfsplcqr mgamvafrrf edftrnfdev iscfanvpkd pplfsearts lyseddcksl
1441 reepihilnv siqcadhled ealvpilrtf vqskknilvd yglrripfli aqekefpkff
1501 tfrardefae driyrhlepa lafqlelnrm rnfdltavpc anhkmhlylg aakvegryev
1561 tdhrffirai irhsdlitke asfeylqneg erllleamde levafnntnv rtdcnhifln
1621 fvptvimdpn kieesvrymv mrygsrlwkl rvlqaevkin irqtttgsav pirlfitnes
1681 gyyldislyk evtdsrsgni mfhsfgnkqg pqhgmlintp yvtkdllqak rfqaqtlgtt
1741 yiydfpemfr qalfklwgsp dkypkdilty telvldsqgq lvemnrlpgg nevgmvafkm
1801 rfktqeypeg rdvivigndi tfrigsfgpg edllylrase maraeaipki yvaansgari
1861 gmaeeikhmf hvawvdpedp hkgfkylylt pqdytrissl nsvhckhiee ggesrymitd
1921 iigkddglgv enlrgsgmia gesslayeei vtislvtcra igigaylvrl gqrviqvens
1981 hiiltgasal nkvlgrevyt snnqlggvqi mhyngvshit vpddfegvyt ilewlsympk
2041 dnhspvpiit ptdpidreie flpsrapydp rwmlagrphp tlkgtwqsgf fdhgsfkeim
2101 apwaqtvvtg rarlggipvg viavetrtve vavpadpanl dseakiiqqa gqvwfpdsay
2161 ktaqaikdfn reklplmifa nwrgfsggmk dmydqvlkfg ayivdglrqy kqpiliyirp
2221 mrelrggswv vidatinplc iemyadkesr ggvlepegtv eikfrkedli ksmrridpay
2281 kklmeqlgep dlsdkdrkdl egrlkaredl llpiyhqvav qfadfhdtpg rmlekgvisd
2341 ilewktartf lywrlrrlll edqvkqeilq asgelshvhi qsmlrrwfve tegavkaylw
2401 dnnqvvvqwl eqhwqagdgp rstirenity lkhdsvlkti rglveenpev avdcviylsq
2461 hispaeraqv vhllstmdsp ast (SEQ ID NO:9)
```

FIG. 17B

```
  1    rvlqaevkin  irqtttgsav  pirlfitnes  gyyldislyk  evtdsrsgni  mfhsfgnkqg
 61    pqhgmlintp  yvtkdllqak  rfqaqtlgtt  yiydfpemfr  qalfklwgsp  dkypkdlilty
121    telvldsqgq  lvemnrlpgg  nevgmvafkm  rfktqeypeg  rdvivigndi  tfrigsfgpg
181    edllylrase  maraeaipki  yvaansgari  gmaeeikhmf  hvawvdpedp  hkgfkylylt
241    pqdytrissl  nsvhckhiee  ggesrymitd  iigkddglgv  enlrgsgmia  gesslayeei
301    vtislvtcra  igigaylvrl  gqrviqvens  hiiltgasal  nkvlgrevyt  snnqlggvqi
361    mhyngvshit  vpddfegvyt  ilewlsympk  dnhspvpiit  ptdpidreie  flpsrapydp
421    rwmlagrphp  tlkgtwqsgf  fdhgsfkeim  apwaqtvvtg  rarlggipvg  viavetrtve
481    vavpadpanl  dseakiiqqa  gqvwfpdsay  ktaqaikdfn  reklplmifa  nwrgfsggmk
541    dmydqvlkfg  ayivdglrqy  kqpiliyirp  mrelrggswv  vidatinplc  iemyadkesr
601    ggvlepegtv  eikfrkedli  ksmrridpay  kklmeqlgep  dlsdkdrkdl  egrlkaredl
661    llpiyhqvav  qfadfhdtpg  rmlekgvisd  ilewktartf  lywrlrrlll  edqvkqeilq
721    asgelshvhi  qsmlrrwfve  tegavkaylw  dnnqvvvqwl  eqhwqagdgp  rstirenity
781    lkhdsvlkti  rglveenpev  avdcviylsq  hispaeraqv  vhllstmdsp  ast
       (SEQ ID NO:10)
```

FIG. 18

```
  1 ldvldrcasd prvsatasgr lflhivspln lasakavteh fhkmmkrfrs ehnerllrlr
 61 vdqievkmhl rkggsgsdge krssreegae atgsqakeke rlqvlrlsvs shqgswlhtk
121 asedvphvlt gdpiaqrsfv fdegeetdae gfvaqaspag sgaegadgak sratektgqr
181 egdaapvvrr eppeaegllg risvglktlr gtqtsatgsa gagempaass sppgrweggd
241 rkkqellsvs rreeneffrh ekdadpypev driamarsaa rragstyifd flglmeiall
301 qswqthlkek gekdggvggw deavprdlfk aeafkvsaqg tlyldpdwrv adnkigmvgf
361 litlktpeyp sgrqvvllgn ditfqggsfg vpehlfftqv srfsreqglp rvyiacnsga
421 riglyenlkd kikvewndas npslgfknly lsaedyaalp pgvvsghfee avngdqrrfv
481 ldaiigdpdk figvenlrgs gtiagetsra ydetftlsyv tgrsvgigay ivrlaqrtiq
541 mvrgplllltg yqalnkllgr evyasqdqlg gpevmfrngv shlvvqndqe gmkevlrwla
601 ytpktardsv ssaemfssdp verevaftpt kapydvrhml agytkedgtf vsgffdknsf
661 keylagwgks vvvgrarlgg ipfgaiavet rttearvpad psspdsresv imhagqvwfp
721 dsayktaqai ndfnrgenlp liifanwrgf sggtrdmfee ilkfgsqivd alrtykqpvf
781 iyipphgelr ggswvvvdpt inlqkmemya danarggvle ppgiceikyr aadqkalmhr
841 vddvlkeldk qlqdcqtasd aidlkekikr reaaleplyl siarfyadlh drpermkarg
901 vissivnwkn srcifywrak rrllqddlea rilaadarld ytkarakied llkshgvdia
961 gdkaacefls stegkeatqa iversrrega iekirdilss lpeserretl esaatpac
```
(SEQ ID NO:11)

FIG. 19

```
   1  mgsthlpivg  lnasttpsls  tirpvnsaga  afqpsapsrt  skkksrrvqs  lrdggdggvs
  61  dpnqsirqgl  agiidlpkeg  tsapevdish  gseeprgsyq  mngilneahn  grhaslskvv
 121  efcmalggkt  pihsvlvann  gmaaakfmrs  vrtwanetfg  sekaiqliam  atpedmrina
 181  ehiriadqfv  evpggtnnnn  yanvqlivei  avrtgvsavw  pgwghasenp  elpdalnang
 241  ivflgppsss  mnalgdkvgs  aliaqaagvp  tlpwsgsqve  iplevcldsi  paemyrkacv
 301  stteealasc  qmigypamik  aswggggkgi  rkvnndddvr  alfkqvqgev  pgspifimrl
 361  asqsrhlevq  llcdqygnva  alhsrdcsvq  rrhqkiieeg  pvtvapretv  keleqaarrl
 421  akavgyvgaa  tveylysmet  geyyflelnp  rlqvehpvte  wiaevnlpaa  qvavgmgipl
 481  wqvpeirrfy  gmdngggydi  wrktaalatp  fnfdevdsqw  pkghcvavri  tsedpddgfk
 541  ptggkvkeis  fkskpnvway  fsvksgggih  efadsqfghv  faygvsraaa  itnmslalke
 601  iqirgeihsn  vdytvdllna  sdfkenriht  gwldnriamr  vqaerppwyi  svvggalykt
 661  itsntdtvse  yvsylvkgqi  ppkhislvhs  tvslnieesk  ytietirsgq  gsyrlrmngs
 721  vieanvqtlc  dggllmqldg  nshviyaeee  aggtrllidg  ktcllqndhd  psrllaetpc
 781  kllrflvadg  ahveadvpya  evevmkmcmp  llspaagvin  vllsegqpmq  agdliarldl
 841  ddpsavkrae  pfngsfpems  lpiaasgqvh  krcatslnaa  rmvlagydhp  inkvvqdlvs
 901  cldapelpfl  qweelmsvla  trlprllkse  legkyseykl  nvghgkskdf  pskmlreiie
 961  enlahgseke  iatnerlvep  lmsllksyeg  greshahfiv  kslfedylsv  eelfsdgiqs
1021  dvierlrqqh  skdlqkvvdi  vlshqgvrnk  tkliltlmek  lvypnpavyk  dqltrfssln
1081  hkryyklalk  aselleqtkl  selrtsiars  lselemftee  rtaiseimgd  lvtaplpved
1141  alvslfdcsd  qtlqqrviet  yisrlyqphl  vkdsiqlkyq  esgvialwef  aeahsekrlg
1201  amvivksles  vsaaigaalk  gtsryasseg  nimhiallga  dnqmhgteds  gdndqaqvri
```

FIG. 20A

```
1261 dklsatleqn tvtadlraag vkviscivqr dgalmpmrht fllsdeklcy eeepvlrhve
1321 pplsallelg klkvkgynev kytpsrdrqw niytlrnten pkmlhrvffr tlvrqpgasn
1381 kftsgnisdv evggaeesls ftsssilrsl mtaieelelh airtghshmf lcilkeqkll
1441 dlvpvsgnkv vdigqdeata clllkemalq ihelvgarmh hlsvcqwevk lkldsdgpas
1501 gtwrvvttnv tshtctvdiy revedtesqk lvyhsapsss gplhgvalnt pyqplsvidl
1561 krcsarnnrt tycydfplaf etavqkswsn issdtnrcyv katelvfahk ngswgtpvip
1621 merpaglndi gmvawildms tpeypngrqi vvianditfr agsfgpreda ffetvtnlac
1681 erklpliyla ansgarigia devkscfrvg wsddgsperg fqyiylteed harisasvia
1741 hkmqldngei rwvidsvvgk edglgvenih gsaaiasays rayeetftlt fvtgrtvgig
1801 aylarlgirc iqrtdqpiil tgfsalnkll grevysshmq lggpkimatn gvvhltvsdd
1861 legvsnilrw lsyvpanigg plpitksldp pdrpvayipe ntcdpraais giddsqgkwl
1921 ggmfdkdsfv etfegwaksv vtgraklggi pvgviavetq tmmqlipadp gqldshersv
1981 pragqvwfpd satktaqaml dfnreglplf ilanwrgfsg gqrdlfegil qagstivenl
2041 rtynqpafvy ipkaaelrgg awvvidskin pdriefyaer takgnvlepq glieikfrse
2101 elqecmgrld pelinlkakl qgvkhengsl peseslqksi earkkqllpl ytqiavrfae
2161 lhdtslrmaa kgvikkvvdw edsrsffykr lrrrisedvl akeirgvsgk qfshqsaiel
2221 iqkwylaskg aetgstewdd ddafvawren penyqeyike lraqrvsqll sdvadsspdl
2281 ealpqglsml lekmdpsrra qfveevkkvl k (SEQ ID NO:12)
```

FIG. 20B

```
   1 mwalgdkias sivaqtagip tlpwsgsglr vdwqendfsk rilnvpqdly ekgyvkdvdd
  61 glkaaeevgy pvmikasegg ggkgirkvnn addfpnlfrq vqaevpgspi fvmrlakqsr
 121 hlevqiladq ygnaislfgr dcsvqrrhqk iieeapaaia tpavfehmeq cavklakmvg
 181 yvsagtveyl ysqdgsfyfl elnprlqveh pctemvadvn lpaaqlqiam giplfrikdi
 241 rmmygvspwg dapidfensa hvpcprghvi aaritsenpd egfkpssgtv qelnfrsnkn
 301 vwgyfsvaaa gglhefadsq fghcfswgen reeaisnmvv alkelsirgd frttveylik
 361 lletesfqln ridtgwldrl iaekvqaerp dtmlgvvcga lhvadvslrn sisnflhsle
 421 rgqvlpahtl lntvdveliy egikyvlkvt rqspnsyvvi mngscvevdv hrlsdggll
 481 sydgssytty mkeevdryri tignktcvfe kendpsvmrs psagkliqyi vedgghvfag
 541 qcyaeievmk mvmtltaves gcihyvkrpg aaldpgcvia kmqldnpskv qqaelhtgsl
 601 pqiqstalrg eklhrvfhyv ldnlvnvmng yclpdpffss rvkdwverlm ktlrdpslpl
 661 lelqdimtsv sgriplnvek sikkemaqya snitsvlcqf psqqianild shaatlnrks
 721 erevffmntq sivqlvqryr sgirghmkav vmdllrqylr vetqfqnghy dkcvfalree
 781 nksdmntvln yifshaqvtk knllvtmlid qlcgrdptlt dellniltel tqlskttnak
 841 valrarqvli ashlpsyelr hnqvesifls aidmyghqfc ienlqklils etsifdvlpn
 901 ffyhsnqvvr maalevyvrr ayiayelnsv qhrqlkdntc vvefqfmlpt shpnrgnipt
 961 lnrmsfasnl nhygmthvas vsdvlldnaf tppcqrmggm vsfrtfedfv rifdeimgcf
1021 cdsppqsptf pesghtslyd edkvprdepi hilnvaiktd gdieddrlaa mfreftqqnk
1081 atlvehgirr ltflvaqkdf rkqvncevdq rfhrefpkff tfrardkfee driyrhlepa
1141 lafqlelnrm rnfdltaipc anhkmhlylg aakvevgtev tdyrffvrai irhsdlvtke
1201 asfeylqneg erllleamde levafnntnv rtdcnhifln fvptvimdps kieesvrsmv
```

FIG. 21A

```
1261  mrygsrlwkl  rvlqaelkin  irltttgkai  pirlfltnes  gyyldislyk  evtdsrtaqi
1321  mfqaygdkqg  plhgmlintp  yvtkdllqsk  rfqaqslgtt  yiydipemfr  qsliklwesm
1381  stqaflpspp  lpsdiltyte  lvlddqgqlv  hmnrlpggne  igmvawkmsl  kspeypdgrd
1441  iivigndity  rigsfgpqed  llflrasela  raegipriyv  aansgarigl  aeeirhmfhv
1501  awvdpedpyk  gykylyltpq  dykrvsalns  vhcehvedeg  esrykitdii  gkeeglgaen
1561  lrgsgmiage  sslaydevit  islvtcraig  igaylvrlgq  rtiqvenshl  iltgagalnk
1621  vlgrevytsn  nqlggiqimh  nngvthstvc  ddfegvftvl  hwlsympksv  hssvpllnsk
1681  dpidriiefv  ptkapydprw  mlagrphptq  kgqwlsgffd  ygsfseimqp  waqtvvvgra
1741  rlggipvgvv  avetrtvels  ipadpanlds  eakiiqqagq  vwfpdsafkt  yqaikdfnre
1801  glplmvfanw  rgfsggmkdm  ydqvlkfgay  ivdglrecsq  pvmvyippqa  elrggswvvi
1861  dptinprhme  myadresrgs  vlepegtvei  kfrkkdlvkt  mrrvdpvyir  laerlgtpel
1921  spterkeles  klkereefli  piyhqvavqf  adlhdtpgrm  qekgvindil  dwktsrtffy
1981  wrlrrllled  lvkkkihnan  peltdgqiqa  mlrrwfveve  gtvkayvwdn  nkdlvewlek
2041  qlteedgvrs  vieenikyis  rdyvlkqirs  lvqanpevam  dsivhmtqhi  sptqraevvr
2101  ilstmdspst  (SEQ ID NO:13)
```

FIG. 21B

| | | | | | |
|---|---|---|---|---|---|
| 1 | lfltnesgyy | ldislykevt | dsrtaqimfq | aygdkqgplh | gmlintpyvt | kdllqskrfq |
| 61 | aqslgttyiy | dipemfrqsl | iklwesmstq | aflpspplps | diltytelvl | ddqgqlvhmn |
| 121 | rlpggneigm | vawkmslksp | eypdgrdiiv | igndityrig | sfgpqedllf | lraselarae |
| 181 | gipriyvaan | sgariglaee | irhmfhvawv | dpedpykgyk | ylyltpqdyk | rvsalnsvhc |
| 241 | ehvedegesr | ykitdiigke | eglgaenlrg | sgmiagessl | aydevitisl | vtcraigiga |
| 301 | ylvrlgqrti | qvenshlilt | gagalnkvlg | revytsnnql | ggiqimhnng | vthstvcddf |
| 361 | egvftvlhwl | sympksvhss | vpllnskdpi | driiefvptk | apydprwmla | grphptqkgq |
| 421 | wlsgffdygs | fseimqpwaq | tvvvgrarlg | gipvgvvave | trtvelsipa | dpanldseak |
| 481 | iiqqagqvwf | pdsafktyqa | ikdfnreglp | lmvfanwrgf | sggmkdmydq | vlkfgayivd |
| 541 | glrecsqpvm | vyippqaelr | ggswvvidpt | inprhmemya | dresrgsvle | pegtveikfr |
| 601 | kkdlvktmrr | vdpvyirlae | rlgtpelspt | erkelesklk | ereeflipiy | hqvavqfadl |
| 661 | hdtpgrmqek | gvindildwk | tsrtffywrl | rrllledlvk | kkihnanpel | tdgqiqamlr |
| 721 | rwfvevegtv | kayvwdnnkd | lvewlekqlt | eedgvrsvie | enikyisrdy | vlkqirslvq |
| 781 | anpevamdsi | vhmtqhispt | qraevvrils | tmdspst (SEQ ID NO:14) | | |

FIG. 22

CARBOXYLTRANSFERASE DOMAIN OF ACETYL-COA CARBOXYLASE

This disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights. This application claims the benefit of the priority of the following four U.S. Provisional Applications: U.S. Ser. No. 60/439,383, filed Jan. 10, 2003; 60/459,464, filed Mar. 31, 2003; 60/491,640, filed Jul. 31, 2003; and 60/514,636, filed Oct. 27, 2003 and the entire contents of these applications are hereby incorporated by reference into this application.

All patent applications, published patent applications, issued and granted patents, texts, and literature references cited in this specification are hereby incorporated herein by reference in their entirety to more fully describe the state of the art to which the present invention pertains.

BACKGROUND OF THE INVENTION

Acetyl-coenzyme A carboxylases (ACCs) are crucial for the biosynthesis and oxidation of long-chain fatty acids, and they are important targets for the development of therapeutic agents against obesity, diabetes, and bacterial infections. See Alberts and Vagelos, 1972, *The Enzymes*, Boyer, ed., Academic Press, New York, vol. 6, pp. 37-82; Wakil et al., 1983, *Ann. Rev. Biochem.* 52:537-579; McGarry and Brown, 1997, *Eur. J. Biochem.* 244:1-14; Abu-Elheiga et al., 2001, *Science* 291:2613-2616; Ramsay et al., 2001, *Biochim. Biophys. Acta* 1546:21-43; Cronan, Jr. and Waldrop, 2002, *Prog. Lipid Res.* 41:407-435; Lenhard and Gottschalk, 2002, *Advanced Drug Delivery Reviews* 54:1199-1212. In addition, the carboxyltransferase (CT) domain of this enzyme from some plants is the site of action of widely-used commercial herbicides such as haloxyfop and sethoxydim (Gronwald, 1991, *Weed Science* 39:435-449; Devine and Shukla, 2000, *Crop Protection* 19:881-889; Zagnitko et al., 2001, *Proc. Natl. Acad. Sci. USA* 98:6617-6622; Delye et al., 2003, *Plant Physiol.* 132:1716-1723).

ACCs catalyze the formation of malonyl-CoA from acetyl-CoA and $CO_2$, a reaction that also requires the hydrolysis of ATP. Two isoforms of this enzyme have been identified in mammals. ACC 1, a cytosolic enzyme, catalyzes the committed step in the biosynthesis of long-chain fatty acids. Wakil et al, 1983, *Ann. Rev. Biochem.* 52:537-579. In comparison, ACC2 is associated with the mitochondrial membrane and its malonyl-CoA product potently inhibits the shuttle that transports long-chain acyl-CoAs from the cytosol to the mitochondria for oxidation. McGarry and Brown, 1997, *Eur. J. Biochem.* 244:1-14; Ramsay et al., 2001, *Biochim. Biophys. Acta* 1546:21-43.

The malonyl-CoA produced in the ACC-catalyzed reaction is a negative regulator of carnitine palmitoyltransferase 1, which is involved in fatty acid oxidation. During starvation, ACC levels and consequently malonyl-CoA levels are decreased and fatty acid oxidation is increased. The reduction of malonyl-CoA results in an increase in ATP synthesis which is directly linked to an increase in fatty acid oxidation, and also results in a decrease in ATP consumption for fatty acid synthesis which is consequently decreased. Interestingly, mice lacking ACC2 exhibit a higher rate of fatty acid oxidation and reduced body fat and body weight, while genetic ablation of ACC1 in mice was found to be embryonically lethal, possibly due to lack of $C_2$ units for the synthesis of fatty acid needed for biomembrane synthesis. See Abu-Elheiga et al., *Science* 291:2613-2616 (2001); see also U.S. Patent Application Publication No. 20030028912 of Matzuk et al. published Feb. 6, 2003.

Mammalian, yeast, and most other eukaryotic ACCs are large, multi-functional enzymes, containing the biotin carboxylase (BC) domain, the biotin carboxyl carrier protein (BCCP) domain, and the carboxyltransferase (CT) domain. See FIG. 1A. BC catalyzes the ATP-dependent carboxylation of a biotin group covalently linked to a lysine residue in BCCP, and then CT catalyzes the transfer of the carboxyl group from biotin to acetyl-CoA to produce malonyl-CoA. In *E. coli* and other bacteria, ACCs are multi-subunit enzymes composed of 3 distinct protein subunits, with a BC subunit, a BCCP subunit, and two subunits for the CT. See FIG. 1A. Crystal structures are available for the BC and BCCP subunits of *E. coli* ACC (see Cronan Jr. and Waldrop, 2002, *Prog. Lipid Res.* 41:407-435).

SUMMARY OF THE INVENTION

The present invention provides compositions and crystals of the carboxyltransferase (CT) domain (the C-terminal ~90 kDa fragment) of various acetyl-CoA carboxylase (ACC) proteins, including yeast, mouse and human ACCs. Further, the present invention provides methods for identifying and designing compounds that can modulate ACC activity. These methods are based, in part, on the X-ray crystallographic structures of the CT domain of yeast ACC as produced by construct yCTACC (the yeast CT domain comprising residues 1429-2233 (SEQ ID NO:2) of the *S. cerevisiae* ACC set forth in GenBank Entry No. Q00955 (SEQ ID NO:1)), either alone or bound to acetyl-CoA or a CT inhibitor, such as haloxyfop or diclofop; or the CT domain of yeast ACC as produced by construct yCT2ACC (the yeast CT domain comprising residues 1476-2233 (SEQ ID NO:3) of the *S. cerevisiae* ACC set forth in GenBank Entry No. Q00955) either alone, or bound to a CT inhibitor, such as haloxyfop, diclofop or CP-640186. Thus, the present invention relates to the crystal structures of the carboxyltransferase ("CT") domain of acetyl-CoA carboxylase ("ACC"), to the use of these domains for identifying inhibitors of ACCs, and to the use of these structures in the design of anti-obesity compounds, anti-diabetes compounds, antibiotic compounds, herbicide compounds, fungicide compounds and in the design of herbicide resistant plants.

The disclosure includes seven (7) tables provided as an appendix on compact disc, Tables 1, 2, 3, 4, 5, 6 and 7. The compact disc is formatted for IBM-PC using an MS-Windows operating system, and contains 7 files, entitled: "Table 1" of size 1,319 KB created on Dec. 30, 2003; "Table 2" of size 916 KB created on Dec. 30, 2003; "Table 3" of size 1,229 KB created on Dec. 30, 2003; "Table 4" of size 856 KB created on Dec. 30, 2003; "Table 5" of size 1,264 KB created on Dec. 30, 2003; "Table 6" of size 1,042 KB created on Dec. 30, 2003; and "Table 7" of size 1,236 KB created on Dec. 30, 2003. These tables contain a list of the atomic coordinates of amino acids within the crystals of carboxyltransferase ("CT") domains of yeast acetyl-CoA carboxylase ("ACC") either in uncomplexed ("free") or complexed form. Table 1 presents a list of the atomic coordinates of an uncomplexed CT domain crystal, where the CT domain polypeptide has the amino acid sequence of SEQ ID NO:2. For the present invention, the sequences that refer to a CT domain, i.e. SEQ ID NOS: 2, 3, 4, 6, 8, 10 and 14, refer to the sequence of one monomer of the CT domain. A CT domain comprises a dimer composed of two identical monomers, and from the crystal structures, it is generally the case that sequence residues below 1800 (in relation to SEQ ID NO: 1 numbering) comprise one face of a binding pocket from one monomer and sequence residues above 1800 comprise the other face of a binding pocket from the other monomer. Table 2 presents a list of the atomic coordinates of a complexed CT domain crystal, where the CT domain is complexed to acetyl-CoA, and where the CT domain polypeptide has the amino acid sequence of SEQ ID NO:2. Table 3 presents a list of the atomic coordinates of a complexed CT domain crystal, where the CT domain is complexed to the inhibitor haloxyfop, and where the CT domain polypeptide has the amino acid sequence of SEQ ID NO:2. Table 4 presents a list of the atomic coordinates of a complexed CT domain crystal, where the CT domain is complexed to the inhibitor diclofop, and where the CT domain polypeptide has the amino acid sequence of SEQ ID NO:3. Table 5 presents a list of the atomic coordinates of a complexed CT domain crystal, where the CT domain is complexed to the inhibitor CP-640186, and where the CT domain polypeptide has the amino acid sequence of SEQ ID NO:3. Table 6 presents a list of the atomic coordinates of an uncomplexed CT domain crystal, where the CT domain polypeptide has the amino acid sequence of SEQ ID NO:4. Table 7 presents a list of the atomic coordinates of an uncomplexed CT domain crystal, where the CT domain polypeptide has the amino acid sequence of SEQ ID NO:3. These atomic coordinate listings will not appear in the printed patent, but are provided herewith as separate files named by Table number on duplicate copies of a single electronically readable compact disc in compliance with 37 C.F.R. §1.52(e). The contents of these files are hereby incorporated by reference in their entireties.

In one aspect of the present invention, a crystallizable composition comprises a carboxyltransferase domain of acetyl-coenzyme A (CoA) carboxylase. The carboxyltransferase domain of the crystallizable composition can comprise a human carboxyltransferase domain, a mouse carboxyltransferase domain, or a yeast carboxyltransferase domain. The carboxyltransferase domain of the crystallizable composition can be complexed with a ligand. The ligand can comprise acetyl-CoA or a compound that inhibits activity of the carboxyltransferase domain. Compounds that inhibit activity of the CT domain include, for example, haloxyfop (FIG. 5A), diclofop (FIG. 5A) and CP-640186 (FIG. 23; and see U.S. Patent Application Publication No.US2003/0187254 A1; Harwood, J. H. et al., *J. Biol. Chem.* 278(39): 37099-37111 (2003)).

In another aspect of the present invention, the carboxyltransferase domain of the crystallizable composition can comprise two monomers, each monomer comprising consecutive amino acid residues at least 50% identical to SEQ ID NO:2; SEQ ID NO:3, SEQ ID NO:4, SEQ ID NO: 6, SEQ ID NO:8, SEQ ID NO:10 or SEQ ID NO:14. In other aspects, each monomer comprises consecutive amino acid residues at least 60%, 65%, 70%, 75%, 80%, 85%, 90%, 95% or 99% identical to SEQ ID NO:2; SEQ ID NO:3, SEQ ID NO:4, SEQ ID NO: 6, SEQ ID NO:8, SEQ ID NO:10 or SEQ ID NO:14.

The present invention also provides various crystals comprising a carboxyltransferase domain of acetyl-CoA carboxylase. In one aspect, a crystal comprises a carboxyltransferase domain of acetyl-CoA carboxylase, wherein the domain comprises two monomers. In other aspects, a crystal comprises a carboxyltransferase domain of acetyl-CoA carboxylase complexed with acetyl-CoA, haloxyfop, diclofop or CP-640186. The CT domain of the crystals can comprise, for example, a human carboxyltransferase domain, a mouse carboxyltransferase domain, or a yeast carboxyltransferase domain.

In another aspect, the crystal comprises a carboxyltransferase domain of acetyl-CoA carboxylase, wherein the CT domain comprises two monomers, and the crystal comprises unit cell dimensions of about: (a) a=247±2 Å; b=125±2 Å; c=145±2 Å; α=90°; β=94±2°; γ=90°; and space group C2 (b) a=255±2 Å; b=113+2 Å; c=135±2 Å; α=90°; β=101 ±2°; γ=90°; and space group C2 (c) a=246±2 Å; b=124±2 Å; c=145±2 Å; α=90°; β=94±2°; γ=90°; and space group C2; (d) a=93±2 Å; b=138±2 Å; c=101±2 Å; c=90°; β=114±20; γ=90°; and space group P2, (e) a=137±2 Å; b=137±2 Å; c=244±2 Å; α=90°; β=90°; γ=120°; and space group P3$_2$21; or (f) a=247±2 Å; b=125±2 Å; c=146±2 Å; a=90°; β=94±°; γ=90°; and space group C2.

In another aspect, the crystal comprises a carboxyltransferase domain of acetyl-CoA carboxylase, wherein the CT domain comprises two monomers, and wherein each monomer of the carboxyltransferase domain comprises consecutive amino acid residues at least 50% identical to SEQ ID NO:2; SEQ ID NO:3, SEQ ID NO:4, SEQ ID NO: 6, SEQ ID NO:8 or SEQ ID NO: 10. In other aspects, each monomer of the CT domain comprises consecutive amino acid residues of at least 60%, 65%, 70%, 75%, 80%, 85%, 90%, 95% or 99% identical to SEQ ID NO:2; SEQ ID NO:3, SEQ ID NO:4, SEQ ID NO: 6, SEQ ID NO:8, SEQ ID NO:10 or SEQ ID NO:14.

In another aspect, the crystal comprises a carboxyltransferase domain of acetyl-CoA carboxylase, wherein the CT domain comprises two monomers, and wherein the carboxyltransferase domain comprises a three-dimensional structure characterized by the atomic coordinates of Table 1, Table 2, Table 3, Table 4, Table 5, Table 6 or Table 7.

The present invention also provides an isolated carboxyltransferase domain comprising two monomers, each monomer comprising consecutive amino acid residues at least 50%, 60%, 65%, 70%, 75%, 80%, 85%, 90%, 95% or 99% identical to SEQ ID NO:2; SEQ ID NO:3, SEQ ID NO:4, SEQ ID NO: 6, SEQ ID NO:8, SEQ ID NO:10 or SEQ ID NO:14. The isolated CT domain can comprise, for example, a human carboxyltransferase domain, a mouse carboxyltransferase domain, or a yeast carboxyltransferase domain.

In another aspect, the isolated CT domain comprises two monomers, each monomer comprising consecutive amino acid residues at least 50%, 60%, 65%, 70%, 75%, 80%, 85%, 90%, 95% or 99% identical to the amino acid residues of SEQ ID NO:2; SEQ ID NO:3, SEQ ID NO:4, SEQ ID NO: 6, SEQ ID NO:8, SEQ ID NO:10 or SEQ ID NO:14, except that amino acid residues of each of the aforementioned SEQ ID NOS. identified in Table G as corresponding to amino acid residues 11974, V2002, G1998, V2001, V2024, L1968, F1956, W1924, Y1738, S1708, A1627, 11735, G1734 and L1756 of SEQ ID NO:1 do not vary. In another aspect, these residues can vary conservatively. The residue numbering is in relation to SEQ ID NO: 1, and the corresponding residues for SEQ ID NO:2; SEQ ID NO:3, SEQ ID NO:4, SEQ ID NO: 6, SEQ ID NO:8, SEQ ID NO:10 or SEQ ID NO:14 have been determined as listed in Table G. Further, residues corresponding to SEQ ID NO: 1 that are not listed in Table G can be determined by Blast alignment (for example, see FIG. 4). Further, the reference to a first monomer or a second monomer is in relation to the three-dimensional structure of an isolated CT domain, as a CT domain comprises two monomers that are identical in amino acid sequence. Additionally, as a CT domain comprises two monomer units, a binding site of a CT domain is comprised of residues from both monomers. Generally, where residues are listed as comprising a binding site or some other feature of a CT domain that involves both monomer units, residues below 1800 (in relation to SEQ ID NO:1 numbering) are from one monomer, and residues above 1800 are from the other monomer. Thus, in the disclosure, residues above 1800 are sometimes denoted with an apostrophe symbol (i.e. Ala 1908') to indicate their location within a separate monomer, however, it is not necessary to denote the residue with an apostrophe.

In another aspect, the isolated CT domain comprises two monomers, each monomer comprising consecutive amino acid residues at least 50%, 60%, 65%, 70%, 75%, 80%, 85%, 90%, 95% or 99% identical to the amino acid residues of SEQ ID NO:2; SEQ ID NO:3, SEQ ID NO:4, SEQ ID NO: 6, SEQ ID NO:8, SEQ ID NO:10 or SEQ ID NO:14, except that amino acid residues of each of the aforementioned SEQ ID NOS. identified in Table G as corresponding to amino acid residues A1761, K1764, L2025, E2026, G2029 of SEQ ID NO:1 do not vary, and amino acid residue Met 1765 can be Val. In another aspect, these residues can vary conservatively. The residue numbering is in relation to SEQ ID NO:1, and the corresponding residues for SEQ ID NO:2; SEQ ID NO:3, SEQ ID NO:4, SEQ ID NO: 6, SEQ ID NO:8, SEQ ID NO:10 or SEQ ID NO:14 is listed in Table G.

In another aspect, the isolated CT domain comprises two monomers, each monomer comprising consecutive amino acid residues at least 50%, 60%, 65%, 70%, 75%, 80%, 85%, 90%, 95% or 99% identical to the amino acid residues of SEQ ID NO:2; SEQ ID NO:3, SEQ ID NO:4, SEQ ID NO: 6, SEQ ID NO:8 or SEQ ID NO:10, except that amino acid residues of each of the aforementioned SEQ ID NOS. identified in Table G as corresponding to amino acid residues Ile1593, Ser1595, Phe1596, Asn1624, Ser1625, Gly1626, Ala1627, Arg1628, Ile1629, Gly1630, Gly1699, Leu1705, Arg1731, Gly1734, Ile1735, Tyr1738, Ile1755, Leu1756, Thr1757, Gly1758, Ala1759, Ala1761, Asn1774, Gly1955, Phe1956, Arg1996, Gly1997, Gly1998, Ser1999, Val2001, Val2024, Leu2025, Gly2029, Ile2033, Lys2034 and Arg2036 of SEQ ID NO:1 do not vary. In another aspect, these residues can vary conservatively. The residue numbering is in relation to SEQ ID NO:1, and the corresponding residues for SEQ ID NO:2; SEQ ID NO:3, SEQ ID NO:4, SEQ ID NO: 6, SEQ ID NO:8, SEQ ID NO:10 or SEQ ID NO:14 are listed in Table G.

In another aspect, the isolated CT domain comprises two monomers, each monomer comprising consecutive amino acid residues at least 50%, 60%, 65%, 70%, 75%, 80%, 85%, 90%, 95% or 99% identical to the amino acid residues of SEQ ID NO:2; SEQ ID NO:3, SEQ ID NO:4, SEQ ID NO: 6, SEQ ID NO:8 or SEQ ID NO:10, except that amino acid residues of each of the aforementioned SEQ ID NOS. identified in Table G as corresponding to amino acid residues Phe1596, Ser1625, Gly1626, Ala1627, Arg1628, Ile1629, Leu1705, Ser1708, Ala1712, Gly1734, Ile1735, Gly1736, Ala1737, Tyr1738, Leu1739, Arg1741, Leu1742, Ile1755, Leu1756, Thr1757, Val1923, Trp1924, Pro1926, Ser1928, Ala1929, Trp1953, Gly1955, Phe1956, Ser1957, Val1967, Leu1968, Lys1969, Gly1971, Ile1974, Arg1996, Gly1997, Gly1998, Ser1999, Trp2000, Val2001, Val2002, Val2024 and Leu2025 of SEQ ID NO:1 do not vary. In another aspect, these residues can vary conservatively. The residue numbering is in relation to SEQ ID NO: 1, and the corresponding residues for SEQ ID NO:2; SEQ ID NO:3, SEQ ID NO:4, SEQ ID NO: 6, SEQ ID NO:8, SEQ ID NO: 10 or SEQ ID NO: 14 is listed in Table G.

In another aspect, the isolated CT domain comprises two monomers, each monomer comprising consecutive amino acid residues at least 50%, 60%, 65%, 70%, 75%, 80%, 85%, 90%, 95% or 99% identical to the amino acid residues of SEQ ID NO:2; SEQ ID NO:3, SEQ ID NO:4, SEQ ID NO: 6, SEQ ID NO:8 or SEQ ID NO:10, except that amino acid residues of each of the aforementioned SEQ ID NOS. identified in Table G as corresponding to amino acid residues Ile1629, Leu1756, Thr1757, Gly1758, Ala1761, Asn1763, Lys1764, Leu1766, Tyr1771, Ala1908, Gln1922, Val1923, Trp1924, Trp1953, Arg1954, Gly1955, Phe1956, Ser1957, Gly1958, Gly1959, Asp1962, Arg1996, Gly1997, Ser1999, Val2024, Leu2025, Glu2026, Pro2027, Gly2029, Val2031 and Ile2033 of SEQ ID NO:1 do not vary. The residue numbering is in relation to SEQ ID NO:1, and the corresponding residues for SEQ ID NO:2; SEQ ID NO:3, SEQ ID NO:4, SEQ ID NO: 6, SEQ ID NO:8, SEQ ID NO:10 or SEQ ID NO:14 is provided in Table G.

In yet another aspect, an isolated carboxyltransferase domain comprises two monomers, each monomer comprising amino acid residues at least 50%, 60%, 65%, 70%, 75%, 80%, 85%, 90%, 95% or 99% identical to the amino acid residues of SEQ ID NO:2; SEQ ID NO:3, SEQ ID NO:4, SEQ ID NO: 6, SEQ ID NO:8, SEQ ID NO:10 or SEQ ID NO:14, which are shown to be corresponding to the following amino acid residues of SEQ ID NO:1 in Table G: Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761,Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Tyr1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 (wherein the residue numbering is in relation to SEQ ID NO:1, and the corresponding residues for SEQ ID NOS:2, 3, 4, 6, 8, 10 and 14 are listed in Table G), wherein linear spatial relationship of the residues of SEQ ID NO:1 are preserved in the CT domain.

The crystal structures of the present invention is useful, inter alia, for the rational design of compounds that modulate the activity of the CT domain of ACC. In view of the biological importance of ACC, modulators of the CT domain of ACC may be used in the treatment of various diseases and disorders, including but not limited to, obesity, metabolic syndrome, diabetes, cardiovascular disease, atherosclerosis and infections. The present invention may also be used to design and/or screen metabolic enhancers that may be used to promote endurance or survival under stressful conditions. The structural models of the present invention are based, at least in part, on the X-ray crystallographic structure of the CT domains encoded by the vectors yCTACC or yCT2ACC, both free and bound to the inhibitors haloxyfop, diclofop or CP-640186. These models are useful for the rational design of therapeutic compounds, herbicide compounds, pesticide compounds, as well as for the design and optimization of herbicide resistant plants.

Thus, the present invention provides a method for identifying a compound that modulates activity of acetyl-CoA carboxylase comprising: (a) providing the atomic coordinates for at least 10, 20, 30 or 50 amino acid residues for a carboxyltransferase domain of acetyl-CoA carboxylase as set forth in any of Tables 1 to 7, or coordinates having a root mean square deviation therefrom, with respect to at least 50% of Cα atoms, of not more than ±2 Å or ±1.5 Å in computer readable form; (b) converting the atomic coordinates into electrical signals readable by a computer processor; (c) providing a structure of a candidate compound in computer readable form; and (d) determining whether or not the candidate compound fits into a binding cavity of the carboxyltransferase domain, so as to identify a compound that modulates activity of acetyl-CoA carboxylase. This method can further comprise determining whether contacting the candidate compound to the carboxyltransferase domain under enzymatically acceptable conditions modulates carboxyltransferase domain activity.

The present invention also provides a method for rationally designing a compound that modulates activity of acetyl-CoA carboxylase, comprising: (a) generating a computer readable model of a binding site of a carboxyltransferase domain of acetyl-CoA carboxylase; and (b) using the model to design a compound having a structure and a charge distribution compatible with the binding site, wherein the compound comprises a functional group that interacts with the binding site to modulate acetyl-CoA carboxylase activity. Additionally, the method can further comprise outputting the design of the compound to a user.

In the method for rationally designing a compound that modulates activity of acetyl-CoA carboxylase, compatibility of the compound to the binding site can be determined by determining whether the compound has a proximity of at least 2-10 Å, 2-7 Å or of at least 2.5-4 Å to residues Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036, Leu2189 of SEQ ID NO:1, or to the corresponding residues for SEQ ID NO:2, 3, 4, 6, 8, 10 and 14 as listed in Table G.

In another aspect of the method for rationally designing a compound that modulates activity of acetyl-CoA carboxylase, the compatibility of the compound to the binding site can be determined by determining whether the compound has a proximity of at least 2-10 Å, 2-7 Å or of at least 2.5-4 Å of the compound to residues Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, Leu2025 of SEQ ID NO: 1, or to the corresponding residues for SEQ ID NO:2, 3, 4, 6, 8, 10 or 14 as listed in Table G.

In yet another aspect, the compatibility of the compound to the binding site can be determined by determining whether the compound has a proximity of at least 2-10 Å, 2-7 Å or of at least 2.5-4 Å of the compound to residues Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val923, Trp1924, His1925, Trp1953, Arg1954, Gly1955, Phe1956, Ser1957, Gly1958, Gly1959, Gln1960, Asp1962, Arg1996, Gly1997, Ser1999, Val2024, Leu2025, Glu2026, Pro2027, Gly2029, Met2030, Val2031, Gly2032, Ile2033 of SEQ ID NO:1, or to the corresponding residues for SEQ ID NO:2, 3, 4, 6, 8, 10 or 14 as listed in Table G.

The present invention also provides a method for identifying a compound that binds to a carboxyltransferase domain of acetyl-CoA carboxylase comprising: (a) providing a set of atomic coordinates defining the three-dimensional structure of a crystal of a carboxyltransferase domain of acetyl-CoA carboxylase as in any of Table 1 to 7, or coordinates having a root mean square deviation therefrom, with respect to at least 50% of Cα atoms, of not more than ±1.5 Å or ±2 Å, in computer readable form; and (b) selecting a compound by performing rational drug design with the atomic coordinates, wherein the selecting is performed in conjunction with computer modeling, so as to identify a compound that binds to the carboxyltransferase domain of acety-CoA carboxylase. This method can further comprise outputting the identity of the compound to a user.

In another aspect, the present invention provides a method for identifying an inhibitor compound capable of binding to, and inhibiting the enzymatic activity of a carboxyltransferase domain of acetyl-CoA carboxylase comprising: (a) introducing into a suitable computer program information defining a carboxyltransferase binding site conformation of an acetyl-CoA carboxylase molecule comprising a conformation defined by at least 30 of the atomic coordinates of any of Tables 1 to 7, wherein the program displays the three-dimensional structure thereof; (b) providing a three dimensional structure of a test compound in the computer program; (c) displaying and superimposing the model of the test compound on the model of the binding site; (d) assessing whether the test compound model fits spatially into the binding site; and (e) determining whether the test compound inhibits enzymatic activity, so as to identify an inhibitor compound capable of binding to, and inhibiting the enzymatic activity of a carboxyltransferase domain of acetyl-CoA carboxylase. This method can further comprise outputting the identity of the inhibitor compound to a user.

In another aspect, the present invention provides a method for identifying a compound that modulates acetyl-CoA carboxylase activity comprising: (a) providing a model of a binding cavity of carboxyltransferase of acetyl-CoA carboxylase, wherein the model comprises atomic coordinates of residues: (i) Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761, Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Tyr1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 and Leu2189, according to Table 1, 2, 3, 4, 5, 6 or 7, or coordinates having a root mean square deviation therefrom, with respect to at least 50% of Cα atoms, of not more than ±1.5 Å or 2 Å, in computer readable form; (ii) Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036 and Leu2189, according to Table 1, 2, 3, 4, 5, 6 or 7, or coordinates having a root mean square deviation therefrom, with respect to at least 50% of Cα atoms, of not more than ±1.5 Å or 2 Å, in computer readable form; (iii) Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024 and Leu2025 according to Table 1, 2, 3, 4, 5, 6 or 7, or coordinates having a root mean square deviation therefrom, with respect to at least 50% of Cα atoms, of not more than ±1.5 Å or 2 Å, in computer readable form; (iv) Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val1923, Trp1924, His1925, Trp1953, Arg1954, Gly1955, Phe1956, Ser1957, Gly1958, Gly1959, Gln1960, Asp1962, Arg1996, Gly1997, Ser1999, Val2024, Leu2025, Glu2026, Pro2027, Gln2028, Gly2029, Met2030, Val2031, Gly2032 and Ile2033, according to Table 1, 2, 3, 4, 5, 6 or 7, or coordinates having a root mean square deviation therefrom, with respect to at least 50% of Cα atoms, of not more than ±1.5 Å or 2 Å, in computer readable form; (v) Ile1593, Ser1595, Ser1625, Gly1626, Ala1627, Arg1628, Ile1629, Arg1731, Val1733, Gly1734, Ile1755, Leu1756, Thr1757, Gly1758, Gly1997, Gly1998, Val2024, Leu2025, Ile2033, Lys2034 and Arg2036, according to Table 1, 2, 3, 4, 5, 6 or 7, or coordinates having a root mean square deviation therefrom, with respect to at least 50% of Cα atoms, of not more than ±1.5 Å or 2 Å, in computer readable form; (vi) Thr1757, Ala1761, Ile1762, Lys1764, Met1765, Leu1766, Val1923, Arg1954, Gly1955, Phe1956, Ser1957, Gly1958, Gly1959, Leu2025, Glu2026, Gln2028, Gly2029, Gly2032 and Ile2033, according to Table 1, 2, 3, 4, 5, 6 or 7, or coordinates having a root mean square deviation therefrom, with respect to at least 50% of Cα atoms, of not more than ±1.5 Å or 2 Å, in computer readable form; or (vii) Gly1626, Ala1627, Leu1705, Ser1708, Gly1734, Ile1735, Tyr1738, Leu1756, Trp1924, Ala1929, Phe1956, Val1967, Leu1968, Tyr1970, Gly1971, Ile1974, Gly1997, Gly1998, Ser1999, Val2001, Val2002 and Val2024, according to Table 1, 2, 3, 4, 5, 6 or 7, or coordinates having a root mean square deviation therefrom, with respect to at least 50% of Cα atoms, of not more than ±1.5 Å or 2 Å, in computer readable form; (b) providing the structure of a candidate compound; (c) determining whether the structure of the candidate compound fits into the binding cavity, comprising determining interactions between the candidate compound and at least one of the residues; and (d) selecting the fitted candidate compound, so as to identify a compound that modulates acetyl-CoA carboxylase activity. The method for identifying a compound that modulates acetyl-CoA carboxylase activity can further comprise outputting the structure of the fitted candidate compound to a user.

The present invention also provides a computer readable medium comprising: the methods for identifying a compound that modulates activity of ACC; the methods for rationally designing a compound that modulates activity of ACC; the methods for identifying a compound that binds to a CT domain of ACC; the methods for identifying an inhibitor compound capable of binding to and inhibiting the enzymatic activity of a CT domain of ACC; or any other methods of the present invention that includes the use of the atomic coordinates provided herein.

The present invention also provides an antibody that specifically binds to any one of the isolated carboxyltransferase domains described herein.

In another aspect, the present invention provides a compound from using any of the methods for identifying a compound that modulates activity of ACC; the methods for rationally designing a compound that modulates activity of ACC; the methods for identifying a compound that binds to a CT domain of ACC; the methods for identifying an inhibitor compound capable of binding to and inhibiting the enzymatic activity of a CT domain of ACC; and any other methods of the present invention that includes the use of the atomic coordinates provided herein; wherein the compound binds to a carboxyltransferase domain of acetyl-CoA carboxylase and comes within about 2-10 Å, 2-7 Å or within about 2.5-4 Å of amino acid residues Ala1761, Lys1764, Met1765 of one monomer of the carboxyltransferase domain and residues Leu2025', Glu2026', and Gly2029' of a second monomer of the carboxyltransferase domain (where the residue numbering is in relation to SEQ ID NO:1, and thus encompasses corresponding residues as listed in Table G or that can be determined by alignment, for example, in FIG. 4); and wherein both monomers combined or together comprise a three-dimensional structure characterized by atomic coordinates of at least 30 amino acid amino residues according to at least one of Tables 1-7; with the proviso that the compound is not haloxyfop, diclofop, or an anthracene-containing compound.

In another aspect, the present invention provides a compound identified by any of the methods for identifying a compound that modulates activity of ACC; the methods for rationally designing a compound that modulates activity of ACC; the methods for identifying a compound that binds to a CT domain of ACC; the methods for identifying an inhibitor compound capable of binding to and inhibiting the enzymatic activity of a CT domain of ACC; and any other methods of the present invention that includes the use of the atomic coordinates provided herein; wherein the compound binds to a carboxyltransferase domain, and wherein the bound compound comes within about 2-10, 2-7 or within about 2.5-4 Å of residues Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036, Leu2189 of the CT domain (where the residue numbering is in relation to SEQ ID NO:1, and thus encompasses corresponding residues as listed in Table G or that can be determined by alignment, for example, in FIG. 4), with the proviso that the compound is not haloxyfop, diclofop, or an anthracene-containing compound.

In another aspect, the present invention provides a compound identified by any of the methods for identifying a compound that modulates activity of ACC; the methods for rationally designing a compound that modulates activity of ACC; the methods for identifying a compound that binds to a CT domain of ACC; the methods for identifying an inhibitor compound capable of binding to and inhibiting the enzymatic activity of a CT domain of ACC; and any other methods of the present invention that includes the use of the atomic coordinates provided herein; wherein the compound binds to a carboxyltransferase domain, and wherein the bound compound comes within about 2-10, 2-7 or within about 2.5-4 Å of residues Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val1923, Trp1924, His1925, Trp1953, Arg1954, Gly1955, Phe1956, Ser1957, Gly1958, Gly1959, Gln1960, Asp1962, Arg1996, Gly1997, Ser1999, Val2024, Leu2025, Glu2026, Pro2027, Gln2028, Gly2029, Met2030, Val2031, Gly2032, Ile2033 of the CT domain (where the residue numbering is in relation to SEQ ID NO: 1, and thus encompasses corresponding residues as listed in Table G or that can be determined by alignment, for example, in FIG. 4), with the proviso that the compound is not haloxyfop, diclofop, or an anthracene-containing compound.

In another aspect, the present invention provides a compound identified by any of the methods for identifying a compound that modulates activity of ACC; the methods for rationally designing a compound that modulates activity of ACC; the methods for identifying a compound that binds to a CT domain of ACC; the methods for identifying an inhibitor compound capable of binding to and inhibiting the enzymatic activity of a CT domain of ACC; and any other methods of the present invention that includes the use of the atomic coordinates provided herein; wherein the compound binds to a carboxyltransferase domain, and wherein the bound compound comes within about 2-10, 2-7 or within about 2.5-4 Å of residues Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, Leu2025 of the CT domain (where the residue numbering is in relation to SEQ ID NO:1, and thus encompasses corresponding residues as listed in Table G or that can be determined by alignment, for example, in FIG. 4), with the proviso that the compound is not haloxyfop, diclofop, or an anthracene-containing compound.

The present invention also provides for a composition comprising any compound isolated, designed or identified by the methods described herein and a physiologically acceptable carrier.

In another aspect, the present invention provides a three-dimensional model of a carboxyltransferase domain of acetyl-CoA carboxylase, comprising two monomers, wherein both monomers combined comprise a three-dimensional structure characterized by atomic coordinates of at least 30 amino acid residues according to one or more of Tables 1-7.

In another aspect, the present invention provides a data structure comprising atomic coordinates for a carboxyltransferase domain of acetyl-CoA carboxylase, as set forth in any of Tables 1-7, or coordinates having a root mean square deviation therefrom, with respect to at least 50% of Cα atoms, of not more than 1.5 Å or 2 Å.

In one aspect, the present invention provides a computer displaying a virtual model of carboxyltranferase domain of acetyl-CoA carboxylase based on at least twenty amino acid residues having atomic coordinates as set forth in any of Tables 1-7, or coordinates having a root mean square deviation therefrom, with respect to at least 50% of Cα atoms, of not more than about 1.5 Å or 2 Å.

In yet another aspect, the present invention provides a storage medium containing atomic coordinates for a carboxyltransferase domain of acetyl-CoA carboxylase, as set forth in any of Tables 1-7, or coordinates having a root mean square deviation therefrom, with respect to at least 50% of Cα atoms, of not more than about 1.5 Å or 2 Å.

In another aspect, the invention provides a computer system for performing rational drug design comprises atomic coordinate data according to any of Tables 1-7, defining the three-dimensional structure of a crystallized carboxyltransferase domain or of a crystallized carboxyltransferase complex.

In another aspect, the invention provides a computer method for identifying a compound capable of binding to the three-dimensional structure of a carboxyltransferase domain, the computer method comprises a step of determining whether the compound fits into a binding pocket of the carboxyltransferase domain. In this method, the binding pocket can comprise a three-dimensional structure set forth by atomic coordinates of any of Tables 1-7, or any subset of atomic coordinates thereof.

In another aspect, the present invention provides a computer readable media with atomic coordinate data according to Table 1, 2, 3, 4, 5, 6 or 7, recorded thereon, said data defining the three-dimensional structure of crystallized carboxyltransferase or crystallized carboxyltransferase complex.

In one aspect, the present invention provides a method for treating a metabolic syndrome or an insulin resistance syndrome in a subject in need of such treatment, comprising administering to the subject a first compound capable of binding to a second compound having atomic coordinates defined by Table 1 or 7, or coordinates having a root mean square deviation therefrom, with respect to at least 50% of Cα atoms, of not more than 1.5 Å. The metabolic syndrome can comprise, for example, diabetes, obesity, cardiovascular disease, atherosclerosis, depression, cancer, hyperlipidemia, dislipidemia, hypertension, hyperuricemia, renal dysfunction or any combination thereof.

In another aspect, the present invention provides a method for identifying a compound that modulates activity of acetyl-CoA carboxylase, comprising: (a) contacting a carboxyltransferase domain comprising two monomers, each monomer comprising consecutive amino acid residues at least 50% identical to the amino acid residues of SEQ ID NO:2, SEQ ID NO:3, SEQ ID NO:4, SEQ ID NO:6, SEQ ID NO:8, SEQ ID NO:10 or SEQ ID NO:14, with a test compound; (b) determining whether or not the test compound binds to the carboxyltransferase domain; where a determination that the test compound binds to the domain identifies a compound that modulates activity of acetyl-CoA carboxylase. The method can further comprise determining whether the test compound identified in step (b) increases or decreases acetyl-CoA carboxylase activity. The test compound can comprise, for example, a peptide, an organic compound, an antibody or a nucleic acid. Additionally, such test compounds can also be from a library of compounds. The test compounds can also comprise herbicides or fungicides.

BRIEF DESCRIPTION OF THE FIGURES

The patent or application file contains at least one drawing executed in color. Copies of this patent or patent application publication with color drawings will be provided by the Office upon request and payment of the necessary fee.

FIGS. 1A-1B. Primary structures of ACCs. FIG. 1A presents a schematic drawing of the primary structures of an eukaryotic (yeast), multi-domain ACC (top) and a bacterial (E. coli), multi-subunit ACC (bottom) The N (terminal) subdomain of CT is from about 1484-1830, and the C (terminal)

sub-domain of CT is from about 1830-2233. FIG. 1B shows an alignment of CT domain sequences between yeast ACC, human ACC2 and wheat ACC. The "yeast" sequence spans residues 1481-2210 of SEQ ID NO:1 (GenBank No. Q00955). The "human" sequence spans residues 1715-2452 of SEQ ID NO:7 (GenBank No. AAH22940 (Q13805)). The "wheat" sequence spans residues 1546-2303 of SEQ ID NO:12 (GenBank No. T06161). The residue numbers shown are for yeast ACC. Residues in the core of the monomer structure of the CT domain are colored green, while residues in the dimer interface are colored magenta. The "s.s" abbreviation stands for "secondary structure", which is either an alpha-helix ($\alpha$) or a beta-strand ($\beta$). A dash "–" represents a residue that is identical to that in yeast ACC, whereas an equal sign represents a residue that is strictly conserved among ACCs (for example, see GenBank Nos. BAA11238; T30568; P32874; S60200; AAK16499; T30568; AAL02056; T02235; AAA81579; T09538; BAA07012; CAA54683; NP_776649; CAA56352; NP_071529; AAP94122; A29924; NP_446374; XP_132282; CAE01471; NP_610342; and NP_493922; the sequence conservation between species in the CT domain (in relation to the span of residues 1484-1830 of SEQ ID NO:1) is high, generally showing a conservation of at least 50% sequence identity. Dots represent gaps in the alignment.

FIG. 2A presents a schematic drawing in stereo of the structure of the CT domain dimer of yeast ACC. The N and C domains of one monomer are colored cyan and yellow, while those of the other monomer are colored purple and green. The acetyl-CoA molecule bound to one monomer is shown as a stick model. The acetyl portion of the compound is not visible in the electron density map (possibly due to disorder), so only the CoA portion is shown. Only the adenine base was observed in other other monomer (labeled A). FIG. 2B shows a schematic drawing of the structure of the N sub-domain of the CT domain, in stereo. FIG. 2C shows a schematic stereo drawing of the structure of the C domain of the CT domain. Secondary structure elements that are equivalent to those in the N domain are given the same name. FIG. 2D presents a schematic drawing of the structure of crotonase in complex with octanoyl-CoA. In FIGS. 2B, 2C, and 2D, the secondary structure elements are shown and labeled. The residue numbers shown are for yeast ACC.

FIG. 3A presents a schematic drawing in stereo of the active site of the yeast CT domain. The N domain is shown in cyan, and the C domain of the other monomer in green. The side chains of residues in the active site are shown in purple. The prime (') in the labels indicates the C domain of the other monomer of the dimer. FIG. 3B shows the molecular surface of the active site region of the CT domain, depicting a three-dimensional view of the binding mode of CoA. The side chain of Lys 1764 ($\alpha$6) has been removed to facilitate the viewing of the active site. FIG. 3C presents a chemical structure of the commercial herbicide haloxyfop. FIG. 3D presents a double-reciprocal plot showing the competitive inhibition of wild-type yeast CT domain by haloxyfop.

FIGS. 4A-4H. Sequence alignment of the CT domains of ACCs from different species. The sequence alignments were conducted using the Blast alignment program (Tatiana A. et al. (1999), "Blast 2 sequences—a new tool for comparing protein and nucleotide sequences", *FEMS Microbiol Lett.* 174:247-250; and see National Center for Biotechnology Information website for Blast tools). Specifically, the Blast alignment program used was BlastP Version 2.2.6, where the Matrix used was Blosum 62. FIGS. 4A-4B show an alignment between SEQ ID NO:2 (yeast CT domain) and SEQ ID NO:6 (mouse CT domain of ACC1). The alignment shows that there is a 51% sequence identity and a 65% sequence similarity ("positives") between SEQ ID NO:2 and SEQ ID NO:6. FIGS. 4C-4D show an alignment between SEQ ID NO:2 and SEQ ID NO:8 (human ACC1 CT domain). This alignment shows that there is a 50% identity and a 66% similarity between SEQ ID NO:2 and SEQ ID NO:8. FIGS. 4E-4F show an alignment between SEQ ID NO:2 and SEQ ID NO:10 (human ACC2 CT domain). This alignment shows that there is a 51% identity and a 66% similarity between SEQ ID NO:2 and SEQ ID NO:10. FIGS. 4G-4H show an alignment between SEQ ID NO:2 and SEQ ID NO:14 (mouse ACC1 CT domain). This alignment shows that there is a 51% identity and a 67% similarity between SEQ ID NO:2 and SEQ ID NO:14.

FIGS. 5A-5C. Crystal structure of the yeast CT domain in complex with haloxyfop. FIG. 5A presents the chemical structures of the herbicides R-haloxyfop, R-diclofop, and sethoxydim. FIG. 5B shows the final $2F_0$-$F_c$ electron density at 2.8 Å resolution for haloxyfop, contoured at 16. FIG. 5C presents a schematic stereo drawing of the structure of yeast CT domain dimer in complex with haloxyfop. The N domains of the two monomers are colored in cyan and magenta, while the C domains are colored in yellow and green. The inhibitor is shown in stick models. The FIG. 5B drawing was produced with SETOR (Evans, 1993, *J. Mol. Graphics* 11:134-138). The FIG. 5C drawing was produced with Ribbons (Carson, 1987, *J. Mol. Graphics* 5:103-106).

FIG. 6A presents a stereographic drawing showing the binding site for haloxyfop. The N domain of one monomer is colored in cyan, and the C domain of the other monomer in green. The side chains of residues in the binding site are shown in yellow and magenta, respectively. The dashed segment indicates the disordered residues 1959'-1964'. Produced with Ribbons (Carson, 1987, J. Mol. Graphics 5:103-106). FIG. 6B shows a schematic drawing of the interactions between haloxyfop and the yeast CT domain. FIG. 6C presents an overlay of the binding mode of haloxyfop and diclofop. The conformations of residues Tyr1738 and Phe1956' in the haloxyfop and diclofop complexes are also shown.

FIGS. 7A-7F. Conformational change in the yeast CT domain upon inhibitor binding. FIG. 7A presents a structural overlay of the CT domain free enzyme (in magenta) and the haloxyfop complex (in cyan and green for the N and C domains) near the inhibitor binding site. The binding mode of CoA (Zhang et al., 2003, *Science* 299:2064-2067) is also shown. The poorer structural overlap in the C domain is due to the change in the dimer organization. FIG. 7B shows the molecular surface of the active site of the free enzyme. The model of haloxyfop is included for reference. Most of the inhibitor is in steric clash with the enzyme. FIG. 7C shows the molecular surface of the binding site in the haloxyfop complex. For both FIGS. 7B and 7C, residues 1759-1772 and 2026'-2098' have been removed to give a better view of the binding site. FIG. 7D presents a sequence alignment of residues in the haloxyfop binding pocket. Residues that interact with haloxyfop are colored in magenta. The two residues that confer resistance when mutated, Leu1705 and Val1967, are colored in red. A dash represents a residue that is identical to that in yeast ACC, whereas an equal sign represents a residue that is strictly conserved among ACCs. The sequence numbering is in reference to SEQ ID NO: 1 ("yeast ACC"). The human ACC1 sequence is from SEQ ID NO:7, the human ACC2 sequence is from SEQ ID NO:9; the wheat ACC sequence is from SEQ ID NO:12; and the *T. gondii* sequence is from SEQ ID NO: 11. FIG. 7E shows the inhibition of the wild-type and mutant yeast CT domains by haloxyfop. The activity shown is relative to that in the absence of inhibitor for each enzyme. FIG. 7F shows the inhibition of the wild-type yeast CT domain by haloxyfop, diclofop and sethoxydim. FIG. 7A was produced with Ribbons (Carson, 1987, *J. Mol. Graphics* 5:103-106). FIGS. 7B and 7C were produced with GRASP (Nicholls et al., 1991, *Proteins* 11:281-296).

FIG. 8A presents the structure of the dimer of the L1705I/V1967I mutant, in the same color scheme as FIG. 5C. FIG. 8B shows a structural overlay of the wild-type (in magenta) and the L1705I/V1967I mutant CT domains (in cyan and green for the two monomers) near the active site. FIG. 8C shows the molecular surface near the active site region of the L1705I/V1967I double mutant. The CoA molecule is shown for reference. FIGS. 8A and 8B were produced with Ribbons (Carson, 1987, *J. Mol. Graphics* 5:103-106). FIG. 8C was produced with GRASP (Nicholls et al., 1991, *Proteins* 11:281-296).

FIGS. 9A-9B. The amino acid sequence for yeast ACC (SEQ ID NO: 1; GenBank Accession No. Q00955).

FIG. 10. The amino acid sequence encompassing the yeast CT domain encoded by the vector yCTACC. This amino acid sequence (SEQ ID NO:2) corresponds to residues 1429-2233 of SEQ ID NO: 1.

FIG. 11. The amino acid sequence encompassing the yeast CT domain encoded by the vector yCT2ACC. This amino acid sequence (SEQ ID NO:3) corresponds to residues 1476-2233 of SEQ ID NO:1.

FIG. 12. The amino acid sequence of a mutated yeast CT domain (SEQ ID NO:4). The mutations are in reference to the residue numbering of SEQ ID NO: 1, and the amino acid sequence of SEQ ID NO:4 spans residues 1476-2233 as the mutations were introduced on the yCT2ACC background. The mutations consisted of changing Leu1705 into an isoleucine ("L1705I") and of changing Val 1967 to an isoleucine ("V1967I").

FIG. 13. The amino acid sequence of mouse ACC2 (SEQ ID NO:5; GenBank Accession No. AAH22940; the corresponding mRNA GenBank Accession No. is BC022940).

FIG. 14. The amino acid sequence (SEQ ID NO:6) encompassing the CT domain of mouse ACC2. The sequence corresponds to residues 35-767 of SEQ ID NO:5.

FIGS. 15A-15B. The amino acid sequence of human ACC1 (SEQ ID NO:7; GenBank Accession No. AAP94122; the corresponding mRNA GenBank Accession No. is AY315627).

FIG. 16. The amino acid sequence (SEQ ID NO:8) encompassing the CT domain of human ACC1. The sequence corresponds to residues 1548-2346 of SEQ ID NO:7.

FIGS. 17A-17B. The amino acid sequence of human ACC2 (SEQ ID NO:9; GenBank Accession No. AAB58382; the corresponding mRNA GenBank Accession No. is U89344).

FIG. 18. The amino acid sequence (SEQ ID NO:10) encompassing the CT domain of human ACC2. The sequence corresponds to residues 1651-2483 of SEQ ID NO:9.

FIG. 19. The amino acid sequence of *T. gondii* ACC (SEQ ID NO: 11; GenBank Accession No. AAK16499).

FIGS. 20A-20B. The amino acid sequence of wheat ACC (SEQ ID NO:12; GenBank Accession No. T06161).

FIGS. 21A-21B. The amino acid sequence of mouse ACC1 (SEQ ID NO:13; GenBank Accession No. XP_109883.

FIG. 22. The amino acid sequence (SEQ ID NO:14) encompassing the CT domain of mouse ACC1. The sequence corresponds to residues 1294-2110 of SEQ ID NO:13.

FIG. 23A provides the chemical structure of CP-640186. FIG. 23B presents a stereographic drawing showing the binding site for haloxyfop. FIG. 23C presents a schematic of the molecular surface of the active site of the yeast CT domain. The figure shows CP-640186 is bound in the active site, at the interface between two monomers of the ACC enzyme. FIG. 23D shows that the binding site for the CP-640186 compound is distinct or non-competitive from that for CoA or for the herbicides, and this is consistent with kinetic studies that show that the CP-640186 compound is non-competitive with respect to malonyl-CoA.

FIG. 24A shows crystals of free enzyme of yeast CT domain (1429-2233). FIG. 24B shows crystals of an acetyl-CoA complex of yeast CT domain.

DETAILED DESCRIPTION OF THE INVENTION

Figure 1A:
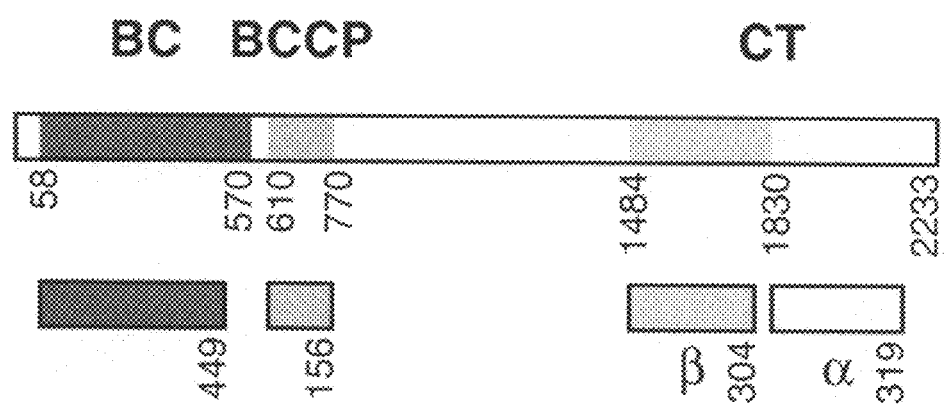

In general, the present invention is directed to the provision of a detailed three-dimensional structure of the CT domain of the family of acetyl-CoA carboxylases, including yeast, mouse and human ACC. The present invention also provides the three-dimensional structure of the CT domain of ACC, bound to substrates, including, but not limited to, the CT domain of ACC bound to CoA, or bound to inhibitors, including, but not limited to, the CT domain of ACC bound to haloxyfop, diclofop or CP-640186. The present invention also provides methods of using the three-dimensional crystal structures in order to identify and design compounds that can modulate ACC activity. Compositions comprising solated CT domains are also provided.

The following Index of Tables lists the Tables disclosed herein:

| INDEX OF TABLES | | |
|---|---|---|
| TABLE | TITLE/DESCRIPTION OF TABLE | |
| 1 | Atomic Coordinates of Yeast CT Domain (1429-2233) | |
| 2 | Atomic Coordinates of Yeast CT Domain Complexed with CoA | |
| 3 | Atomic Coordinates for Yeast CT Domain Complexed with Haloxyfop | |
| 4 | Atomic Coordinates for Yeast CT Domain Complexed with Diclofop | |
| 5 | Atomic Coordinates for Yeast CT Domain Complexed with CP-640186 | |
| 6 | Atomic Coordinates for Mutant Yeast CT Domain | |
| 7 | Atomic Coordinates for Yeast CT Domain (1476-2233) | |
| A | CT Domain Table | |
| B | Constructs Created and Tested For Production of Proteins Comprising the CT Domain of Yeast ACC | |
| C | Summary of Crystallographic Information for the Free Enzyme (Table 1) and the CoA Complex (Table 2) | |
| D | Kinetic Parameters of Wild-Type and Mutant CT | |
| E | Summary of Crystallographic Information for the Free Enzyme (Table 7), Haloxyfop Complex (Table 3), Diclofop Complex (Table 4) and the L1705I/V1967I Mutant (Table 6) | |
| F | Constructs Created and Tested for Production of Proteins Comprising the CT Domain of Mouse ACC2 | |
| G | Corresponding Residues Between SEQ ID NO: 1, 2, 3, 4, 6, 8, 10 and 14 | |

TABLE A

CT DOMAIN TABLE

| Row # | Description | SEQ ID NO: | Unit Cell Info. | Atomic Coord. | Comments |
|---|---|---|---|---|---|
| 1 | S. cerevisiae - ACC gene GenBank Q00955 | 1 FIG. 9 | N/A | N/A | |
| 2 | Yeast ACC gene GenBank AAA20073 | — | N/A | N/A | Prior GenBank sequence for yeast ACC - replaced by Q00955 due to sequence errors |
| 3 | Yeast CT domain (1429-2233 of SEQ ID NO: 1) Vector name: yCTACC | 2 FIG. 10 | a = 247; b = 125; c = 145; β = 94; space group C2; Cystal Form I | Table 1 | (1) Residues in/near the active site of the CT domain and/or of a binding pocket: Met1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly1736, Ala 1737, Tyr1738, Leu 1739, Arg1741, Leu1742, Pro1753, Ile 1755, Leu1756, Thr1757, Gly1758, Ala1759, Pro1760, Ala1761, Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Tyr1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 and Leu2189 (2) Acetyl CoA binding pocket residues (for a compound within at least 7 angstroms of) comprise: Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036, Leu2189. (3) "Herbicide" binding pocket residues (for a compound within at least 7 angstroms of) comprise: Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, Leu2025. (4) "CP compound" binding pocket residues (for a compound within at least 7 angstroms of) comprise: Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val1923, Trp1924, His1925, Trp1953, Arg1954, Gly1955, Phe1956, Ser1957, Gly1958, Gly1959, |

TABLE A-continued

CT DOMAIN TABLE

| Row # | Description | SEQ ID NO: | Unit Cell Info. | Atomic Coord. | Comments |
|---|---|---|---|---|---|
| | | | | | Gln1960, Asp1962, Arg1996, Gly1997, Ser1999, Val2024, Leu2025, Glu2026, Pro2027, Gln2028, Gly2029, Met2030, Val2031, Gly2032, Ile2033. |
| 4 | Yeast CT domain 1429-2233 of SEQ ID NO: 1 | 2 | A = 255; b = 113; c = 135; β = 101; space group C2 Crystal Form II | | Another Crystal Form of the Free Enzyme |
| 5 | Yeast CT domain (1476-2233 of SEQ ID NO: 1) Vector name: yCT2ACC | 3 FIG. 11 | a = 246; b = 124; c = 145; β = 94; space group C2 | Table 7 | See Example 2 |
| 6 | SEQ ID NO: 2 complexed with acetyl-CoA | N/A | a = 93; b = 138; c = 101; β = 114; space group P2$_1$ Crystal Form III | Table 2 | See Example 1 |
| 7 | SEQ ID NO: 2 complexed with haloxyfop | N/A | a = 247; b = 125; c = 146; β = 94; space group C2 (complex formed by soaking crystals of SEQ ID NO: 2 with haloxyfop) | Table 3 | See Example 2 |
| 8 | SEQ ID NO: 3 complexed with diclofop | N/A | a = 137; b = 137; c = 244; space group P3$_2$21 (complex formed by co-crystallization of SEQ ID NO: 3 with diclofop) Crystal Form IV | Table 4 | See Example 2 |
| 9 | SEQ ID NO: 3 Complexed with CP-640186 | N/A | a = 247; b = 125; c = 146; β = 94; space group C2 (complex formed by soaking crystals of SEQ ID NO: 3 with CP-640186) | Table 5 | See Example 4 |
| 10 | Yeast CT domain of yCTACC with mutations: L1705I and V1967I in SEQ ID NO: 3 | 4 FIG. 12 | a = 247; b = 125; c = 146; β = 94; space group C2 | Table 6 | See Example 2 |
| 11 | Mouse ACC2 GenBank BC022940 mRNA, this entry refers to: | 5 FIG. 13 | | | See Example 3 |

TABLE A-continued

CT DOMAIN TABLE

| Row # | Description | SEQ ID NO: | Unit Cell Info. | Atomic Coord. | Comments |
|---|---|---|---|---|---|
| | AAH22940 protein | | | | |
| 12 | CT domain of mouse ACC2 (35-767 of GenBank AAH22940) Vector: mCTACC2 | 6 | FIG. 14 | | FIG. 4A-B alignment |
| 13 | human ACC1 GenBank AY315627 mRNA, this entry refers to: AAP94122 protein | 7 | FIG. 15 | | FIG. 1B, FIG. 7D alignments |
| 14 | CT domain of human ACC1 (1548-2346 of GenBank AAP94122) Vector: hCTACC1 | 8 | FIG. 16 | | FIG. 4C-4D alignment |
| 15 | Human ACC2 GenBank U89344 mRNA refers to AAB58382 protein | 9 | FIG. 17 | | FIG. 7D alignment |
| 16 | CT domain of human ACC2 (1651-2483 of GenBank AAB58382) | 10 | FIG. 18 | | FIG. 4E-4F alignment |
| 17 | *T. gondii* ACC GenBank AAK16499 | 11 | FIG. 19 | | FIG. 7D alignment |
| 18 | Wheat ACC GenBank T06161 | 12 | FIG. 20 | | FIG. 1 and FIG. 7D alignments |
| 19 | Mouse ACC1 GenBank XP_109883 | 13 | FIG. 21 | | |
| 20 | CT Domain of Mouse ACC1 (1294-2110 of GenBank XP_109883) | 14 | FIG. 22 | | FIG. 4G-H alignment |

In one embodiment, the present invention provides the atomic coordinates which define the three-dimensional structure of the CT domain of ACC, or an active site, substrate binding site or modulator binding site thereof, alone or in complex with a compound, with a root mean square deviation (RMSD) in the positions of the Cα atoms for at least 50% of the amino acids, of from about 0 to about 4 Å, from about 0 to about 2 Å, 0 from about 0 to about 1.5 Å or from about 0 to about 0.5 Å. The RMSD can also apply to the positions of C, N or O atoms. The term "root mean square deviation" is used herein as it is in the art. For example, in one standard definition, RMSD means the square root of the arithmetic mean of the squares of the deviations from the mean. It is a way to express the deviation or variation from a trend or object. The RMSD defines the variation in the backbone of a polypeptide, protein or protein complex from the relevant portion of the backbone of the CT domain as defined by the atomic coordinates provided herein. The atomic coordinates may be included in a computer readable medium, including a database, and may be displayed on a computer.

In one aspect of the present invention, the isolated CT domain polypeptides are crystallizable compositions. For the first time, the present invention provides crystallizable compositions of CT domains, such that the three-dimensional structure of the CT domain has now been provided, as reflected by the tables of structure coordinates listed in Tables 1-7. This has provided for the first time, information about the shape and structure of the ACC CT domain. The atomic coordinates of Tables 1-7 refers to Cartesian coordinates derived from mathematical equations related to the patterns obtained on diffraction of a beam of X-rays by the atoms (scattering centers) of a CT domain, either in free crystal form or in complexed crystal form. The diffraction data are used to calculate an electron density map of the repeating unit of the crystal. The electron density maps are then used to establish the positions of the individual atoms of the free CT domain or a CT domain complex.

Those of skill in the art will understand that a set of atomic coordinates for a CT domain or a CT domain complex or a portion thereof, is a relative set of points that define a shape in three dimensions. Thus, it is possible that a different set of coordinates could define a similar or identical shape. Therefore, slight variations in the individual coordinates will have little effect on overall shape, i.e. see RMSD. For example, variations in coordinates can be generated because of mathematical manipulations of the coordinates. For example, the structure coordinates of Tables 1-7 could be manipulated by crystallographic permutations of the structure coordinates, integer additions or subtractions to sets of the structure coordinates, inversion of the structure coordinates or any combination of the above. Alternatively, modifications in the crystal structure due to mutations, additions, substitutions and/or deletions of amino acids, or other changes in any of the components that make up the crystal could also account for variations in the structure coordinates. If such variations are within an acceptable standard of error as compared to the original coordinates, the resulting three-dimensional shape is considered to be the same. Thus, in one aspect of the present invention, any molecule or molecular complex that has a RMSD of conserved residue backbone atoms (N, Cα, C, O) of less than about 4 Å, 2 Å, 1.5 Å, 1 Å or 0.5 Å when superimposed on the relevant backbone atoms described by the coordinates listed in any one of Tables 1-7 are considered identical.

Various computational analyses are available to determine whether a molecule or a molecular complex or a portion thereof is sufficiently similar to all or parts of a CT domain or a CT domain complex to be considered the same. Such analyses may be carried out in current software applications, for example, the Molecular Similarity application of QUANTA (Molecular Simulations Inc., San Diego, Calif.) version 4.1. The Molecular Similarity application permits comparisons between different structures, different conformations of the same structure, and different parts of the same structure. The procedure used in Molecular Similarity to compare structures is divided into foru steps: 1) load the structures to be compared; 2) define the atom equivalences in these structures; 3) perform a fitting operation; and 4) analyze the results. For structures to be compared, one structure is identified as the target (the fixed structure) and the remaining structures are working structures (the moving structures). Since atom equivalency with QUANTA is defined by user input, in one aspect of the present invention, equivalent atoms can be defined as protein backbone atoms (N, Cα, C, O) for all conserved residues between any two structures being compared. When a fitting method is used to compare whether two structures are essentially the same, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is thereby reported by QUANTA.

The present invention also provides for methods of using a computer to identify modulators of a target CT domain of ACC comprising using a computer-readable three-dimensional structure of the CT domain of an ACC enzyme, a substrate or modulator binding site of the CT domain of ACC, and/or an active site of the CT domain of ACC to design and/or select for a potential modulator of the CT domain of ACC based on the predicted ability of the modulator to bind to a binding site, for example, of the CT domain of ACC. The invention further provides for synthesizing and testing the designed or selected modulator for its ability to modulate the activity of the target CT domain of ACC. For example, a potential modulator may be contacted with the target enzyme in the presence of one or more substrates, and the ability of the target enzyme to act on its substrate in the presence or absence of potential modulator may be measured and compared. As another specific, non-limiting example, the designed or selected potential modulator may be synthesized and introduced into an in vivo or in vitro model system and then the production of malonyl-CoA may be monitored. A modulator that decreases the relative amount of malonyl-CoA may be useful in the treatment of obesity, metabolic syndrome, diabetes, cardiovascular disease, atherosclerosis and infections, whereas a modulator that increases malonyl-CoA may be useful to promote endurance or survival in stressful conditions. In one embodiment, the modulator decreases the activity of ACC2 but not ACC1. A modulator can be essentially any compound, including, a small-molecule, a peptide, a protein, a nucleic acid (including siRNA, anti-sense RNA, catalytic DNA or RNA, DNAzymes, Ribozymes) and antibodies and antibody fragments. A modulator can also be a herbicide or a fungicide.

Modulators identified according to the instant invention also may be used as herbicides. In a further specific, non-limiting example, a designed or selected potential modulator may be contacted with the target enzyme in the presence of a known herbicide that binds to the CT domain of ACC to determine whether the potential modulator competes for binding of the herbicide. The potential modulator also may be tested for its ability to inhibit the growth of certain plants, and the potential modulator may selectively inhibit the growth of "weeds" or other undesired plants. Because the acetyl-CoA carboxylase molecule is large, it is very difficult to crystallize, and has not yet been crystallized. This invention, therefore, provides a solution to a long-felt need, for providing a method to rationally design or modify compounds known to bind to ACC. The provided structure of the CT domain of ACC only now enables one to define, and therefore adjust, the binding mode of any given compound. The virtual models, atomic structure, methods and compositions provided by this invention are useful in the drug discovery of further, as yet unidentified inhibitors or modulators of ACC, and in the design or redesign of modulators of ACC activity.

The present invention also provides for molecules which comprise binding site(s) and/or active sites of the CT domain of ACC, as defined by the atomic coordinates provided by the present invention, in an otherwise synthetic molecule. Such a molecule may be used to screen test compounds, for example compounds in a combinatorial library, for binding to the active site and/or binding sites and/or for suitability as ligands. Within the present invention, a binding site of the CT domain can also be referred to as a binding cavity or a binding pocket. Further, in the present invention, a ligand of a CT domain encompasses essentially any molecule that can bind to the CT domain, including a substrate or a modulator.

The present invention further provides for a method of designing or selecting an inhibitor or agonist of ACC comprising creating a computer model of the negative space present in an unoccupied binding site and/or active site of the CT domain of ACC, which can take into account the electron densities at the boundaries of this space, and using such a model to design or select molecules that modulate the activity of ACC. Such a negative space, particularly a space presented in the context of electrophilic and electrophobic boundaries, in computer readable, electronic form, stored or storable on a floppy disc or computer hard drive, may provide a simple template for the design and/or selection of modulator compounds.

In addition, the present invention provides for a method of evaluating the binding properties of a potential modulator comprising co-crystallizing the modulator with the CT domain of ACC, determining the three-dimensional structure of the modulator bound to the CT domain of ACC and analyzing the three-dimensional structure of the CT domain of ACC bound to the modulator to evaluate the structural aspects of binding. Such a structure may further be used to design and/or select improved potential modulator compounds.

In another embodiment, the present invention provides for polynucleotides encoding an ACC polypeptide having a mutation in one or more residues of the active site and/or a binding site of the CT domain, as those residues are defined herein. Further, CT domain polynucleotides are useful, inter alia, for producing herbicide resistant plants. Accordingly, the present invention also relates to genetically modified herbicide resistant plants.

The present invention further provides for an isolated and purified peptide fragment comprising the CT domain of ACC. In various embodiments, a CT domain of ACC is that provided by the yCTACC, yCT2ACC, mCTACC2, and hCTACC constructs. The isolated and purified peptide fragment comprising the CT domain of ACC is useful, inter alia, for the screening and assay of compounds which modulate the activity of the CT domain of ACC. As noted supra, modulators of the CT domain of ACC may be used in the treatment of various diseases and disorders, including but not limited to, obesity, metabolic syndrome, diabetes, cardiovascular disease, atherosclerosis and infections. The isolated and purified peptide fragment comprising the CT domain of ACC also may be used to design and/or screen metabolic enhancers that may be used to promote endurance or survival under stressful conditions.

The modulators of the activity of the CT domain of ACC to be screened or assayed using the isolated and purified CT domain of ACC of the instant invention may be those designed or identified using the crystal structures concerning the CT domain of ACC provided herein, or they may be existing compounds not previously known to be modulators of the CT domain of ACC.

In one aspect, the following set of amino acids, or a subset thereof: Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761,Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Tyr1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098 and Val2108, can be involved as comprising a binding of a substrate or a modulator, or can be involved as comprising an active site. These residues, or a subset thereof, can help form a three-dimensional binding pocket or cavity for a substrate or a modulator and/or can actually make direct or indirect interactions with a substrate or a modulator. The residue numbering is in relation to SEQ ID NO:1. However, the corresponding residues for other polypeptides, including polypeptides of other species, can easily be determined. For example, SEQ ID NO:2 is a polypeptide identical to residues 1429-2233 of SEQ ID NO:1; and hence, Met1503 would correspond to Met75 of SEQ ID NO:2. Similarly, SEQ ID NO:3 is a polypeptide identical to residues 1476-2233 of SEQ ID NO:1; and hence, Met1503 would correspond to Met28 of SEQ ID NO:3. Further, from FIG. 4, SEQ ID NO:2 is aligned with SEQ ID NO:6 (FIGS. 4A-4B), SEQ ID NO:8 (FIGS. 4C-4D) and SEQ ID NO:10 (FIGS. 4E-4F). Thus, corresponding residues in SEQ ID NOS:6, 8 and 10 can be determined for SEQ ID NO:1 numbering. For example, as Met1503 is Met75 in SEQ ID NO:2, Met75 aligns with Leu46 of SEQ ID NO:6 in FIG. 4C; and hence, Leu46 would be the corresponding residue to Met1503. A list of corresponding residues between SEQ ID NOS:1, 2, 3, 4, 6, 8, 10 and 14 is provided in Table G.

Thus, for example, one subset of residues of the binding site that are important for CoA binding is: Ile1593, Ser1595, Ser1625, Ala1627, Arg1628, Ile1629, Gly1630, Met1631, Gly1701, Glu1703, Leu1705, Ser1708, Ala1712, Arg1731, Val1733, Gly1734, Ile1735, Tyr1738, Leu1742, Pro1753, Leu1756, Thr1757, Ala1761, Ile1762, Lys1764, Met1765, Leu 1766, Tyr1771, Pro1920, Gly1921, Val1923, Trp 1924, Arg1954, Gly1955, Phe1956, Ser1957, Gly1958, Gly1959, Gln1960, Arg1961, Asp1962, Met1963, Phe1964, Asn1965, Val1967, Leu1968, Gly1971, Ile1974, Val1975, Glu1994, Gly1997, Gly1998, Trp2000, Val2001, Val2002, Arg2021, Gly2023, Val2024, Leu2025, Glu2026, Pro2027, Gln2028, Ile2033, Lys2034, Arg2036, Asp2098, and Val2108 (where the numbering corresponds to SEQ ID NO:1). These residues can be considered to comprise one set of residues relevant for the design/analysis of a three-dimensional binding pocket or binding cavity for acetyl-CoA or for a modulator.

Further, from the study of the crystal structure of the yeast CT domain in complex with acetyl-CoA, the following residues have been determined to be within 7 Å of acetyl-CoA, and thus comprise another subset of residues of the CoA binding site: Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036, and Leu2189 (where the numbering corresponds to SEQ ID NO:1; and wherein residues numbered below 1800 reside on one monomer and wherein residues numbered above 1800 reside on the other monomer of the CT domain). In addition, these residues can be considered to comprise one set of residues relevant for the design/analysis of a three-dimensional binding pocket or binding cavity for acetyl-CoA or for a modulator.

Further, from the study of the crystal structure of the yeast CT domain in complex with CoA, the following residues have been determined to be within 7 Å of CoA, and thus comprise another subset of residues of the CoA binding site: Ile1593, Ser1595, Ser1625, Gly1626, Ala1627, Arg1628, Ile1629, Arg1731, Val1733, Gly1734, Ile755, Leu1756, Thr1757, Gly1758, Gly1997, Gly1998, Val2024, Leu2025, Ile2033, Lys2034, and Arg2036, (where the numbering corresponds to SEQ ID NO: 1; and wherein residues numbered below 1800 reside on one monomer and wherein residues numbered above 1800 reside on the other monomer of the CT domain). In addition, these residues can be considered to comprise one set of residues relevant for the design/analysis of a three-dimensional binding pocket or binding cavity for acetyl-CoA or for a modulator.

From the study of the crystal structure of the yeast CT domain in complex with haloxyfop, the following residues have been determined to be within 7 Å of haloxyfop, and thus comprise one set of residues for a binding site: Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, and Leu2025 (where the numbering corresponds to SEQ ID NO: 1; and wherein residues numbered below 1800 reside on one monomer and wherein residues numbered above 1800 reside on the other monomer of the CT domain). In addition, these residues can be considered to comprise one set of residues relevant for the design/analysis of a three-dimensional binding pocket or binding cavity for modulator compounds.

From the study of the crystal structure of the yeast domain in complex with haloxyfop, the following residues have been determined to be within 7 Å of haloxyfop, and thus comprise one set of residues for a binding site: Gly1626, Ala1627, Leu1705, Ser1708, Gly1734, Ile1735, Tyr1738, Leu1756, Trp1924, Ala1929, Phe1956, Val1967, Leu1968, Tyr1970, Gly1971, Ile1974, Gly1997, Gly1998, Ser1999, Val2001, Val2002 and Val2024, (where the numbering corresponds to SEQ ID NO: 1; and wherein residues numbered below 1800 reside on one monomer and wherein residues numbered above 1800 reside on the other monomer of the CT domain). In addition, these residues can be considered to comprise one set of residues relevant for the design/analysis of a three-dimensional binding pocket or binding cavity for modulator compounds.

From the study of the crystal structure of the yeast CT domain in complex with CP-640186, the following residues have been determined to be within 7 Å of CP-640186, and thus comprise yet another subset of residues of a binding site: Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val1923, Trp1924, His1925, Trp1953, Arg1954, Gly1955, Phe1956, Ser1957, Gly1958, Gly1959, Gln1960, Asp1962, Arg1996, Gly1997, Ser1999, Val2024, Leu2025, Glu2026, Pro2027, Gln2028, Gly2029, Met2030, Val2031, Gly2032, and Ile2033 (where the numbering corresponds to SEQ ID NO:1; and wherein residues numbered below 1800 reside on one monomer and wherein residues numbered above 1800 reside on the other monomer of the CT domain). In addition, these residues can be considered to comprise one set of residues relevant for the design/analysis of a three-dimensional binding pocket or binding cavity for non-competitive (non-competitive in respect to the concentration of acetyl-CoA, for example, as acetyl-CoA does not bind in a pocket or cavity that is comprised by the above list of residues) modulator compounds.

From the study of the crystal structure of the yeast CT domain in complex with CP-640186, the following residues have been determined to be within 7 Å of CP-640186, and thus comprise yet another subset of residues of a binding site: Thr1757, Ala1761, Ile1762, Lys1764, Met1765, Leu1766, Val1923, Arg1954, Gly1955, Phe1956, Ser1957, Gly1958, Gly1959, Leu2025, Glu2026, Gln2028, Gly2029, Gly2032, Ile2033, (where the numbering corresponds to SEQ ID NO: 1; and wherein residues numbered below 1800 reside on one monomer and wherein residues numbered above 1800 reside on the other monomer of the CT domain). In addition, these residues can be considered to comprise one set of residues relevant for the design/analysis of a three-dimensional binding pocket or binding cavity for non-competitive (non-competitive in respect to the concentration of acetyl-CoA, for example, as acetyl-CoA does not bind in a pocket or cavity that is comprised by the above list of residues) modulator compounds.

An α-helix refers to the most abundant helical conformation found in globular proteins and the term is used in accordance with the standard meaning of the art. In an α helix, all amide protons point toward the N-terminus and all carbonyl oxygens point toward the C-terminus. The repeating nature of the phi, psi pairs ensure this orientation. Hydrogen bonds within an α helix also display a repeating pattern in which the backbone C=O of residue X (wherein X refers to any amino acid) hydrogen bonds to the backbone HN of residue X+4. The α helix is a coiled structure characterized by 3.6 residues per turn, and translating along its axis 1.5 Å per amino acid. Thus the pitch is 3.6×1.5 or 5.4 Å. The screw sense of alpha helices is always right-handed.

A β-sheet refers to two or more polypeptide chains (or β-strands) that run alongside each other and are linked in a regular manner by hydrogen bonds between the main chain C=O and N—H groups. Therefore all hydrogen bonds in a beta-sheet are between different segments of polypeptide. Hydrogen bonds in anti-parallel sheets are perpendicular to the chain direction and spaced evenly as pairs between strands. Hydrogen bonds in parallel sheets are slanted with respect to the chain direction and spaced evenly between strands.

A loop refers to any other conformation of amino acids (i.e. not a helix, strand or sheet). Additionally, a loop may contain bond interactions between amino acid side chains, but not in a repetitive, regular fashion.

In one embodiment, the present invention encompasses allelic variants and mutations of the CT domain sequences disclosed herein that are at least 85 percent, at least 90 percent, or at least 95 percent homologous to the naturally occurring CT domain, with homology being determined by standard computer software, such as BLASTP, or ClustalW used with a scoring matrix such as BLOSUM or PAM.

A modulator of ACC enzyme activity refers to a compound which can alter the amount of product generated by a reaction catalyzed by the enzyme. The alteration may be an increase or a decrease. A compound that increases the amount of product is considered an agonist and a compound that decreases the amount of product is considered an inhibitor. Where the biological function of an enzyme encompasses both directions of a reaction (for example ACC catalyzes the carboxylation of acetyl-CoA to produce malonyl-CoA and the decarboxylation of malonyl-CoA to produce acetyl-CoA), whether a modulator is acting as an agonist or an inhibitor depends upon the amount of malonyl-CoA produced. A modulator which decreases the production of malonyl-CoA is an inhibitor. A decrease in malonyl-CoA results in an increase in fatty acid oxidation and a decrease in fatty acid synthesis. Such a decrease may be useful for the treatment of obesity, metabolic syndrome, diabetes, cardiovascular disease, atherosclerosis and infections.

Figure 3A:
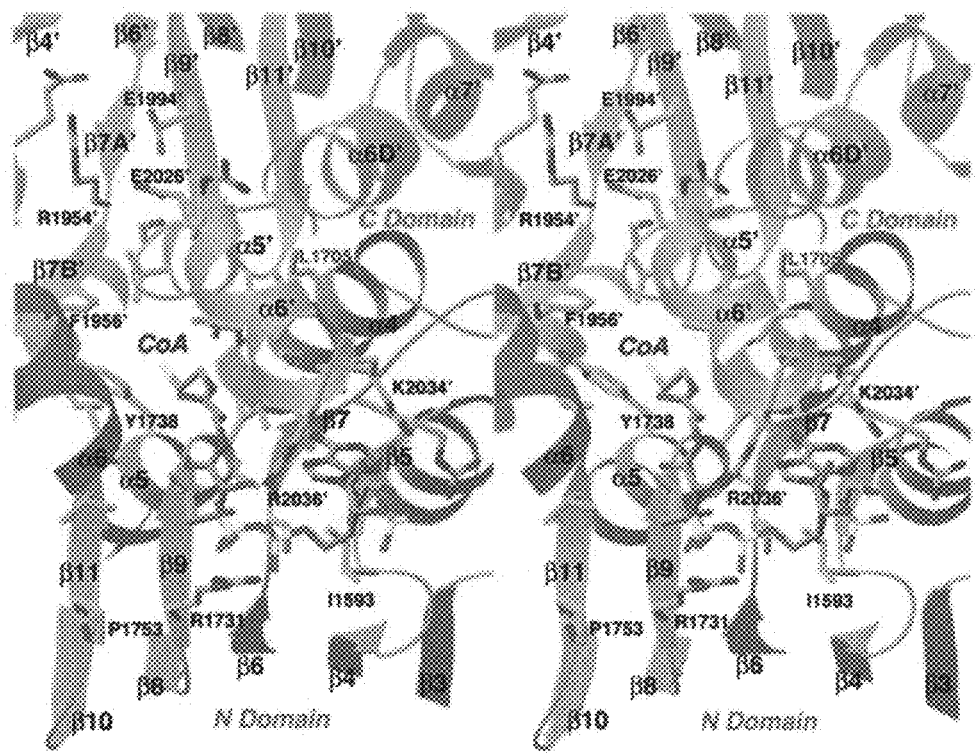
FIGS. 3A-3D.
Figure 3B:
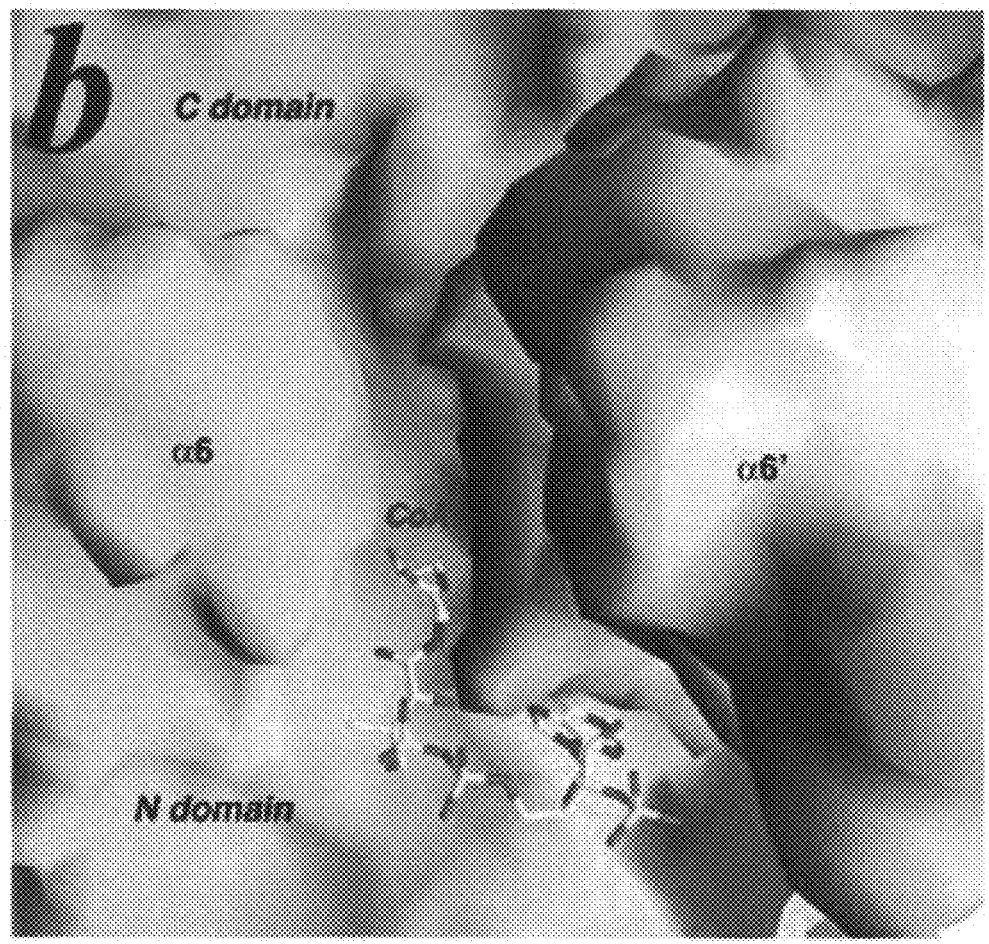
Figure 3C:
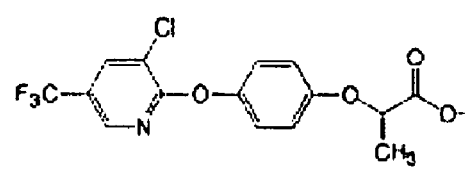
Figure 3D:
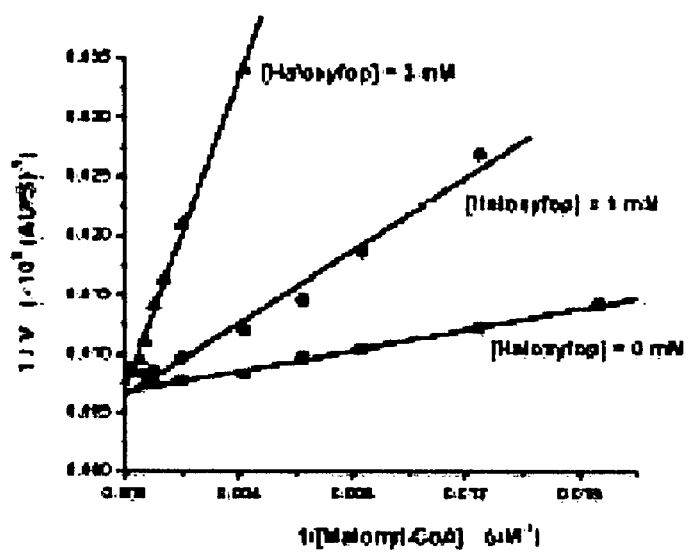

A substrate binding site refers to a region of the CT domain of ACC that retains substrate (for example, acetyl-CoA, malonyl-CoA, biotin) in a position suitable for acyl transfer to occur. The configuration of the substrate binding site is likely to be different in the presence and absence of bound substrate, and both configurations are optimally considered in the design and/or selection of enzyme modulators. Specifically, for the CT domain of yeast ACC, the substrate binding site is schematically depicted in FIGS. 3A and 3B. In one set of non-limiting embodiments of the invention, the acetyl-CoA binding site of ACC is comprised in a protein structure in which the following amino acids, or a subset thereof, may directly contact substrate or otherwise participate in or affect acetyl transfer: Ile1593, Ser1595, Ser1625, Ala1627, Arg1628, Ile1629, Gly1630, Met1631, Gly1701, Glu1703, Leu1705, Ser1708, Ala1712, Arg1731, Val1733, Gly1734, Ile1735, Tyr1738, Leu1742, Pro1753, Leu1756, Thr1757, Ala1761, Ile1762, Lys1764, Met1765, Leu1766, Tyr1771, Pro1920, Gly1921, Val1923, Trp1924, Arg1954, Gly1955, Phe1956, Ser1957, Gly1958, Gly1959, Gln1960, Arg1961, Asp1962, Met1963, Phe1964, Asn1965, Val1967, Leu1968, Gly1971, Ile1974, Val1975, Glu1994, Gly1997, Gly1998, Trp2000, Val2001, Val2002, Arg2021, Gly2023, Val2024, Leu2025, Glu2026, Pro2027, Gln2028, Ile2033, Lys2034, Arg2036, Asp2098, and Val2108 of yeast ACC and the corresponding amino acids in other ACCs and ACC-related enzymes (see Table G and FIGS. 1, 4 and 7). In another set of non-limiting embodiments of the invention, the acetyl-CoA binding site of ACC is comprised in a protein structure in which the following amino acids, or a subset thereof, may directly contact substrate or otherwise participate in or affect acetyl transfer: Ile1593, Ser1595, Ser1625, Gly1626, Ala1627, Arg1628, Ile1629, Arg1731, Val1733, Gly1734, Ile1755, Leu1756, Thr1757, Gly1758, Gly1997, Gly1998, Val2024, Leu2025, Ile2033, Lys2034, and Arg2036. In another set of non-limiting embodiments of the invention, the acetyl-CoA binding site of ACC is comprised in a protein structure in which the following amino acids, or a subset thereof, may directly contact substrate or otherwise participate in acetyl transfer: Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036 and Leu2189 (where the residue numbering is in reference to SEQ ID NO: 1—note: whenever the disclosure lists residues with SEQ ID NO: 1 numbering, the invention encompasses the corresponding residues to other CT domains, including the corresponding residues listed in Table G, or the corresponding residues aligned in FIGS. 1, 4 and 7, or the corresponding residues of other CT domains that can be aligned to SEQ ID NO: 1).

Where amino acid residues are designated by numbers, the numbers are sometimes used to refer to specific amino acids as present in a structurally defined CT domain of ACC to convey the three-dimensional relationship between the residues. Thus, for example, a virtual model of a binding site (for CoA or for a modulator, for example) may consist essentially of residues, or a subset thereof, of: Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761, Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Tyr1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 and Leu2189 (where the numbering is in relation to SEQ ID NO:1, and thus encompasses corresponding residues of any CT domain, where the corresponding residues can be identified/determined by Blast alignment and/or Blast homology), with their atoms oriented according to the coordinates set forth in Tables 1-7, without intervening amino acids, and may be referred to as a "molecule" despite the fact that it is only a virtual molecule. Alternatively, additional atoms may be comprised in the site.

Additionally, a virtual model of a CoA binding site may consist essentially of residues Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val2001, Val2024, Leu2025, Gly2029, Ile2033, Lys2034, Arg2036, and Leu2189, or a subset thereof (where the numbering corresponds to SEQ ID NO: 1; and wherein residues numbered below 1800 reside on one monomer and wherein residues numbered above 1800 reside on the other monomer of the CT domain), with their atoms oriented according to the coordinates set forth in any one of Tables 1-7, without intervening amino acids, and may be referred to as a "molecule" despite the fact that it is only a virtual molecule. Alternatively, additional atoms may be comprised in the site.

A virtual model of a binding site for a modulator may consist essentially of residues: Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, and Leu2025, or a subset thereof (where the numbering corresponds to SEQ ID NO:1; and wherein residues numbered below 1800 reside on one monomer and wherein residues numbered above 1800 reside on the other monomer of the CT domain), with their atoms oriented according to the coordinates set forth in any one of Tables 1-7, without intervening amino acids, and may be referred to as a "molecule" despite the fact that it is only a virtual molecule. Alternatively, additional atoms may be comprised in the site.

A virtual model of another binding site for a modulator may consist essentially of residues: Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val1923, Trp1924, His1925, Trp1953, Arg1954, Gly1955, Phe1956, Ser1957, Gly1958, Gly1959, Gln1960, Asp1962, Arg1996, Gly1997, Ser1999, Val2024, Leu2025, Glu2026, Pro2027, Gln2028, Gly2029, Met2030, Val2031, Gly2032, and Ile2033, or a subset thereof, (where the numbering corresponds to SEQ ID NO:1; and wherein residues numbered below 1800 reside on one monomer and wherein residues numbered above 1800 reside on the other monomer of the CT domain) with their atoms oriented according to the coordinates set forth in any one of Tables 1-7, without intervening amino acids, and may be referred to as a "molecule" despite the fact that it is only a virtual molecule. Alternatively, additional atoms may be comprised in the site.

A virtual model of another binding site for a modulator may consist essentially of residues: Gly1626, Ala1627, Leu1705, Ser1708, Gly1734, Ile1735, Tyr1738, Leu1756, Trp1924, Ala1929, Phe1956, Val1967, Leu1968, Tyr1970, Gly1971, Ile1974, Gly1997, Gly1998, Ser1999, Val2001, Val2002 and Val2024, or a subset thereof, (where the numbering corresponds to SEQ ID NO:1; and wherein residues numbered below 1800 reside on one monomer and wherein residues numbered above 1800 reside on the other monomer of the CT domain) with their atoms oriented according to the coordinates set forth in any one of Tables 1-7, without intervening amino acids, and may be referred to as a "molecule" despite the fact that it is only a virtual molecule. Alternatively, additional atoms may be comprised in the site.

A virtual model of another binding site for a modulator may consist essentially of residues: Thr1757, Ala1761, Ile1762, Lys1764, Met1765, Leu1766, Val1923, Arg1954, Gly1955, Phe1956, Ser1957, Gly1958, Gly1959, Leu2025, Glu2026, Gln2028, Gly2029, Gly2032, Ile2033, or a subset thereof, (where the numbering corresponds to SEQ ID NO:1; and wherein residues numbered below 1800 reside on one monomer and wherein residues numbered above 1800 reside on the other monomer of the CT domain) with their atoms oriented according to the coordinates set forth in any one of Tables 1-7, without intervening amino acids, and may be referred to as a "molecule" despite the fact that it is only a virtual molecule. Alternatively, additional atoms may be comprised in the site.

For purposes of clarity, and not by way of limitation, the detailed description is divided into the following subsections:

a. determination of crystal structure;
b. design of modulators;
c. screening for modulators;
d. assay systems;
e. mutant ACC polypeptides and polynucleotides encoding them
f. herbicide resistant plants

Determination of Crystal Structure

The three-dimensional structure of a CT domain of ACC may be determined by obtaining its crystal structure directly and/or by comparing the primary and/or secondary structure of the CT domain of ACC, and/or an incomplete set of components of its three-dimensional structure, with a crystal structure that has already been solved.

The three-dimensional structures obtained from crystals of the CT domain of yeast ACC ("yACC") and the CT domain in complex with a modulator, may be employed to solve the structures of the CT domains of other ACC species, including but not limited to the CT domains of human ACC (hACC) and mouse ACC (mACC), as well as the structures of the CT domains of other acetyl-CoA carboxylases. The atomic coordinates calculated for yCTACC (SEQ ID NO:2) are set forth in Table 1. The atomic coordinates calculated for yCTACC in complex with CoA are set forth in Table 2. The atomic coordinates calculated for yCTACC in complex with haloxyfop are set forth in Table 3. The atomic coordinates calculated for yCT2ACC (SEQ ID NO:3) in complex with diclofop are set forth in Table 4. The atomic coordinates calculated for yCT2ACC (SEQ ID NO:3) in complex with CP-640186 are set forth in Table 5. The atomic coordinates calculated for yCT2ACC with the L17051 and V19671 mutations (SEQ ID NO:4) are set forth in Table 6. The atomic coordinates calculated for yCT2ACC (SEQ ID NO:3) are set forth in Table 7.

The CT domain of ACC may be prepared from a natural source, may be produced by recombinant DNA technology, or may be chemically synthesized (although this last possibility would be extremely cumbersome). For example, a full-length cDNA encoding an acetyl-CoA carboxylase such as ACC may be subcloned from a cDNA preparation by the polymerase chain reaction (PCR), using at least one primer design based on known, homologous, or obtained protein sequence, and inserted into an expression vector. Standard deletion mutagenesis techniques then may be used to remove those regions of the ACC cDNA not encoding the CT domain.

In specific, non-limiting embodiments, the isolated CT domain of ACC may be obtained from ACC proteins found in yeasts, such as *S. cerevisiae*, or in mammalian species, such as *Mus musculus* or *Homo sapiens*. Specific, non-limiting examples of the CT domains for the ACC of *S. cerevisiae* comprise amino acids 1429-2233 (SEQ ID NO:2) or 1476-2233 (SEQ ID NO:3), respectively, of the amino acid sequence set forth in GenBank Entry No. Q00955 (SEQ ID NO: 1). Specific, non-limiting examples of the CT domains for the ACC of *M. musculus* ACC2 comprise amino acids 35-767 (SEQ ID NO:6) of the amino acid sequence set forth in GenBank Entry No. AAH22940 (SEQ ID NO:5) (the corresponding mRNA sequence is set forth in GenBank Entry No. BC022940). Specific, non-limiting examples of the CT domains for the ACC of *M. musculus* ACC1 comprise amino acids 1294-2110 (SEQ ID NO: 14) of the amino acid sequence set forth in GenBank Entry No. XP_109883 (SEQ ID NO:13). Specific, non-limiting examples of the CT domains for the ACC of *H. sapiens* ACC1 comprise amino acids 1548-2346 (SEQ ID NO:8) of GenBank Entry No. AAP94122 (SEQ ID NO:7) (the corresponding mRNA sequence is set forth in GenBank Entry No. AY315627). Specific, non-limiting examples of the CT domains for the ACC of *H. sapiens* ACC2 comprise amino acids 1651-2483 (SEQ ID NO:10) of GenBank Entry No. AAB58382 (SEQ ID NO:9) (the corresponding mRNA sequence is set forth in GenBank Entry No. U89344).

A nucleic acid encoding a CT domain of ACC, or a fusion protein comprising said CT domain of ACC, may be operably linked to other elements which aid in its expression, such as a promoter element. One of skill in the art would know, based on the degeneracy of the genetic code, how to set out the many possible nucleotide sequences that would code for the amino acids of SEQ ID NOS:2-14. A large number of suitable vector-host systems are known in the art. Possible vectors include, but are not limited to, plasmids or modified viruses, but the vector system must be compatible with the host cell used. Examples of vectors include *E. coli* bacteriophages such as lambda derivatives, or plasmids such as pBR322 derivatives or pUC plasmid derivatives, e.g., pGEX vectors (Amersham-Pharmacia, Piscataway, N.J.), pET vectors (Novagen, Madison, Wis.), pmal-c vectors (Amersham-Pharmacia, Piscataway, N.J.), pFLAG vectors (Chiang and Roeder, 1993, *Pept. Res.* 6:62-64), baculovirus vectors (Invitrogen, Carlsbad, Calif.; Pharmingen, San Diego, Calif.), etc. The insertion into a cloning vector can, for example, be accomplished by ligating the DNA fragment into a cloning vector which has complementary cohesive termini, by blunt end ligation if no complementary cohesive termini are available or through nucleotide linkers using techniques standard in the art. E.g., Ausubel et al. (eds.), *Current Protocols in Molecular Biology*, (1992). Recombinant vectors comprising the nucleic acid of interest may then be introduced into a host cell compatible with the vector (e.g. *E. coli*, insect cells, mammalian cells, etc.) via transformation, transfection, infection, electroporation, etc. The nucleic acid may also be placed in a shuttle vector which may be cloned and propagated to large quantities in bacteria and then introduced into a eukaryotic host cell for expression. The vector systems of the present invention may provide expression control sequences and may allow for the expression of proteins in vitro.

The CT domains of any of the afore-mentioned ACCs, produced either naturally, synthetically or by recombinant means, may be purified by methods known in the art, including, but not limited to, selective precipitation, dialysis, chromatography, and/or electrophoresis. Purification may be monitored by measuring the ability of a fraction to perform the catalytic activity. Any standard method of measuring acetyl-CoA carboxylase activity may be used.

For certain embodiments, it may be desirable to express the CT domain of ACC as a fusion protein. In specific non-limiting embodiments, the fusion protein comprises a tag which facilitates purification. As referred to herein, a "tag" is any added series of amino acids which are provided in a protein at either the C-terminus, the N-terminus, or internally. Suitable tags include but are not limited to tags known to those skilled in the art to be useful in purification such as, but not limited to, His tag, glutathione-s-transferase tag, flag tag, mbp (maltose binding protein) tag, etc. Such tagged proteins may also be engineered to comprise a cleavage site, such as a thrombin, enterokinase or factor X cleavage site, for ease of removal of the tag before, during or after purification. Vector systems which provide a tag and a cleavage site for removal of the tag are particularly useful to make the expression constructs of the present invention. A tagged ACC may be purified by immuno-affinity or conventional chromatography, including but not limited to, chromatography employing the following: glutathione-Sepharose™ (Amersham-Pharmacia, Piscataway, N.J.) or an equivalent resin, nickel or cobalt-purification resins, nickel-agarose resin, anion exchange chromatography, cation exchange chromatography, hydrophobic resins, gel filtration, antiflag epitope resin, reverse phase chromatography, etc.

In certain embodiments, the CT domain of ACC is expressed as His-tagged protein by subcloning a DNA sequence encoding residues 1429-2233 (SEQ ID NO:2) of the *S. cerevisiae* ACC protein disclosed by Zhang et al. (*Science* 2003;299:2064-2067) or SEQ ID NO:3 into the pET24 d vector (Novagen) and over-expressing the His-tagged fusion protein expressed from the resulting vector in *E. coli* at 20° C.; the soluble protein then may be purified by nickel-agarose affinity and anion exchange chromatography. The purified protein may be concentrated to 10 mg/ml and flash-frozen in liquid nitrogen.

After purification, at least 90 to at least 95 percent of total protein is the CT domain of ACC, the enzyme, or a mixture of the enzyme and one or more substrates or modulators thereof, may be concentrated to greater than 1 mg/ml for crystallization purposes. In one embodiment, the concentration is greater than 5 mg/ml.

Figure 24A:
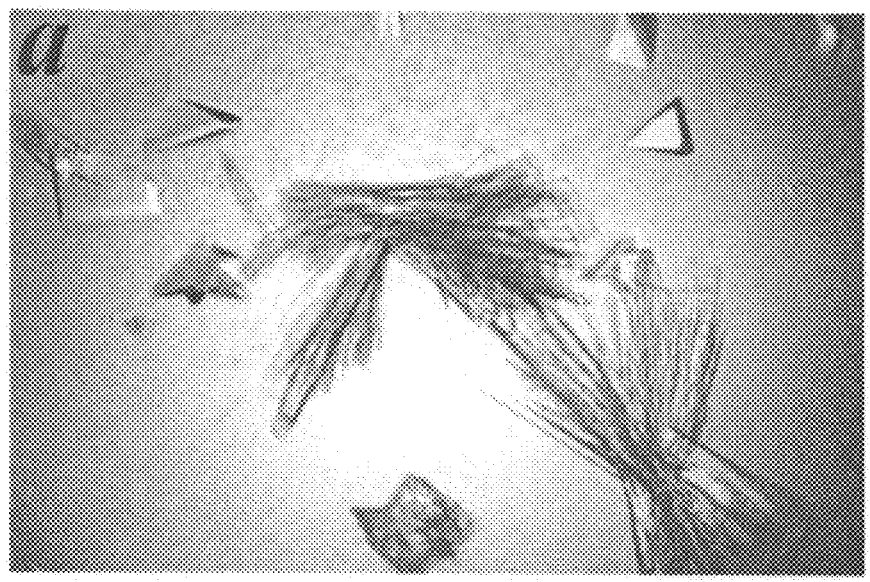
FIGS. 24A-24B.
Figure 24B:
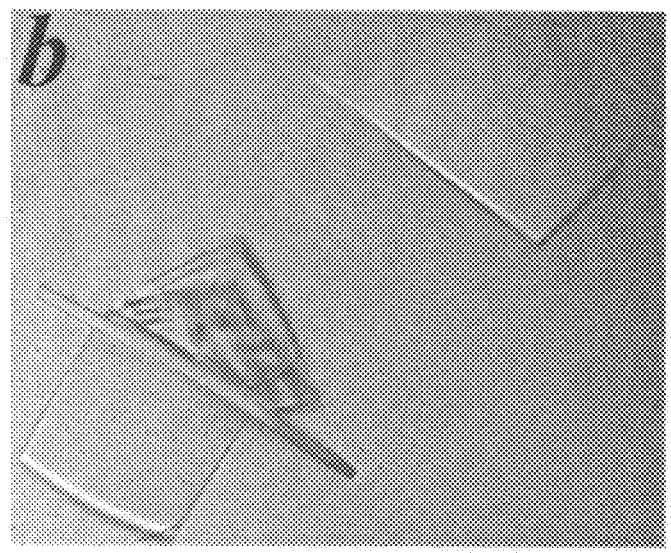

Any crystallization technique known to those skilled in the art may be employed to obtain the crystals of the present invention, including, but not limited to, batch crystallization, vapor diffusion (either by sitting drop or hanging drop) and micro dialysis. Seeding of the crystals in some instances may be required to obtain X-ray quality crystals. Standard micro and/or macro seeding of crystals may therefore be used. In one embodiment, the crystals are obtained using the sitting-drop vapor diffusion method. Different crystallization methods can result in the formation of different crystal forms (i.e., polymorphs or solvates), and thus, the present invention encompasses the different crystal forms for the CT domain of ACC. For example, the yeast CT domain has been crystallized in at least four different crystal forms (denoted herein as "Form I", "Form II", "Form III" and "Form IV"), as manifested by their different crystal unit cell parameters: Form I refers to the crystal that comprises the unit cell information: a=247±2 Å; b=125±2 Å; c=145±2 Å; $\alpha$=90°; $\beta$=94±2°; $\gamma$=90°; and space group C2. The atomic coordinates for this crystal is set forth in Table 1, and a picture of the crystals is presented in FIG. 24A. Form II refers to the crystal that comprises the unit cell information: a=255±2 Å; b=113±2 Å; c=135±2 Å; $\alpha$=90°; $\beta$=101+2°; $\gamma$=90°; and space group C2. Form III refers to the crystal that comprises the unit cell information: a=93±2 Å; b=138±2 Å; c=101±2 Å; $\alpha$=90'; $\beta$=114±2°; $\gamma$=90°; and space group P2$_1$. The atomic coordinates for this crystal is set forth in Table 2, and a picture of the crystals is presented in FIG. 24B. Form IV refers to the crystal that comprises the unit cell information: a=137±2 Å; b=137±2 Å; c=244±2 Å; $\alpha$=90°; $\beta$=90°; $\gamma$=120; and space group P3$_2$21. The atomic coordinates for this crystal is set forth in Table 4.

To collect diffraction data from the crystals of the present invention, the crystals may be flash-frozen in the crystallization buffer employed for the growth of said crystals, however with preferably higher precipitant concentration (see, Examples below). For example, but not by way of limitation, if the precipitant used was 20% PEG 3350, the crystals may be flash frozen in the same crystallization solution employed for the crystal growth wherein the concentration of the precipitant is increased to 25% (see Examples below). If the precipitant is not a sufficient cryoprotectant (i.e. a glass is not formed upon flash-freezing), cryoprotectants (e.g. glycerol, ethylene glycol, low molecular weight PEGs, alcohols, etc.) may be added to the solution in order to achieve glass formation—upon flash-freezing, providing the cryoprotectant is compatible with preserving the integrity of the crystals. The flash-frozen crystals are maintained at a temperature of less than −110° C. or less than −150° C. during the collection of the crystallographic data by X-ray diffraction.

In certain embodiments, the protein crystals and protein-substrate complex co-crystals of the present invention diffract to a high resolution limit of at least greater than or equal to 3.5 angstrom (Å) or greater than or equal to 3 Å; it should be noted that a greater resolution is associated with the ability to distinguish atoms placed closer together. In one embodiment, the protein crystals and protein-substrate complex co-crystals of the present invention diffract to a high resolution limit of greater than 2.5 Å or 1.5 Å.

Thus, a crystal of the present invention may take a variety of forms. In one embodiment, the crystallized CT domain of ACC has a space group of C2 with three molecules in the asymmetric unit and with unit dimensions for the free enzyme of: a=247±2 Å; b=125±2 Å; c=145±2 Å; $\alpha$=90°; $\beta$=94±2°; $\gamma$=90° (see e.g., Examples, below). In another embodiment, the crystallized CT domain of ACC has a space group of C2 with three molecules in the asymmetric unit and with unit dimensions for the free enzyme of: a=255±2 Å; b=113±2 Å; c=135±2 Å; $\alpha$=90°; $\beta$=101±2°; $\gamma$=90°. In another embodiment, the crystallized CT domain of ACC has a space group of C2 with three molecules in the asymmetric unit and with unit dimensions for the free enzyme of: a=246±2.5 Å; b=124±2 Å; c=145±2 Å; $\alpha$=90°; $\beta$=94±2°; $\gamma$=90°. In another embodiment, the crystallized mutant CT domain (SEQ ID NO:4) of ACC has a space group of C2 with three molecules in the asymmetric unit and with unit dimensions for the free enzyme of a=247±2 Å; b=125+2 Å; c=146±2 Å; $\alpha$=90°; $\beta$=94±2°; $\gamma$=90°. In another embodiment, the CT domain: acetyl-CoA complex has a crystal with a space group of P2$_1$, with two molecules in the asymmetric unit and with unit dimensions of: a=93±2 Å; b=138±2 Å; c=101+2 Å; $\alpha$=90; $\beta$=114±2°; $\gamma$=90°. In another embodiment, the CT domain: diclofop complex has a crystal with a space group of P3$_2$21, with two molecules in the asymmetric unit and with unit dimensions of: a=137±2 Å; b=137+2 Å; c=244±2 Å; $\alpha$=90°; $\beta$=90°; $\gamma$=1200. In another embodiment, the CT domain: haloxyfop complex has a crystal with a space group of C2, with three molecules in the asymmetric unit and with unit dimensions of: a=247±2 Å; b=125±2 Å; c=146±2 Å; α=90°; β=94±°; γ=90°. In another embodiment, the CT domain:CP-640186 complex has a crystal with a space group of C2, with three molecules in the asymmetric unit and with unit dimensions of: a=247±2 Å; b=125±2 Å; c=146±2 Å; α=90°; β=94±2°°; γ=90°.

Data obtained from the diffraction pattern may be solved directly or may be solved by comparing it to a known structure, for example, the three-dimensional structure of the CT domain of yACC (with or without substrates or modulators). If the crystals are in a different space group than the known structure, molecular replacement may be employed to solve the structure, or if the crystals are in the same space group, refinement and difference Fourier methods may be employed. The structure of the CT domain of ACC, as defined herein, exhibits no greater than about 4.0 Å, 1.5 Å or 0.5 Å root mean square deviation (RMSD) in the positions of the Cα atoms for at least 50% or more of the amino acids.

In a specific, non-limiting embodiment of the present invention, seleno-methionyl proteins may be used to directly determine the structure of a CT domain of an ACC. Hendrickson, 1991, *Science*, 254:51-58. For example, a seleno-methionyl single wavelength anomalous diffraction (SAD) data set may be collected at 100K on the free enzyme and native reflection data sets may be collected for enzyme/substrate complexes. X-ray diffraction data may be processed with the HKL package. Otwinowski and Minor, 1997, *Methods Enzymol.* 276:307-326. The location of seleno-methionyl atoms may be determined with the program SnBv2.0 (Weeks and Miller, 1999, *Acta Crystallogr D Biol Crystallogr* 55:492-500) and may further be confirmed with SHELXS (Sheldrick, 1990, *Acta Crystal.* A46:467-473). Reflection phases, which can be, for example, less than or equal to 4.0 Å, may be calculated based on the SAD data and may further be improved with the program SOLVE (Terwilliger and Berendzen, 1999, *Acta Cryst.* D55:849-861). The resulting atomic model may be built into the electron density with the problem O (Jones et al., 1991, *Acta Crystal* A47:110-119). A structure of the enzyme/substrate complex may be determined by molecular replacement with the program COMO (Jogl et al., 2001, *Acta Cryst.* D57:1127-1134) and structural refinement may be carried out with the program CNS (Brunger et al., 1998, *Acta Cryst.* D54:905-921).

Any method known to those skilled in the art may be used to process the X-ray diffraction data. In addition, in order to determine the atomic structure of an ACC according to the present invention, multiple isomorphous replacement (MIR) analysis, model building and refinement may be performed. For MIR analysis, the crystals may be soaked in heavy-atoms to produce heavy atom derivatives necessary for MIR analysis. As used herein, heavy atom derivative or derivatization refers to the method of producing a chemically modified form of a protein or protein complex crystal wherein said protein is specifically bound to a heavy atom within the crystal. In practice a crystal is soaked in a solution containing heavy metal atoms or salts, or organometallic compounds, e.g., lead chloride, gold cyanide, thimerosal, lead acetate, uranyl acetate, mercury chloride, gold chloride, etc., which can diffuse through the crystal and bind specifically to the protein. The location(s) of the bound heavy metal atom(s) or salts can be determined by X-ray diffraction analysis of the soaked crystal. This information is used to generate MIR phase information which is used to construct the three-dimensional structure of the crystallized CT domain of ACC of the present invention. Thereafter, an initial model of the three-dimensional structure may be built using the program O (Jones et al., 1991, *Acta Crystallogr. A*47:110-119). The interpretation and building of the structure may be further facilitated by use of the program CNS (Brunger et al, 1998, *Acta Crystallogr.* D54:905-921).

The method of molecular replacement broadly refers to a method that involves generating a preliminary model of the three-dimensional structure of crystal of a CT domain of an ACC of the present invention whose structural coordinates were previously unknown. Molecular replacement is achieved by orienting and positioning a molecule whose structural coordinates are known (e.g. yCTACC or yCT2ACC, as described herein) within the unit cell as defined by the X-ray diffraction pattern obtained from the CT domain of an ACC under study (or the corresponding enzyme/substrate complex or enzyme/inhibitor complex) so as to best account for the observed diffraction pattern of the unknown crystal. Phases can then be calculated from this model and combined with the observed amplitudes to give an approximate Fourier synthesis of the structure whose coordinates are unknown. This in turn can be subject to any of several forms of refinement to provide a final, accurate structure.

The molecular replacement method may be applied using techniques known to the skilled artisan. For example, the program COMO may be employed to determine the previously unknown structure of a CT domain of an ACC or its enzyme/substrate or enzyme/inhibitor complexes by molecular replacement using the coordinates or a subset of coordinates, of yCTACC set forth in Table 1, the coordinates or a subset of coordinates, of yCTACC in complex with acetyl-CoA set forth in Table 2, the coordinates or a subset of coordinates, of yCTACC in complex with haloxyfop set forth in Table 3, the coordinates or a subset of coordinates, of yCTACC in complex with diclofop set forth in Table 4, the coordinates or a subset of coordinates, of yCT2ACC in complex with CP-640186 set forth in Table 5, the coordinates or a subset of coordinates, of yCTACC with mutations LI 7051 and VI 9671 set forth in Table 6, or the coordinates or a subset of coordinates, of yCT2ACC set forth in Table 7, as reference structures.

The three-dimensional structures and the specific atomic coordinates associated with said structures of the CT domain of yeast ACC, alone or in complex with a substrate such as acetyl-CoA or a modulator, are useful for solving the structure of crystallized forms of CT domains of other ACCs. This technique may could also be applied to solve the structures of ACC-related proteins, where there is sufficient sequence identity. Such ACC-related proteins comprise a root mean square deviation (RMSD) of no greater than 2.0 Å, 1.5 Å, 1.0 Å or 0.5 Å in the positions of Cα atoms for at least 50 percent or more of the amino acids of the structure of the CT domain of ACC of the present invention. Such an RMSD may be expected based on the amino acid sequence identity. Chothia and Lesk, 1986, *EMBO J.* 5:823-826.

The refined three-dimensional structures of the CT domains of ACCs of the present invention, specifically different spans of the CT domain (SEQ ID NO:2; SEQ ID NO:3) of yeast ACC, a mutant CT domain of yeast ACC, the CT domain of yeast ACC in complex with CoA, the CT domain of yeast ACC in complex with haloxyfop, diclofop or CP-640186, are represented by the atomic coordinates set forth in Tables 1-7. A description of various specific features of these structures is presented in the Examples section below. Such description may be useful for solving the structures of other ACCs.

Design of Modulators

Modulators of ACC may be designed, according to the invention, using three-dimensional structures obtained as set forth in the preceding section and the Examples section below. These structures may be used to design or screen for molecules that are able to form the desired interactions with one or more binding sites of the CT domain of ACC.

The models of the CT domain (and sub-regions, including active sites, binding sites or cavities thereof) of ACC described herein may be used to either directly develop a modulator for ACC or indirectly develop a modulator of an ACC-related enzyme for which the structure has not yet been solved. A modulator designed to interact with a CT domain may be reasonably expected to interact not only with the CT domain but also with the other ACC-related enzymes. The ability for such a modulator to modulate the activity of a CT domain of ACC can be confirmed by further computer analysis, and/or by in vitro and/or in vivo testing.

In non-limiting embodiments, the present invention provides for a model, actual or virtual, of the CT domain (the whole domain, or parts, such as a particular substrate or modulator binding site) of ACC. The reactive site or the active site of the CT domain of ACC is located the interface of a dimer of CT and comprises the N and C domains of the two monomers of the dimer (see FIGS. 2A and 3A). More specifically, the active site comprises a cavity between the small β-sheets (with strands β5, β7, β9, and β11) of the β-β-α super-helix of the two domains (see Examples below and FIG. 3A). The CoA molecule is mostly associated with the N domain of one molecule in the dimer (FIG. 3A). The biotin substrate is mostly associated with the small β-sheet in the C domain of the other monomer in the active site (see FIG. 3A). The three-dimensional orientation of atoms in the cavity at the interface of the dimers is as set forth by the atomic coordinates for these elements provided for yACC herein, to within about 2 Å, 1.5 Å, or 0.5 Å thereof.

Characteristics of the active site include, but are not limited to, one or more of the following features: 1) binding of haloxyfop, diclofop, CP-640186 or other modulators to the CT active site at the interface between two monomers of the ACC enzyme; 2) interaction between the $CF_3$ group of haloxyfop or similar ACC inhibitors with the side chains of Trp1924', Val 1967', Ile1974', wherein the presence of the prime sign after the numerical identifier indicates that the designated residue is in the second monomer; 3) the pyridyl ring of haloxyfop is π-stacked with the side chains of Tyr1738 and Phe1956'; 4) the phenyl ring of haloxyfop interacts with the main chains of Gly1734-Ile1735, and Gly1997'-Gly1998'; 5) one carboxylate oxygen of haloxyfop is hydrogen-bonded to the main chain amides of Ile1735 and Ala1627, and the other carboxylate oxygen of haloxyfop is exposed to the solvent; 6) the methyl group of the propionate moiety of haloxyfop interacts with Leu1705 and Ala1627; 7) binding of haloxyfop induces significant conformational changes for the side chains of Tyr1738 and Phe1956', which in turn open up the hydrophobic core of the dimer; 8) the trifluoropyridyl group of haloxyfop is inserted into this hydrophobic core; 9) residues Phe1956'-1965' become disordered upon binding of haloxyfop; 10) other than Leu1705 and Val1967', most of the residues of the binding site of the CT domain of ACC that interact with haloxyfop are strictly or highly conserved among the CT domains; 11) there are only small conformational changes in the ACC enzyme upon binding of CP-640186, in contrast to the binding of herbicides; 12) the binding site for the CP-640186 compound is distinct from that for CoA or for the herbicides; 13) the anthracene group of CP-640186 is placed in the narrow channel between helices α6 and β6', interacting with residues Ala1761, Lys1764, Met1765 on one face and residues Leu2025', Glu2026', and Gly2029' on the other; 14) the carbonyl oxygen next to the anthracene group is hydrogen-bonded to the main-chain amide of Gln2028'; 15) the remainder of the CP-640186 compound (the two piperidine rings and morpholine ring) is placed next to the peptide segment Arg1954'-Gly1959', and has interactions with Val 1923', Thr1757, and Ile1762; 16) one face of these piperidine rings and morpholine ring is exposed to the solvent in the CT complex; 17) the carbonyl oxygen next to the morpholine ring is hydrogen-bonded to the main-chain amide of Gly1958'; and 18) most of the residues that interact with the CP compound are strictly or highly conserved among the CT domains, two exceptions are Met1765 which is Val in most mammalian ACCs, and Ile1762, which is Leu in most other ACCs—additional residues may also be important for binding, for example, Gly2032 is replaced by Glu in most other ACCs, and this Glu side chain could ion-pair with Lys1764, forming a lid over the anthracene group.

A model of an active site may be comprised in a virtual or actual protein structure that is smaller than, larger than, or the same size as a native CT domain of an ACC protein. The protein environment surrounding the active site model may be homologous or identical to native CT domain of an ACC, or it may be partially or completely non-homologous.

In particular non-limiting embodiments of the invention, the CoA binding site of a model is as schematically depicted in FIG. 3, In another set of specific, non-limiting embodiments, the acetyl CoA binding site comprises amino acid residues Ile1593, Ser1595, Ser1625, Ala1627, Arg1628, Ile1629, Gly1630, Met1631, Gly1701, Glu1703, Leu1705, Ser1708, Ala1712, Arg1731, Val1733, Gly1734, Ile1735, Tyr1738, Leu1742, Pro1753, Leu1756, Thr1757, Ala1761, Ile1762, Lys1764, Met1765, Leu1766, Tyr1771, Pro1920, Gly1921, Val1923, Trp 1924, Arg1954, Gly1955, Phe1956, Ser1957, Gly1958, Gly1959, Gln1960, Arg1961, Asp1962, Met1963, Phe1964, Asn1965, Val1967, Leu1968, Gly1971, Ile1974, Val1975, Glu1994, Gly1997, Gly1998, Trp2000, Val2001, Val2002, Arg2021, Gly2023, Val2024, Leu2025, Glu2026, Pro2027, Gln2028, Ile2033, Lys2034, Arg2036, Asp2098, and Val2108, or a subset thereof, of yACC or the equivalent residues from another ACC, in a configuration as defined by the atomic coordinates set forth in Tables 1-7. In another set of specific, non-limiting embodiments, the acetyl CoA binding site comprises amino acid residues: Met1503, Lys1592, Ile1593, Ser1595, Phe1596, Asn1624, Ser1625, Gly1626, Ala1627, Arg1628, Ile1629, Gly1630, Gly1699, Leu1705, Arg1731, Val1733, Gly1734, Ile1735, Tyr1738, Ile1755, Leu1756, Thr1757, Gly1758, Ala1759, Pro1760, Ala1761, Asn1774, Gly1955, Phe1956, Arg1996, Gly1997, Gly1998, Ser1999, Val9001, Val2024, Leu2025, Gly2099, Ile2033, Lys2034, Arg2036, and Leu2189, or a subset thereof, of yACC or the equivalent residues from another ACC, in a configuration as defined by the atomic coordinates set forth in Tables 1-7.

Figure 5C:
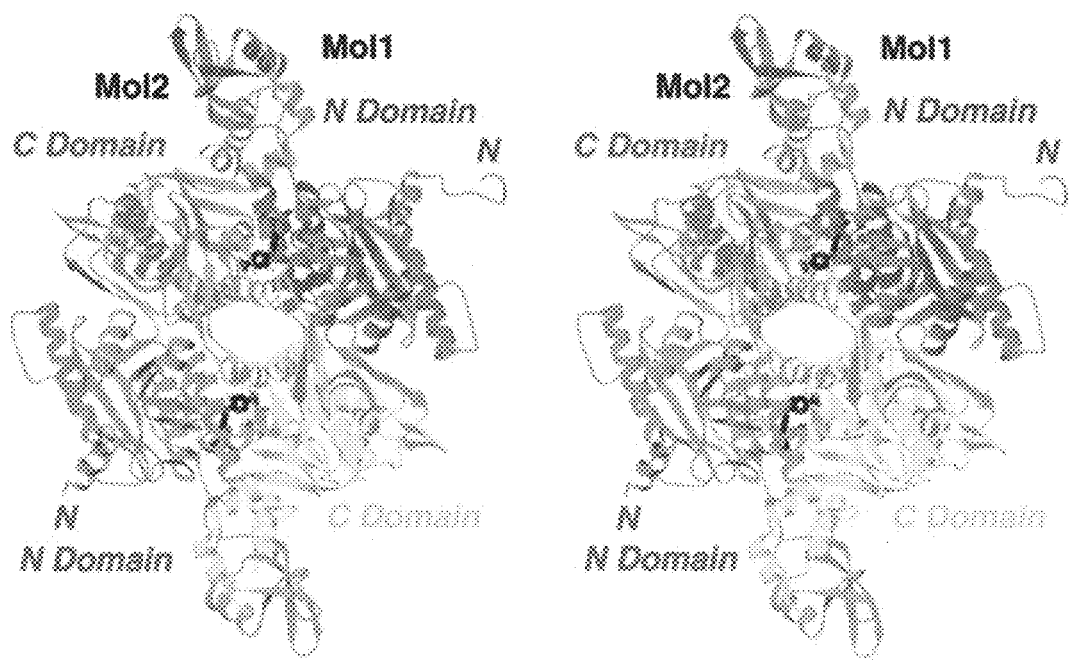

In particular non-limiting embodiments of the invention, one binding site for modulators is schematically depicted in FIGS. 5, 6 and 7. In another set of specific, non-limiting embodiments, one modulator binding site comprises amino acid residues Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, and Leu2025, or a subset thereof, of yACC or the equivalent residues from another ACC, in a configuration as defined by the atomic coordinates set forth in Tables 1-7.

In particular non-limiting embodiments of the invention, one binding site for modulators is schematically depicted in FIG. 23. In another set of specific, non-limiting embodiments, one modulator binding site comprises amino acid residues Ile1629, Leu1756, Thr1757, Gly1758, Pro1760, Ala1761, Ile1762, Asn1763, Lys1764, Met1765, Leu1766, Tyr1771, Ala1908, Pro1920, Gln1922, Val923, Trp1924, His1925, Trp1953, Arg1954, Gly1955, Phe1956, Ser1957, Gly1958, Gly1959, Gln1960, Asp1962, Arg1996, Gly1997, Ser1999, Val2024, Leu2025, Glu2026, Pro2027, Gln2028, Gly2029, Met2030, Val2031, Gly2032, and Ile2033 or a subset thereof, of yeast ACC ("yACC") or the equivalent residues from another ACC, in a configuration as defined by the atomic coordinates set forth in Tables 1-7.

Thus, the present invention provides for a method for rationally designing a modulator of an ACC, comprising the steps of (i) producing a computer readable model of a molecule comprising a region (i.e., an active site, reactive site, or a binding site) of a CT domain of ACC (e.g. yACC); and (ii) using the model to design a test compound having a structure and a charge distribution compatible with (i.e. able to be accommodated within) the region of the CT domain, wherein the test compound can comprise a functional group that may interact with the active site to modulate acetyl-CoA carboxylase activity. If the crystal structure is not available for the CT domain to be examined, homology modeling methods known to those of ordinary skill in the art may be used to produce a model, which then may be used to design test compounds as described above.

The atomic coordinates of atoms of the CT domain (or a region/portion thereof) of an ACC or an ACC-related enzyme may be used in conjunction with computer modeling using a docking program such as GRAM, DOCK, HOOK or AUTODOCK (Dunbrack et al., 1997, *Folding & Design* 2:27-42) to identify potential modulators. This procedure can include computer fitting of potential modulators to a model of a CT domain (including models of regions of a CT domain, for example, an active site, or a binding site) to ascertain how well the shape and the chemical structure of the potential modulator will complement the active site or to compare the potential modulators with the binding of substrate or known inhibitor molecules in the active site.

Computer programs may be employed to estimate the attraction, repulsion and/or steric hindrance associated with a postulated interaction between the reactive site model and the potential modulator compound. Generally, characteristics of an interaction that are associated with modulator activity include, but are not limited to, tight fit, low stearic hindrance, positive attractive forces, and specificity.

Modulator compounds of the present invention may also be designed by visually inspecting the three-dimensional structure of a reactive site of the CT domain of an ACC or ACC-related enzymes, a technique known in the art as "manual" drug design. Manual drug design may employ visual inspection and analysis using a graphics visualization program known in the art.

In designing potential modulator compounds according to the invention, the functional aspect of a modulator may be directed at a particular step of the ACC catalytic mechanism, as illustrated by the following non-limiting example.

In ACC, the CT domain catalyzes the carboxylation of acetyl-CoA, by transferring a carboxyl group from biotin to acetyl-CoA, to produce malonyl-CoA, and also catalyzes the decarboxylation of malonyl-CoA, by transferring a carboxyl group to a biotin methyl ester, to produce acetyl-CoA. According to the invention, a modulator intended to decrease malonyl-CoA levels decreases the carboxylation of acetyl-CoA. Correspondingly, a modulator that is intended to increase malonyl-CoA levels facilitates the carboxylation of acetyl-CoA.

Because it is known that ACC2 knockout mice (see U.S. Patent Application Publication No. US2003/0028912 A1) are "skinny" and that knockout of ACC1 is embryonically lethal in mice, it may be desirable to design modulators which selectively inhibit ACC2 and not ACC1 (Abu-Elheiga et al., *Science*, 291, 2613, (2001). This may be achieved as discussed further below under the heading assay systems.

In various non-limiting embodiments, the present invention provides for virtual or actual models of the active site of the CT domain of ACC. As set forth above, such a model may or alternatively may not comprise additional amino acid residues in addition to amino acid residues of the active site. Characteristics of the active site model in the actual or virtual presence of bound haloxyfop provide a non-limiting physical description of the active site model which pertain in the presence or absence of haloxyfop. As examples, active site models of the invention may, in the presence of haloxyfop, comprise the $CF_3$ group of haloxyfop interacting with side chains of Trp1924', Val1967', Ile1974 of the active site model; and/or comprise a pyridyl ring of haloxyfop π-stacked with the side chains of Tyr1738 and Phe1956' of the active site model; and/or comprise an interaction between the phenyl ring of haloxyfop and the main chains of Gly1734-Ile1735, and Gly1997'-Gly1998' in the active site model; and/or comprise one carboxylate oxygen of haloxyfop hydrogen-bonded to the main chain amides of Ile1735 and Ala1627 of the active site model, where the other carboxylate oxygen of haloxyfop is exposed to the exterior; and/or comprise the methyl group of the propionate moiety of haloxyfop interacting with Leu1705 and Ala1627; and/or comprise significant conformational changes for the side chains of Tyr1738 and Phe1956' which open up a hydrophobic core into which the trifluoropyridyl group of haloxyfop is inserted; and/or comprise disordered residues Phe1956'-1965'.

Figure 6A:
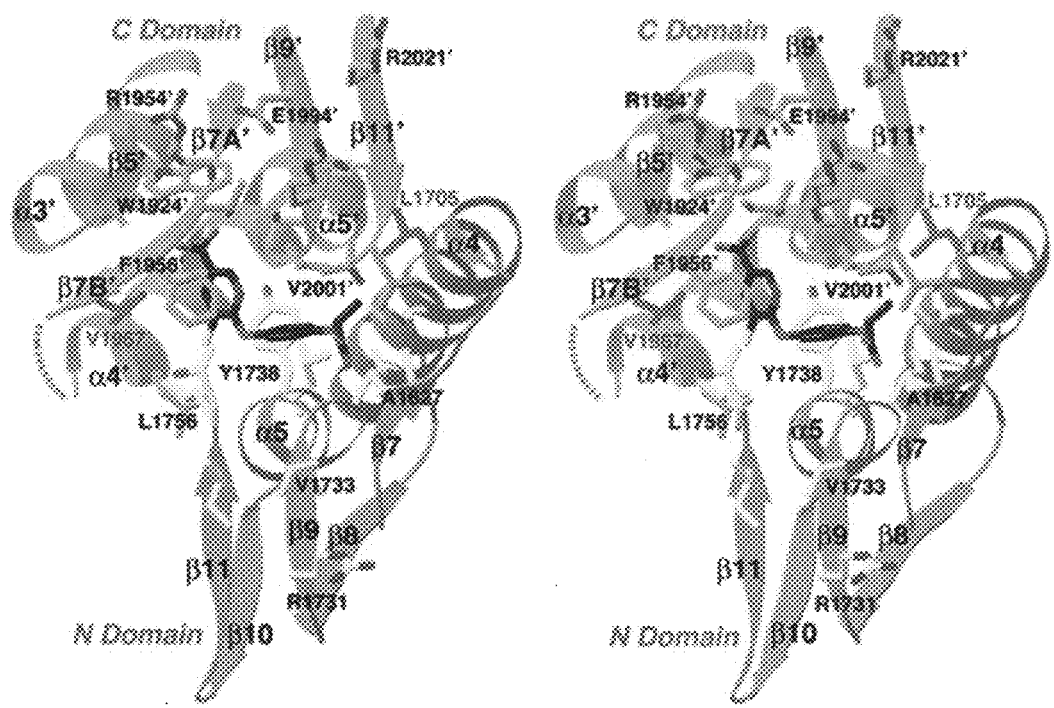
FIGS. 6A-6C. The binding mode of haloxyfop.
Figure 6B:
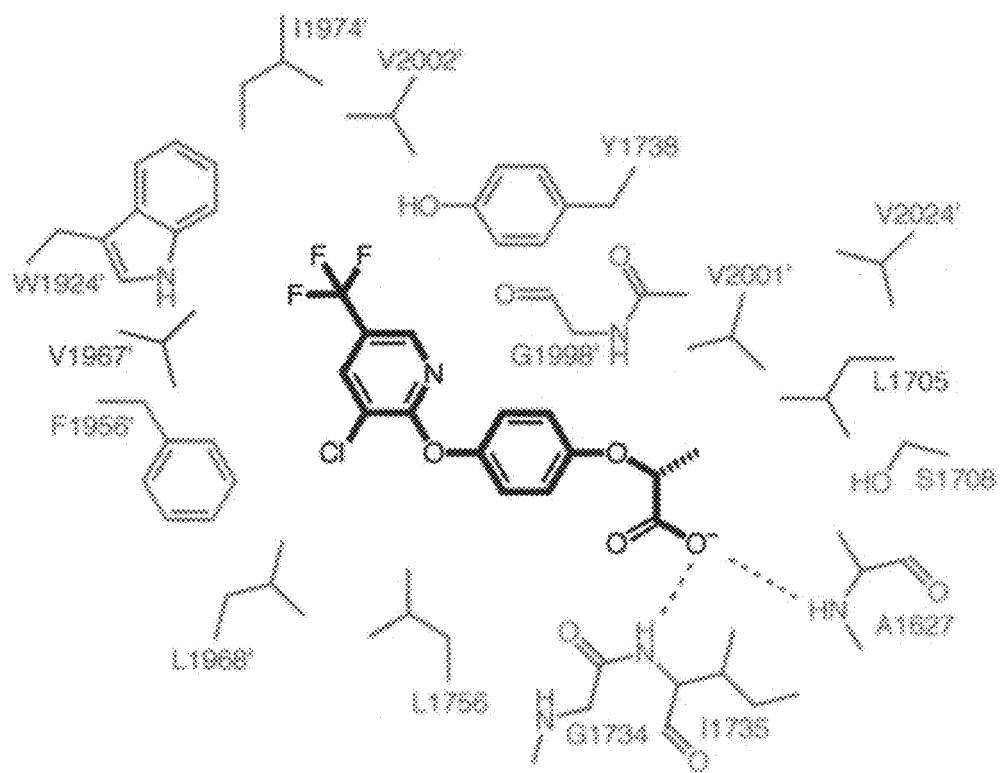
Figure 6C:
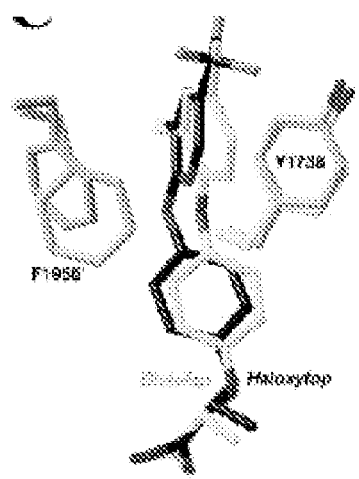

Further, the binding mode of diclofop is essentially the same as for haloxyfop (see FIG. 6C and Examples). The carboxyl groups of the two inhibitors essentially have the same binding mode, and the aromatic rings of diclofop show small but recognizable differences in their positions as compared to those of halxofop, but the two chloro substituents in diclofop superimpose well with the substituents in haloxyfop. For the enzyme, the Phe1956' side chain has a different conformation, which may be linked to the change in the position of diclofop. On the other hand, the Tyr1738 side chains show little structural differences, and the other residues in the binding site have essentially the same conformation in the two complexes. The α4 helix is disordered in the co-crystals with diclofop as well. Moreover, the dimer organization in the diclofop complex is the same as the haloxyfop complex, as it also has the 2.5° rotation of the second monomer relative to the first monomer. Thus, characteristics of the active site model in the actual or virtual presence of bound diclofop provide a non-limiting physical description of the active site model which pertain in the presence or absence of diclofop.

The present invention, in further non-limiting embodiments, provides for methods of designing an ACC inhibitor, comprising virtually or physically constructing, identifying or designing a compound which, when actually or virtually bound to the active site model, interacts with side chains of Trp1924', Val1967', Ile1974 of the active site model; and/or n-stacks with the side chains of Tyr1738 and Phe1956'; and/or interacts with the main chains of Gly1734-Ile1735, and Gly1997'-Gly1998'; and/or comprises one carboxylate oxygen hydrogen-bonded to the main chain amides of Ile1735 and Ala1627; and/or comprises a methyl group which interacts with Leu1705 and Ala1627; and/or induces conformational changes for the side chains of Tyr1738 and Phe1956', which may open a hydrophobic core; and/or causes residues Phe1956'-1965' of the model to become disordered. Such methods may comprise the step of designing the compound to have one or more of the above-listed effects on the active site model.

Further, active site models of the invention may, in the presence of CP-640186, comprise a model for a binding site that is distinct from the binding sites for CoA or for herbicides such as haloxyfop or diclofop. Such a binding site can comprise the interaction with a modulator with residues Ala1761, Lys1764, Met1765 on one face of the ACC dimer and residues Leu2025', Glu2026', and Gly2029' on the other. Since the carbonyl oxygen next to the anthracene group of CP-640186 is hydrogen-bonded to the main-chain amide of Gln2028', Gln2028' may be involved in the binding of a modulator in this binding site. Similarly, residues Arg1954'-Gly1959', Val1923', Thr1757, Ile1762, Gly1958', Met1765, Ile1762, Gly2032 and Lys1764 may comprise important residues for a model of this binding site.

Screening for Modulator Compounds

As an alternative or an adjunct to rationally designing modulators, random screening of a small molecule library, a peptide library or a phage library for compounds that interact with and/or bind to a site/region of interest (i.e., a binding site, active site or a reactive site, for example) of the CT domain of ACC or ACC-related enzymes may be used to identify useful compounds. Such screening may be virtual; small molecule databases can be computationally screened for chemical entities or compounds that can bind to or otherwise interact with a virtual model of an active site, binding site or reactive site of a CT domain of an ACC. Alternatively, screening can be against actual molecular models of the CT domain or portions thereof. In one embodiment, modulators which selectively bind ACC2 and not ACC1, or vice versa, are screened. Further, antibodies can be generated that bind to a site of interest of the CT domain. After candidate (or "test") compounds that can bind to the CT domain are identified, the compounds can then be tested to determine whether they can modulate CT domain enzymatic activity (see Assay Systems section below).

In one embodiment, CT domain proteins, nucleic acids, and cells containing the CT domains are used in screening assays. Screens may be designed to first find candidate compounds that can bind to a CT domain or portion thereof, and then these compounds may be used in assays that evaluate the ability of the candidate compound to modulate CT domain or ACC enzymatic activity. Thus, as will be appreciated by those in the art, there are a number of different assays which may be run, including binding assays and activity assays. In one aspect, candidate compounds are first tested to determine whether they can bind to a particular binding site of the CT domain, i.e., the binding site for CoA, the binding site used by diclofop/haloxyfop or the binding site used by anthracene comprising compounds.

Thus, in one embodiment, the methods comprise combining a CT domain or portion thereof and a candidate compound, and determining the binding of the candidate compound to the CT domain or portion thereof. In some embodiments of the methods herein, the CT domain (or portion thereof) or the candidate agent is non-diffusably bound to an insoluble support having isolated sample receiving areas (e.g., a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples—i.e., they enable high-throuput screening. Following binding of the CT domain, excess unbound material is removed by washing. The sample receiving areas may then be blocked through incubation with bovine serum albumin (BSA), casein or other innocuous protein or other moiety.

A candidate compound is added to the assay. Candidate compounds include, but are not limited to, specific antibodies, compounds from chemical libraries, peptide analogs, etc. Of particular interest are screening assays for compounds that have a low toxicity for human cells. A wide variety of assays may be used for this purpose, including labeled in vitro protein-protein binding assays, immunoassays for protein binding, NMR assays to determine protein-protein or protein-chemical compound binding, and the like. Candidate compounds can also include herbicides or fungicides.

The term "candidate compound" as used herein describes any molecule, e.g., protein, oligopeptide, small organic molecule, polysaccharide, polynucleotide, etc., with the capability of directly or indirectly modulating CT domain or ACC enzymatic activity. Generally a plurality of assay mixtures are run in parallel with different compound concentrations to obtain a differential response to the various concentrations. Typically, one of these concentrations serves as a negative control, i.e., at zero concentration or below the level of detection.

Candidate compounds can encompass numerous chemical classes, though typically they are organic molecules, and in one embodiment they are small organic compounds having a molecular weight of more than 100 and less than about 2,500 daltons. Candidate compounds can comprise functional groups necessary for structural interaction with proteins, for example hydrogen bonding, and typically include at least an amine, carbonyl, hydroxyl or carboxyl group, preferably at least two of the functional chemical groups. The candidate compounds can comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate compounds can be obtained from a wide variety of sources including libraries of synthetic or natural compounds. For example, numerous means are available for random and directed synthesis of a wide variety of organic compounds and biomolecules, including combinatorial chemical synthesis and the expression of randomized peptides or oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. In one embodiment, the library is fully randomized, with no sequence preferences or constants at any position. In another, the library is biased. That is, some positions within the sequence are either held constant, or are selected from a limited number of possibilities.

The determination of the binding of the candidate compound to the CT domain may be done in a number of ways. In one embodiment, the candidate compound is labelled, and binding determined directly. For example, this may be done by attaching all or a portion of the CT domain to a solid support, adding a labelled candidate compound (for example a fluorescent label or radioactive label), washing off excess reagent, and determining whether the label is present on the solid support. Various blocking and washing steps may be utilized as is known in the art.

By "labeled" herein is meant that the compound is either directly or indirectly labelled with a label which provides a detectable signal, e.g., radioisotope, fluorescers, enzyme, antibodies, particles such as magnetic particles, chemiluminescers, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal.

In one embodiment, the binding of the candidate compound is determined through the use of competitive binding assays. In this embodiment, the competitor is a binding moiety known to bind to the CT domain, such as an antibody, peptide, ligand (i.e., acetyl-CoA, haloxyfop, diclofop or CP-640186), etc. Under certain circumstances, there may be competitive binding as between the candidate compound and the known binding moiety, with the binding moiety displacing the bioactive agent.

In one embodiment, the candidate compound is labeled. Either the candidate compound, or the competitor, or both, is added first to the CT domain for a time sufficient to allow binding, if present. Incubations may be performed at any temperature which facilitates optimal binding, typically between 4 and 40° C. Incubation periods are selected for optimum binding but may also be optimized to facilitate rapid high-throughput screening. Typically between 0.1 and 1 hour will be sufficient. Excess reagent is generally removed or washed away. The second component is then added, and the presence or absence of the labeled component is followed, to indicate binding.

In one embodiment, the competitor is added first, followed by the candidate compound. Displacement of the competitor is an indication that the candidate compound is binding to the CT domain and thus is capable of binding to, and potentially modulating, the activity of the CT domain or ACC enzyme. In this embodiment, either component can be labeled. Thus, for example, if the competitor is labeled, the presence of label in the wash solution indicates displacement of the competitor by the candidate compound. Alternatively, if the candidate compound is labeled, the presence of the label on the support indicates displacement of the candidate compound.

In one embodiment, a potential ligand for a CT domain can be obtained by screening a recombinant bacteriophage library (Scott and Smith, *Science*, 249:386-390 (1990); Cwirla et al., *Proc. Natl. Acad. Sci.*, 87:6378-6382 (1990); Devlin et al., *Science*, 249:404-406 (1990). Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive CT domain (or portion thereof). After a specified incubation period, the filters can be thoroughly washed and developed for autoradiography. Plaques containing the phage that bind to the radioactive CT domain or portion thereof can then be identified. These phages can be further cloned and then retested for their ability to bind to the CT domain as before. Once the phages have been purified, the binding sequence contained within the phage can be determined by standard DNA sequencing techniques. Once the DNA sequence is known, synthetic peptides can be generated which represents these sequences, and further binding studies can be performed as discussed herein.

In another embodiment, a potential ligand for a CT domain can be obtained by screening a candidate compounds by NMR (see for example, U.S. Patent Application Publication No. US2003/0148297A1 or Pellecchia et al., *Nature Reviews Drug Discovery*, 1:211-219 (2002)). As mentioned, a CT domain or portions thereof can be immobilized to all types of solid supports. It is not needed that the binding be a covalent binding. It is only required that the target is kept immobilized in the NMR measuring environment. Moreover, the immobilization need not be directly to the solid support; it may also occur indirectly through suitable bridging moieties or molecules, or through spacers. Very suitable supports are solid polymers used in chromatography, such as polystyrene, sepharose and agarose resins and gels, e.g. in bead form or in a porous matrix form. Additionally, appropriately chemically modified silicon based materials are also very suitable supports.

Any soluble molecule can be used as a compound that is a candidate to binding to the CT domain. It is not necessary that the said soluble molecule is water-soluble. Any liquid medium that does not denature the said compound nor the CT domain molecule can be used in the NMR measurements. The CT domain target molecule is immobilized to a suitable support, such as a solid resin, and additionally placed in a suitable NMR probe, for example, a flow injection NMR probe, for the duration of the screening. Each sample of the compounds to be screened, e.g. the compounds from a library, is then applied to the immobilized target by pumping it through, along or via the solid support. The sample to be assayed may contain a single component suspected of binding to the CT domain target molecule, or may contain multiple components of a compound library or other type of collection or mixture. The flow may be stopped when a desired level of concentration of the compounds to be assayed is reached in the target containing probe or vessel.

For the acquisition of the NMR spectra, in principle any NMR pulse sequence capable of detecting resonances from dissolved molecule samples and, preferably suppressing residual solvent signals, such as by pulsed field gradients, may be used to detect binding. In practice, however, a one-dimensional 1H-NMR spectrum is acquired with sufficient resolution and sensitivity to detect and quantitate resonances derived from each compound being assayed in the presence of the control solid support. In addition, a second spectrum recorded using the same NMR protocol, is acquired for the same solution of screenable compounds in the presence of the solid support containing the immobilized CT domain target molecule. Optionally, a third spectrum may be acquired in the presence of the solid support containing the immobilized CT domain target molecule in order to detect extremely weak target binding. This spectrum can be recorded while using a diffusion or T2 filter.

After acquisition of the NMR spectrum, the sample of small compound or compounds is washed out of the NMR probe containing the target immobilized solid support. Subsequently, the next sample can be applied to the probe in a stopped-flow manner. Throughout the entire screening process a single sample of the target immobilized solid support remains in the NMR probe. The target immobilized solid support need only be changed should the target become denatured, chemically degraded or saturated by a tight-binding compound that cannot be washed away. In order to safeguard that certain compounds do not bind in such a way that the target molecule is blocked, at certain stages, a control is carried out to check the availability of binding opportunities to the target molecule.

The NMR spectra are preferably compared by subtracting one of the two NMR data sets from the other, thereby creating a difference spectrum. In general, since the target molecule is essentially in the solid phase, the resonances from compounds that bind to the target molecule are broadened beyond detection while in the bound state. Thus, binding is sensitively and reliably detectable by a decrease in height of peaks that derive exclusively from the solution form of compounds binding to the target molecule. This effect is most easily seen in the difference spectra. An alternative approach that can be used to quantitate the affinity of the target-ligand interaction is to determine peak areas (e.g. by integrating) in the control and experimental spectra and compare the values of these areas. Although it is possible to carry out the NMR screening method in batch mode, in the flow-injection set-up, one sample of target may be used to screen an entire library.

The present invention also encompasses antibodies that can specifically bind to the CT domain, including specific regions of the CT domain, such as binding sites. Antibodies include, for example, monoclonal antibodies and antibody fragments, such as Fab', Fab, F(ab')$_2$, single domain antibodies (DABs), Fv, and scFv (single chain Fv). The techniques for preparing and characterizing antibodies are well known in the art (see, for example, Antibodies: A Laboratory Manual, Cold Spring Harbor Laboratory, 1988). Monoclonal antibodies may be readily prepared through the use of well-known techniques, such as those exemplified in U.S. Pat. No. 4,196,265. Typically, this technique involves immunizing a suitable animal with a selected immunogen composition, e.g., a purified or partially purified ACC protein, ACC polypeptide, ACC peptide, CT domain or fragment thereof. The immunizing composition is administered in a manner effective to stimulate antibody-producing cells. These antibody-producing cells are then isolated and fused with tumor cells. The result of this cell fusion is a "hybridoma," which will continually produce antibodies. These antibodies are called monoclonal because they come from only one type of cell, the hybridoma cell; polyclonal antibodies, on the other hand, are derived from preparations containing many kinds of cells.

Assay Systems

Potential modulators of acetyl-CoA carboxylase activity, produced, for example, by rational drug design or by screening of libraries as described above, may be subjected to one of the following assays to confirm their activity.

After identifying candidate compounds that can bind to the CT domain, these candidate compounds are then tested to determine whether they can modulate ACC enzymatic activity. For example, the candidate compounds can be tested by using enzyme kinetic assays to test the effects of a candidate compound upon CT domain catalytic activity (see, Examples, FIGS. 7E and 7F, Kuchhait et al. 1974, *J. Biol. Chem.* 249: 6633-6645 (1974), and Harwood, H. J. et al., *J. Biol. Chem.* 278:37099-37111 (2003)). The CT domain can catalyze the decarboxylation of malonyl-CoA to produce acetyl-CoA in the presence of biotin methyl ester. Thus, the enzyme kinetic assays monitor the production of acetyl-CoA by coupling it to citrate synthase and malate dehydrogenase, which ultimately lead to the reduction of NAD$^+$.

A potential modulator may be subjected to virtual testing using a computer model of the CT domain of ACC or portions thereof, using the methods set forth for screening libraries of compounds. In other embodiments, a potential modulator may be evaluated for its ability to physically interact with the CT domain of an ACC or an ACC-related enzyme by co-crystallizing the potential modulator with the CT domain of the ACC or the ACC-related enzyme and then determining the structure of the resulting co-crystal. For example, the structure of the co-crystal may be determined by molecular replacement to assess the binding characteristics. The ability of the compound to modulate enzyme activity may be correlated with its ability to physically interact with the reactive site and/or to assume an orientation that would facilitate or inhibit carboxylation of malonyl.

In one specific example, a modulator may be determined to interact with the reactive site of the CT domain of yACC if, in a co-crystal of the modulator and yACC, the modulator contains an atom, (and in one embodiment, the atom is of functional group) within about 2-10 Å, 2-7 Å or within about 2.5-4 Å of an atom comprised in one or more of the following yACC amino acid residues (or corresponding amino acid residues for other ACCs): Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761, Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Try1970, Gly1971, Ser1972, Ile974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 and Leu2189 (residue numbering of SEQ ID NO:1). Co-crystallization with the CT domain of ACC2 and ACC1 can be accomplished in order to determine whether the modulator is selective for either ACC2 or ACC1.

The present invention further provides for assays comprising incubating the potential modulator with a purified CT domain of an ACC, such as yACC, mACC (ACC1 or ACC2)

or hACC (ACC 1 or ACC2), or a plant ACC, performing gel filtration to separate any free potential modulator from ACC-bound modulator, and determining the amount of acetyl carboxylation activity of the modulator-bound enzyme. To measure binding constants (e.g., $K_d$), methods known to those in the art may be employed such as Biacore™ analysis, isothermal titration calorimetry, fluorescence, ELISA with substrate on the plate to show competitive binding, or by a malonyl carboxylation activity assay. Similarly, the reaction rate may be measured by methods known in the art. In addition, relative binding affinities can be calculated, for example, to determine whether the modulator selectively binds ACC2 and not ACC1.

The present invention further provides for methods that determine the effect of a potential modulator in vivo. Such methods may provide important information, including the effect of the modulator on molecules involved in interrelated pathways may be determined. For example, a potential modulator may be administered to a cell, such as a liver cell, a fat cell, a heart cell, or a skeletal cell, that is capable of regulating fatty acid oxidation, and/or the biosynthesis of long-chain fatty acids, and then the level of one or more molecules involved in fatty oxidation, the Embden-Meyerhoff pathway, the Krebs cycle, mitochondrial electron transport, fatty acid synthesis, and gluconeogenesis, including insulin, glycogen, cholesterol, and ketone bodies, may be measured, and the success or failure of the potential modulator to achieve the desired effect may be determined. For example, a modulator intended to effect preferential metabolism of fats (for example, in the treatment of obesity) may have one or more of the following effects: an increase in the acetyl-CoA/CoA ratio; increased intermediates or products of fatty acid oxidation; decreased intermediates or products of the Embden-Meyerhoff pathway, including lactic acid or lactate; decreased intermediates and products of fatty acid synthesis; decreased glycogen stores, increased ATP production, decreased ATP consumption, and decreased insulin sensitivity. The foregoing in vivo assays may be performed in a cell in the context of a cell culture, a tissue explant, and/or an organism. Equivalent in vitro systems that duplicate one or more of the recited pathways may also be used to assay the modulator for desired activity.

Further in vivo systems include plant in vivo systems in which the modulators of the present invention are administered to plants, and in particular weeds, to determine whether the modulator is a potential herbicide. The ability to slow or inhibit plant growth indicates that the modulator is a candidate herbicide. Alternatively, a modulator may improve the growth of plants, in which case, the modulator may be useful as a fertilizer. The modulators may also be tested for their ability to selectively slow or inhibit unwanted plant growth, while having a lesser effect on the herbicide resistant plants of the present invention.

Mutant Acc Polynucleotides and Polypeptides

The amino acid sequences of the CT domains are highly conserved among the eukaryotic multi-functional ACCs (FIG. 1B and FIG. 4), and they share very limited homology to the two subunits of the bacterial ACCs (FIG. 1A). However, the CT domains do not share any recognizable sequence homology with other proteins in public databases. The carboxyltransferase (CT) domain contains about 800 residues (90 kD) (about residues 1429-2233 or residues 1476-2233 or residues 1484-2233 of SEQ ID NO:1, where SEQ ID NO:1 has the Genbank accession number Q00955), and constitutes approximately the C-terminal one-third of the eukaryotic, multi-domain ACCs. The amino acid sequences of this domain are highly conserved; for example, there is about 50% sequence identity between the CT domains of yeast ACC and mouse ACC2, human ACC1 and human ACC2 (see FIG. 4A-F). Further, when the degree of conservation is even higher when examining particular residues of the CT that are considered important in a structural sense. For example, Table G provides a list of residues that are important for substrate and modulator binding, and the degree of identity of these residues between yeast and mouse or human is greater than about 70%. Further, the present invention provides the crystal structures of the free enzyme and CoA complex of the CT domain of yeast ACC, as well as the crystal structures of the haloxyfop, diclofop and CP-640186 complexes. The structure contains two sub-domains, the N and C domains, and the active site is located at the interface of a dimer of the enzyme.

The present invention provides for isolated and purified CT domains of ACCs comprising at least one amino acid mutation. The present invention further provides for polynucleotides encoding these isolated and purified polypeptides. Such polypeptides preferably include a mutation in one or more amino acids selected from the group consisting of Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731, Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761, Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Try1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 and Leu2189 of yACC (residue numbering of SEQ ID NO:1) or the corresponding amino acid from any ACC or ACC-related enzyme. The corresponding amino acids may be determined by amino acid alignment methods known in the art and referenced herein above. For a review of sequence alignment methodology, see Phillips et al., 2000, *Mol Phylogenet Evol.* 16:317-330.

The mutant CT domain polypeptides of the present invention may comprise a deletion and/or mutation in one or more of the above-enumerated amino acids. As used herein, a mutation includes a deletion, a conserved amino acid change and/or non-conserved amino acid change. The polypeptides of the present invention may comprise all or a portion of the remaining amino acids of the CT domain of ACC. For example, the polypeptide may comprise one or more mutations in the above-enumerated amino acids. The polypeptide may further comprise additional deletions/additions/mutations, so long as the resultant polypeptide comprises one or more mutations in the above-enumerated amino acids and the resultant polypeptide has reduced or increased acetyl-CoA carboxylase activity as compared to the CT domain of wild-type ACC, wherein the reduction or increase in the activity is a direct result of the mutation in one or more of the above-enumerated amino acid residues.

The polynucleotides of the present invention which encode the mutated CT domain polypeptide can be made by any means known in the art. For example, PCR may be employed to generate a polynucleotide comprising codons which result in a mutation in one or more of the above-enumerated amino acid residues. Commercial kits are also available for producing mutants, such as QuikChange™ (Stratagene). In addition, site directed mutagenesis may be employed, as well as chemical synthesis. The skilled artisan is well versed in the methods available for producing the polynucleotides and polypeptides of the present invention.

The present invention further provides for vectors comprising the polynucleotides of the present invention, including expression vectors in which the polynucleotide is operably linked to expression control sequences. In one embodiment, the vector is suitable for expression in plants and/or suitable for creating a genetically modified plant, such as a plant in which the native CT domain of ACC is replaced by the mutated CT domain of ACC of the present invention or a plant in which the mutated CT domain of ACC of the present invention is overexpressed, as further described in the following section.

Herbicide Resistant Plants

The CT domain of ACC is also the site of action of two different classes of commercial herbicides (Gronwald, 1991, *Weed Science* 39:435-449; Devine and Shukla, 2000, *Crop Protection* 19:881-889; Zagnitko et al., 2001, *Proc. Natl. Acad. Sci. USA* 98:6617-6622; Delye et al., 2003, *Plant Physiol.* 132:1716-1723), as represented by haloxyfop and sethoxydim, respectively. See FIG. 5A. These compounds are potent inhibitors of ACCs from sensitive plants and kill them by shutting down fatty acid biosynthesis. This observation confirms that an inhibitor of the CT domain is sufficient to block the function of ACC, and establishes this domain as a valid target for the development of inhibitors against these enzymes, especially the human ACCs.

The present invention also provides for herbicide resistant plants. Such plants are resistant to herbicides which modulate the activity of the CT domain of ACC and ACC-related enzymes. An herbicide resistant plant made in accordance with the present invention has a mutation in one or more amino acids, possibly in or near the active site of the CT domain of ACC or an ACC-related enzyme. Such mutations reduce or inhibit the acetyl-CoA carboxylase activity of ACC and include mutations in one or more of the amino acids of the CT domains of plant ACCs and/or ACC-related enzymes which correspond to Met 1503, Lys 1592, Ile1593, Ser1595, Phe 1596, Asn 1624, Ser1625, Gly 1626, Ala1627, Arg1628, Ile1629, Gly1630, Met1631, Gly 1699, Gly1701, Glu1703, Cys 1704, Leu1705, Ser1708, Ala1712, Arg1731; Val1733, Gly1734, Ile1735, Gly 1736, Ala 1737, Tyr1738, Leu 1739, Arg 1741, Leu1742, Pro1753, Ile 1755, Leu1756, Thr1757, Gly1758, Ala1759, Pro1760, Ala1761, Ile1762, Asn1763, Lys1764, Met1765, Leu1766, Tyr1771, Asn1774, Ala1908, Pro1920, Gly1921, Gln1922, Val1923, Trp1924, His1925, Pro1926, Ser1928, Ala1929, Phe1930, Trp1953, Arg1954, Gly1955, Phe1956, Ser1957, Gly1958, Gly1959, Gln1960, Arg1961, Asp1962, Met1963, Phe1964, Asn1965, Glu1966, Val1967, Leu1968, Lys1969, Try1970, Gly1971, Ser1972, Ile1974, Val1975, Glu1994, Arg1996, Gly1997, Gly1998, Ser1999, Trp2000, Val2001, Val2002, Val2003, Arg2021, Gly2023, Val2024, Leu2025, Glu2026, Pro2027, Gln2028, Gly 2029, Met2030, Val2031, Gly2032, Ile2033, Lys2034, Arg2036, Asp2098, Val2108 and Leu2189 of yACC (residue numbering of SEQ ID NO:1). In a specific subset of the above residues, mutations reduce or inhibit the acetyl-CoA carboxylase activity of ACC and include mutations in one or more of the amino acids of the CT domains of plant ACCs and/or ACC-related enzymes which correspond to Phe1596, Ser1625, Gly1626, Ala1627, Arg1628, Ile1629, Cys1704, Leu1705, Ser1708, Ala1712, Val1733, Gly1734, Ile1735, Gly1736, Ala1737, Tyr1738, Leu1739, Arg1741, Leu1742, Ile1755, Leu1756, Thr1757, Val1923, Trp1924, His1925, Pro1926, Ser1928, Ala1929, Phe1930, Trp1953, Gly1955, Phe1956, Ser1957, Asn1965, Glu1966, Val1967, Leu1968, Lys1969, Tyr1970, Gly1971, Ser1972, Ile1974, Arg1996, Gly1997, Gly1998, Ser1999, Trp2000, Val2001, Val2002, Val2003, Gly2023, Val2024, Leu2025 (residue numbering of SEQ ID NO:1). A genetically modified herbicide resistant plant of the present invention may be made by any technique known in the art.

Prior to constructing a genetically modified plant, it may first be desirable to select a candidate polynucleotide encoding a mutant CT domain of an ACC polypeptide by determining whether it has reduced acetyl-CoA carboxylase activity.

Once a candidate polynucleotide encoding the mutant CT domain of an ACC polypeptide is selected, the genome of a target plant may be modified by incorporation of the polynucleotide. Modification includes providing a vector comprising the polynucleotide, insertion of the polynucleotide into the genome at any location, insertion of the polynucleotide into the endogenous ACC gene, replacement of all or part of the endogenous ACC gene with the polynucleotide.

To produce a herbicide resistant plant of the present invention shoot cultures of the target plant material may be employed as a starting material. Micropropagated shoot cultures may be generated by surface sterilizing young shoots from field grown juvenile and mature stage target plants in a sterilization medium, rinsing the sterilized shoots, and then exposing them to a multiplication or elongation medium. Suitable sterilization media, such as 0.01% mercuric chloride solution, are known, and repeated rinsing may be performed with sterile, distilled water. Alternatively, micropropagated shoot cultures may be obtained from forestry companies.

According to certain embodiments, in vitro micropropagated shoot cultures are grown for a period of from one week to several weeks, preferably three weeks, on a multiplication medium. The shoot cultures may preferably be transferred to a shoot elongation medium. The shoot elongation medium additionally comprises a plant growth promoter. Shoot cultures are preferably exposed to the shoot elongation medium for at least three weeks, more preferably for four to six weeks. Shoot cultures are preferably subcultured to fresh medium every two to four weeks, and are preferably transferred to fresh medium about two to three weeks before transformation. Shoots of the target plant material are preferably allowed to grow to a size of from 1 to 8 cm in length, more preferably from about 3 to 4 cm in length, before they are transformed to incorporate the desired polynucleotide encoding a mutant CT domain of an ACC polypeptide of the present invention.

The polynucleotide encoding the mutant CT domain of an ACC polypeptide of the invention may be transformed into the target plant material, by, for example, introducing a genetic construct, such as a vector, into the target plant. Genetic constructs introduced into the target plant material may comprise. The mutant CT domain of an ACC polypeptide encoded by the polynucleotide is preferably functional in the target plant.

According to one embodiment, the polynucleotide is incorporated into a vector which includes expression control sequences. A target plant may be transformed with more than one vector of the present invention, thereby expressing more than one mutant CT domain of an ACC polypeptide capable of modulating acetyl-CoA carboxylase activity. Similarly, a vector may be assembled containing more than one open reading frame coding for one or more mutant CT domains of ACC polypeptides of the present invention.

Polynucleotides include, but are not limited to, a polymeric collection of nucleotides and includes DNA and corresponding RNA molecules, both sense and anti-sense strands, and comprehends cDNA, genomic DNA and recombinant DNA, as well as wholly or partially synthesized polynucleotides. A polynucleotide may be an entire gene, or any portion thereof. All of the polynucleotides described herein are isolated and purified, as those ten-s are commonly used in the art.

The vector may further comprise expression control sequences, as indicated above, such as, a gene promoter sequence and a gene termination sequence operably linked to the polynucleotide to be transcribed. The gene promoter sequence is generally positioned at the 5' end of the polynucleotide to be transcribed, and is employed to initiate transcription of the polynucleotide. Promoter sequences are generally found in the 5' non-coding region of a gene but they may exist in introns or in the coding region. When the vector includes an open reading frame in a sense orientation, the gene promoter sequence also initiates translation of the open reading frame.

A variety of gene promoter sequences which may be usefully employed in the vectors of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of a polypeptide in all parts of the plant. Use of a tissue specific promoter will result in production of the desired RNA only in the tissue of interest. With vectors employing inducible gene promoter sequences, the rate of RNA polymerase binding and initiation may be modulated by external stimuli, such as light, heat, anaerobic stress, alteration in nutrient conditions and the like. Temporally regulated promoters may be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, are used. Other examples of gene promoters which may be usefully employed in the present invention include mannopine synthase (mas), octopine synthase (ocs) and those reviewed by Chua et al (*Science* 1989;244:174-181).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, gene terminator sequences may be those from the original ACC polypeptide gene, or from the target species being transformed.

The vectors of the present invention may also comprise a reporter gene or a selection marker that is effective in target plant cells to permit the detection of transformed cells containing the vector. Such reporter genes and selection markers, which are well known in the art, typically confer resistance to one or more toxins. A chimeric gene that expresses β-D-glucuronidase (GUS) in transformed plant tissues but not in bacterial cells is a preferred selection marker for use in methods of the present invention. The binary vector pKIWI 105, constructed as described by Janssen and Gardner, 1989, *Plant Molecular Biology* 14:61-72, is one such selection marker. Plant material expressing GUS is resistant to antibiotics such as kanamycin. Another suitable marker is the NPTII gene, whose expression results in resistance to kanamycin or hygromycin, antibiotics which are generally toxic to plant cells at a moderate concentration. Rogers et al., 1988, *Methods for Plant Molecular Biology*, Weissbach and Weissbach, eds., Academic Press Inc., San Diego, Calif. Alternatively, the presence of the desired polynucleotide encoding a mutant CT domain of an ACC polypeptide of the present invention in transformed cells may be determined by means of other techniques that are well known in the art, such as Southern and Western blots.

In another embodiment, nucleotide sequences including a non-coding region of a polynucleotide encoding for an endogenous ACC, or a nucleotide sequence complementary to such a non-coding region may be employed. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences of endogenous ACC. Transformation of a target plant with a vector comprising such non-coding sequences of an endogenous ACC may lead to a reduction in the amount of endogenous ACC synthesized by the plant by the process of cosuppression, in a manner similar to that discussed, for example, by Napoli et al. (*Plant Cell* 1990;2:279-290) and de Carvalho Niebel et al. (*Plant Cell* 1995;7:347-358).

The vectors of the present invention may be used to transform a variety of plants using the methods of the present invention, including monocotyledons (e.g. grasses, corn, grains, oat, wheat and barley), dicotyledons (e.g. *Arabidopsis*, tobacco, legumes, alfalfa, oaks, eucalyptus, maple), and Gymnosperms (e.g. Scots pine; Aronen, 1996, Finnish Forest Res. Papers, vol. 595), white spruce (Ellis et al, 1993, *Biotechnology* 11:94-92), larch (Huang et al., 1991, *In vitro Cell* 27:201-207).

Techniques for stably incorporating vectors into the genome of target plants are well known in the art and include *Agrobactenum*-mediated introduction, electroporation, protoplast fusion, injection into reproductive organs, injection into immature embryos, high velocity projectile introduction, and the like. The choice of technique will depend upon the target plant to be transformed. For example, dicotyledonous plants and certain monocots and gymnosperms may be transformed by *Agrobacterium Ti* plasmid technology as described, for example by Bevan (*Nucl. Acid Res.* 1984;12: 8711-8721). Targets for the introduction of the genetic constructs of the present invention include tissues, such as leaf tissue, disseminated cells, protoplasts, seeds, embryos, meristematic regions, cotyledons, hypocotyls, and the like. Target plant materials for transformation according to methods of the present invention include in vitro micropropagated shoot cultures prepared as described above.

Transfer of one or more vectors into target plant shoots may be accomplished using *Agrobacterium*-mediated transformation techniques. *Agrobacterium* strains are suitable and are commercially available. *Agrobacterium tumefaciens* strain AGL1 (*Bio-Technology* 1991;9:963-967) is available. Methods for transforming a population of the *Agrobacterium* strain with a vector are well known. The freeze thaw method described in An et al., 1988, *Plant Molecular Biology*

Manual, Dordrecht: Kluwer Academic Publishers, 1988, pp. A3/1-A3119, is one method for transforming the *Agrobacterium* culture with the vector of interest.

Colonies of *Agrobacterium* carrying the genetic construct of interest are prepared for inoculation of the target plant material according to known techniques. See e.g. U.S. Pat. No. 6,255,559. Mature shoots of the target plant material are selected for transformation. Stem segments from each node are excised. Stem segments from the second and third nodes are possible. All leaves are peeled from the stems, and additional wounding may be inflicted, for example, by light longitudinal cutting of both sides of the stem with a scalpel blade. The selected stem segments, preferably including the second and third nodes, are inoculated with the *Agrobacterium* culture prepared as described above.

Inoculation of stem segments with the *Agrobacterium* suspension takes place under conditions that optimize infection of the stem segments. Suitable techniques are well known. After incubation, excess suspension is removed and stem segments are transferred to a co-cultivation medium. Following the co-cultivation period, stem segments are removed from the medium and washed. Stem segments are cultured until adventitious buds are produced from the stem segments.

Putative transformed shoots are excised from the stem segments and transferred to growth medium which may include a selection agent, such as kanamycin. Transformed shoots are transferred to a suitable rooting medium known in the art. Rooting is accomplished in a period of from about two to four weeks and may involve an initial culture period in the dark to allow initial root development, followed by transfer to standard photoperiod conditions. During elongation and rooting, explants may be transferred to larger culture vessels. Rooted shoots, or plantlets, may be transferred to a growth medium and grown to mature, genetically modified plants. Genetically modified plants produced according to the methods disclosed herein may be reproduced, for example, using standard clonal propagation techniques such as axillary bud multiplication techniques. The genetically modified plants may then be tested for herbicide resistance by growing the plants in the presence of an herbicide. The polypeptide encoded by the polynucleotides of the present invention can be preselected for its inability to bind to and/or be inhibited by an herbicide compound of interest before the genetically modified plants of the present invention are prepared.

The following examples are representative of techniques employed by the inventors in carrying out aspects of the present invention. It should be appreciated that while these techniques are exemplary for the practice of the invention, those of skill in the art, in light of the present disclosure, will recognize that numerous modifications can be made without departing from the spirit and intended scope of the invention.

EXAMPLES

The examples described below are provided to illustrate the present invention and are not included for the purpose of limiting the invention.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

Example 1

Determination of the Crystal Structure of the CT Domain of Yeast ACC, Alone or Complexed with Acetyl CoA Materials and Methods Protein expression and purification. Various constructs comprising the CT domain of *S. cerevisiae* ACC were subcloned into the pET24d vector (Novagen) to produce the constructs listed in Table A, which were then over-expressed in *E. coli* incubated at 20° C. The soluble proteins that were produced were purified by nickel-agarose affinity and anion exchange chromatography. The proteins were concentrated to 10 mg/ml in a buffer containing 20 mM Tris (pH 7.0), 100 mM NaCl, 5% (v/v) glycerol, and 10 mM DTT. The samples were flash-frozen in liquid nitrogen and stored at −80° C. The C-terminal His-tag was not removed for crystallization. For the production of selenomethionyl proteins, the expression constructs were transformed into DL41 (DE3) cells. The bacterial growth was carried out in defined LeMaster media, and the proteins were purified using the same protocol as for the wild-type protein.

Protein Crystallization. Crystals of the proteins were obtained at 4° C. by the vapor diffusion method. The reservoir solution contained 100 mM NaCitrate (pH 5.5), 10% (w/v) PEG8000, and 5% (v/v) glycerol. The protein was at 7 mg/ml in a solution that also contained 1 mM acetyl-CoA. Microseeding was used to obtain crystals of sufficient size for data collection. Three different crystal forms were observed under this condition, and our structural analyses showed only very weak electron density for the acetyl-CoA. A fourth crystal form was obtained using the crystallization condition 100 mM Tris (pH 7.0), 13% (w/v) PEG8000 and 10% (v/v) glycerol. The protein was pre-incubated with 2 mM acetyl-CoA, and the binding of this compound to the enzyme was observed in the electron density map. The crystals were cryo-protected with the introduction of 25% (v/v) ethylene glycol and flash frozen in liquid propane.

Data Collection. X-ray diffraction data were collected on an ADSC CCD at the X4A beamline of Brookhaven National Laboratory. For initial structure determination, a seleno-methionyl single-wavelength anomalous diffraction (SAD) data set to 2.7 Å resolution was collected at 100K on a crystal grown at pH 5.5. Significant decay in the crystal diffraction quality precluded data collection at other wavelengths. The diffraction images were processed and scaled with the HKL package. See Otwinowski and Minor, 1997, *Meth. Enzymol.* 276:307-326. One crystal form (Form 1) of the CT domain encoded by SEQ ID NO:2 belongs to the space group C2, with unit cell dimensions of a=247 Å, b=125 Å, c=145 Å, and β=94°. There are three molecules in the asymmetric unit. Another crystal form (Form II) of the CT domain encoded by SEQ ID NO:2 belongs to the space group C2, with unit cell dimensions of a=255 Å, b=113 Å, c=135 Å, and β=101°. To determine the binding mode for acetyl-CoA, a native data set to 2.7 Å resolution was collected on a crystal grown at pH 7.

It belongs to space group P2₁, with cell dimensions of a= 92.9 Å, b=138.1 Å, c=101.4 Å, and β=114.40. There are two molecules in the asymmetric unit. The data processing statistics are summarized in Table C.

Structure determination and refinement. The locations of Se atoms were determined with the program SnB (Weeks and Miller, 1999, *J. Appl. Cryst.* 32:120-124) and further confirmed with SHELXS (Sheldrick, 1990, *Acta Cryst.* A46:467-473) based on the anomalous differences in the SAD data set. Reflection phases to 2.7 Å resolution were calculated and improved with the program SOLVE (Terwilliger and Berendzen, *Acta Cryst.* D55:849-861). The atomic model was built into the electron density with the program O (Jones et al., 1991, *Acta Cryst.* A47:110-119). The structure of the CoA complex was determined by the molecular replacement method with the program COMO (Jogl et al., 2001, *Acta Cryst.* D57:1127-1134). The structure refinement was carried out with the program CNS (Brunger et al., *Acta Cryst.* D54:905-921). The statistics on the structure refinement are summarized in Table C.

Enzyme kinetic assays. The CT domain can catalyze the decarboxylation of malonyl-CoA to produce acetyl-CoA in the presence of biotin methyl ester. The kinetic assays monitored the production of acetyl-CoA by coupling it to citrate synthase and malate dehydronase, which ultimately lead to the reduction of NAD⁺ (Guchhait et al., 1974, *J. Biol. Chem.* 9:6633-6645). Mutations in the active site were designed based on the structural information. The mutants were made with the QuikChange kit (Stratagene) and sequenced for confirmation. They were purified and assayed kinetically under the same condition as the wild-type protein. The kinetic parameters for each enzyme were obtained by non-linear least-squares fitting to the initial velocity data.

TABLE B

Constructs created and tested for production of proteins comprising the CT domain of yeast ACC

| Construct | 1st residue* | Last residue* | Induced | Soluble | Crystallized |
|---|---|---|---|---|---|
| 1 | 1476 | 2147 | − | NA† | NA |
| 2 (yCTACC) (SEQ ID NO: 2) | 1429 | 2233 | + | + | + |
| 3 | 1476 | 2233 | − | NA | NA |
| 4 | 1412 | 2041 | − | NA | NA |
| 5 | 1423 | 2041 | + | − | NA |
| 6 | 1435 | 2041 | − | NA | NA |
| 7 | 1441 | 2041 | + | − | NA |
| 8 | 1429 | 2041 | + | + | |
| 9 | 1412 | 2135 | + | − | NA |
| 10 | 1435 | 2135 | − | NA | NA |
| 11 | 1441 | 2135 | + | + | |
| 12 | 1429 | 2135 | − | NA | NA |
| 13 | 1493 | 2135 | + | − | NA |
| 14 | 1525 | 2233 | + | − | NA |
| 15 | 1452 | 2233 | + | − | NA |
| 16 | 1476 | 2135 | + | − | NA |
| 17 | 1476 | 2190 | + | + | |
| 18 | 1485 | 2135 | + | − | NA |
| 19 | 1493 | 2135 | + | − | NA |
| 20 | 1493 | 2190 | + | + | |
| 21 | 1476 | 2210 | + | + | |
| 22 | 1476 | 2233 | + | + | + |

TABLE B-continued

Constructs created and tested for production of proteins comprising the CT domain of yeast ACC

| Construct | 1st residue* | Last residue* | Induced | Soluble | Crystallized |
|---|---|---|---|---|---|
| (yCT2ACC) (SEQ ID NO: 3) | | | | | |
| 23 | 1493 | 2210 | + | + | |
| 24 | 1493 | 2233 | + | + | |

*Residue numbering based on GenBank Entry No. Q00955
†NA—Not applicable

TABLE C

Summary of crystallographic information

| Crystal | Free enzyme (see Table 1 for atomic coordinates) | CoA complex (see Table 2 for atomic coordinates) |
|---|---|---|
| Maximum resolution (Å) | 2.7 | 2.7 |
| Number of observations | 533,916 | 168,936 |
| $R_{merge}^1$ (%) | 7.6 (18.1) | 5.2 (11.6) |
| Resolution range for refinement | 30-2.7 Å | 30-2.7 Å |
| Number of reflections | 113,103 | 59,546 |
| Completeness (%) | 94.5 | 93.1 |
| R factor² (%) | 22.9 (35.4) | 22.7 (33.0) |
| free R factor (%) | 26.4 (40.4) | 27.9 (36.4) |
| rms deviation in bond lengths (Å) | 0.009 | 0.009 |
| rms deviation in bond angles (°) | 1.4 | 1.4 |

$$^1 R_{merge} = \sum_h \sum_i |I_{hi} - \langle I_h \rangle| \bigg/ \sum_h \sum_i I_{hi}$$

The numbers in parentheses are for the highest resolution shell.

$$^2 R = \sum_h |F_h^o - F_h^c| \bigg/ \sum_h F_h^o$$

Results

To obtain crystals for structural analysis, the CT domain of yeast ACC, which constitutes the 90 kD fragment at the C-terminus of the protein was expressed and purified. The CT domain of yeast ACC shares 50% sequence identity with those of human ACCs, and its structure is therefore a good model for the human enzymes. The structure of the free enzyme was determined at 2.7 Å resolution by the selenomethionyl single-wavelength anomalous diffraction (SAD) method (Table C) (Hendrickson, 1991, *Science* 254:51-58) and the atomic coordinates are shown in Table 1. The structure of CT in complex with CoA was determined at 2.7 Å resolution from a crystal grown in the presence of 2 mM acetyl-CoA (Table C) and the atomic coordinates are shown in Table 2.

Figure 2A:
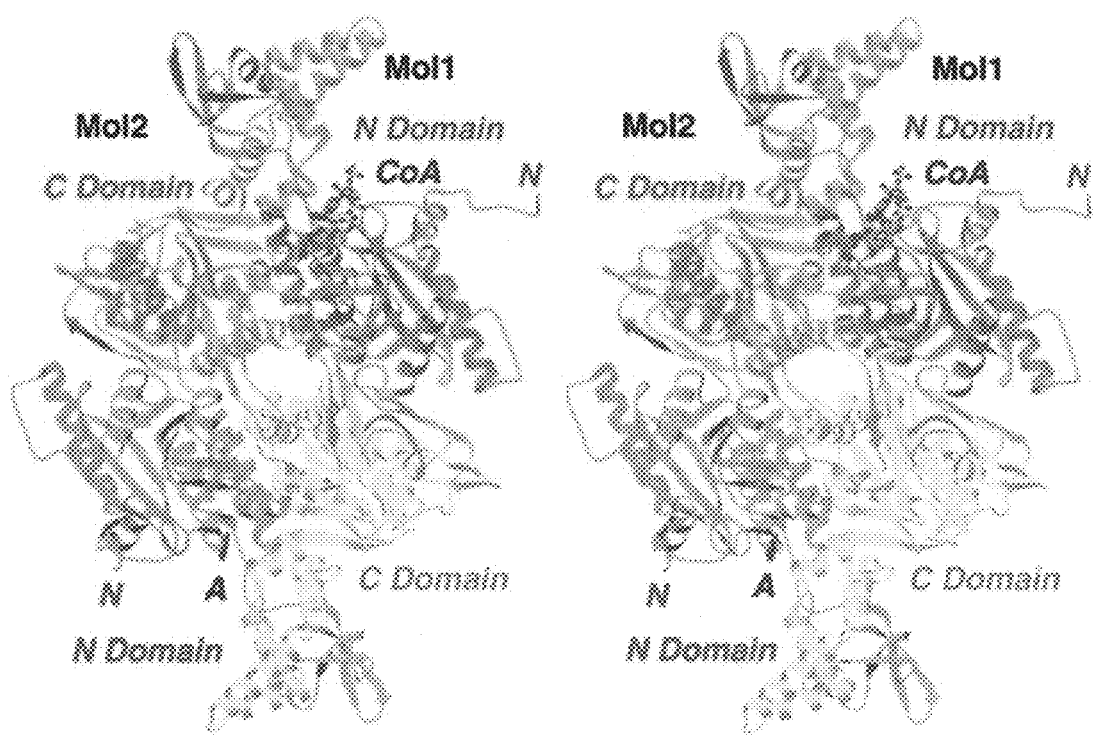
FIGS. 2A-2D. Structure of the CT domain.
Figure 2B:
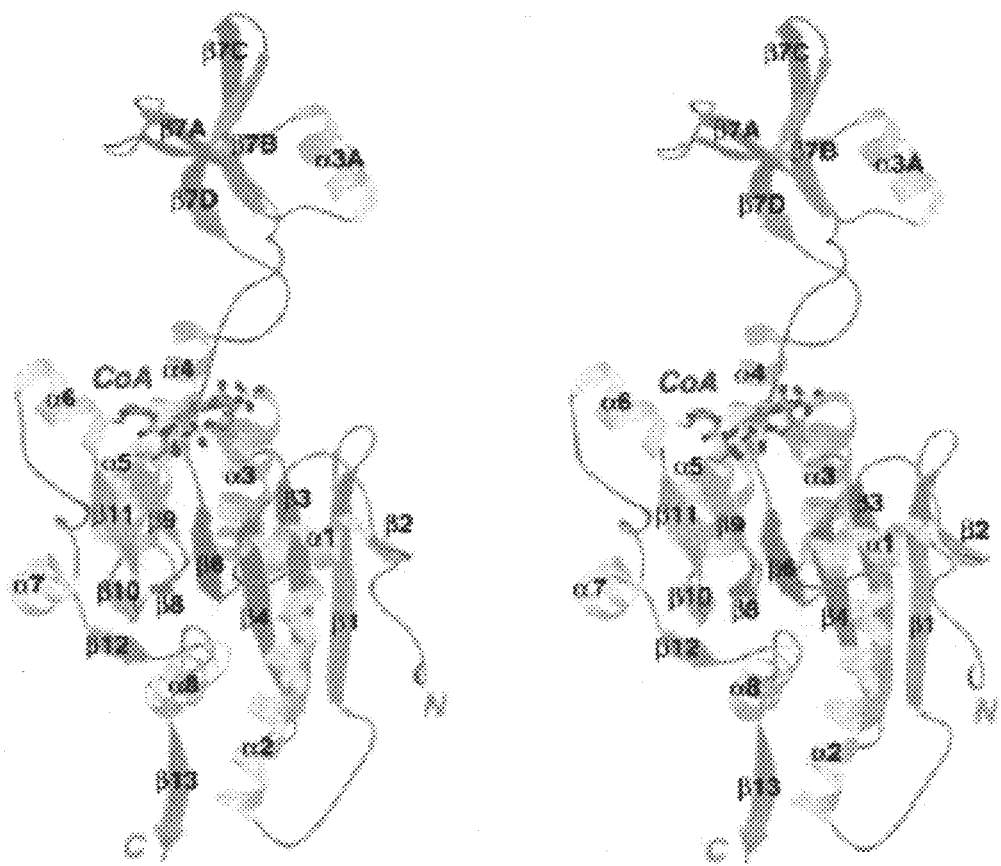
Figure 2C:
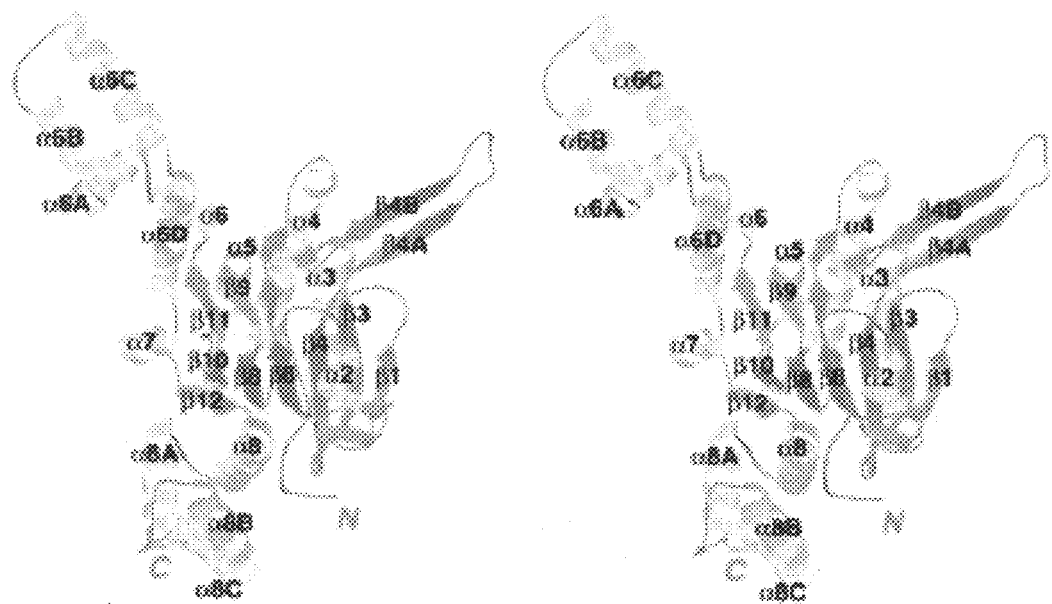

The crystal structures show that each CT domain molecule is made up of two sub-domains, which are intimately associated with each other (FIG. 2A). The N domain contains residues 1484-1824, in the N-terminal half of the CT (FIG. 2B), whereas the C domain contains residues 1825-2202, in the C-terminal half (FIG. 2C). In FIGS. 2A, 2B, and 2C, the schematics were generated with Ribbons (Carson, 1987, *J. Mol. Graphics* 5:103-106). This domain organization of CT is consistent with the fact that the N- and C-terminal halves show limited sequence homology to the β and α subunits of the bacterial CT, respectively (FIG. 1A). More than 50 residues at the N-terminus and 30 residues at the C-terminus (together with the His-tag) are disordered in the crystal of the CoA complex.

The N and C domains share similar polypeptide backbone folds, with a central β-β-α super-helix (FIGS. 2A, 2B). A total of 127 equivalent Cα atoms can be superimposed to within 2.5 Å of each other between the two domains, and the root-mean-squares (rms) distance for these atoms is 1.3 Å. However, the amino acid sequence identity among these structurally equivalent residues is only 12%, underscoring the lack of sequence conservation between the two domains. The backbone fold of the two domains is also similar to that of the crotonase/ClpP superfamily (FIG. 2D) (Benning et al. 1996, Biochem. 35:8103-8109; Engel et al., 1996, EMBO J. 15:5135-5145; Wang et al., 1997, Cell 91:447-456; Benning et al., 2000, Biochem. 39:4630-4639; Mursula et al., 2001, J. Mol. Biol. 309:845-853), even though the amino acid sequence identity between the domains in CT and these other proteins are less than 14%. Interestingly, crotonase and several other members of the family are acyl-CoA-dependent enzymes that catalyze various reactions for fatty-acid β-oxidation (Engel et al., 1996, EMBO J. 15:5135-5145; Benning et al., 2000, Biochem. 39:4630-4639; Mursula et al., 2001, J. Mol. Biol. 309:845-853; Cronan, Jr. and Waldrop, 2002, Prog. Lipid Res. 41:407-435). Despite the similarity in their backbone folds, however, there are significant differences in the oligomerization state and the composition of the active site between CT and other crotonase family members (see below). In addition, the domains in CT contain significant insertions to the crotonase/Clp fold (FIGS. 2B-D), and some of these inserted segments are important for the oligomerization of the enzyme (FIG. 2A).

A dimer of the CT domain is observed in all the structures of the present invention (FIG. 2A), and the organization of this dimer is essentially the same in these different structures. About 5300 Å² of the surface area of each monomer is buried in the dimer interface, involving mostly residues that are highly conserved among the ACCs (FIG. 2B). This suggests that the observed dimer should be a stable and conserved oligomerization state of the domain, in agreement with gel-filtration and light-scattering studies performed in solution as well as the $\alpha_2\beta_2$ stoichiometry of the bacterial CT subunits (Cronan, Jr. and Waldrop, 2002, Prog. Lipid Res. 41:407-435). The dimer is formed by the side-to-side arrangement of the two monomers, such that the N domain of one molecule is placed next to the C domain of the other (FIG. 2A). The α6A-α6D insertion in the C domain of one monomer (FIG. 2C) is inter-digitated between the β7A-β7D insertion (FIG. 2B) and the core of the N domain of the other monomer (FIG. 2A). The insertion between β4 and β5 of the C domain (FIG. 2C) also contributes to the formation of the dimer.

Figure 1B:
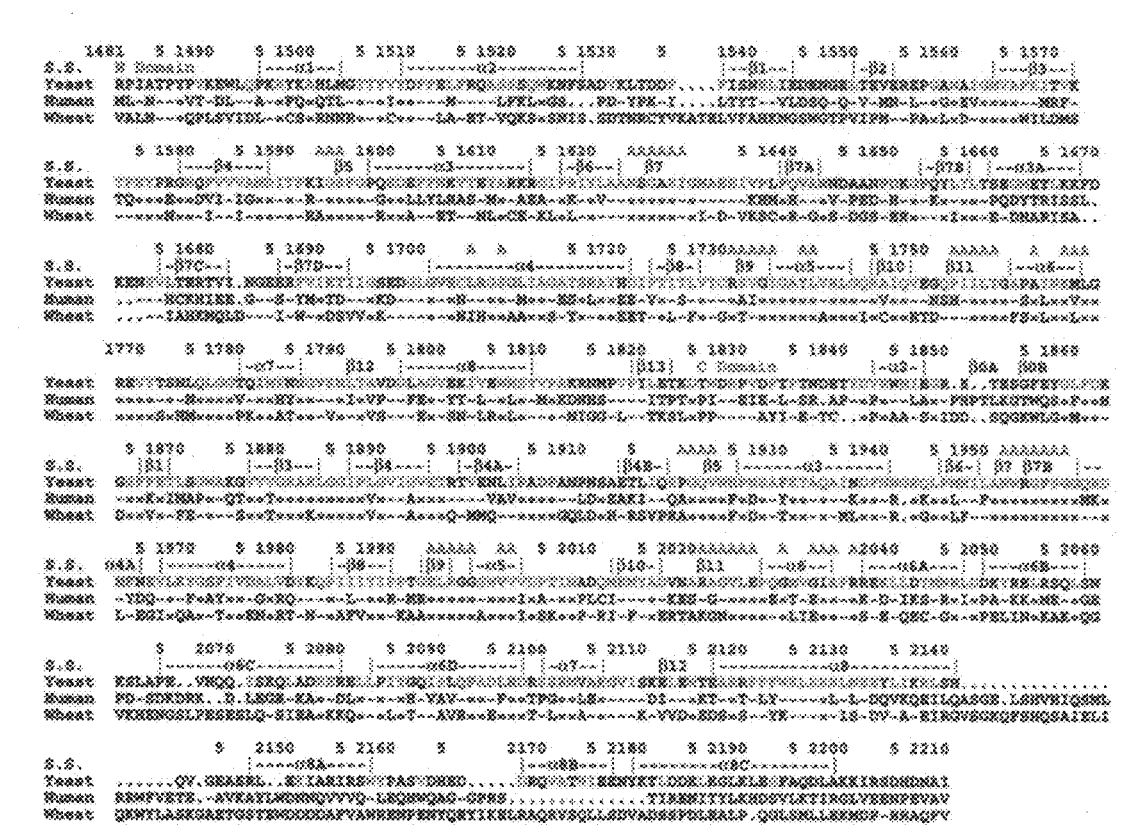

The structure of the CoA complex of the present invention, at 2.7 Å resolution, revealed that the active site of the enzyme is located at the interface of the dimer and with mostly equal contribution from the N and C domains of the two monomers (FIGS. 2A, 3A). This is in sharp contrast to other members of the crotonase family where the active site is either located within the monomer or has only small contributions from another monomer, and where the enzyme is generally a trimer or hexamer (dimer of trimers). Engel et al., 1996, EMBO J. 15:5135-5145; Benning et al., 2000, Biochem. 39:4630-4639; Mursula et al., 2001, J. Mol. Biol. 309:845-853. In the structures of the present invention, the active site is located in a cavity between the small β-sheets (with strands β5, β7, β9 and β11) of the β-β-α super-helix of the two domains (FIG. 3A). Above these two β-sheets, the α6 helices of the two domains form two walls, providing additional binding surfaces for the CoA and biotin substrates as well as restricting their directions of approach (FIGS. 3A, 3B). FIG. 3A was produced with Ribbons (Carson, 1987, J. Mol. Graphics 5:103-106), and FIG. 3B was produced with GRASP (Nicholls et al., 1991, Proteins 11:281-296). Residues in this active site are generally well conserved among the various CT domains (FIG. 1B). FIG. 4 is a sequence alignment of ACC from different species showing that the amino acids in or near the active site are conserved.

The CoA molecule is mostly associated with the N domain of one molecule in the dimer (FIG. 3A). The N1 and N6 atoms of the adenine base are recognized by hydrogen-bonds with the main chain of residues immediately after β7 in the N domain (FIG. 3A). The phosphate groups of CoA are located near the side chains of Arg1731, Lys2034' and Arg2036' (the primed residue numbers indicate the second monomer). The pantotheine arm lies on the surface of the small β-sheet in the N domain, and the thiol group is placed in the cavity between the two domains (FIG. 3A). Although acetyl-CoA was used in the crystallization, there was no electron density for the acetyl group, and only the CoA molecule is included in the current atomic model. In the other active site of the dimer, only the electron density for the adenine base of the coenzyme was observed (FIG. 2A).

Based on the structures of the present invention, it is likely that the biotin substrate is mostly associated with the small β-sheet in the C domain of the other monomer in the active site (FIG. 3A). This is partly supported by observations with the E. coli biotin ligase/repressor BirA, where the biotin molecule is bound on the surface of a β-sheet. Weaver et al., 2001, Protein Sci 10:2618-2622. Therefore, two domains with similar backbone folds are used to recognize completely different chemical entities in CT.

There are only minor changes in the conformation of the core of the monomer or the organization of the dimer when CoA is bound to the enzyme. The RMS distance between 1200 equivalent Cα atoms of the dimers of the free enzyme and CoA complex is 0.4 Å. Residues in α6B-α6C (2046-2080) of the C domain are disordered in the free enzyme structure, but this is most likely due to differences in crystal packing interactions between the two crystals.

To characterize the functional roles of the conserved residues in the active site, many of them were mutated and the kinetic parameters of the mutants for the reverse reaction, which transfers the carboxyl group of malonyl-CoA to biotin (Table D) were determined. The largest effect on the catalytic activity was observed with the mutation of the Arg1954 residue, in the C domain (FIG. 3A), which lead to a 75-fold increase in the $K_m$ for malonyl-CoA and a 300-fold decrease in the overall $k_{cat}/K_m$ of the enzyme (Table D). Based on the structures of the invention, it is likely that this residue is important for recognizing the carboxyl group of malonyl-CoA, and this is also consistent with the hypothesis that the biotin substrate may be mostly associated with the C domain. Of the charged side chains that interact with the phosphate groups of CoA, mutation of Arg1731 gave rise to a 14-fold increase in the $K_m$ for malonyl-CoA (Table D), consistent with the structural observations. On the other hand, mutation of Arg2036 had minimal effects on the enzyme catalysis.

TABLE D

Kinetic parameters of wild-type and mutant CT

| Enzyme | $V_{max}$* ($\times 10^{-5}$ AU/s) | $K_m$ (µM) (for malonyl-CoA) | $V_{max}/K_m$ |
|---|---|---|---|
| Wild-type | 148 ± 3 | 67 ± 5 | 2.2 ± 0.1 |
| L1705I | 12 ± 0.3 | 1342 ± 180 | 0.009 ± 0.001 |
| R1731S | 385 ± 10 | 909 ± 72 | 0.42 ± 0.02 |
| Y1738F | 152 ± 3 | 53 ± 6 | 2.9 ± 0.3 |
| R1954S | 39 ± 6 | 5100 ± 1200 | 0.0076 ± 0.0008 |
| E1994Q | 272 ± 3 | 109 ± 5 | 2.5 ± 0.1 |
| E2026Q | 144 ± 6 | 218 ± 24 | 0.66 ± 0.05 |
| R2036E | 133 ± 3 | 41 ± 4 | 3.3 ± 0.3 |

*All reactions contain 2.5 µM of the enzyme.

Figure 2D:
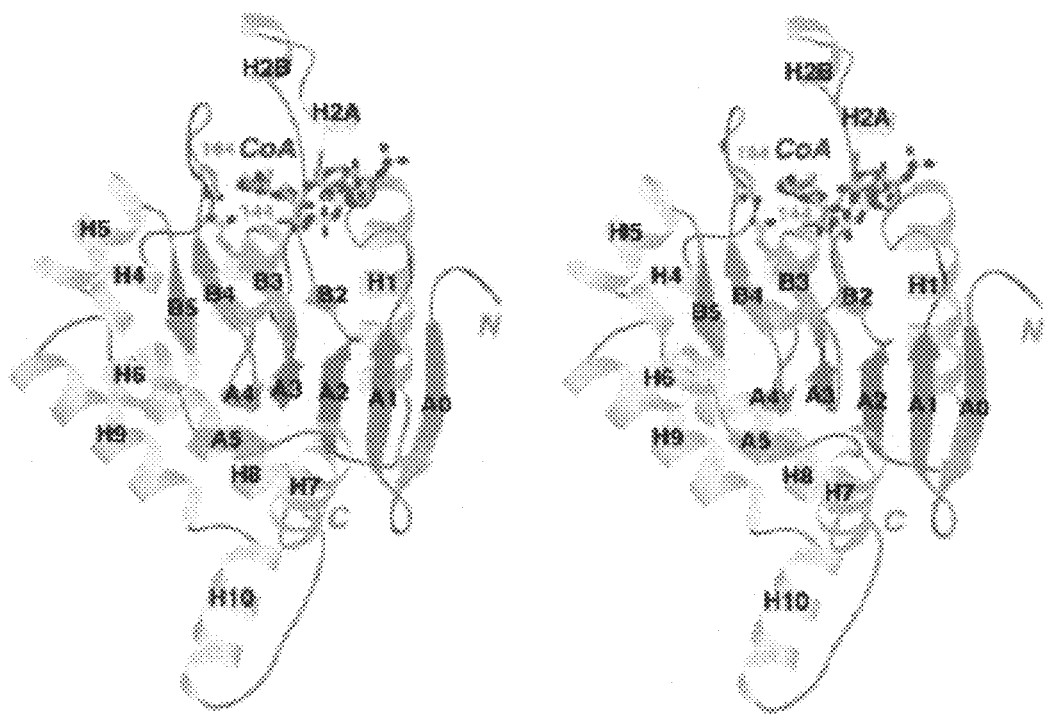

The results of the structure-based mutagenesis experiments of the invention also help to clarify the catalytic mechanism of this enzyme. A general base is needed to extract the proton from the acetyl group of acetyl-CoA to initiate the carboxylation reaction. Kinetic and chemical modification studies of *E. coli* CT have suggested that a cysteine residue may serve this function. Cronan, Jr. and Waldrop, 2002, *Prog. Lipid Res.* 41:407-435. However, the structures of the invention do not show a cysteine residue in the active site (FIG. 3A). In addition, those residues in the active site that could function as a general base (Tyr1738, Glu1994, Glu2026) were mutated, and kinetic studies were performed which showed that these residues are not required for the catalysis (Table D). Therefore, the structural and mutagenesis studies support the catalytic mechanism where the N1 atom of biotin itself functions as the general base. Knowles, 1989, *Ann. Rev. Biochem.* 58:195-221. This is in strong contrast to the crotonases where an acidic side chain of the enzyme is required for catalysis (FIG. 2D).

Example 2

Molecular Basis for the Inhibition of the CT Domain of ACC

Obesity is associated with a variety of serious human diseases, especially type 2 diabetes, cardiovascular diseases, depression, and cancer. There is clearly a critical need for therapeutic agents that can regulate body weight and obesity. Acetyl-coenzyme A carboxylases (ACCs) are crucial for the metabolism of longchain fatty acids. They catalyze the production of malonyl-CoA from acetyl-CoA and $CO_2$, a reaction that also requires the hydrolysis of ATP. Two isoforms of this enzyme have been identified in mammals. ACC1, a cytosolic enzyme, catalyzes the first and the committed step in the biosynthesis of long-chain fatty acids. In comparison, ACC2 is associated with the mitochondrial membrane and its malonyl-CoA product potently inhibits the shuttle that transports longchain acyl-CoAs from the cytosol to the mitochondria for oxidation. Mice lacking ACC2 have elevated fatty acid oxidation and reduced body fat and body weight, establishing ACC2 as a target for anti-obesity, anti-diabetes, cardiovascular, metabolic and anti-infection agents.

The CT domain is the site of action of two different classes of widely-used commercial herbicides, as represented by haloxyfop (FOPs) and sethoxydim (DIMs) (FIG. 5A). These compounds are potent inhibitors of ACCs from sensitive plants and kill them by shutting down fatty acid biosynthesis. This confirms that an inhibitor of the CT domain is sufficient to block the function of ACC, and establishes this domain as a valid target for the development of inhibitors against these enzymes, especially the human ACCs.

However, the molecular mechanism for the inhibitory action of the herbicides was previously not known. Until recently, the herbicides were the only known potent inhibitors of the CT domain.

The present invention provides the crystal structures of the CT domain of yeast ACC in complex with two different FOP inhibitors, haloxyfop and diclofop, at up to 2.5 Å resolution. These are the first structures of inhibitor complexes of any CT domains. They demonstrate that the herbicides are active site inhibitors of the CT domain, and are located at the interface of the dimer. Surprisingly, a large conformational change in the active site of the enzyme is required for the binding of these compounds. Most of the residues in this binding site are strictly conserved among the various CT domains. Therefore, this binding site likely exists in the other CT domains as well, and the herbicides are expected to share a similar binding mode to these domains, especially those from human ACCs.

The crystal structure of the CT domain of yeast ACC in complex with haloxyfop has been determined at 2.8 Å resolution (Table E). The enzyme:inhibitor complex was prepared by soaking pre-formed free-enzyme crystals of the CT domain with the inhibitor. The crystals were very sensitive to the herbicide, and most soaking experiments destroyed the diffraction of the crystal. The current diffraction data set was collected on a crystal that had been soaked for 1 hour in a solution containing 1 mM haloxyfop. Prior kinetic experiments showed that haloxyfop has a $K_i$ of about 0.5 mM against this CT domain. Nonetheless, the crystallographic analysis clearly revealed the presence of haloxyfop in the structure, with well-defined electron density (FIG. 5B).

To assess whether there are conformational changes in the enzyme upon inhibitor binding, the structure at 2.5 Å resolution of the free enzyme of the CT domain was determined (Table E). The free enzyme structure in Example 1 was based on a crystal that was grown in the presence of acetyl-CoA (Zhang et al., 2003). For the current structure, acetyl-CoA was not included in the crystallization solution. In addition, a new expression construct (yCT2ACC; SEQ ID NO:3) to prepare the protein samples for this crystal. This construct covers residues 1476-2233 of yeast ACC, removing about 50 residues at the N terminus (1429-1475) that were found to be completely disordered in the earlier structure (Zhang et al., 2003). This new protein sample readily produces large crystals of the CT domain.

The enzyme:diclofop complex was prepared by co-crystallization, using the new CT domain protein sample covering residues 1476-2233. These co-crystals are in a different crystal form compared to the crystals of the free enzyme and the haloxyfop complex, and the structure was determined by the molecular replacement method (Jogl, G., et al. (2001). COMO: A program for combined molecular replacement. *Acta Cryst.* D57, 1127-1134.) (Fable E).

Binding mode of haloxyfop. The haloxyfop herbicide is bound in the active site, at the interface between the two monomers of the dimer (FIG. 1D). Structural comparison with the CoA complex in Example 1 shows that the haloxyfop molecule in the active site will disrupt the binding of the acetyl- and malonyl-CoA substrates for catalysis (FIG. 5C, and see FIG. 7A for a detailed view), consistent with the kinetic observations suggesting that haloxyfop is a competitive inhibitor with respect to malonyl-CoA (Zhang et al., 2003). Previous studies with wheat ACC showed that the herbicides are nearly competitive with respect to the substrate acetyl-CoA (Rendina et al., 1990).

Haloxyfop is located in a groove between the N domain of one monomer and the C domain of the other monomer (FIG. 6A). The pyridyl ring of haloxyfop is sandwiched between the side chains of Tyr1738 and Phe1956' (primed residue numbers indicate the C domain of the other monomer), showing π-π interactions (FIG. 6B). The chloro substituent on this ring is pointed towards the side chains of Leu1756 and Leu1968', although the chlorine atom has relatively weaker electron density based on the crystallographic analysis (FIG. 5B). The trifluoromethyl group is positioned over the plane of the Trp1924' side chain. It also has interactions with the side chains of Val1967', Ile1974', and Val2002'. The ring nitrogen of the pyridyl group and the two ether oxygen atoms of the inhibitor are not involved in hydrogen-bonding interactions with the enzyme. The phenyl ring in the center of the inhibitor is situated between the amide bonds linking residues Gly1734 to Ile1735, and Gly1997' to Gly1998' (FIG. 6B). For the carboxylate group of the inhibitor, one of its oxygen atoms is hydrogen-bonded to the main-chain amides of Ala1627 and Ile1735 (FIG. 6B), whereas the other oxygen atom is exposed to the solvent. The negative charge on the carboxylate is not formally balanced by a positively-charged side chain of the enzyme. The methyl group of the propionate has van der Waals interactions with the side chains of Ala1627 and Leu1705.

The structure of haloxyfop as modeled into the electron density is the R stereoisomer (FIG. 6A), in agreement with results from earlier kinetic studies (Gronwald, J. W. (1991). Lipid biosynthesis inhibitors. *Weed Science* 39, 435-449; Rendina, A. R., et al. (1990) Inhibition of acetyl-coenzyme A carboxylase by two classes of grass-selective herbicides. *J Agric Food Chem* 38, 1282-1287). The S stereoisomer cannot assume this binding mode as the methyl group would clash with one of the carboxylate oxygens (FIG. 6A), indicating the molecular mechanism for the stereoselectivity of the CT domain for this class of compounds.

Figure 7A:
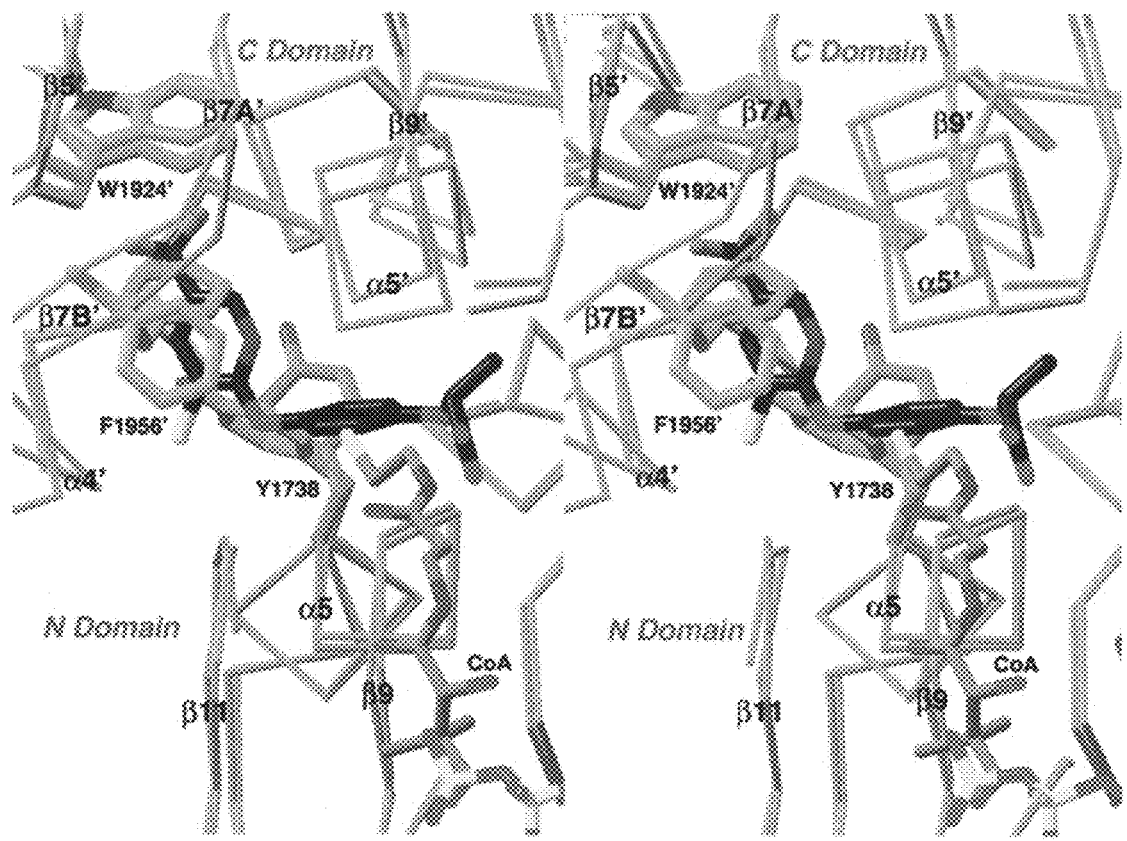

The binding mode of haloxyfop can also explain earlier observations that the CoA ester of this herbicide is a more potent inhibitor of ACC. The CoA molecule could be linked to haloxyfop, as the thiol group of CoA is located close to the carboxylic oxygen that is exposed to the solvent (FIG. 7A). A conformational change for the pantotheine portion of the CoA molecule is needed to form the covalent link to haloxyfop, but the adenine nucleotide portion of CoA should be able to maintain its interaction with the enzyme (Zhang et al., 2003). The establishment of these additional interactions is likely the basis for the enhanced potency of the CoA ester of haloxyfop.

Figure 7B:
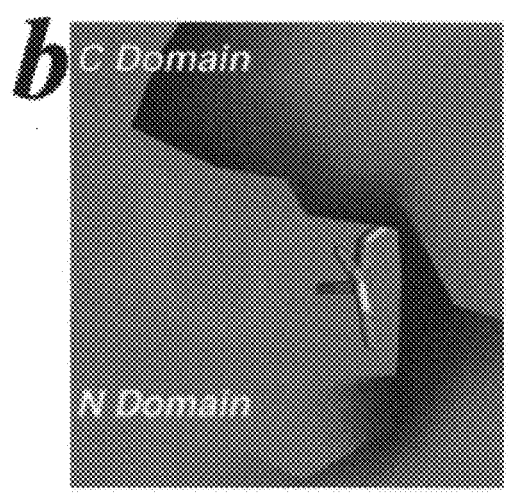
Figure 7C:
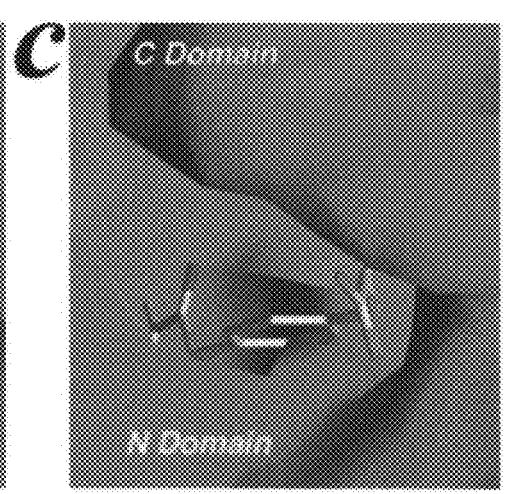
Figure 7E:
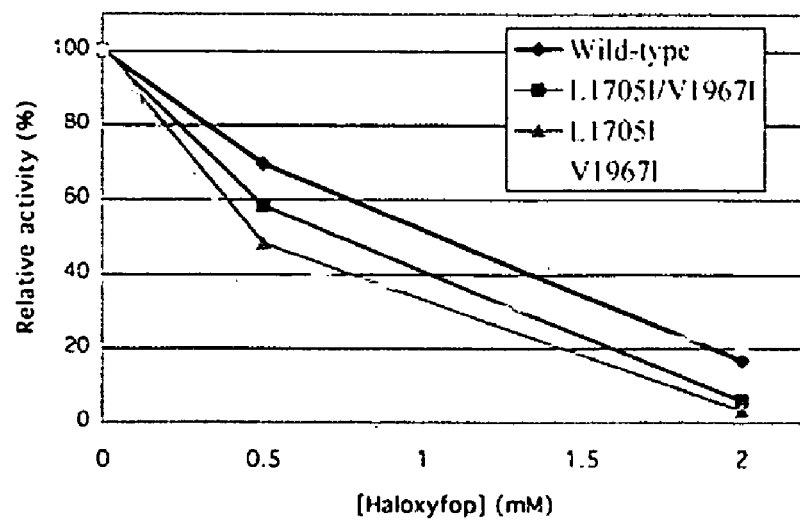
Figure 7F:
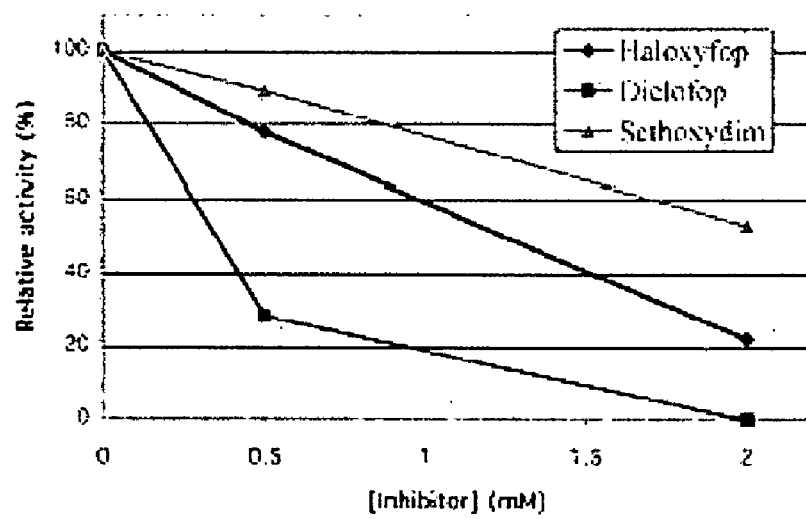

Large conformational changes in the enzyme for haloxyfop binding. Unexpectedly, significant conformational changes in the active site of the enzyme are needed for inhibitor binding. Most importantly, the side chains of Tyr1738 and Phe1956' assume new positions in the inhibitor complex to become 1-stacked with the pyridyl ring of haloxyfop (FIG. 7A). These two side chains help cover the hydrophobic core of the dimer interface in the free enzyme and the CoA complex. Their positions in the free enzyme actually clash with the bound conformation of haloxyfop (FIG. 7A), and the inhibitor binding pocket does not exist in the free enzyme (FIG. 7B). With the conformational changes for these and other residues in the active site, a binding pocket is revealed on the surface of the CT domain and the trifluoro-pyridyl group of the inhibitor is inserted deep into the hydrophobic core of the dimer (FIG. 7C). It is unlikely that this hydrophobic pocket is used by the substrates (acetyl-CoA or biotin) during the catalysis by the enzyme (FIG. 7A).

Extensive structural changes are observed near the Phe1956' residue (FIG. 7A), even though residues 1952'-1959' are highly conserved among the CT domains (FIG. 7D). The side chain rotates by about 120° around its $\chi 1$ torsion angle. Moreover, the main chain also moves, by about 2 Å, such that the side chain does not clash with the inhibitor (FIG. 7A). This triggers a conformational change for an entire segment of the CT domain, residues 1955'-1967' (FIG. 7A). Several residues in this segment (1959'-1964') have no electron density and are likely disordered in the current structure. This region corresponds to the α4A helix in the free enzyme structure, and is weakly conserved among the CT domains (FIG. 7D). This helix is probably unwound in the inhibitor complex.

In comparison, the conformational change for Tyr1738 is mostly limited to its side chain (FIG. 7A), which rotates by about 70° around the $\chi 1$ and $\chi 2$ torsion angles. It interacts with the side chains of Ala1712, Leu1742 and Val1975' in its new position, and its hydroxyl group forms a hydrogen-bond with the main chain carbonyl oxygen of Gly1971'.

Inhibitor binding at the dimer interface also causes a change in the organization of the dimer (FIG. 7A). With one monomer of the dimer in superposition, a rotation of about 2.5° is needed to bring the second monomer into overlap. The conformational changes in the monomer, and especially the change in dimer organization, may explain the detrimental effects of inhibitor binding on the diffraction quality of the crystals in the soaking experiments.

Diclofop has a similar binding mode. The binding mode of the herbicide as well as the conformational changes in the monomer and dimer of the CT domain are confirmed by the structure of the complex with diclofop (FIG. 5A), at 2.5 Å resolution (Table E). This complex was produced by cocrystallization, and the crystals are in a different space group as compared to the free enzyme and the haloxyfop complex. Nonetheless, the structure of the diclofop complex is essentially the same as that of the haloxyfop complex. This confirms that the structural changes observed for the haloxyfop complex is unlikely biased by crystal packing interactions.

The carboxyl groups of the two inhibitors essentially have the same binding mode (FIG. 6C). The aromatic rings of diclofop show small but recognizable differences in their positions as compared to those of haloxyfop, but the two chloro substituents in diclofop superimpose well with the substituents in haloxyfop (FIG. 6C). For the enzyme, the Phe1956' side chain has a different conformation, which may be linked to the change in the position of the inhibitor (FIG. 6C). On the other hand, the Tyr1738 side chains show little structural differences, and the other residues in the binding site have essentially the same conformation in the two complexes. The α4A helix is disordered in the co-crystals with diclofop as well. Moreover, the dimer organization in the diclofop complex is the same as the haloxyfop complex, as it also has the 2.5° rotation of the second monomer relative to the first monomer.

This binding pocket is likely present in most CT domains. Most of the residues that interact with the herbicides are either strictly or highly conserved among all the CT domains (FIG. 1B, FIG. 4, FIG. 7D; and alignments with SEQ ID NO:1 or 2 with GenBank Nos. BAA11238; T30568; P32874; S60200; AAK16499; T30568; AAL02056; T02235; AAA81579; T09538; BAA07012; CAA54683; NP_776649; CAA56352; NP_071529; AAP94122; A29924; NP_446374; XP_132282; CAE01471; NP_610342; and NP_493922). Therefore, it may be expected that this binding site also exists in most other CT domains, and that haloxyfop, diclofop and other FOPs can share a similar binding mode to these domains. Structures of the herbicide complexes of the yeast CT domain should be directly relevant for the design and optimization of inhibitors against the human ACCs.

The formation of this binding site requires conformational variability for several residues in the active site of the enzyme (FIG. 7A). The structure of the CT domain as observed here in the inhibitor complex is unlikely to be stable on its own, because of the significant exposure of the hydrophobic core of the dimer. Factors that regulate the conformational dynamics of residues in this region may affect the inhibitor sensitivity of the CT domain. This could be one mechanism for the herbicide resistance mutations that have been observed against the plant ACCs (see below).

Residues that confer resistance to herbicides are in the binding pocket. Only two residues in the binding site show appreciable variation among the different CT domains, Leu1705 and Val1967' (FIG. 7D). Remarkably, it is exactly the variation/mutation of these two residues that can confer resistance to the herbicides in plants. The residue that is equivalent to Leu1705 in the CT domains of wheat and other sensitive ACCs is Ile, and the Ile to Leu mutation, a subtle change in the side chain of this residue, renders the enzyme resistant to both haloxyfop and sethoxydim. The residue that is equivalent to Val1967 in sensitive plants is Ile, and the Ile to Asn mutation makes the plants resistant to the FOPs, but not the DIMs. The Ile to Val mutation may also confer resistance to haloxyfop, although it does not affect the sensitivity to clodinafop. The structural information herein would predict that there may be natural mutations in the other residues in this binding pocket (FIG. 6A) that can confer resistance to the herbicides, even though these residues are highly conserved.

To assess whether mutations of the Leu1705 and Val 967 residues have similar effects on inhibitor sensitivity by the yeast CT domain, we created the L1705UV1967I double mutant as well as the L1705I and V1967I single mutants of this domain. These mutants are still dimeric in solution based on light scattering experiments. Kinetic studies show, however, that the single and double mutations have only minimal effects on the sensitivity of the CT domain to haloxyfop (FIG. 7E), with $K_i$ remaining in the 0.5 mM range. Interestingly, the $IC_{50}$ values of herbicides against resistant plant ACCs are also in the 0.1 to 0.5 mM range. At the same time, the L1705I and V1967I mutants generally have 50-fold or more reduction in catalytic activity as compared to the wild-type CT domain, with roughly a 10- to 20-fold increase in the $K_m$ for the malonyl-CoA substrate.

These experiments demonstrate that the Leu1705 and Val1967 residues do not have a major contribution to herbicide sensitivity by the yeast CT domain. In the structure of the complex, these two residues make mostly peripheral contacts with the inhibitor (FIG. 6A), consistent with the kinetic observations. The apicoplast ACC enzyme from the parasite *Toxoplasma gondii* has a Leu residue at position 1705 (FIG. 7D), but it is still sensitive to the FOPs, although insensitive to the DIMs.

Figure 8A:
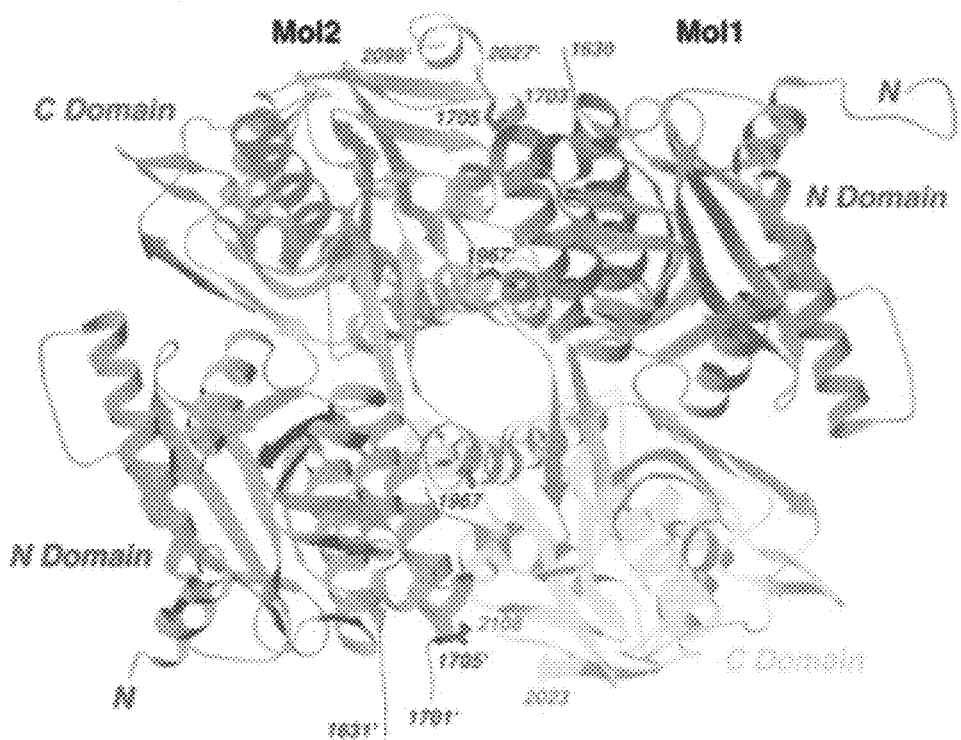
FIGS. 8A-8C. Structure of the L1705I/V1967I double mutant.

Large segments of the CT domain are disordered in the L1705I/V1967I double mutant. To reveal the impact of the mutations on the conformation of the CT domain, the crystal structure of the L1705I/V1967I double mutant at 2.6 Å resolution was determined (Table E). Surprisingly, a significant portion of the mutant structure, residues 1632-1702 (β7A-β7D insertion in the N domain) and 2026-2099 (α6 and α6A-α6D insertion in the C domain), are disordered, even though the mutant crystal is isomorphous to the wild-type crystal. These two inserted segments have intimate contacts with each other in the wild-type dimer interface (Zhang et al., 2003) (FIG. 5C), which are now missing in the mutant dimer (FIG. 8A).

Figure 8B:
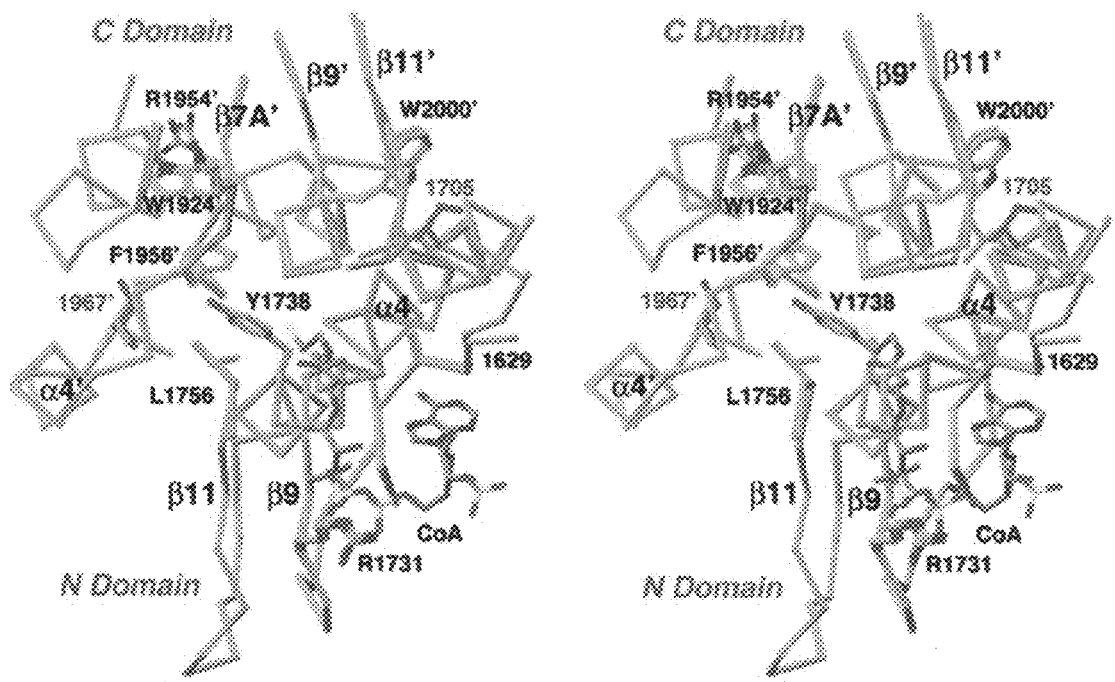

Besides the disordered segments, conformational changes near the Leu1705 mutation site cause partial unwinding of the beginning of the α4 helix (FIG. 8B), and the new Ile side chain at this position has weak electron density. Therefore, it is likely that the L1705I mutation produces conformational changes for residues near the mutation site, which in turn gives rise to the disordering of the inserted segment (1632-1702) just prior to it. The new Ile side chain at the 1967 position is well defined, and the extra methyl group is placed between the side chains of Pro1926 and Phe1956 (FIG. 8B). However, kinetic studies show that the V1967I mutation is also detrimental to the catalytic activity of the CT domain.

Figure 8C:
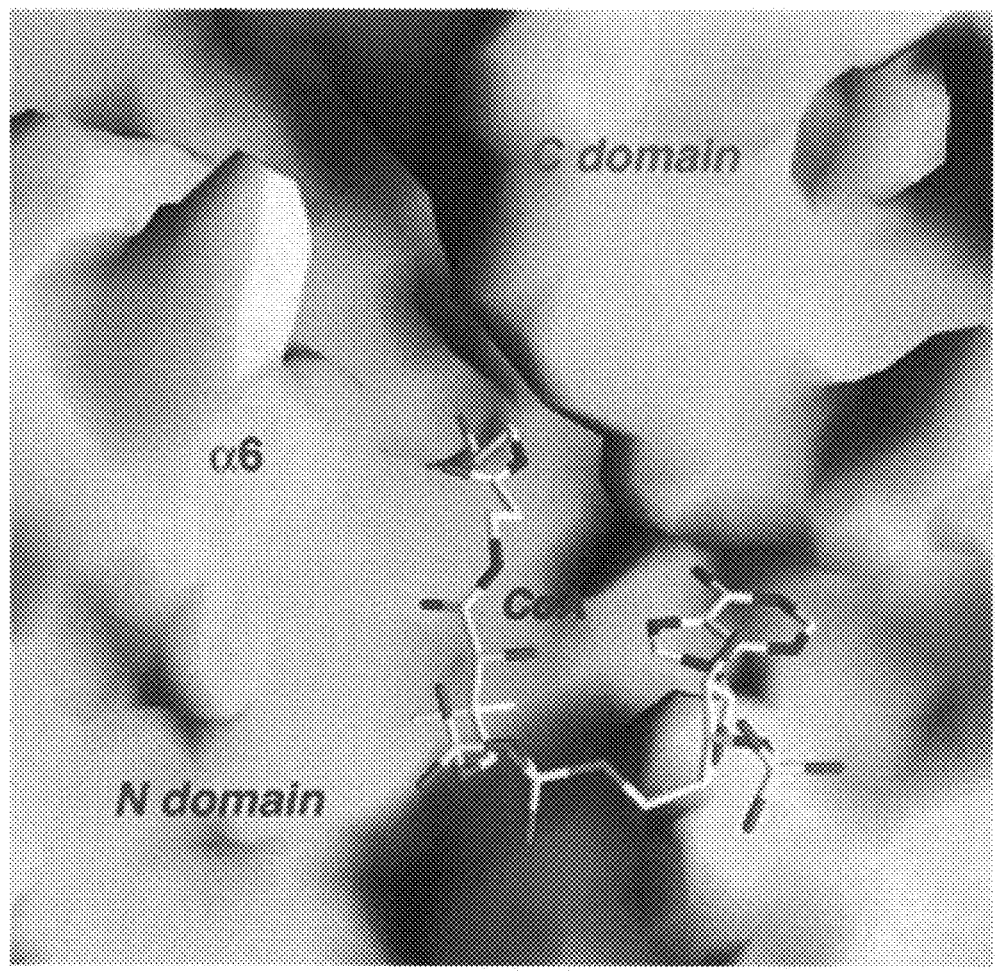
Figure 23A:
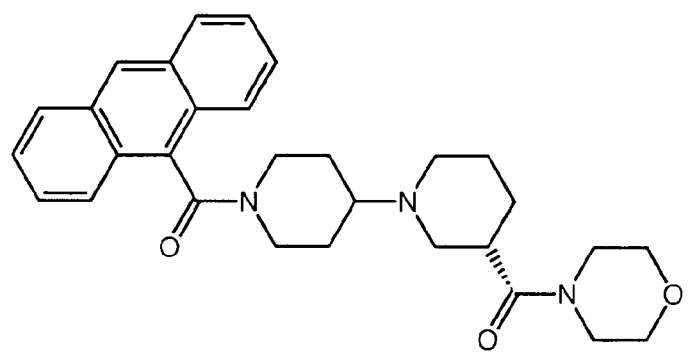
FIGS. 23A-23D.
Figure 23B:
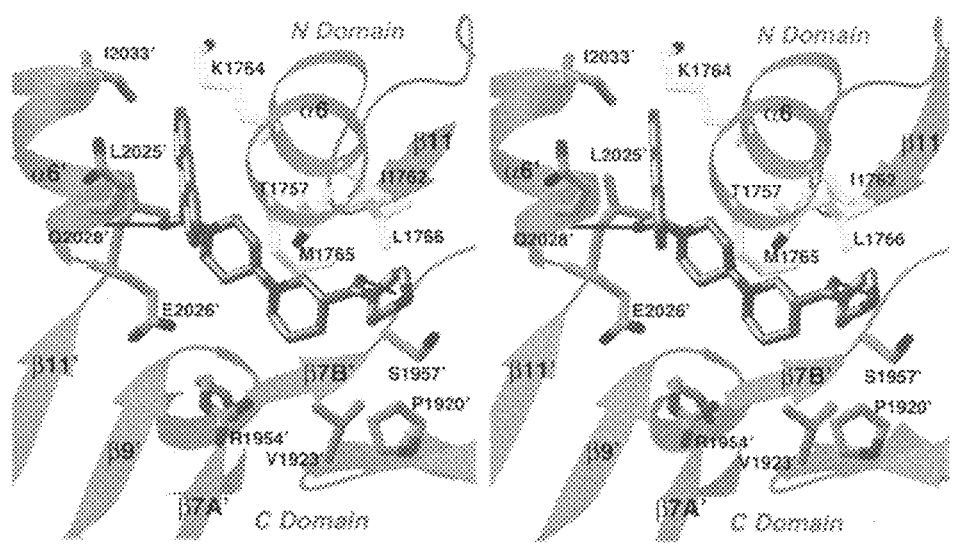
Figure 23C:
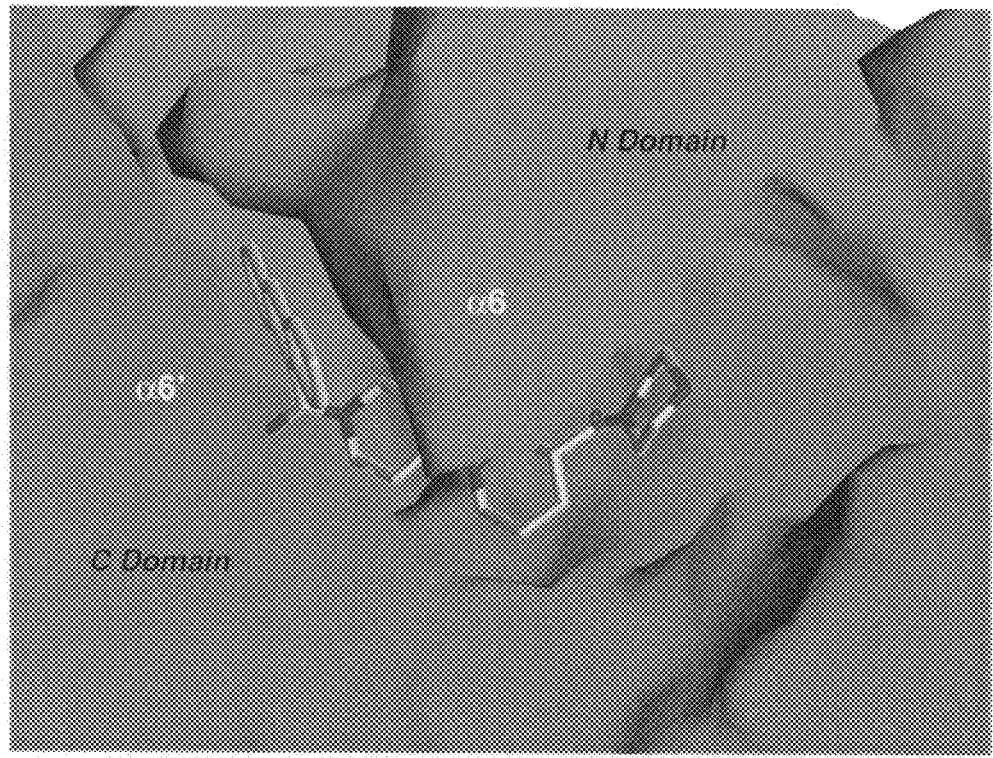
Figure 23D:
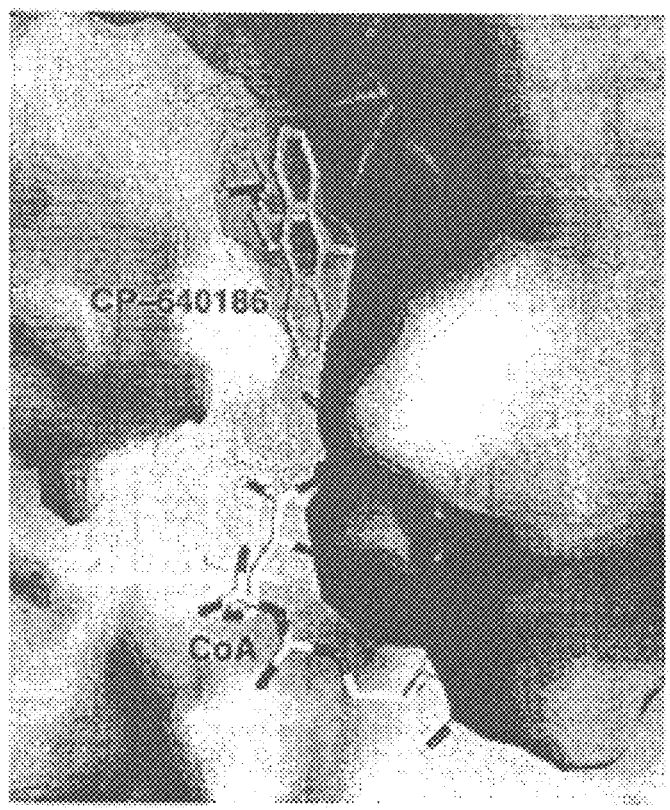

The structural observations herein provide a molecular explanation for the reduced catalytic activity of these mutants. In the structure of the L1705I/V1967I double mutant, the α6 helix in the C domain is disordered, significantly changing the molecular surface in the active site (FIG. 8C). In addition, there are conformational differences for residues 1629-1631, just prior to the disordered segment (1632-1702), between the wild-type and the mutant (FIG. 8B). The main chain amide of residue 1629 is hydrogen-bonded to the N1 atom of the adenine base in acetyl-CoA (Zhang et al., 2003). Therefore, the mutations may have indirectly disrupted the binding of CoA to the enzyme, consistent with the increase in the $K_m$ of the malonyl-CoA substrate.

Compounds that strongly inhibit both isoforms of human ACC have recently been reported, representing the first known potent inhibitors of the human enzymes. Kinetic studies suggest that they probably also function by interfering with the CT activity, confirming that the CT domain is a valid target for inhibiting the human ACCs. (Harwood Jr., et al. (2003) Isozyme-nonselective N-substituted bipiperidylcarboxamide acetyl-CoA carboxylase inhibitors reduce tissue malonyl-CoA concentrations, inhibit fatty acid synthesis, and increase fatty acid oxidation in cultured cells and in experimental animals. *J Biol Chem* 278, 37099-37111) Moreeover, these compounds can both inhibit de novo fatty acid biosynthesis as well as stimulate fatty acid oxidation, which may be clinically more efficacious (Harwood Jr. et al., 2003). The structures of the inhibitor complexes of the CT domain provided herein reveal a large conformational change in the active site of the enzyme, which produces a highly conserved and highly hydrophobic binding pocket that leads deep into the dimer interface.

Experimental Procedures

Protein production and crystallization. The cloning, expression, purification, and crystallization of the CT domain (residues 1429-2233(SEQ ID NO:2; yCTACC)) of yeast ACC followed protocols as described earlier (Zhang et al., 2003; Example 1). Based on that first crystal structure, additional bacterial expression constructs for this domain were designed, and it was found that the construct covering residues 1476-2233 (SEQ ID NO:3; yCT2ACC) produces a large amount of soluble protein in *E. coli*. This protein can be purified following the same protocol, and readily produces large crystals of the free enzyme. The reservoir solution contains 0.1 M sodium citrate (pH 5.5), 200 mM NaCl, 8% (w/v) PEG8000, and 10% (v/v) glycerol. The protein is at 10 mg/ml concentration. These free enzyme crystals were cryo-protected by the introduction of 25% (v/v) ethylene glycol and flash-frozen in liquid propane for data collection at 100K.

To prepare the haloxyfop complex, crystals of the free enzyme (covering residues 1429-2233) were soaked with various concentrations of the herbicide for different lengths of time. Noting the poor affinity of the inhibitor, initial attempts used high concentration of the compound (5 mM and higher), however this invariably led to dissolution of the crystal or loss of X-ray diffraction. Good quality diffraction was maintained after soaking a crystal for 1 hour at 1 mM concentration of haloxyfop. The crystal was flash-frozen in liquid propane.

To prepare the diclofop complex, CT domain (residues 1476-2233) was mixed with the reservoir solution containing 2 mM of the compound. The reservoir solution contains 0.1 M sodium citrate (pH 5.5), 200 mM NaCl, 8% (w/v) PEG8000, and 10% (v/v) glycerol.

Structure Determination. X-ray diffraction data were collected at the X4A beamline of the National Synchrotron Light Source (NSLS). The diffraction images were processed with the HKL package (Otwinowski and Minor, 1997). The wild-type free enzyme, the haloxyfop complex, and the L1705I/V1967I mutant crystals belong to space group C2 and are isomorphous with each other, as well as with that of the free enzyme structure in Example 1 (Zhang et al., 2003). The unit cell parameters for the free enzyme crystal are a=247 Å, b=125 Å, c=145 Å, and β=94 for SEQ ID NO:2; and the unit cell parameters for the free enzyme crystal are a=246 Å, b=124 Å, c=145 Å, and β=94 for SEQ ID NO:3. The structure refinement was carried out with the program CNS (Brunger et al., 1998). Clear electron density for the herbicides was observed from the crystallographic analysis. The atomic model was built with the program O (Jones, T. A. (1978) A graphics model building and refinement system for macromolecules. *J Appl Cryst* 11, 268-272.). The crystallographic information is summarized in Table E.

Crystals of the diclofop complex are in a new crystal form. They belong to space group $P3_221$, with cell parameters of a=b=137 Å and c=244 Å. There is one dimer of the CT domain in the asymmetric unit. The structure was solved by the molecular replacement method with the program COMO (Jogl, G., Tao, X., Xu, Y., and Tong, L. (2001). COMO: A program for combined molecular replacement. *Acta Cryst* D57, 1127-1134.), using the structure of the haloxyfop complex as the search model.

Mutagenesis and kinetic assays. The L1705I and V1967I single-site mutants as well as the L1705I/V1967I double mutant were made with the QuikChange kit (Stratagene), from the expression construct that covers residues 1476-2233. The mutants were sequenced, expressed in *E. coli*, and purified following the same protocol as that for the wild-type CT domain. The catalytic activity of the CT domain was assayed following protocols described earlier (Guchhait, R. B. et al. (1974) Acetyl coenzyme A carboxylase system from *Escherichia coli*. Purification and properties of the biotin carboxylase, carboxyltransferase, and carboxyl carrier protein components. *J Biol Chem* 249, 6633-6645; Zhang et al., 2003). For the inhibition studies shown in FIG. 7E, the activity of the enzyme in the presence of 0, 0.5 or 2 mM haloxyfop was determined. The concentration of the malonyl-CoA substrate was kept close to the expected $K_m$, 75 μM for the wild-type enzyme and 750 μM for the mutants. The wild-type enzyme was at 2.5 μM concentration, whereas the mutants were at 20 μM concentration.

TABLE E

Summary of Crystallographic Information

| Structure | Free enzyme | Haloxyfop complex | Diclofop complex | L1705I/V1967I |
|---|---|---|---|---|
| Maximum resolution (Å) | 2.5 | 2.8 | 2.5 | 2.6 |
| Number of observations | 420,147 | 285,486 | 584,662 | 315,564 |
| $R_{merge}$[1] (%) | 6.9 (31.4) | 9.3 (28.8) | 7.6 (31.7) | 5.0 (25.6) |
| Resolution range for refinement | 27-2.5 | 27-2.8 | 27-2.5 | 27-2.6 |
| Number of reflections | 130,501 | 96,167 | 88,661 | 117,132 |
| Completeness (%) | 86 (64) | 88 (74) | 96 (89) | 87 (69) |
| R factor[2] (%) | 21.9 (26.7) | 21.8 (27.9) | 23.7 (28.5) | 21.2 (26.8) |
| Free R factor[2] (%) | 25.0 (29.0) | 25.2 (30.9) | 26.5 (31.6) | 23.7 (28.5) |
| rms deviation in bond lengths (Å) | 0.007 | 0.009 | 0.009 | 0.008 |
| rms deviation in bond angles (°) | 1.2 | 1.2 | 1.1 | 1.2 |

$$^1 R_{merge} = \sum_h \sum_i |I_{hi} - \langle I_h \rangle| \Big/ \sum_h \sum_i I_{hi}$$

The numbers in parentheses are for the highest resolution shell.

$$^2 R = \sum_h |F_h^o - F_h^c| \Big/ \sum_h F_h^o$$

Example 3

Expression, Purification and Assay of the CT Domain of Mouse ACC2

Materials and Methods

Various constructs comprising the CT domain of *M. musculus* ACC2 were subcloned into the pET26b vector (Novagen) to produce the constructs listed in Table F, which were then over-expressed in *E. coli* and purified as described above in Example 1.

Kinetic assays of CT activity also were performed as described in Example 1, and the activity of the enzyme was assayed in the reverse direction, i.e. measuring the transfer of the carboxyl group from malonyl-CoA to biotin methyl ester, as previously described (Zhang et al., 2003, *Science* 299: 2064-2067).

Results

The mouse CT domain is enzymatically active and the $V_{max}$ and $K_m$ values have been determined using malonyl-CoA as a substrate. The $V_{max}$ is $50 \times 10^5$ AU/s, and the $K_m = 120$ µM, comparable to the kinetic parameters of the yeast CT domain

TABLE F

Constructs created and tested for production of proteins comprising the CT domain of mouse ACC2

| Row | 1st residue* | Last residue* | Induced | Soluble |
|---|---|---|---|---|
| 1 | 54 | 810 | + | − |
| 2 | 43 | 810 | + | − |
| 3 | 35 | 810 | + | − |
| 4 | 24 | 810 | + | − |
| 5 | 11 | 810 | + | − |
| 6 | 1 | 810 | + | − |
| 7 | 54 | 767 | + | + |
| 8 | 43 | 767 | + | + |
| 9 (mCTACC2) | 35 | 767 | + | + |
| 10 | 24 | 767 | + | − |
| 11 | 11 | 767 | + | − |
| 12 | 1 | 767 | + | − |
| 13 | 54 | 713 | + | − |
| 14 | 43 | 713 | + | − |
| 15 | 35 | 713 | + | − |
| 16 | 24 | 713 | + | − |
| 17 | 11 | 713 | + | − |
| 18 | 1 | 713 | + | − |
| 19 | 54 | 695 | + | − |
| 20 | 43 | 695 | + | − |
| 21 | 35 | 695 | + | − |
| 22 | 24 | 695 | + | − |
| 23 | 11 | 695 | + | − |
| 24 | 1 | 695 | + | − |

*Residue numbering based on GenBank Entry No. AAH22940
†NA—Not applicable

Example 4
Determination of the Crystal Structure of the CT Domain of Yeast ACC Complexed With CP-640186

Free crystals of the yeast CT domain (SEQ ID NO:3) was prepared as in Example 2. To prepare the CP-640186 complex, crystals of the free enzyme (covering residues 1476-2233) were soaked with the CP compound.

Structure Determination. X-ray diffraction data were collected at the X4A beamline of the National Synchrotron Light Source (NSLS). The diffraction images were processed with the HKL package (Otwinowski and Minor, 1997). The unit cell parameters for the complex crystal are a=247 Å, b=125 Å, c=146 Å, and β=94, with a space group of C2. The structure refinement was carried out with the program CNS (Brunger et al., 1998). Clear electron density for the herbicides was observed from the crystallographic analysis. The atomic model was built with the program O (Jones, T. A. (1978) A graphics model building and refinement system for macromolecules. *J Appl Cryst* 11, 268-272.).

Results. The crytal structure of yeast CT in complex with CP-640186 was determined at 2.8 Å resolution. This compound was recently reported by Pfizer to be a potent inhibitor of mammalian ACC1 and ACC2, with $IC_{50}$ values of about 55 nM (FIG. 23).

From the crystal structure, several salient features of the complex should be noted. For example, the inhibitor is bound in the active site (FIG. 23), at the interface between two monomers of the enzyme. This proves that the inhibitor functions at the active site of the CT domain. In contrast the studies with the herbicides (diclfop or haloxyfop), there are only small conformational changes in the enzyme upon binding of the CP compound. The binding site for the CP compound is distinct from that for CoA or for the herbicides, and this is consistent with kinetic studies showing that the CP compound is non-competitive with respect to malonyl-CoA. The structure suggests that this binding site (i.e., the binding site for the CP compound) may overlap with that for biotin.

The anthracene group of the CP compound is placed in the narrow channel between helices α6 and α6', interacting with residues Ala1761, Lys1764, Met1765 on one face, and residues Leu2025', Gln2026' and Gly2029' on the other. The carbonyl oxygen next to the anthracene group is hydrogen-bonded to the main-chain amide of Gln2028'. The remainder of the inhibitor (the two piperidine rings and the morpholine ring) is placed next to the peptide segment Arg1954'-Gly1959'. In addition, it has interactions with Val1923', Thr1757 and Ile1762. One face of these rings is exposed to the solvent in the CT complex. The carbonyl oxygen next to the morpholine ring is hydrogen-bonded to the main chain amide of Gly1958'.

Kinetic studies show that the inhibitor is non-competitive versus the substrate malonyl-CoA. The Ki values are about 4 µM, however, this value must be considered in relation to the fact that about 3 µM of enzyme is in the reaction buffer.

Most of the residues that interact with the CP compound are strictly or highly conserved among the CT domains. Two exceptions are Met1765, which is Val in most mammalian ACCs, and Ile1762, which is Leu in most other ACCs. Additional residues may also be important for inhibitor binding. For example, Gly2032 is replaced by Glu in most other ACCs, and this Glu side chain could ion-pair with Lys1764, forming a lid over the anthracene group.

The structural information proves that yeast CT is a valid surrogate for defining the binding modes of inhibitors against human ACCs, and provides a basis for the design of modulators against human ACC and other enzymes.

TABLE G

CT Domain Corresponding Residues (The residues correspond by row)

| SEQ ID NO: 1 (yeast) | SEQ ID NO: 2 (yeast) | SEQ ID NO: 3 (yeast) | SEQ ID NO: 4 (yeast) | SEQ ID NO: 6 (mouse ACC2) | SEQ ID NO: 8 (human ACC1) | SEQ ID NO: 10 (human ACC2) | SEQ ID NO: 14 (mouse ACC1) |
|---|---|---|---|---|---|---|---|
| Met 1503 | Met 75 | Met 28 | Met 28 | Leu 30 | Leu 46 | Leu 87 | Leu 64 |
| Lys 1592 | Lys 164 | Lys 117 | Lys 117 | Gln 116 | Arg 140 | Arg 173 | Arg 158 |
| Ile 1593 | Ile 165 | Ile 118 | Ile 118 | Ile 117 | Ile 141 | Ile 174 | Ile 159 |

TABLE G-continued

CT Domain Corresponding Residues (The residues correspond by row)

| SEQ ID NO: 1 (yeast) | SEQ ID NO: 2 (yeast) | SEQ ID NO: 3 (yeast) | SEQ ID NO: 4 (yeast) | SEQ ID NO: 6 (mouse ACC2) | SEQ ID NO: 8 (human ACC1) | SEQ ID NO: 10 (human ACC2) | SEQ ID NO: 14 (mouse ACC1) |
|---|---|---|---|---|---|---|---|
| Ser 1595 | Ser 167 | Ser 120 | Ser 120 | Ser 119 | Ser 143 | Ser 176 | Ser 161 |
| Phe 1596 | Phe 168 | Phe 121 | Phe 121 | Phe 120 | Phe 144 | Phe 177 | Phe 162 |
| Asn 1624 | Asn 196 | Asn 149 | Asn 149 | Asn 148 | Asn 172 | Asn 205 | Asn 190 |
| Ser 1625 | Ser 197 | Ser 150 | Ser 150 | Ser 149 | Ser 173 | Ser 206 | Ser 191 |
| Gly 1626 | Gly 198 | Gly 151 | Gly 151 | Gly 150 | Gly 174 | Gly 207 | Gly 192 |
| Ala 1627 | Ala 199 | Ala 152 | Ala 152 | Ala 151 | Ala 175 | Ala 208 | Ala 193 |
| Arg 1628 | Arg 200 | Arg 153 | Arg 153 | Arg 152 | Arg 176 | Arg 209 | Arg 194 |
| Ile 1629 | Ile 201 | Ile 154 | Ile 154 | Met 153 | Ile 177 | Ile 210 | Ile 195 |
| Gly 1630 | Gly 202 | Gly 155 | Gly 155 | Gly 154 | Gly 178 | Gly 211 | Gly 196 |
| Met 1631 | Met 203 | Met 156 | Met 156 | Leu 155 | Leu 179 | Met 212 | Leu 197 |
| Gly 1699 | Gly 271 | Gly 224 | Gly 224 | Asn 220 | Gly 244 | Gly 277 | Gly 262 |
| Gly 1701 | Gly 273 | Gly 226 | Gly 226 | Gly 222 | Gly 246 | Gly 279 | Gly 264 |
| Glu 1703 | Glu 275 | Glu 228 | Glu 228 | Glu 224 | Glu 248 | Glu 281 | Glu 266 |
| Cys 1704 | Cys 276 | Cys 229 | Cys 229 | Asn 225 | Asn 249 | Asn 282 | Asn 267 |
| Leu 1705 | Leu 277 | Leu 230 | Ile 230 | Leu 226 | Leu 250 | Leu 283 | Leu 268 |
| Ser 1708 | Ser 280 | Ser 233 | Ser 233 | Ser 229 | Ser 253 | Ser 286 | Ser 271 |
| Ala 1712 | Ala 284 | Ala 237 | Ala 237 | Ala 233 | Ala 257 | Ala 290 | Ala 275 |
| Arg 1731 | Arg 303 | Arg 256 | Arg 256 | Arg 252 | Arg 276 | Arg 309 | Arg 294 |
| Val 1733 | Val 305 | Val 258 | Val 258 | Leu 254 | Ile 278 | Ile 311 | Ile 296 |
| Gly 1734 | Gly 306 | Gly 259 | Gly 259 | Gly 255 | Gly 279 | Gly 312 | Gly 297 |
| Ile 1735 | Ile 307 | Ile 260 | Ile 260 | Ile 256 | Ile 280 | Ile 313 | Ile 298 |
| Gly 1736 | Gly 308 | Gly 261 | Gly 261 | Gly 257 | Gly 281 | Gly 314 | Gly 299 |
| Ala 1737 | Ala 309 | Ala 262 | Ala 262 | Ala 258 | Ala 282 | Ala 315 | Ala 300 |
| Tyr 1738 | Tyr 310 | Tyr 263 | Tyr 263 | Tyr 259 | Tyr 283 | Tyr 316 | Tyr 301 |
| Leu 1739 | Leu 311 | Leu 264 | Leu 264 | Leu 260 | Leu 284 | Leu 317 | Leu 302 |
| Arg 1741 | Arg 313 | Arg 266 | Arg 266 | Arg 262 | Arg 286 | Arg 319 | Arg 304 |
| Leu 1742 | Leu 314 | Leu 267 | Leu 267 | Leu 263 | Leu 287 | Leu 320 | Leu 305 |
| Pro 1753 | Pro 325 | Pro 278 | Pro 278 | His 274 | His 298 | His 331 | His 316 |
| Ile 1755 | Ile 327 | Ile 280 | Ile 280 | Ile 276 | Ile 300 | Ile 333 | Ile 318 |
| Leu 1756 | Leu 328 | Leu 281 | Leu 281 | Leu 277 | Leu 301 | Leu 334 | Leu 319 |
| Thr 1757 | Thr 329 | Thr 282 | Thr 282 | Thr 278 | Thr 302 | Thr 335 | Thr 320 |
| Gly 1758 | Gly 330 | Gly 283 | Gly 283 | Gly 279 | Gly 303 | Gly 336 | Gly 321 |
| Ala 1759 | Ala 331 | Ala 284 | Ala 284 | Ala 280 | Ala 304 | Ala 337 | Ala 322 |
| Pro 1760 | Pro 332 | Pro 285 | Pro 285 | Gly 281 | Gly 305 | Ser 338 | Gly 323 |
| Ala 1761 | Ala 333 | Ala 286 | Ala 286 | Ala 282 | Ala 306 | Ala 339 | Ala 324 |
| Ile 1762 | Ile 334 | Ile 287 | Ile 287 | Leu 283 | Leu 307 | Leu 340 | Leu 325 |
| Asn 1763 | Asn 335 | Asn 288 | Asn 288 | Asn 284 | Asn 308 | Asn 341 | Asn 326 |
| Lys 1764 | Lys 336 | Lys 289 | Lys 289 | Lys 285 | Lys 309 | Lys 342 | Lys 327 |
| Met 1765 | Met 337 | Met 290 | Met 290 | Val 286 | Val 310 | Val 343 | Val 328 |
| Leu 1766 | Leu 338 | Leu 291 | Leu 291 | Leu 287 | Leu 311 | Leu 344 | Leu 329 |
| Tyr 1771 | Try 343 | Tyr 296 | Tyr 296 | Tyr 292 | Tyr 316 | Tyr 349 | Tyr 334 |
| Asn 1774 | Asn 346 | Asn 299 | Asn 299 | Asn 295 | Asn 319 | Asn 352 | Asn 337 |
| Ala 1908 | Ala 480 | Ala 433 | Ala 433 | Ala 431 | Ala 455 | Ala 488 | Ala 473 |
| Pro 1920 | Pro 492 | Pro 445 | Pro 445 | Ala 443 | Ala 467 | Ala 500 | Ala 485 |
| Gly 1921 | Gly 493 | Gly 446 | Gly 446 | Gly 444 | Gly 468 | Gly 501 | Gly 486 |
| Gln 1922 | Gln 494 | Gln 447 | Gln 447 | Gln 445 | Gln 469 | Gln 502 | Gln 487 |
| Val 1923 | Val 495 | Val 448 | Val 448 | Val 446 | Val 470 | Val 503 | Val 488 |
| Trp 1924 | Trp 496 | Trp 449 | Trp 449 | Trp 447 | Trp 471 | Trp 504 | Trp 489 |
| His 1925 | His 497 | His 450 | His 450 | Phe 448 | Phe 472 | Phe 505 | Phe 490 |
| Pro 1926 | Pro 498 | Pro 451 | Pro 451 | Pro 449 | Pro 473 | Pro 506 | Pro 491 |
| Ser 1928 | Ser 500 | Ser 453 | Ser 453 | Ser 451 | Ser 475 | Ser 508 | Ser 493 |
| Ala 1929 | Ala 501 | Ala 454 | Ala 454 | Ala 452 | Ala 476 | Ala 509 | Ala 494 |
| Phe 1930 | Phe 502 | Phe 455 | Phe 455 | Tyr 453 | Phe 477 | Tyr 510 | Phe 495 |
| Trp 1953 | Trp 525 | Trp 478 | Trp 478 | Trp 475 | Trp 499 | Trp 532 | Trp 517 |
| Arg 1954 | Arg 526 | Arg 479 | Arg 479 | Arg 476 | Arg 500 | Arg 533 | Arg 518 |
| Gly 1955 | Gly 527 | Gly 480 | Gly 480 | Gly 477 | Gly 501 | Gly 534 | Gly 519 |
| Phe 1956 | Phe 528 | Phe 481 | Phe 481 | Phe 478 | Phe 502 | Phe 535 | Phe 520 |
| Ser 1957 | Ser 529 | Ser 482 | Ser 482 | Ser 479 | Ser 503 | Ser 536 | Ser 521 |
| Gly 1958 | Gly 530 | Gly 483 | Gly 483 | Gly 480 | Gly 504 | Gly 537 | Gly 522 |
| Gly 1959 | Gly 531 | Gly 484 | Gly 484 | Gly 481 | Gly 505 | Gly 538 | Gly 523 |
| Gln 1960 | Gln 532 | Gln 485 | Gln 485 | Met 482 | Met 506 | Met 539 | Met 524 |
| Arg 1961 | Arg 533 | Arg 486 | Arg 486 | Lys 483 | Lys 507 | Lys 540 | Lys 525 |
| Asp 1962 | Asp 534 | Asp 487 | Asp 487 | Asp 484 | Asp 508 | Asp 541 | Asp 526 |
| Met 1963 | Met 535 | Met 488 | Met 488 | Met 485 | Met 509 | Met 542 | Met 527 |
| Phe 1964 | Phe 536 | Phe 489 | Phe 489 | Tyr 486 | Tyr 510 | Tyr 543 | Tyr 528 |
| Asn 1965 | Asn 537 | Asn 490 | Asn 490 | Glu 487 | Asp 511 | Asp 544 | Asp 529 |
| Glu 1966 | Glu 538 | Glu 491 | Glu 491 | Gln 488 | Gln 512 | Gln 545 | Gln 530 |
| Val 1967 | Val 539 | Val 492 | Ile 492 | Met 489 | Val 513 | Val 546 | Val 531 |
| Leu 1968 | Leu 540 | Leu 493 | Leu 493 | Leu 490 | Leu 514 | Leu 547 | Leu 532 |
| Lys 1969 | Lys 541 | Lys 494 | Lys 494 | Lys 491 | Lys 515 | Lys 548 | Lys 533 |
| Tyr 1970 | Tyr 542 | Tyr 495 | Tyr 495 | Phe 492 | Phe 516 | Phe 549 | Phe 534 |
| Gly 1971 | Gly 543 | Gly 496 | Gly 496 | Gly 493 | Gly 517 | Gly 550 | Gly 535 |

TABLE G-continued

CT Domain Corresponding Residues (The residues correspond by row)

| SEQ ID NO: 1 (yeast) | SEQ ID NO: 2 (yeast) | SEQ ID NO: 3 (yeast) | SEQ ID NO: 4 (yeast) | SEQ ID NO: 6 (mouse ACC2) | SEQ ID NO: 8 (human ACC1) | SEQ ID NO: 10 (human ACC2) | SEQ ID NO: 14 (mouse ACC1) |
|---|---|---|---|---|---|---|---|
| Ser 1972 | Ser 544 | Ser 497 | Ser 497 | Ala 494 | Ala 518 | Ala 551 | Ala 536 |
| Ile 1974 | Ile 546 | Ile 499 | Ile 499 | Ile 496 | Ile 520 | Ile 553 | Ile 538 |
| Val 1975 | Val 547 | Val 500 | Val 500 | Val 497 | Val 521 | Val 554 | Val 539 |
| Glu 1994 | Glu 566 | Glu 519 | Glu 519 | Glu 516 | Glu 540 | Glu 573 | Glu 558 |
| Arg 1996 | Arg 568 | Arg 521 | Arg 521 | Arg 518 | Arg 542 | Arg 575 | Arg 560 |
| Gly 1997 | Gly 569 | Gly 522 | Gly 522 | Gly 519 | Gly 543 | Gly 576 | Gly 561 |
| Gly 1998 | Gly 570 | Gly 523 | Gly 523 | Gly 520 | Gly 544 | Gly 577 | Gly 562 |
| Ser 1999 | Ser 571 | Ser 524 | Ser 524 | Ser 521 | Ser 545 | Ser 578 | Ser 563 |
| Trp 2000 | Trp 572 | Trp 525 | Trp 525 | Trp 522 | Trp 546 | Trp 579 | Trp 564 |
| Val 2001 | Val 573 | Val 526 | Val 526 | Val 523 | Val 547 | Val 580 | Val 565 |
| Val 2002 | Val 574 | Val 527 | Val 527 | Val 524 | Val 548 | Val 581 | Val 566 |
| Val 2003 | Val 575 | Val 528 | Val 528 | Leu 525 | Ile 549 | Ile 582 | Ile 567 |
| Arg 2021 | Arg 593 | Arg 546 | Arg 546 | Arg 543 | Arg 567 | Arg 600 | Arg 585 |
| Gly 2023 | Gly 595 | Gly 548 | Gly 548 | Gly 545 | Ser 569 | Gly 602 | Ser 587 |
| Val 2024 | Val 596 | Val 549 | Val 549 | Val 546 | Val 570 | Val 603 | Val 588 |
| Leu 2025 | Leu 597 | Leu 550 | Leu 550 | Leu 547 | Leu 571 | Leu 604 | Leu 589 |
| Glu 2026 | Glu 598 | Glu 551 | Glu 551 | Glu 548 | Glu 572 | Glu 605 | Glu 590 |
| Pro 2027 | Pro 599 | Pro 552 | Pro 552 | Pro 549 | Pro 573 | Pro 606 | Pro 591 |
| Gln 2028 | Gln 600 | Gln 553 | Gln 553 | Glu 550 | Glu 574 | Glu 607 | Glu 592 |
| Gly 2029 | Gly 601 | Gly 554 | Gly 554 | Gly 551 | Gly 575 | Gly 608 | Gly 593 |
| Met 2030 | Met 602 | Met 555 | Met 555 | Thr 552 | Thr 576 | Thr 609 | Thr 594 |
| Val 2031 | Val 603 | Val 556 | Val 556 | Val 553 | Val 577 | Val 610 | Val 595 |
| Gly 2032 | Gly 604 | Gly 557 | Gly 557 | Glu 554 | Glu 578 | Glu 611 | Glu 596 |
| Ile 2033 | Ile 605 | Ile 558 | Ile 558 | Ile 555 | Ile 579 | Ile 612 | Ile 597 |
| Lys 2034 | Lys 606 | Lys 559 | Lys 559 | Lys 556 | Lys 580 | Lys 613 | Lys 598 |
| Arg 2036 | Arg 608 | Arg 561 | Arg 561 | Arg 558 | Arg 582 | Arg 615 | Arg 600 |
| Asp 2098 | Asp 670 | Asp 623 | Asp 623 | Asp 620 | Asp 644 | Asp 677 | Asp 662 |
| Val 2108 | Val 680 | Val 633 | Val 633 | Ile 630 | Ile 654 | Val 687 | Val 672 |
| Leu 2189 | Leu 761 | Leu 714 | Leu 714 | N/A | N/A | N/A | N/A |

What is claimed is:

1. A composition comprising a non-crystalline polypeptide consisting of:
    (a) the amino acid sequence of SEQ ID NO:2,
    (b) the amino acid sequence of SEQ ID NO:3, or
    (c) an amino acid sequence that is at least 95% identical to the amino acid sequence of (a) or (b) and wherein the polypeptide binds acetyl-CoA, haloxyfop, diclofop, or CP-640186.

2. The composition of claim 1, wherein the composition comprises one or more dimers of said non-crystalline polypeptide.

3. The composition of claim 2, wherein the non-crystalline polypeptide consists of an amino acid sequence that is at least 99% identical to the amino acid sequence of (a) or (b) of claim 1 and wherein the polypeptide binds acetyl-CoA, haloxyfop, diclofop, or CP-640186.

4. The composition of claim 2, wherein each polypeptide of the dimer consists of the amino acid sequence of SEQ ID NO:2 or SEQ ID NO:3.

5. The composition of claim 1, wherein the polypeptide is complexed with a ligand, wherein the ligand is selected from the group consisting of haloxyfop, diclofop and CP-640186.

6. The composition of claim 1, wherein the polypeptide consists of the amino acid sequence of SEQ ID NO:2 or SEQ ID NO:3.

7. A composition comprising a non-crystalline carboxyltransferase domain dimer of two polypeptides, wherein each polypeptide of the dimer is selected from the group consisting of:
    a) the amino acid sequence of SEQ ID NO:3, and
    b) an amino acid sequence that is at least 95% identical to the amino acid sequence of SEQ ID NO:3, wherein each polypeptide binds acetyl-CoA, haloxyfop, diclofop, or CP-640186 and wherein the following amino acid residues corresponding to SEQ ID NO:3 are conserved or conservatively substituted: Ile 499, Val 527, Gly 523, Val 526, Val 549, Leu 493, Phe 481, Trp 449, Tyr 263, Ser 233, Ala 152, Ile 260, Gly 259, and Leu 281.

8. A composition comprising a non-crystalline dimer of two polypeptides, wherein each polypeptide of the dimer consists of the amino acid sequence of SEQ ID NO:2 or SEQ ID NO:3.

9. A composition comprising a non-crystalline dimer of two polypeptides, wherein each polypeptide of the dimer consists of:
    (a) the amino acid sequence of SEQ ID NO:3, or an amino acid sequence that is at least 95% identical to the amino acid sequence of SEQ ID NO:3, wherein the polypeptide binds acetyl-CoA, haloxyfop, diclofop, or CP-640186 and wherein the following amino acid residues corresponding to SEQ ID NO:3 are conserved or conservatively substituted: Ala 286, Lys 289, Leu 550, Glu 551, and Gly 554, or
    (b) the amino acid sequence of SEQ ID NO:2, or an amino acid sequence that is at least 95% identical to the amino acid sequence of SEQ ID NO:2, wherein the polypeptide binds acetyl-CoA, haloxyfop, diclofop, or CP-640186 and wherein the following amino acid residues corresponding to SEQ ID NO:2 are conserved or conservatively substituted: Ala 333, Lys 336, Leu 597, Glu 598, and Gly 601.

10. A composition comprising a non-crystalline dimer of two polypeptides, wherein each polypeptide of the dimer consists of:
    (a) the amino acid sequence of SEQ ID NO:3, or an amino acid sequence that is at least 95% identical to the amino acid sequence of SEQ ID NO:3, wherein the polypeptide binds acetyl-CoA, haloxyfop, diclofop, or CP-640186 and wherein the following amino acid residues corresponding to SEQ ID NO:3 are conserved or conservatively substituted: Ile 118, Ser 120, Phe 121, Asn 149, Ser 150, Gly 151, Ala 152, Arg 153, Ile 154, Gly 155, Gly 224, Leu 230, Arg 256, Gly 259, Ile 260, Tyr 263, Ile 280, Leu 281, Thr 282, Gly 283, Ala 284, Ala 286, Asn 299, Gly 480, Phe 481, Arg 521, Gly 522, Gly 523, Ser 524, Val 526, Val 549, Leu 550, Gly 554, Ile 558, Lys 559, and Arg 561, or
    (b) the amino acid sequence of SEQ ID NO:2, or an amino acid sequence that is at least 95% identical to the amino acid sequence of SEQ ID NO:2, wherein the polypeptide binds acetyl-CoA, haloxyfop, diclofop, or CP-640186 and wherein the following amino acid residues corresponding to SEQ ID NO:2 are conserved or conservatively substituted: Ile 165, Ser 167, Phe 168, Asn 196, Ser 197, Gly 198, Ala 199, Arg 200, Ile 201, Gly 202, Gly 271, Leu 277, Arg 303, Gly 306, Ile 307, Tyr 310, Ile 327, Leu 328, Thr 329, Gly 330, Ala 331, Ala 333, Asn 346, Gly 527, Phe 528, Arg 568, Gly 569, Gly 570, Ser 571, Val 573, Val 596, Leu 597, Gly 601, Ile 605, Lys 606, and Arg 608.

11. A composition comprising a non-crystalline dimer of two polypeptides, wherein each polypeptide of the dimer consists of:
    (a) the amino acid sequence of SEQ ID NO:3, or an amino acid sequence that is at least 95% identical to the amino acid sequence of SEQ ID NO:3, wherein the polypeptide binds acetyl-CoA, haloxyfop, diclofop, or CP-640186 and wherein the following amino acid residues corresponding to SEQ ID NO:3 are conserved: Ile 154, Leu 281, Thr 282, Gly 283, Ala 286, Asn 288, Lys 289, Leu 291, Tyr 296, Ala 433, Gln 447, Val 448, Trp 449, Trp 478, Arg 479, Gly 480, Phe 481, Ser 482, Gly 483, Gly 484, Asp 487, Arg 521, Gly 522, Ser 524, Val 549, Leu 550, Glu 551, Pro 552, Gly 554, Val 556, and Ile 558, or
    (b) the amino acid sequence of SEQ ID NO:2, or an amino acid sequence that is at least 95% identical to the amino acid sequence of SEQ ID NO:2, wherein the polypeptide binds acetyl-CoA, haloxyfop, diclofop, or CP-640186 and wherein the following amino acid residues corresponding to SEQ ID NO:2 are conserved: Ile 201, Leu 328, Thr 329, Gly 330, Ala 333, Asn 335, Lys 336, Leu 338, Tyr 343, Ala 480, Gln 494, Val 495, Trp 496, Trp 525, Arg 526, Gly 527, Phe 528, Ser 529, Gly 530, Gly 531, Asp 534, Arg 568, Gly 569, Ser 571, Val 596, Leu 597, Glu 598, Pro 599, Gly 601, Val 603, and Ile 605.

12. A composition comprising a non-crystalline dimer of two polypeptides, wherein each polypeptide of the dimer consists of:
    (a) the amino acid sequence of SEQ ID NO:3, or an amino acid sequence that is at least 95% identical to the amino acid sequence of SEQ ID NO:3, wherein the polypeptide binds acetyl-CoA, haioxyfop, diciofop, or CP-640186 and wherein the following amino acid residues corresponding to SEQ ID NO:3 are conserved: Phe 121, Ser 150, Gly 151, Ala 152, Arg 153, Ile 154, Leu 230, Ser 233, Ala 237, Gly 259, Ile 260, Gly 261, Ala 262, Tyr 263, Leu 264, Arg 266, Leu 267, Ile 280, Leu 281, Thr 282, Val 448, Trp 449, Pro 451, Ser 453, Ala 454, Trp 478, Gly 480, Phe 481, Ser 482, Val 492, Leu 493, Lys 494, Gly 496, Ile 499, Arg 521, Gly 522, Gly 523, Ser 524, Trp 525, Val 526, Val 527, Val 549, and Leu 550, or (b) the amino acid sequence of SEQ ID NO:2, or an amino acid sequence that is at least 95% identical to the amino acid sequence of SEQ ID NO:2, wherein the polypeptide binds acetyl-CoA, haloxyfop, diclofop, or CP-640186 and wherein the following amino acid residues corresponding to SEQ ID NO:2 are conserved: Phe 168, Ser 197, Gly 198, Ala 199, Arg 200, Ile 201, Leu 277, Ser 280, Ala 284, Gly 306, Ile 307, Gly 308, Ala 309, Tyr 310, Leu 311, Arg 313, Leu 314, Ile 327, Leu 328, Thr 329, Val 495, Trp 496, Pro 498, Ser 500, Ala 501, Trp 525, Gly 527, Phe 528, Ser 529, Val 539, Leu 540, Lys 541, Gly 543, Ile 546, Arg 568, Gly 569, Gly 570, Ser 571, Trp 572, Val 573, Val 574, Val 596, and Leu 597.

13. A composition comprising a non-crystalline dimer, wherein each polypeptide of the dimer consists of:
(a) the amino acid sequence of SEQ ID NO:2,
(b) the amino acid sequence of SEQ ID NO:3, or
(c) an amino acid sequence that is at least 95% identical to the amino acid sequence of (a) or (b) and wherein the polypeptide binds acetyl-CoA, haloxyfop, diclofop, or CP-640186.

14. A crystal comprising a dimer of a carboxyltransferase (CT) domain of an acetyl-CoA carboxylase, wherein the CT domain consists of the amino acid sequence of SEQ ID NO:3;
(a) wherein the CT domain is unliganded and the crystal has unit cell dimensions of a=247±2 Å; b=125±2 Å; c=145±2 Å; $\alpha$=90°; $\beta$+94±2°; $\gamma$=90°; and space group C2;
(b) wherein the CT domain is unliganded and the crystal has unit cell dimensions of a=255±2 Å; b=113±2 Å; c=135±2 Å; $\alpha$=90°; $\beta$=101±2°; $\gamma$=90°;and space group C2;
(c) wherein the CT domain is unliganded and the crystal has unit cell dimensions of a=246±2 Å; b=124±2 Å; c=145±2 Å; $\alpha$=90°; $\beta$=94±2°; $\gamma$=90°; and space group C2;
(d) wherein the CT domain is complexed with diclofop and the crystal has unit cell dimensions of a=137±2 Å; b=137±2 Å; c=244±2 Å; $\alpha$=90°; $\mu$=90°; $\gamma$=120°; and space group P3$_2$21; or
(e) wherein the CT domain is complexed with CP-640186 or haloxyfop and the crystal has unit cell dimensions of a=247±2 Å; b=125±2 Å; c=146±2 Å; $\alpha$=90°; $\beta$=94±2°; $\gamma$=90°; and space group C2.

15. The crystal of claim 14, wherein the CT domain is unliganded and the crystal has unit cell dimensions of : a=246±2 Å; b=124±2 Å; c=145±2 Å; $\alpha$=90°; $\beta$=94±2°; $\gamma$=90°; and space group C2.

16. The crystal of claim 14, wherein the CT domain is complexed with haloxyfop and the crystal has unit cell dimensions of a=247±2 Å; b=125±2 Å; c=146±2 Å; $\alpha$=90°; $\beta$=94±2°; $\gamma$=90°; and space group C2.

17. The crystal of claim 16, wherein the CT domain of the crystal comprises a three-dimensional structure having the atomic coordinates of Table 3.

18. The crystal of claim 14, wherein the CT domain is complexed with diclofop and the crystal has unit cell dimensions of a=137±2 Å; b=137±2 Å; c=244±2 Å; $\alpha$=90°; $\beta$=90°; $\gamma$=120°; and space group P3$_2$21.

19. The crystal of claim 18, wherein the CT domain of the crystal comprises a three-dimensional structure having the atomic coordinates of Table 4.

20. The crystal of claim 14, wherein the CT domain is complexed with CP-640186 and the crystal has unit cell dimensions of a=247±2 Å; b=125±2 Å; c =146±2 Å; $\alpha$=90°; $\beta$=94±2°; $\gamma$=90°; and space group C2.

21. The crystal of claim 20, wherein the CT domain of the crystal comprises a three-dimensional structure having the atomic coordinates of Table 5.

22. A crystal comprising a dimer of a carboxyltransferase (CT) domain of an acetyl-CoA carboxylase, wherein the CT domain consists of the amino acid sequence of SEQ ID NO:2 and is complexed with acetyl-CoA and wherein the crystal has unit cell dimensions of: a=93±2 Å; b=138±2 Å; c= 101±2 Å; $\alpha$=90°; $\beta$=114±2°; $\gamma$=90°; and space group P21.

23. The crystal of claim 22, wherein the CT domain of the crystal comprises a three-dimensional structure having the atomic coordinates of Table 2.

\* \* \* \* \*

SEQUENCE LISTING

<160> NUMBER OF SEQ ID NOS: 14

<210> SEQ ID NO 1
<211> LENGTH: 2233
<212> TYPE: PRT
<213> ORGANISM: Saccharomyces cerevisiae

<400> SEQUENCE: 1

```
Met Ser Glu Glu Ser Leu Phe Glu Ser Ser Pro Gln Lys Met Glu Tyr
1               5                   10                  15

Glu Ile Thr Asn Tyr Ser Glu Arg His Thr Glu Leu Pro Gly His Phe
            20                  25                  30

Ile Gly Leu Asn Thr Val Asp Lys Leu Glu Glu Ser Pro Leu Arg Asp
        35                  40                  45

Phe Val Lys Ser His Gly Gly His Thr Val Ile Ser Lys Ile Leu Ile
    50                  55                  60

Ala Asn Asn Gly Ile Ala Ala Val Lys Glu Ile Arg Ser Val Arg Lys
65                  70                  75                  80

Trp Ala Tyr Glu Thr Phe Gly Asp Asp Arg Thr Val Gln Phe Val Ala
                85                  90                  95

Met Ala Thr Pro Glu Asp Leu Glu Ala Asn Ala Glu Tyr Ile Arg Met
            100                 105                 110

Ala Asp Gln Tyr Ile Glu Val Pro Gly Gly Thr Asn Asn Asn Asn Tyr
        115                 120                 125

Ala Asn Val Asp Leu Ile Val Asp Ile Ala Glu Arg Ala Asp Val Asp
```

-continued

```
            130                 135                 140
Ala Val Trp Ala Gly Trp Gly His Ala Ser Glu Asn Pro Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
                180                 185                 190

Ala Gln Ser Ala Lys Val Pro Cys Ile Pro Trp Ser Gly Thr Gly Val
            195                 200                 205

Asp Thr Val His Val Asp Glu Lys Thr Gly Leu Val Ser Val Asp Asp
210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
                260                 265                 270

Ala Leu Tyr His Gln Ala Ala Asn Glu Ile Pro Gly Ser Pro Ile Phe
            275                 280                 285

Ile Met Lys Leu Ala Gly Arg Ala Arg His Leu Glu Val Gln Leu Leu
            290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

Ala Lys Ala Glu Thr Phe His Glu Met Glu Lys Ala Ala Val Arg Leu
                340                 345                 350

Gly Lys Leu Val Gly Tyr Val Ser Ala Gly Thr Val Glu Tyr Leu Tyr
            355                 360                 365

Ser His Asp Asp Gly Lys Phe Tyr Phe Leu Glu Leu Asn Pro Arg Leu
            370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
                405                 410                 415

Asp Ile Arg Thr Leu Tyr Gly Met Asn Pro His Ser Ala Ser Glu Ile
                420                 425                 430

Asp Phe Glu Phe Lys Thr Gln Asp Ala Thr Lys Lys Gln Arg Arg Pro
            435                 440                 445

Ile Pro Lys Gly His Cys Thr Ala Cys Arg Ile Thr Ser Glu Asp Pro
450                 455                 460

Asn Asp Gly Phe Lys Pro Ser Gly Gly Thr Leu His Glu Leu Asn Phe
465                 470                 475                 480

Arg Ser Ser Ser Asn Val Trp Gly Tyr Phe Ser Val Gly Asn Asn Gly
                485                 490                 495

Asn Ile His Ser Phe Ser Asp Ser Gln Phe Gly His Ile Phe Ala Phe
            500                 505                 510

Gly Glu Asn Arg Gln Ala Ser Arg Lys His Met Val Val Ala Leu Lys
            515                 520                 525

Glu Leu Ser Ile Arg Gly Asp Phe Arg Thr Val Glu Tyr Leu Ile
            530                 535                 540

Lys Leu Leu Glu Thr Glu Asp Phe Glu Asp Asn Thr Ile Thr Thr Gly
545                 550                 555                 560
```

```
Trp Leu Asp Asp Leu Ile Thr His Lys Met Thr Ala Glu Lys Pro Asp
                565                 570                 575

Pro Thr Leu Ala Val Ile Cys Gly Ala Ala Thr Lys Ala Phe Leu Ala
            580                 585                 590

Ser Glu Glu Ala Arg His Lys Tyr Ile Glu Ser Leu Gln Lys Gly Gln
        595                 600                 605

Val Leu Ser Lys Asp Leu Leu Gln Thr Met Phe Pro Val Asp Phe Ile
    610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
                645                 650                 655

Gln Leu Ser Asp Gly Gly Leu Leu Ala Ile Gly Lys Ser His
            660                 665                 670

Thr Ile Tyr Trp Lys Glu Val Ala Ala Thr Arg Leu Ser Val Asp
        675                 680                 685

Ser Met Thr Thr Leu Glu Val Glu Asn Asp Pro Thr Gln Leu Arg
    690                 695                 700

Thr Pro Ser Pro Gly Lys Leu Val Lys Phe Leu Val Glu Asn Gly Glu
705                 710                 715                 720

His Ile Ile Lys Gly Gln Pro Tyr Ala Glu Ile Glu Val Met Lys Met
                725                 730                 735

Gln Met Pro Leu Val Ser Gln Glu Asn Gly Ile Val Gln Leu Leu Lys
            740                 745                 750

Gln Pro Gly Ser Thr Ile Val Ala Gly Asp Ile Met Ala Ile Met Thr
        755                 760                 765

Leu Asp Asp Pro Ser Lys Val Lys His Ala Leu Pro Phe Glu Gly Met
    770                 775                 780

Leu Pro Asp Phe Gly Ser Pro Val Ile Glu Gly Thr Lys Pro Ala Tyr
785                 790                 795                 800

Lys Phe Lys Ser Leu Val Ser Thr Leu Glu Asn Ile Leu Lys Gly Tyr
                805                 810                 815

Asp Asn Gln Val Ile Met Asn Ala Ser Leu Gln Gln Leu Ile Glu Val
            820                 825                 830

Leu Arg Asn Pro Lys Leu Pro Tyr Ser Glu Trp Lys Leu His Ile Ser
        835                 840                 845

Ala Leu His Ser Arg Leu Pro Ala Lys Leu Asp Glu Gln Met Glu Glu
    850                 855                 860

Leu Val Ala Arg Ser Leu Arg Arg Gly Ala Val Phe Pro Ala Arg Gln
865                 870                 875                 880

Leu Ser Lys Leu Ile Asp Met Ala Val Lys Asn Pro Glu Tyr Asn Pro
                885                 890                 895

Asp Lys Leu Leu Gly Ala Val Val Glu Pro Leu Ala Asp Ile Ala His
            900                 905                 910

Lys Tyr Ser Asn Gly Leu Glu Ala His Glu His Ser Ile Phe Val His
        915                 920                 925

Phe Leu Glu Glu Tyr Tyr Glu Val Glu Lys Leu Phe Asn Gly Pro Asn
    930                 935                 940

Val Arg Glu Glu Asn Ile Ile Leu Lys Leu Arg Asp Glu Asn Pro Lys
945                 950                 955                 960

Asp Leu Asp Lys Val Ala Leu Thr Val Leu Ser His Ser Lys Val Ser
                965                 970                 975
```

-continued

```
Ala Lys Asn Asn Leu Ile Leu Ala Ile Leu Lys His Tyr Gln Pro Leu
            980             985             990

Cys Lys Leu Ser Ser Lys Val Ser Ala Ile Phe Ser Thr Pro Leu Gln
            995             1000            1005

His Ile Val Glu Leu Glu Ser Lys Ala Thr Ala Lys Val Ala Leu
        1010            1015            1020

Gln Ala Arg Glu Ile Leu Ile Gln Gly Ala Leu Pro Ser Val Lys
        1025            1030            1035

Glu Arg Thr Glu Gln Ile Glu His Ile Leu Lys Ser Ser Val Val
        1040            1045            1050

Lys Val Ala Tyr Gly Ser Ser Asn Pro Lys Arg Ser Glu Pro Asp
        1055            1060            1065

Leu Asn Ile Leu Lys Asp Leu Ile Asp Ser Asn Tyr Val Val Phe
        1070            1075            1080

Asp Val Leu Leu Gln Phe Leu Thr His Gln Asp Pro Val Val Thr
        1085            1090            1095

Ala Ala Ala Ala Gln Val Tyr Ile Arg Arg Ala Tyr Arg Ala Tyr
        1100            1105            1110

Thr Ile Gly Asp Ile Arg Val His Glu Gly Val Thr Val Pro Ile
        1115            1120            1125

Val Glu Trp Lys Phe Gln Leu Pro Ser Ala Ala Phe Ser Thr Phe
        1130            1135            1140

Pro Thr Val Lys Ser Lys Met Gly Met Asn Arg Ala Val Ser Val
        1145            1150            1155

Ser Asp Leu Ser Tyr Val Ala Asn Ser Gln Ser Ser Pro Leu Arg
        1160            1165            1170

Glu Gly Ile Leu Met Ala Val Asp His Leu Asp Asp Val Asp Glu
        1175            1180            1185

Ile Leu Ser Gln Ser Leu Glu Val Ile Pro Arg His Gln Ser Ser
        1190            1195            1200

Ser Asn Gly Pro Ala Pro Asp Arg Ser Gly Ser Ser Ala Ser Leu
        1205            1210            1215

Ser Asn Val Ala Asn Val Cys Val Ala Ser Thr Glu Gly Phe Glu
        1220            1225            1230

Ser Glu Glu Glu Ile Leu Val Arg Leu Arg Glu Ile Leu Asp Leu
        1235            1240            1245

Asn Lys Gln Glu Leu Ile Asn Ala Ser Ile Arg Arg Ile Thr Phe
        1250            1255            1260

Met Phe Gly Phe Lys Asp Gly Ser Tyr Pro Lys Tyr Tyr Thr Phe
        1265            1270            1275

Asn Gly Pro Asn Tyr Asn Glu Asn Glu Thr Ile Arg His Ile Glu
        1280            1285            1290

Pro Ala Leu Ala Phe Gln Leu Glu Leu Gly Arg Leu Ser Asn Phe
        1295            1300            1305

Asn Ile Lys Pro Ile Phe Thr Asp Asn Arg Asn Ile His Val Tyr
        1310            1315            1320

Glu Ala Val Ser Lys Thr Ser Pro Leu Asp Lys Arg Phe Phe Thr
        1325            1330            1335

Arg Gly Ile Ile Arg Thr Gly His Ile Arg Asp Asp Ile Ser Ile
        1340            1345            1350

Gln Glu Tyr Leu Thr Ser Glu Ala Asn Arg Leu Met Ser Asp Ile
        1355            1360            1365

Leu Asp Asn Leu Glu Val Thr Asp Thr Ser Asn Ser Asp Leu Asn
```

```
                   1370             1375             1380
His Ile Phe Ile Asn Phe Ile Ala Val Phe Asp Ile Ser Pro Glu
    1385             1390             1395

Asp Val Glu Ala Ala Phe Gly Gly Phe Leu Glu Arg Phe Gly Lys
    1400             1405             1410

Arg Leu Leu Arg Leu Arg Val Ser Ser Ala Glu Ile Arg Ile Ile
    1415             1420             1425

Ile Lys Asp Pro Gln Thr Gly Ala Pro Val Pro Leu Arg Ala Leu
    1430             1435             1440

Ile Asn Asn Val Ser Gly Tyr Val Ile Lys Thr Glu Met Tyr Thr
    1445             1450             1455

Glu Val Lys Asn Ala Lys Gly Glu Trp Val Phe Lys Ser Leu Gly
    1460             1465             1470

Lys Pro Gly Ser Met His Leu Arg Pro Ile Ala Thr Pro Tyr Pro
    1475             1480             1485

Val Lys Glu Trp Leu Gln Pro Lys Arg Tyr Lys Ala His Leu Met
    1490             1495             1500

Gly Thr Thr Tyr Val Tyr Asp Phe Pro Glu Leu Phe Arg Gln Ala
    1505             1510             1515

Ser Ser Ser Gln Trp Lys Asn Phe Ser Ala Asp Val Lys Leu Thr
    1520             1525             1530

Asp Asp Phe Phe Ile Ser Asn Glu Leu Ile Glu Asp Glu Asn Gly
    1535             1540             1545

Glu Leu Thr Glu Val Glu Arg Glu Pro Gly Ala Asn Ala Ile Gly
    1550             1555             1560

Met Val Ala Phe Lys Ile Thr Val Lys Thr Pro Glu Tyr Pro Arg
    1565             1570             1575

Gly Arg Gln Phe Val Val Ala Asn Asp Ile Thr Phe Lys Ile
    1580             1585             1590

Gly Ser Phe Gly Pro Gln Glu Asp Glu Phe Phe Asn Lys Val Thr
    1595             1600             1605

Glu Tyr Ala Arg Lys Arg Gly Ile Pro Arg Ile Tyr Leu Ala Ala
    1610             1615             1620

Asn Ser Gly Ala Arg Ile Gly Met Ala Glu Glu Ile Val Pro Leu
    1625             1630             1635

Phe Gln Val Ala Trp Asn Asp Ala Ala Asn Pro Asp Lys Gly Phe
    1640             1645             1650

Gln Tyr Leu Tyr Leu Thr Ser Glu Gly Met Glu Thr Leu Lys Lys
    1655             1660             1665

Phe Asp Lys Glu Asn Ser Val Leu Thr Glu Arg Thr Val Ile Asn
    1670             1675             1680

Gly Glu Glu Arg Phe Val Ile Lys Thr Ile Ile Gly Ser Glu Asp
    1685             1690             1695

Gly Leu Gly Val Glu Cys Leu Arg Gly Ser Gly Leu Ile Ala Gly
    1700             1705             1710

Ala Thr Ser Arg Ala Tyr His Asp Ile Phe Thr Ile Thr Leu Val
    1715             1720             1725

Thr Cys Arg Ser Val Gly Ile Gly Ala Tyr Leu Val Arg Leu Gly
    1730             1735             1740

Gln Arg Ala Ile Gln Val Glu Gly Gln Pro Ile Ile Leu Thr Gly
    1745             1750             1755

Ala Pro Ala Ile Asn Lys Met Leu Gly Arg Glu Val Tyr Thr Ser
    1760             1765             1770
```

-continued

Asn Leu Gln Leu Gly Gly Thr Gln Ile Met Tyr Asn Asn Gly Val
    1775                1780                1785

Ser His Leu Thr Ala Val Asp Asp Leu Ala Gly Val Glu Lys Ile
    1790                1795                1800

Val Glu Trp Met Ser Tyr Val Pro Ala Lys Arg Asn Met Pro Val
    1805                1810                1815

Pro Ile Leu Glu Thr Lys Asp Thr Trp Asp Arg Pro Val Asp Phe
    1820                1825                1830

Thr Pro Thr Asn Asp Glu Thr Tyr Asp Val Arg Trp Met Ile Glu
    1835                1840                1845

Gly Arg Glu Thr Glu Ser Gly Phe Glu Tyr Gly Leu Phe Asp Lys
    1850                1855                1860

Gly Ser Phe Phe Glu Thr Leu Ser Gly Trp Ala Lys Gly Val Val
    1865                1870                1875

Val Gly Arg Ala Arg Leu Gly Gly Ile Pro Leu Gly Val Ile Gly
    1880                1885                1890

Val Glu Thr Arg Thr Val Glu Asn Leu Ile Pro Ala Asp Pro Ala
    1895                1900                1905

Asn Pro Asn Ser Ala Glu Thr Leu Ile Gln Glu Pro Gly Gln Val
    1910                1915                1920

Trp His Pro Asn Ser Ala Phe Lys Thr Ala Gln Ala Ile Asn Asp
    1925                1930                1935

Phe Asn Asn Gly Glu Gln Leu Pro Met Met Ile Leu Ala Asn Trp
    1940                1945                1950

Arg Gly Phe Ser Gly Gly Gln Arg Asp Met Phe Asn Glu Val Leu
    1955                1960                1965

Lys Tyr Gly Ser Phe Ile Val Asp Ala Leu Val Asp Tyr Lys Gln
    1970                1975                1980

Pro Ile Ile Ile Tyr Ile Pro Pro Thr Gly Glu Leu Arg Gly Gly
    1985                1990                1995

Ser Trp Val Val Val Asp Pro Thr Ile Asn Ala Asp Gln Met Glu
    2000                2005                2010

Met Tyr Ala Asp Val Asn Ala Arg Ala Gly Val Leu Glu Pro Gln
    2015                2020                2025

Gly Met Val Gly Ile Lys Phe Arg Arg Glu Lys Leu Leu Asp Thr
    2030                2035                2040

Met Asn Arg Leu Asp Asp Lys Tyr Arg Glu Leu Arg Ser Gln Leu
    2045                2050                2055

Ser Asn Lys Ser Leu Ala Pro Glu Val His Gln Gln Ile Ser Lys
    2060                2065                2070

Gln Leu Ala Asp Arg Glu Arg Glu Leu Leu Pro Ile Tyr Gly Gln
    2075                2080                2085

Ile Ser Leu Gln Phe Ala Asp Leu His Asp Arg Ser Ser Arg Met
    2090                2095                2100

Val Ala Lys Gly Val Ile Ser Lys Glu Leu Glu Trp Thr Glu Ala
    2105                2110                2115

Arg Arg Phe Phe Phe Trp Arg Leu Arg Arg Arg Leu Asn Glu Glu
    2120                2125                2130

Tyr Leu Ile Lys Arg Leu Ser His Gln Val Gly Glu Ala Ser Arg
    2135                2140                2145

Leu Glu Lys Ile Ala Arg Ile Arg Ser Trp Tyr Pro Ala Ser Val
    2150                2155                2160

```
Asp His Glu Asp Asp Arg Gln Val Ala Thr Trp Ile Glu Glu Asn
2165                2170                2175

Tyr Lys Thr Leu Asp Asp Lys Leu Lys Gly Leu Lys Leu Glu Ser
2180                2185                2190

Phe Ala Gln Asp Leu Ala Lys Lys Ile Arg Ser Asp His Asp Asn
2195                2200                2205

Ala Ile Asp Gly Leu Ser Glu Val Ile Lys Met Leu Ser Thr Asp
2210                2215                2220

Asp Lys Glu Lys Leu Leu Lys Thr Leu Lys
2225                2230

<210> SEQ ID NO 2
<211> LENGTH: 805
<212> TYPE: PRT
<213> ORGANISM: Saccharomyces cerevisiae

<400> SEQUENCE: 2

Ile Lys Asp Pro Gln Thr Gly Ala Pro Val Pro Leu Arg Ala Leu Ile
1               5                   10                  15

Asn Asn Val Ser Gly Tyr Val Ile Lys Thr Glu Met Tyr Thr Glu Val
                20                  25                  30

Lys Asn Ala Lys Gly Glu Trp Val Phe Lys Ser Leu Gly Lys Pro Gly
            35                  40                  45

Ser Met His Leu Arg Pro Ile Ala Thr Pro Tyr Pro Val Lys Glu Trp
        50                  55                  60

Leu Gln Pro Lys Arg Tyr Lys Ala His Leu Met Gly Thr Thr Tyr Val
65                  70                  75                  80

Tyr Asp Phe Pro Glu Leu Phe Arg Gln Ala Ser Ser Ser Gln Trp Lys
                85                  90                  95

Asn Phe Ser Ala Asp Val Lys Leu Thr Asp Asp Phe Phe Ile Ser Asn
            100                 105                 110

Glu Leu Ile Glu Asp Glu Asn Gly Glu Leu Thr Glu Val Glu Arg Glu
        115                 120                 125

Pro Gly Ala Asn Ala Ile Gly Met Val Ala Phe Lys Ile Thr Val Lys
    130                 135                 140

Thr Pro Glu Tyr Pro Arg Gly Arg Gln Phe Val Val Ala Asn Asp
145                 150                 155                 160

Ile Thr Phe Lys Ile Gly Ser Phe Gly Pro Gln Glu Asp Glu Phe Phe
                165                 170                 175

Asn Lys Val Thr Glu Tyr Ala Arg Lys Arg Gly Ile Pro Arg Ile Tyr
            180                 185                 190

Leu Ala Ala Asn Ser Gly Ala Arg Ile Gly Met Ala Glu Glu Ile Val
        195                 200                 205

Pro Leu Phe Gln Val Ala Trp Asn Asp Ala Ala Asn Pro Asp Lys Gly
    210                 215                 220

Phe Gln Tyr Leu Tyr Leu Thr Ser Glu Gly Met Glu Thr Leu Lys Lys
225                 230                 235                 240

Phe Asp Lys Glu Asn Ser Val Leu Thr Glu Arg Thr Val Ile Asn Gly
                245                 250                 255

Glu Glu Arg Phe Val Ile Lys Thr Ile Ile Gly Ser Glu Asp Gly Leu
            260                 265                 270

Gly Val Glu Cys Leu Arg Gly Ser Gly Leu Ile Ala Gly Ala Thr Ser
        275                 280                 285

Arg Ala Tyr His Asp Ile Phe Thr Ile Thr Leu Val Thr Cys Arg Ser
    290                 295                 300
```

```
Val Gly Ile Gly Ala Tyr Leu Val Arg Leu Gly Gln Arg Ala Ile Gln
305                 310                 315                 320

Val Glu Gly Gln Pro Ile Ile Leu Thr Gly Ala Pro Ala Ile Asn Lys
                325                 330                 335

Met Leu Gly Arg Glu Val Tyr Thr Ser Asn Leu Gln Leu Gly Gly Thr
                340                 345                 350

Gln Ile Met Tyr Asn Asn Gly Val Ser His Leu Thr Ala Val Asp Asp
                355                 360                 365

Leu Ala Gly Val Glu Lys Ile Val Glu Trp Met Ser Tyr Val Pro Ala
                370                 375                 380

Lys Arg Asn Met Pro Val Pro Ile Leu Glu Thr Lys Asp Thr Trp Asp
385                 390                 395                 400

Arg Pro Val Asp Phe Thr Pro Thr Asn Asp Glu Thr Tyr Asp Val Arg
                405                 410                 415

Trp Met Ile Glu Gly Arg Glu Thr Glu Ser Gly Phe Glu Tyr Gly Leu
                420                 425                 430

Phe Asp Lys Gly Ser Phe Phe Glu Thr Leu Ser Gly Trp Ala Lys Gly
                435                 440                 445

Val Val Val Gly Arg Ala Arg Leu Gly Gly Ile Pro Leu Gly Val Ile
                450                 455                 460

Gly Val Glu Thr Arg Thr Val Glu Asn Leu Ile Pro Ala Asp Pro Ala
465                 470                 475                 480

Asn Pro Asn Ser Ala Glu Thr Leu Ile Gln Glu Pro Gly Gln Val Trp
                485                 490                 495

His Pro Asn Ser Ala Phe Lys Thr Ala Gln Ala Ile Asn Asp Phe Asn
                500                 505                 510

Asn Gly Glu Gln Leu Pro Met Met Ile Leu Ala Asn Trp Arg Gly Phe
                515                 520                 525

Ser Gly Gly Gln Arg Asp Met Phe Asn Glu Val Leu Lys Tyr Gly Ser
                530                 535                 540

Phe Ile Val Asp Ala Leu Val Asp Tyr Lys Gln Pro Ile Ile Ile Tyr
545                 550                 555                 560

Ile Pro Pro Thr Gly Glu Leu Arg Gly Gly Ser Trp Val Val Val Asp
                565                 570                 575

Pro Thr Ile Asn Ala Asp Gln Met Glu Met Tyr Ala Asp Val Asn Ala
                580                 585                 590

Arg Ala Gly Val Leu Glu Pro Gln Gly Met Val Gly Ile Lys Phe Arg
                595                 600                 605

Arg Glu Lys Leu Leu Asp Thr Met Asn Arg Leu Asp Asp Lys Tyr Arg
                610                 615                 620

Glu Leu Arg Ser Gln Leu Ser Asn Lys Ser Leu Ala Pro Glu Val His
625                 630                 635                 640

Gln Gln Ile Ser Lys Gln Leu Ala Asp Arg Glu Arg Glu Leu Leu Pro
                645                 650                 655

Ile Tyr Gly Gln Ile Ser Leu Gln Phe Ala Asp Leu His Asp Arg Ser
                660                 665                 670

Ser Arg Met Val Ala Lys Gly Val Ile Ser Lys Glu Leu Glu Trp Thr
                675                 680                 685

Glu Ala Arg Arg Phe Phe Phe Trp Arg Leu Arg Arg Arg Leu Asn Glu
                690                 695                 700

Glu Tyr Leu Ile Lys Arg Leu Ser His Gln Val Gly Glu Ala Ser Arg
705                 710                 715                 720
```

```
Leu Glu Lys Ile Ala Arg Ile Arg Ser Trp Tyr Pro Ala Ser Val Asp
            725                 730                 735

His Glu Asp Asp Arg Gln Val Ala Thr Trp Ile Glu Glu Asn Tyr Lys
        740                 745                 750

Thr Leu Asp Asp Lys Leu Lys Gly Leu Lys Leu Glu Ser Phe Ala Gln
            755                 760                 765

Asp Leu Ala Lys Lys Ile Arg Ser Asp His Asp Asn Ala Ile Asp Gly
        770                 775                 780

Leu Ser Glu Val Ile Lys Met Leu Ser Thr Asp Lys Glu Lys Leu
785                 790                 795                 800

Leu Lys Thr Leu Lys
            805

<210> SEQ ID NO 3
<211> LENGTH: 758
<212> TYPE: PRT
<213> ORGANISM: Saccharomyces cerevisiae

<400> SEQUENCE: 3

Gly Ser Met His Leu Arg Pro Ile Ala Thr Pro Tyr Pro Val Lys Glu
1               5                   10                  15

Trp Leu Gln Pro Lys Arg Tyr Lys Ala His Leu Met Gly Thr Thr Tyr
            20                  25                  30

Val Tyr Asp Phe Pro Glu Leu Phe Arg Gln Ala Ser Ser Ser Gln Trp
        35                  40                  45

Lys Asn Phe Ser Ala Asp Val Lys Leu Thr Asp Phe Phe Ile Ser
    50                  55                  60

Asn Glu Leu Ile Glu Asp Glu Asn Gly Glu Leu Thr Glu Val Glu Arg
65                  70                  75                  80

Glu Pro Gly Ala Asn Ala Ile Gly Met Val Ala Phe Lys Ile Thr Val
                85                  90                  95

Lys Thr Pro Glu Tyr Pro Arg Gly Arg Gln Phe Val Val Val Ala Asn
            100                 105                 110

Asp Ile Thr Phe Lys Ile Gly Ser Phe Gly Pro Gln Glu Asp Glu Phe
        115                 120                 125

Phe Asn Lys Val Thr Glu Tyr Ala Arg Lys Arg Gly Ile Pro Arg Ile
    130                 135                 140

Tyr Leu Ala Ala Asn Ser Gly Ala Arg Ile Gly Met Ala Glu Glu Ile
145                 150                 155                 160

Val Pro Leu Phe Gln Val Ala Trp Asn Asp Ala Ala Asn Pro Asp Lys
                165                 170                 175

Gly Phe Gln Tyr Leu Tyr Leu Thr Ser Glu Gly Met Glu Thr Leu Lys
            180                 185                 190

Lys Phe Asp Lys Glu Asn Ser Val Leu Thr Glu Arg Thr Val Ile Asn
        195                 200                 205

Gly Glu Glu Arg Phe Val Ile Lys Thr Ile Ile Gly Ser Glu Asp Gly
    210                 215                 220

Leu Gly Val Glu Cys Leu Arg Gly Ser Gly Leu Ile Ala Gly Ala Thr
225                 230                 235                 240

Ser Arg Ala Tyr His Asp Ile Phe Thr Ile Thr Leu Val Thr Cys Arg
                245                 250                 255

Ser Val Gly Ile Gly Ala Tyr Leu Val Arg Leu Gly Gln Arg Ala Ile
            260                 265                 270

Gln Val Glu Gly Gln Pro Ile Ile Leu Thr Gly Ala Pro Ala Ile Asn
        275                 280                 285
```

```
Lys Met Leu Gly Arg Glu Val Tyr Thr Ser Asn Leu Gln Leu Gly Gly
    290                 295                 300

Thr Gln Ile Met Tyr Asn Asn Gly Val Ser His Leu Thr Ala Val Asp
305                 310                 315                 320

Asp Leu Ala Gly Val Glu Lys Ile Val Glu Trp Met Ser Tyr Val Pro
                325                 330                 335

Ala Lys Arg Asn Met Pro Val Pro Ile Leu Glu Thr Lys Asp Thr Trp
                340                 345                 350

Asp Arg Pro Val Asp Phe Thr Pro Thr Asn Asp Glu Thr Tyr Asp Val
            355                 360                 365

Arg Trp Met Ile Glu Gly Arg Glu Thr Glu Ser Gly Phe Glu Tyr Gly
        370                 375                 380

Leu Phe Asp Lys Gly Ser Phe Phe Glu Thr Leu Ser Gly Trp Ala Lys
385                 390                 395                 400

Gly Val Val Val Gly Arg Ala Arg Leu Gly Gly Ile Pro Leu Gly Val
                405                 410                 415

Ile Gly Val Glu Thr Arg Thr Val Glu Asn Leu Ile Pro Ala Asp Pro
            420                 425                 430

Ala Asn Pro Asn Ser Ala Glu Thr Leu Ile Gln Glu Pro Gly Gln Val
        435                 440                 445

Trp His Pro Asn Ser Ala Phe Lys Thr Ala Gln Ala Ile Asn Asp Phe
    450                 455                 460

Asn Asn Gly Glu Gln Leu Pro Met Met Ile Leu Ala Asn Trp Arg Gly
465                 470                 475                 480

Phe Ser Gly Gly Gln Arg Asp Met Phe Asn Glu Val Leu Lys Tyr Gly
                485                 490                 495

Ser Phe Ile Val Asp Ala Leu Val Asp Tyr Lys Gln Pro Ile Ile Ile
            500                 505                 510

Tyr Ile Pro Pro Thr Gly Glu Leu Arg Gly Gly Ser Trp Val Val Val
        515                 520                 525

Asp Pro Thr Ile Asn Ala Asp Gln Met Glu Met Tyr Ala Asp Val Asn
    530                 535                 540

Ala Arg Ala Gly Val Leu Glu Pro Gln Gly Met Val Gly Ile Lys Phe
545                 550                 555                 560

Arg Arg Glu Lys Leu Leu Asp Thr Met Asn Arg Leu Asp Asp Lys Tyr
                565                 570                 575

Arg Glu Leu Arg Ser Gln Leu Ser Asn Lys Ser Leu Ala Pro Glu Val
            580                 585                 590

His Gln Gln Ile Ser Lys Gln Leu Ala Asp Arg Glu Arg Glu Leu Leu
        595                 600                 605

Pro Ile Tyr Gly Gln Ile Ser Leu Gln Phe Ala Asp Leu His Asp Arg
    610                 615                 620

Ser Ser Arg Met Val Ala Lys Gly Val Ile Ser Lys Glu Leu Glu Trp
625                 630                 635                 640

Thr Glu Ala Arg Arg Phe Phe Phe Trp Arg Leu Arg Arg Arg Leu Asn
                645                 650                 655

Glu Glu Tyr Leu Ile Lys Arg Leu Ser His Gln Val Gly Glu Ala Ser
            660                 665                 670

Arg Leu Glu Lys Ile Ala Arg Ile Arg Ser Trp Tyr Pro Ala Ser Val
        675                 680                 685

Asp His Glu Asp Asp Arg Gln Val Ala Thr Trp Ile Glu Glu Asn Tyr
    690                 695                 700
```

```
Lys Thr Leu Asp Asp Lys Leu Lys Gly Leu Lys Leu Glu Ser Phe Ala
705                 710                 715                 720

Gln Asp Leu Ala Lys Lys Ile Arg Ser Asp His Asp Asn Ala Ile Asp
                725                 730                 735

Gly Leu Ser Glu Val Ile Lys Met Leu Ser Thr Asp Lys Glu Lys
            740                 745                 750

Leu Leu Lys Thr Leu Lys
        755

<210> SEQ ID NO 4
<211> LENGTH: 758
<212> TYPE: PRT
<213> ORGANISM: Saccharomyces cerevisiae

<400> SEQUENCE: 4

Gly Ser Met His Leu Arg Pro Ile Ala Thr Pro Tyr Pro Val Lys Glu
1               5                   10                  15

Trp Leu Gln Pro Lys Arg Tyr Lys Ala His Leu Met Gly Thr Thr Tyr
            20                  25                  30

Val Tyr Asp Phe Pro Glu Leu Phe Arg Gln Ala Ser Ser Ser Gln Trp
        35                  40                  45

Lys Asn Phe Ser Ala Asp Val Lys Leu Thr Asp Phe Phe Ile Ser
    50                  55                  60

Asn Glu Leu Ile Glu Asp Glu Asn Gly Glu Leu Thr Glu Val Glu Arg
65                  70                  75                  80

Glu Pro Gly Ala Asn Ala Ile Gly Met Val Ala Phe Lys Ile Thr Val
                85                  90                  95

Lys Thr Pro Glu Tyr Pro Arg Gly Arg Gln Phe Val Val Val Ala Asn
            100                 105                 110

Asp Ile Thr Phe Lys Ile Gly Ser Phe Gly Pro Gln Glu Asp Glu Phe
        115                 120                 125

Phe Asn Lys Val Thr Glu Tyr Ala Arg Lys Arg Gly Ile Pro Arg Ile
    130                 135                 140

Tyr Leu Ala Ala Asn Ser Gly Ala Arg Ile Gly Met Ala Glu Glu Ile
145                 150                 155                 160

Val Pro Leu Phe Gln Val Ala Trp Asn Asp Ala Ala Asn Pro Asp Lys
                165                 170                 175

Gly Phe Gln Tyr Leu Tyr Leu Thr Ser Glu Gly Met Glu Thr Leu Lys
            180                 185                 190

Lys Phe Asp Lys Glu Asn Ser Val Leu Thr Glu Arg Thr Val Ile Asn
        195                 200                 205

Gly Glu Glu Arg Phe Val Ile Lys Thr Ile Gly Ser Glu Asp Gly
    210                 215                 220

Leu Gly Val Glu Cys Ile Arg Gly Ser Gly Leu Ile Ala Gly Ala Thr
225                 230                 235                 240

Ser Arg Ala Tyr His Asp Ile Phe Thr Ile Thr Leu Val Thr Cys Arg
                245                 250                 255

Ser Val Gly Ile Gly Ala Tyr Leu Val Arg Leu Gly Gln Arg Ala Ile
            260                 265                 270

Gln Val Glu Gly Gln Pro Ile Ile Leu Thr Gly Ala Pro Ala Ile Asn
        275                 280                 285

Lys Met Leu Gly Arg Glu Val Tyr Thr Ser Asn Leu Gln Leu Gly Gly
    290                 295                 300

Thr Gln Ile Met Tyr Asn Asn Gly Val Ser His Leu Thr Ala Val Asp
305                 310                 315                 320
```

-continued

```
Asp Leu Ala Gly Val Glu Lys Ile Val Glu Trp Met Ser Tyr Val Pro
                325                 330                 335

Ala Lys Arg Asn Met Pro Val Pro Ile Leu Glu Thr Lys Asp Thr Trp
            340                 345                 350

Asp Arg Pro Val Asp Phe Thr Pro Thr Asn Asp Glu Thr Tyr Asp Val
        355                 360                 365

Arg Trp Met Ile Glu Gly Arg Glu Thr Glu Ser Gly Phe Glu Tyr Gly
    370                 375                 380

Leu Phe Asp Lys Gly Ser Phe Phe Glu Thr Leu Ser Gly Trp Ala Lys
385                 390                 395                 400

Gly Val Val Val Gly Arg Ala Arg Leu Gly Gly Ile Pro Leu Gly Val
                405                 410                 415

Ile Gly Val Glu Thr Arg Thr Val Glu Asn Leu Ile Pro Ala Asp Pro
            420                 425                 430

Ala Asn Pro Asn Ser Ala Glu Thr Leu Ile Gln Glu Pro Gly Gln Val
        435                 440                 445

Trp His Pro Asn Ser Ala Phe Lys Thr Ala Gln Ala Ile Asn Asp Phe
    450                 455                 460

Asn Asn Gly Glu Gln Leu Pro Met Met Ile Leu Ala Asn Trp Arg Gly
465                 470                 475                 480

Phe Ser Gly Gly Gln Arg Asp Met Phe Asn Glu Ile Leu Lys Tyr Gly
                485                 490                 495

Ser Phe Ile Val Asp Ala Leu Val Asp Tyr Lys Gln Pro Ile Ile Ile
            500                 505                 510

Tyr Ile Pro Pro Thr Gly Glu Leu Arg Gly Gly Ser Trp Val Val Val
        515                 520                 525

Asp Pro Thr Ile Asn Ala Asp Gln Met Glu Met Tyr Ala Asp Val Asn
    530                 535                 540

Ala Arg Ala Gly Val Leu Glu Pro Gln Gly Met Val Gly Ile Lys Phe
545                 550                 555                 560

Arg Arg Glu Lys Leu Leu Asp Thr Met Asn Arg Leu Asp Asp Lys Tyr
                565                 570                 575

Arg Glu Leu Arg Ser Gln Leu Ser Asn Lys Ser Leu Ala Pro Glu Val
            580                 585                 590

His Gln Gln Ile Ser Lys Gln Leu Ala Asp Arg Glu Arg Glu Leu Leu
        595                 600                 605

Pro Ile Tyr Gly Gln Ile Ser Leu Gln Phe Ala Asp Leu His Asp Arg
    610                 615                 620

Ser Ser Arg Met Val Ala Lys Gly Val Ile Ser Lys Glu Leu Glu Trp
625                 630                 635                 640

Thr Glu Ala Arg Arg Phe Phe Phe Trp Arg Leu Arg Arg Arg Leu Asn
                645                 650                 655

Glu Glu Tyr Leu Ile Lys Arg Leu Ser His Gln Val Gly Glu Ala Ser
            660                 665                 670

Arg Leu Glu Lys Ile Ala Arg Ile Arg Ser Trp Tyr Pro Ala Ser Val
        675                 680                 685

Asp His Glu Asp Arg Gln Val Ala Thr Trp Ile Glu Glu Asn Tyr
    690                 695                 700

Lys Thr Leu Asp Asp Lys Leu Lys Gly Leu Lys Leu Glu Ser Phe Ala
705                 710                 715                 720

Gln Asp Leu Ala Lys Lys Ile Arg Ser Asp His Asp Asn Ala Ile Asp
                725                 730                 735
```

```
Gly Leu Ser Glu Val Ile Lys Met Leu Ser Thr Asp Lys Glu Lys
            740                 745                 750
Leu Leu Lys Thr Leu Lys
        755
```

<210> SEQ ID NO 5
<211> LENGTH: 810
<212> TYPE: PRT
<213> ORGANISM: Mus musculus

<400> SEQUENCE: 5

```
Leu Phe Ile Thr Asn Glu Ser Gly Tyr Tyr Leu Asp Ile Ser Leu Tyr
1               5                   10                  15

Arg Glu Val Thr Asp Ser Arg Ser Gly Asn Ile Met Phe His Ser Phe
            20                  25                  30

Gly Asn Lys Gln Gly Ser Leu His Gly Met Leu Ile Asn Thr Pro Tyr
        35                  40                  45

Val Thr Lys Asp Leu Leu Gln Ala Lys Arg Phe Gln Ala Gln Ser Leu
    50                  55                  60

Gly Thr Thr Tyr Val Tyr Asp Phe Pro Glu Met Phe Arg Gln Ala Leu
65                  70                  75                  80

Phe Lys Leu Trp Gly Ser Pro Glu Lys Tyr Pro Lys Asp Ile Leu Thr
                85                  90                  95

Tyr Thr Glu Leu Val Leu Asp Ser Gln Gly Gln Leu Val Glu Met Asn
            100                 105                 110

Arg Leu Pro Gly Cys Asn Glu Val Gly Met Val Ala Phe Lys Met Arg
        115                 120                 125

Phe Lys Thr Pro Glu Tyr Pro Glu Gly Arg Asp Ala Val Val Ile Gly
    130                 135                 140

Asn Asp Ile Thr Phe Gln Ile Gly Ser Phe Gly Ile Gly Glu Asp Phe
145                 150                 155                 160

Leu Tyr Leu Arg Ala Ser Glu Met Ala Arg Thr Glu Gly Ile Pro Gln
                165                 170                 175

Ile Tyr Leu Ala Ala Asn Ser Gly Ala Arg Met Gly Leu Ala Glu Glu
            180                 185                 190

Ile Lys Gln Ile Phe Gln Val Ala Trp Val Asp Pro Glu Asp Pro His
        195                 200                 205

Lys Gly Phe Arg Tyr Leu Tyr Leu Thr Pro Gln Asp Tyr Thr Gln Ile
    210                 215                 220

Ser Ser Gln Asn Ser Val His Cys Lys His Ile Glu Asp Glu Gly Glu
225                 230                 235                 240

Ser Arg Tyr Val Ile Val Asp Val Ile Gly Lys Asp Ala Asn Leu Gly
                245                 250                 255

Val Glu Asn Leu Arg Gly Ser Gly Met Ile Ala Gly Glu Ala Ser Leu
            260                 265                 270

Ala Tyr Glu Lys Thr Val Thr Ile Ser Met Val Thr Cys Arg Ala Leu
        275                 280                 285

Gly Ile Gly Ala Tyr Leu Val Arg Leu Gly Gln Arg Val Ile Gln Val
    290                 295                 300

Glu Asn Ser His Ile Ile Leu Thr Gly Ala Gly Ala Leu Asn Lys Val
305                 310                 315                 320

Leu Gly Arg Glu Val Tyr Thr Ser Asn Asn Gln Leu Gly Gly Val Gln
                325                 330                 335

Ile Met His Thr Asn Gly Val Ser His Val Thr Val Pro Asp Asp Phe
            340                 345                 350
```

```
Glu Gly Val Cys Thr Ile Leu Glu Trp Leu Ser Phe Ile Pro Lys Asp
            355                 360                 365
Asn Arg Ser Pro Val Pro Ile Thr Thr Pro Ser Asp Pro Ile Asp Arg
        370                 375                 380
Glu Ile Glu Phe Thr Pro Thr Lys Ala Pro Tyr Asp Pro Arg Trp Met
385                 390                 395                 400
Leu Ala Gly Arg Pro His Pro Thr Leu Lys Gly Thr Trp Gln Ser Gly
                405                 410                 415
Phe Phe Asp His Gly Ser Phe Lys Glu Ile Met Ala Pro Trp Ala Gln
            420                 425                 430
Thr Val Val Thr Gly Arg Ala Arg Leu Gly Gly Ile Pro Val Gly Val
            435                 440                 445
Ile Ala Val Glu Thr Arg Thr Val Glu Val Ala Val Pro Ala Asp Pro
        450                 455                 460
Ala Asn Leu Asp Ser Glu Ala Lys Ile Ile Gln Gln Ala Gly Gln Val
465                 470                 475                 480
Trp Phe Pro Asp Ser Ala Tyr Lys Thr Ala Gln Val Ile Arg Asp Phe
                485                 490                 495
Asn Lys Glu Arg Leu Pro Leu Met Ile Phe Ala Asn Trp Arg Gly Phe
            500                 505                 510
Ser Gly Gly Met Lys Asp Met Tyr Glu Gln Met Leu Lys Phe Gly Ala
            515                 520                 525
Tyr Ile Val Asp Gly Leu Arg Leu Tyr Glu Gln Pro Ile Leu Ile Tyr
        530                 535                 540
Ile Pro Pro Cys Ala Glu Leu Arg Gly Gly Ser Trp Val Val Leu Asp
545                 550                 555                 560
Ser Thr Ile Asn Pro Leu Cys Ile Glu Met Tyr Ala Asp Lys Glu Ser
                565                 570                 575
Arg Gly Gly Val Leu Glu Pro Glu Gly Thr Val Glu Ile Lys Phe Arg
            580                 585                 590
Lys Lys Asp Leu Val Lys Thr Ile Arg Arg Ile Asp Pro Val Cys Lys
            595                 600                 605
Lys Leu Val Gly Gln Leu Gly Lys Ala Gln Leu Pro Asp Lys Asp Arg
        610                 615                 620
Lys Glu Leu Glu Gly Gln Leu Lys Ala Arg Glu Glu Leu Leu Leu Pro
625                 630                 635                 640
Ile Tyr His Gln Val Ala Val Gln Phe Ala Asp Leu His Asp Thr Pro
                645                 650                 655
Gly His Met Leu Glu Lys Gly Ile Ile Ser Asp Val Leu Glu Trp Lys
            660                 665                 670
Thr Ala Arg Thr Phe Phe Tyr Trp Arg Leu Arg Arg Leu Leu Leu Glu
            675                 680                 685
Ala Gln Val Lys Gln Glu Ile Leu Arg Ala Ser Pro Glu Leu Asn His
        690                 695                 700
Glu His Thr Gln Ser Met Leu Arg Arg Trp Phe Val Glu Thr Glu Gly
705                 710                 715                 720
Ala Val Lys Ala Tyr Leu Trp Asp Ser Asn Gln Val Val Gln Trp
                725                 730                 735
Leu Glu Gln His Trp Ser Ala Lys Asp Gly Leu Arg Ser Asn Ile Arg
            740                 745                 750
Glu Asn Ile Asn Tyr Leu Lys Arg Asp Ser Val Leu Lys Thr Ile Gln
            755                 760                 765
```

```
Ser Leu Val Gln Glu His Pro Glu Val Ile Met Asp Cys Val Ala Tyr
    770                 775                 780

Leu Ser Gln His Leu Thr Pro Ala Glu Arg Ile Gln Val Ala Gln Leu
785                 790                 795                 800

Leu Ser Thr Thr Glu Ser Pro Ala Ser Ser
            805                 810

<210> SEQ ID NO 6
<211> LENGTH: 733
<212> TYPE: PRT
<213> ORGANISM: Mus musculus

<400> SEQUENCE: 6

Lys Gln Gly Ser Leu His Gly Met Leu Ile Asn Thr Pro Tyr Val Thr
1               5                   10                  15

Lys Asp Leu Leu Gln Ala Lys Arg Phe Gln Ala Gln Ser Leu Gly Thr
            20                  25                  30

Thr Tyr Val Tyr Asp Phe Pro Glu Met Phe Arg Gln Ala Leu Phe Lys
        35                  40                  45

Leu Trp Gly Ser Pro Glu Lys Tyr Pro Lys Asp Ile Leu Thr Tyr Thr
50                  55                  60

Glu Leu Val Leu Asp Ser Gln Gly Gln Leu Val Glu Met Asn Arg Leu
65                  70                  75                  80

Pro Gly Cys Asn Glu Val Gly Met Val Ala Phe Lys Met Arg Phe Lys
                85                  90                  95

Thr Pro Glu Tyr Pro Glu Gly Arg Asp Ala Val Val Ile Gly Asn Asp
            100                 105                 110

Ile Thr Phe Gln Ile Gly Ser Phe Gly Ile Gly Glu Asp Phe Leu Tyr
        115                 120                 125

Leu Arg Ala Ser Glu Met Ala Arg Thr Glu Gly Ile Pro Gln Ile Tyr
130                 135                 140

Leu Ala Ala Asn Ser Gly Ala Arg Met Gly Leu Ala Glu Glu Ile Lys
145                 150                 155                 160

Gln Ile Phe Gln Val Ala Trp Val Asp Pro Glu Asp Pro His Lys Gly
                165                 170                 175

Phe Arg Tyr Leu Tyr Leu Thr Pro Gln Asp Tyr Thr Gln Ile Ser Ser
            180                 185                 190

Gln Asn Ser Val His Cys Lys His Ile Glu Asp Glu Gly Glu Ser Arg
        195                 200                 205

Tyr Val Ile Val Asp Val Ile Gly Lys Asp Ala Asn Leu Gly Val Glu
210                 215                 220

Asn Leu Arg Gly Ser Gly Met Ile Ala Gly Glu Ala Ser Leu Ala Tyr
225                 230                 235                 240

Glu Lys Thr Val Thr Ile Ser Met Val Thr Cys Arg Ala Leu Gly Ile
                245                 250                 255

Gly Ala Tyr Leu Val Arg Leu Gly Gln Arg Val Ile Gln Val Glu Asn
            260                 265                 270

Ser His Ile Ile Leu Thr Gly Ala Gly Ala Leu Asn Lys Val Leu Gly
        275                 280                 285

Arg Glu Val Tyr Thr Ser Asn Asn Gln Leu Gly Gly Val Gln Ile Met
290                 295                 300

His Thr Asn Gly Val Ser His Val Thr Val Pro Asp Asp Phe Glu Gly
305                 310                 315                 320

Val Cys Thr Ile Leu Glu Trp Leu Ser Phe Ile Pro Lys Asp Asn Arg
                325                 330                 335
```

-continued

```
Ser Pro Val Pro Ile Thr Thr Pro Ser Asp Pro Ile Asp Arg Glu Ile
            340                 345                 350

Glu Phe Thr Pro Thr Lys Ala Pro Tyr Asp Pro Arg Trp Met Leu Ala
        355                 360                 365

Gly Arg Pro His Pro Thr Leu Lys Gly Thr Trp Gln Ser Gly Phe Phe
    370                 375                 380

Asp His Gly Ser Phe Lys Glu Ile Met Ala Pro Trp Ala Gln Thr Val
385                 390                 395                 400

Val Thr Gly Arg Ala Arg Leu Gly Gly Ile Pro Val Gly Val Ile Ala
                405                 410                 415

Val Glu Thr Arg Thr Val Glu Val Ala Val Pro Ala Asp Pro Ala Asn
            420                 425                 430

Leu Asp Ser Glu Ala Lys Ile Ile Gln Gln Ala Gly Gln Val Trp Phe
        435                 440                 445

Pro Asp Ser Ala Tyr Lys Thr Ala Gln Val Ile Arg Asp Phe Asn Lys
    450                 455                 460

Glu Arg Leu Pro Leu Met Ile Phe Ala Asn Trp Arg Gly Phe Ser Gly
465                 470                 475                 480

Gly Met Lys Asp Met Tyr Glu Gln Met Leu Lys Phe Gly Ala Tyr Ile
                485                 490                 495

Val Asp Gly Leu Arg Leu Tyr Glu Gln Pro Ile Leu Ile Tyr Ile Pro
            500                 505                 510

Pro Cys Ala Glu Leu Arg Gly Gly Ser Trp Val Val Leu Asp Ser Thr
        515                 520                 525

Ile Asn Pro Leu Cys Ile Glu Met Tyr Ala Asp Lys Glu Ser Arg Gly
    530                 535                 540

Gly Val Leu Glu Pro Glu Gly Thr Val Glu Ile Lys Phe Arg Lys Lys
545                 550                 555                 560

Asp Leu Val Lys Thr Ile Arg Arg Ile Asp Pro Val Cys Lys Lys Leu
                565                 570                 575

Val Gly Gln Leu Gly Lys Ala Gln Leu Pro Asp Lys Asp Arg Lys Glu
            580                 585                 590

Leu Glu Gly Gln Leu Lys Ala Arg Glu Glu Leu Leu Leu Pro Ile Tyr
        595                 600                 605

His Gln Val Ala Val Gln Phe Ala Asp Leu His Asp Thr Pro Gly His
    610                 615                 620

Met Leu Glu Lys Gly Ile Ile Ser Asp Val Leu Glu Trp Lys Thr Ala
625                 630                 635                 640

Arg Thr Phe Phe Tyr Trp Arg Leu Arg Arg Leu Leu Leu Glu Ala Gln
                645                 650                 655

Val Lys Gln Glu Ile Leu Arg Ala Ser Pro Glu Leu Asn His Glu His
            660                 665                 670

Thr Gln Ser Met Leu Arg Arg Trp Phe Val Glu Thr Glu Gly Ala Val
        675                 680                 685

Lys Ala Tyr Leu Trp Asp Ser Asn Gln Val Val Gln Trp Leu Glu
    690                 695                 700

Gln His Trp Ser Ala Lys Asp Gly Leu Arg Ser Asn Ile Arg Glu Asn
705                 710                 715                 720

Ile Asn Tyr Leu Lys Arg Asp Ser Val Leu Lys Thr Ile
                725                 730
```

<210> SEQ ID NO 7
<211> LENGTH: 2346

```
<212> TYPE: PRT
<213> ORGANISM: Homo sapiens

<400> SEQUENCE: 7

Met Asp Glu Pro Ser Pro Leu Ala Gln Pro Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Leu Glu Glu Lys Glu Gly Ser
        35                  40                  45

Leu Ser Pro Ala Ser Val Gly Ser Asp Thr Leu Ser Asp Leu Gly Ile
    50                  55                  60

Ser Ser Leu Gln Asp Gly Leu Ala Leu His Ile Arg Ser Ser Met Ser
65                  70                  75                  80

Gly Leu His Leu Val Lys Gln Gly Arg Asp Arg Lys Lys Ile Asp Ser
                85                  90                  95

Gln Arg Asp Phe Thr Val Ala Ser Pro Ala Glu Phe Val Thr Arg Phe
            100                 105                 110

Gly Gly Asn Lys Val Ile Glu Lys Val Leu Ile Ala Asn Asn Gly Ile
        115                 120                 125

Ala Ala Val Lys Cys Met Arg Ser Ile Arg Arg Trp Ser Tyr Glu Met
130                 135                 140

Phe Arg Asn Glu Arg Ala Ile Arg Phe Val Val Met Val Thr Pro Glu
145                 150                 155                 160

Asp Leu Lys Ala Asn Ala Glu Tyr Ile Lys Met Ala Asp His Tyr Val
                165                 170                 175

Pro Val Pro Gly Gly Pro Asn Asn Asn Tyr Ala Asn Val Glu Leu
            180                 185                 190

Ile Leu Asp Ile Ala Lys Arg Ile Pro Val Gln Ala Val Trp Ala Gly
        195                 200                 205

Trp Gly His Ala Ser Glu Asn Pro Lys Leu Pro Glu Leu Leu Leu Lys
    210                 215                 220

Asn Gly Ile Ala Phe Met Gly Pro Pro Ser Gln Ala Met Trp Ala Leu
225                 230                 235                 240

Gly Asp Lys Ile Ala Ser Ser Ile Val Ala Gln Thr Ala Gly Ile Pro
                245                 250                 255

Thr Leu Pro Trp Ser Gly Ser Gly Leu Arg Val Asp Trp Gln Glu Asn
            260                 265                 270

Asp Phe Ser Lys Arg Ile Leu Asn Val Pro Gln Glu Leu Tyr Glu Lys
        275                 280                 285

Gly Tyr Val Lys Asp Val Asp Asp Gly Leu Gln Ala Ala Glu Glu Val
    290                 295                 300

Gly Tyr Pro Val Met Ile Lys Ala Ser Glu Gly Gly Gly Lys Gly
305                 310                 315                 320

Ile Arg Lys Val Asn Asn Ala Asp Asp Phe Pro Asn Leu Phe Arg Gln
                325                 330                 335

Val Gln Ala Glu Val Pro Gly Ser Pro Ile Phe Val Met Arg Leu Ala
            340                 345                 350

Lys Gln Ser Arg His Leu Glu Val Gln Ile Leu Val Asp Gln Tyr Gly
        355                 360                 365

Asn Ala Ile Ser Leu Phe Gly Arg Asp Cys Ser Val Gln Arg Arg His
    370                 375                 380

Gln Lys Ile Ile Glu Glu Ala Pro Ala Thr Ile Ala Thr Pro Ala Val
385                 390                 395                 400
```

```
Phe Glu His Met Glu Gln Cys Ala Val Lys Leu Ala Lys Met Val Gly
                405                 410                 415
Tyr Val Ser Ala Gly Thr Val Glu Tyr Leu Tyr Ser Gln Asp Gly Ser
            420                 425                 430
Phe Tyr Phe Leu Glu Leu Asn Pro Arg Leu Gln Val Glu His Pro Cys
        435                 440                 445
Thr Glu Met Val Ala Asp Val Asn Leu Pro Ala Ala Gln Leu Gln Ile
    450                 455                 460
Ala Met Gly Ile Pro Leu Tyr Arg Ile Lys Asp Ile Arg Met Met Tyr
465                 470                 475                 480
Gly Val Ser Pro Trp Gly Asp Ser Pro Ile Asp Phe Glu Asp Ser Ala
                485                 490                 495
His Val Pro Cys Pro Arg Gly His Val Ile Ala Arg Ile Thr Ser
            500                 505                 510
Glu Asn Pro Asp Glu Gly Phe Lys Pro Ser Ser Gly Thr Val Gln Glu
        515                 520                 525
Leu Asn Phe Arg Ser Asn Lys Asn Val Trp Gly Tyr Phe Ser Val Ala
    530                 535                 540
Ala Ala Gly Gly Leu His Glu Phe Ala Asp Ser Gln Phe Gly His Cys
545                 550                 555                 560
Phe Ser Trp Gly Glu Asn Arg Glu Glu Ala Ile Ser Asn Met Val Val
                565                 570                 575
Ala Leu Lys Glu Leu Ser Ile Arg Gly Asp Phe Arg Thr Thr Val Glu
            580                 585                 590
Tyr Leu Ile Lys Leu Leu Glu Thr Glu Ser Phe Gln Met Asn Arg Ile
        595                 600                 605
Asp Thr Gly Trp Leu Asp Arg Leu Ile Ala Glu Lys Val Gln Ala Glu
    610                 615                 620
Arg Pro Asp Thr Met Leu Gly Val Val Cys Gly Ala Leu His Val Ala
625                 630                 635                 640
Asp Val Ser Leu Arg Asn Ser Val Ser Asn Phe Leu His Ser Leu Glu
                645                 650                 655
Arg Gly Gln Val Leu Pro Ala His Thr Leu Leu Asn Thr Val Asp Val
            660                 665                 670
Glu Leu Ile Tyr Glu Gly Val Lys Tyr Val Leu Lys Val Thr Arg Gln
        675                 680                 685
Ser Pro Asn Ser Tyr Val Val Ile Met Asn Gly Ser Cys Val Glu Val
    690                 695                 700
Asp Val His Arg Leu Ser Asp Gly Gly Leu Leu Leu Ser Tyr Asp Gly
705                 710                 715                 720
Ser Ser Tyr Thr Thr Tyr Met Lys Glu Glu Val Asp Arg Tyr Arg Ile
                725                 730                 735
Thr Ile Gly Asn Lys Thr Cys Val Phe Glu Lys Glu Asn Asp Pro Ser
            740                 745                 750
Val Met Arg Ser Pro Ser Ala Gly Lys Leu Ile Gln Tyr Ile Val Glu
        755                 760                 765
Asp Gly Gly His Val Phe Ala Gly Gln Cys Tyr Ala Glu Ile Glu Val
    770                 775                 780
Met Lys Met Val Met Thr Leu Thr Ala Val Glu Ser Gly Cys Ile His
785                 790                 795                 800
Tyr Val Lys Arg Pro Gly Ala Ala Leu Asp Pro Gly Cys Ile Leu Ala
                805                 810                 815
```

-continued

```
Lys Met Gln Leu Asp Asn Pro Ser Lys Val Gln Gln Ala Glu Leu His
            820                 825                 830

Thr Gly Ser Leu Pro Arg Ile Gln Ser Thr Ala Leu Arg Gly Glu Lys
            835                 840                 845

Leu His Arg Val Phe His Tyr Val Leu Asp Asn Leu Val Asn Val Met
    850                 855                 860

Asn Gly Tyr Cys Leu Pro Asp Pro Phe Phe Ser Ser Lys Val Lys Asp
865                 870                 875                 880

Trp Val Glu Arg Leu Met Lys Thr Leu Arg Asp Pro Ser Leu Pro Leu
                885                 890                 895

Leu Glu Leu Gln Asp Ile Met Thr Ser Val Ser Gly Arg Ile Pro Pro
            900                 905                 910

Asn Val Glu Lys Ser Ile Lys Lys Glu Met Ala Gln Tyr Ala Ser Asn
            915                 920                 925

Ile Thr Ser Val Leu Cys Gln Phe Pro Ser Gln Gln Ile Ala Asn Ile
    930                 935                 940

Leu Asp Ser His Ala Ala Thr Leu Asn Arg Lys Ser Glu Arg Glu Val
945                 950                 955                 960

Phe Phe Met Asn Thr Gln Ser Ile Val Gln Leu Val Gln Arg Tyr Arg
                965                 970                 975

Ser Gly Ile Arg Gly His Met Lys Ala Val Val Met Asp Leu Leu Arg
            980                 985                 990

Gln Tyr Leu Arg Val Glu Thr Gln  Phe Gln Asn Gly His  Tyr Asp Lys
            995                 1000                1005

Cys Val  Phe Ala Leu Arg Glu  Glu Asn Lys Ser Asp  Met Asn Thr
        1010                1015                1020

Val Leu  Asn Tyr Ile Phe Ser  His Ala Gln Val Thr  Lys Lys Asn
        1025                1030                1035

Leu Leu  Val Thr Met Leu Ile  Asp Gln Leu Cys Gly  Arg Asp Pro
        1040                1045                1050

Thr Leu  Thr Asp Glu Leu Leu  Asn Ile Leu Thr Glu  Leu Thr Gln
        1055                1060                1065

Leu Ser  Lys Thr Thr Asn Ala  Lys Val Ala Leu Arg  Ala Arg Gln
        1070                1075                1080

Val Leu  Ile Ala Ser His Leu  Pro Ser Tyr Glu Leu  Arg His Asn
        1085                1090                1095

Gln Val  Glu Ser Ile Phe Leu  Ser Ala Ile Asp Met  Tyr Gly His
        1100                1105                1110

Gln Phe  Cys Ile Glu Asn Leu  Gln Lys Leu Ile Leu  Ser Glu Thr
        1115                1120                1125

Ser Ile  Phe Asp Val Leu Pro  Asn Phe Phe Tyr His  Ser Asn Gln
        1130                1135                1140

Val Val  Arg Met Ala Ala Leu  Glu Val Tyr Val Arg  Arg Ala Tyr
        1145                1150                1155

Ile Ala  Tyr Glu Leu Asn Ser  Val Gln His Arg Gln  Leu Lys Asp
        1160                1165                1170

Asn Thr  Cys Val Val Glu Phe  Gln Phe Met Leu Pro  Thr Ser His
        1175                1180                1185

Pro Asn  Arg Gly Asn Ile Pro  Thr Leu Asn Arg Met  Ser Phe Ser
        1190                1195                1200

Ser Asn  Leu Asn His Tyr Gly  Met Thr His Val Ala  Ser Val Ser
        1205                1210                1215

Asp Val  Leu Leu Asp Asn Ser  Phe Thr Pro Pro Cys  Gln Arg Met
```

-continued

```
            1220                1225                1230
Gly Gly Met Val Ser Phe Arg Thr Phe Glu Asp Phe Val Arg Ile
        1235                1240                1245
Phe Asp Glu Val Met Gly Cys Phe Ser Asp Ser Pro Pro Gln Ser
        1250                1255                1260
Pro Thr Phe Pro Glu Ala Gly His Thr Ser Leu Tyr Asp Glu Asp
        1265                1270                1275
Lys Val Pro Arg Asp Glu Pro Ile His Ile Leu Asn Val Ala Ile
        1280                1285                1290
Lys Thr Asp Cys Asp Ile Glu Asp Asp Arg Leu Ala Ala Met Phe
        1295                1300                1305
Arg Glu Phe Thr Gln Gln Asn Lys Ala Thr Leu Val Asp His Gly
        1310                1315                1320
Ile Arg Arg Leu Thr Phe Leu Val Ala Gln Lys Asp Phe Arg Lys
        1325                1330                1335
Gln Val Asn Tyr Glu Val Asp Arg Arg Phe His Arg Glu Phe Pro
        1340                1345                1350
Lys Phe Phe Thr Phe Arg Ala Arg Asp Lys Phe Glu Glu Asp Arg
        1355                1360                1365
Ile Tyr Arg His Leu Glu Pro Ala Leu Ala Phe Gln Leu Glu Leu
        1370                1375                1380
Asn Arg Met Arg Asn Phe Asp Leu Thr Ala Ile Pro Cys Ala Asn
        1385                1390                1395
His Lys Met His Leu Tyr Leu Gly Ala Ala Lys Val Glu Val Gly
        1400                1405                1410
Thr Glu Val Thr Asp Tyr Arg Phe Phe Val Arg Ala Ile Ile Arg
        1415                1420                1425
His Ser Asp Leu Val Thr Lys Glu Ala Ser Phe Glu Tyr Leu Gln
        1430                1435                1440
Asn Glu Gly Glu Arg Leu Leu Leu Glu Ala Met Asp Glu Leu Glu
        1445                1450                1455
Val Ala Phe Asn Asn Thr Asn Val Arg Thr Asp Cys Asn His Ile
        1460                1465                1470
Phe Leu Asn Phe Val Pro Thr Val Ile Met Asp Pro Ser Lys Ile
        1475                1480                1485
Glu Glu Ser Val Arg Ser Met Val Met Arg Tyr Gly Ser Arg Leu
        1490                1495                1500
Trp Lys Leu Arg Val Leu Gln Ala Glu Leu Lys Ile Asn Ile Arg
        1505                1510                1515
Leu Thr Pro Thr Gly Lys Ala Ile Pro Ile Arg Leu Phe Leu Thr
        1520                1525                1530
Asn Glu Ser Gly Tyr Tyr Leu Asp Ile Ser Leu Tyr Lys Glu Val
        1535                1540                1545
Thr Asp Ser Arg Thr Ala Gln Ile Met Phe Gln Ala Tyr Gly Asp
        1550                1555                1560
Lys Gln Gly Pro Leu His Gly Met Leu Ile Asn Thr Pro Tyr Val
        1565                1570                1575
Thr Lys Asp Leu Leu Gln Ser Lys Arg Phe Gln Ala Gln Ser Leu
        1580                1585                1590
Gly Thr Thr Tyr Ile Tyr Asp Ile Pro Glu Met Phe Arg Gln Ser
        1595                1600                1605
Leu Ile Lys Leu Trp Glu Ser Met Ser Thr Gln Ala Phe Leu Pro
        1610                1615                1620
```

-continued

Ser Pro Pro Leu Pro Ser Asp Met Leu Thr Tyr Thr Glu Leu Val
    1625                1630                1635

Leu Asp Asp Gln Gly Gln Leu Val His Met Asn Arg Leu Pro Gly
    1640                1645                1650

Gly Asn Glu Ile Gly Met Val Ala Trp Lys Met Thr Phe Lys Ser
    1655                1660                1665

Pro Glu Tyr Pro Glu Gly Arg Asp Ile Val Ile Gly Asn Asp
    1670                1675                1680

Ile Thr Tyr Arg Ile Gly Ser Phe Gly Pro Gln Glu Asp Leu Leu
    1685                1690                1695

Phe Leu Arg Ala Ser Glu Leu Ala Arg Ala Glu Gly Ile Pro Arg
    1700                1705                1710

Ile Tyr Val Ser Ala Asn Ser Gly Ala Arg Ile Gly Leu Ala Glu
    1715                1720                1725

Glu Ile Arg His Met Phe His Val Ala Trp Val Asp Pro Glu Asp
    1730                1735                1740

Pro Tyr Lys Gly Tyr Arg Tyr Leu Tyr Leu Thr Pro Gln Asp Tyr
    1745                1750                1755

Lys Arg Val Ser Ala Leu Asn Ser Val His Cys Glu His Val Glu
    1760                1765                1770

Asp Glu Gly Glu Ser Arg Tyr Lys Ile Thr Asp Ile Ile Gly Lys
    1775                1780                1785

Glu Glu Gly Ile Gly Pro Glu Asn Leu Arg Gly Ser Gly Met Ile
    1790                1795                1800

Ala Gly Glu Ser Ser Leu Ala Tyr Asn Glu Ile Ile Thr Ile Ser
    1805                1810                1815

Leu Val Thr Cys Arg Ala Ile Gly Ile Gly Ala Tyr Leu Val Arg
    1820                1825                1830

Leu Gly Gln Arg Thr Ile Gln Val Glu Asn Ser His Leu Ile Leu
    1835                1840                1845

Thr Gly Ala Gly Ala Leu Asn Lys Val Leu Gly Arg Glu Val Tyr
    1850                1855                1860

Thr Ser Asn Asn Gln Leu Gly Gly Ile Gln Ile Met His Asn Asn
    1865                1870                1875

Gly Val Thr His Cys Thr Val Cys Asp Asp Phe Glu Gly Val Phe
    1880                1885                1890

Thr Val Leu His Trp Leu Ser Tyr Met Pro Lys Ser Val His Ser
    1895                1900                1905

Ser Val Pro Leu Leu Asn Ser Lys Asp Pro Ile Asp Arg Ile Ile
    1910                1915                1920

Glu Phe Val Pro Thr Lys Thr Pro Tyr Asp Pro Arg Trp Met Leu
    1925                1930                1935

Ala Gly Arg Pro His Pro Thr Gln Lys Gly Gln Trp Leu Ser Gly
    1940                1945                1950

Phe Phe Asp Tyr Gly Ser Phe Ser Glu Ile Met Gln Pro Trp Ala
    1955                1960                1965

Gln Thr Val Val Val Gly Arg Ala Arg Leu Gly Gly Ile Pro Val
    1970                1975                1980

Gly Val Val Ala Val Glu Thr Arg Thr Val Glu Leu Ser Ile Pro
    1985                1990                1995

Ala Asp Pro Ala Asn Leu Asp Ser Glu Ala Lys Ile Ile Gln Gln
    2000                2005                2010

-continued

```
Ala Gly Gln Val Trp Phe Pro Asp Ser Ala Phe Lys Thr Tyr Gln
    2015                2020                2025

Ala Ile Lys Asp Phe Asn Arg Glu Gly Leu Pro Leu Met Val Phe
    2030                2035                2040

Ala Asn Trp Arg Gly Phe Ser Gly Gly Met Lys Asp Met Tyr Asp
    2045                2050                2055

Gln Val Leu Lys Phe Gly Ala Tyr Ile Val Asp Gly Leu Arg Glu
    2060                2065                2070

Cys Cys Gln Pro Val Leu Val Tyr Ile Pro Pro Gln Ala Glu Leu
    2075                2080                2085

Arg Gly Gly Ser Trp Val Val Ile Asp Ser Ser Ile Asn Pro Arg
    2090                2095                2100

His Met Glu Met Tyr Ala Asp Arg Glu Ser Arg Gly Ser Val Leu
    2105                2110                2115

Glu Pro Glu Gly Thr Val Glu Ile Lys Phe Arg Arg Lys Asp Leu
    2120                2125                2130

Val Lys Thr Met Arg Arg Val Asp Pro Val Tyr Ile His Leu Ala
    2135                2140                2145

Glu Arg Leu Gly Thr Pro Glu Leu Ser Thr Ala Glu Arg Lys Glu
    2150                2155                2160

Leu Glu Asn Lys Leu Lys Glu Arg Glu Glu Phe Leu Ile Pro Ile
    2165                2170                2175

Tyr His Gln Val Ala Val Gln Phe Ala Asp Leu His Asp Thr Pro
    2180                2185                2190

Gly Arg Met Gln Glu Lys Gly Val Ile Ser Asp Ile Leu Asp Trp
    2195                2200                2205

Lys Thr Ser Arg Thr Phe Phe Tyr Trp Arg Leu Arg Arg Leu Leu
    2210                2215                2220

Leu Glu Asp Leu Val Lys Lys Ile His Asn Ala Asn Pro Glu
    2225                2230                2235

Leu Thr Asp Gly Gln Ile Gln Ala Met Leu Arg Arg Trp Phe Val
    2240                2245                2250

Glu Val Glu Gly Thr Val Lys Ala Tyr Val Trp Asp Asn Asn Lys
    2255                2260                2265

Asp Leu Ala Glu Trp Leu Glu Lys Gln Leu Thr Glu Glu Asp Gly
    2270                2275                2280

Val His Ser Val Ile Glu Glu Asn Ile Lys Cys Ile Ser Arg Asp
    2285                2290                2295

Tyr Val Leu Lys Gln Ile Arg Ser Leu Val Gln Ala Asn Pro Glu
    2300                2305                2310

Val Ala Met Asp Ser Ile Ile Arg Met Thr Gln His Ile Ser Pro
    2315                2320                2325

Thr Gln Arg Ala Glu Val Ile Arg Ile Leu Ser Thr Met Asp Ser
    2330                2335                2340

Pro Ser Thr
    2345

<210> SEQ ID NO 8
<211> LENGTH: 799
<212> TYPE: PRT
<213> ORGANISM: Homo sapiens

<400> SEQUENCE: 8

Val Thr Asp Ser Arg Thr Ala Gln Ile Met Phe Gln Ala Tyr Gly Asp
1               5                   10                  15
```

-continued

```
Lys Gln Gly Pro Leu His Gly Met Leu Ile Asn Thr Pro Tyr Val Thr
             20                  25                  30

Lys Asp Leu Leu Gln Ser Lys Arg Phe Gln Ala Gln Ser Leu Gly Thr
         35                  40                  45

Thr Tyr Ile Tyr Asp Ile Pro Glu Met Phe Arg Gln Ser Leu Ile Lys
     50                  55                  60

Leu Trp Glu Ser Met Ser Thr Gln Ala Phe Leu Pro Ser Pro Pro Leu
 65                  70                  75                  80

Pro Ser Asp Met Leu Thr Tyr Thr Glu Leu Val Leu Asp Asp Gln Gly
                 85                  90                  95

Gln Leu Val His Met Asn Arg Leu Pro Gly Gly Asn Glu Ile Gly Met
            100                 105                 110

Val Ala Trp Lys Met Thr Phe Lys Ser Pro Glu Tyr Pro Glu Gly Arg
        115                 120                 125

Asp Ile Ile Val Ile Gly Asn Asp Ile Thr Tyr Arg Ile Gly Ser Phe
    130                 135                 140

Gly Pro Gln Glu Asp Leu Leu Phe Leu Arg Ala Ser Glu Leu Ala Arg
145                 150                 155                 160

Ala Glu Gly Ile Pro Arg Ile Tyr Val Ser Ala Asn Ser Gly Ala Arg
                165                 170                 175

Ile Gly Leu Ala Glu Glu Ile Arg His Met Phe His Val Ala Trp Val
            180                 185                 190

Asp Pro Glu Asp Pro Tyr Lys Gly Tyr Arg Tyr Leu Tyr Leu Thr Pro
        195                 200                 205

Gln Asp Tyr Lys Arg Val Ser Ala Leu Asn Ser Val His Cys Glu His
    210                 215                 220

Val Glu Asp Glu Gly Glu Ser Arg Tyr Lys Ile Thr Asp Ile Ile Gly
225                 230                 235                 240

Lys Glu Glu Gly Ile Gly Pro Glu Asn Leu Arg Gly Ser Gly Met Ile
                245                 250                 255

Ala Gly Glu Ser Ser Leu Ala Tyr Asn Glu Ile Ile Thr Ile Ser Leu
            260                 265                 270

Val Thr Cys Arg Ala Ile Gly Ile Gly Ala Tyr Leu Val Arg Leu Gly
        275                 280                 285

Gln Arg Thr Ile Gln Val Glu Asn Ser His Leu Ile Leu Thr Gly Ala
    290                 295                 300

Gly Ala Leu Asn Lys Val Leu Gly Arg Glu Val Tyr Thr Ser Asn Asn
305                 310                 315                 320

Gln Leu Gly Gly Ile Gln Ile Met His Asn Asn Gly Val Thr His Cys
                325                 330                 335

Thr Val Cys Asp Asp Phe Glu Gly Val Phe Thr Val Leu His Trp Leu
            340                 345                 350

Ser Tyr Met Pro Lys Ser Val His Ser Ser Val Pro Leu Leu Asn Ser
        355                 360                 365

Lys Asp Pro Ile Asp Arg Ile Ile Glu Phe Val Pro Thr Lys Thr Pro
    370                 375                 380

Tyr Asp Pro Arg Trp Met Leu Ala Gly Arg Pro His Pro Thr Gln Lys
385                 390                 395                 400

Gly Gln Trp Leu Ser Gly Phe Phe Asp Tyr Gly Ser Phe Ser Glu Ile
                405                 410                 415

Met Gln Pro Trp Ala Gln Thr Val Val Gly Arg Ala Arg Leu Gly
            420                 425                 430
```

```
Gly Ile Pro Val Gly Val Ala Val Glu Thr Arg Thr Val Glu Leu
        435                 440                 445

Ser Ile Pro Ala Asp Pro Ala Asn Leu Asp Ser Glu Ala Lys Ile Ile
    450                 455                 460

Gln Gln Ala Gly Gln Val Trp Phe Pro Asp Ser Ala Phe Lys Thr Tyr
465                 470                 475                 480

Gln Ala Ile Lys Asp Phe Asn Arg Glu Gly Leu Pro Leu Met Val Phe
            485                 490                 495

Ala Asn Trp Arg Gly Phe Ser Gly Gly Met Lys Asp Met Tyr Asp Gln
        500                 505                 510

Val Leu Lys Phe Gly Ala Tyr Ile Val Asp Gly Leu Arg Glu Cys Cys
    515                 520                 525

Gln Pro Val Leu Val Tyr Ile Pro Pro Gln Ala Glu Leu Arg Gly Gly
530                 535                 540

Ser Trp Val Val Ile Asp Ser Ser Ile Asn Pro Arg His Met Glu Met
545                 550                 555                 560

Tyr Ala Asp Arg Glu Ser Arg Gly Ser Val Leu Glu Pro Glu Gly Thr
            565                 570                 575

Val Glu Ile Lys Phe Arg Arg Lys Asp Leu Val Lys Thr Met Arg Arg
        580                 585                 590

Val Asp Pro Val Tyr Ile His Leu Ala Glu Arg Leu Gly Thr Pro Glu
    595                 600                 605

Leu Ser Thr Ala Glu Arg Lys Glu Leu Glu Asn Lys Leu Lys Glu Arg
610                 615                 620

Glu Glu Phe Leu Ile Pro Ile Tyr His Gln Val Ala Val Gln Phe Ala
625                 630                 635                 640

Asp Leu His Asp Thr Pro Gly Arg Met Gln Glu Lys Gly Val Ile Ser
            645                 650                 655

Asp Ile Leu Asp Trp Lys Thr Ser Arg Thr Phe Phe Tyr Trp Arg Leu
        660                 665                 670

Arg Arg Leu Leu Leu Glu Asp Leu Val Lys Lys Ile His Asn Ala
    675                 680                 685

Asn Pro Glu Leu Thr Asp Gly Gln Ile Gln Ala Met Leu Arg Arg Trp
690                 695                 700

Phe Val Glu Val Glu Gly Thr Val Lys Ala Tyr Val Trp Asp Asn Asn
705                 710                 715                 720

Lys Asp Leu Ala Glu Trp Leu Glu Lys Gln Leu Thr Glu Glu Asp Gly
            725                 730                 735

Val His Ser Val Ile Glu Glu Asn Ile Lys Cys Ile Ser Arg Asp Tyr
        740                 745                 750

Val Leu Lys Gln Ile Arg Ser Leu Val Gln Ala Asn Pro Glu Val Ala
    755                 760                 765

Met Asp Ser Ile Ile Arg Met Thr Gln His Ile Ser Pro Thr Gln Arg
770                 775                 780

Ala Glu Val Ile Arg Ile Leu Ser Thr Met Asp Ser Pro Ser Thr
785                 790                 795

<210> SEQ ID NO 9
<211> LENGTH: 2483
<212> TYPE: PRT
<213> ORGANISM: Homo sapiens

<400> SEQUENCE: 9

Met Val Leu Leu Leu Cys Leu Ser Cys Leu Ile Phe Ser Cys Leu Thr
1               5                   10                  15
```

```
Phe Ser Trp Leu Lys Ile Trp Glu Lys Met Thr Asp Ser Lys Pro Ile
            20                  25                  30
Thr Lys Ser Lys Ser Glu Ala Asn Leu Ile Pro Ser Gln Glu Pro Phe
        35                  40                  45
Pro Ala Ser Asp Asn Ser Gly Glu Thr Pro Gln Arg Asn Gly Glu Gly
    50                  55                  60
His Thr Leu His Lys Asp Thr Gln Pro Gly Arg Ala Gln Pro Pro Thr
65                  70                  75                  80
Lys Ala Gln Arg Ser Gly Arg Arg Asn Ser Leu Pro Pro Ser Arg
                85                  90                  95
Gln Lys Pro Pro Arg Asn Pro Leu Ser Ser Ser Asp Ala Ala Pro Ser
            100                 105                 110
Pro Glu Leu Gln Ala Asn Gly Thr Gly Thr Gln Gly Leu Glu Ala Thr
        115                 120                 125
Asp Thr Asn Gly Leu Ser Ser Ser Ala Arg Pro Gln Gly Ser Lys Leu
    130                 135                 140
Val Pro Ser Lys Glu Asp Lys Lys Gln Ala Asn Ile Lys Arg Gln Leu
145                 150                 155                 160
Met Thr Asn Phe Ile Leu Gly Ser Phe Asp Asp Tyr Ser Ser Asp Glu
                165                 170                 175
Asp Ser Val Ala Gly Ser Ser Arg Glu Ser Thr Arg Lys Gly Ser Arg
            180                 185                 190
Ala Ser Leu Gly Ala Leu Ser Leu Glu Ala Tyr Leu Thr Thr Gly Glu
        195                 200                 205
Ala Glu Thr Arg Val Pro Thr Met Arg Pro Ser Met Ser Gly Leu His
    210                 215                 220
Leu Val Lys Arg Gly Arg Glu His Lys Lys Leu Asp Leu His Arg Asp
225                 230                 235                 240
Phe Thr Val Ala Ser Pro Ala Glu Phe Val Thr Arg Phe Gly Gly Asp
                245                 250                 255
Arg Val Ile Glu Lys Val Leu Ile Ala Asn Asn Gly Ile Ala Ala Val
            260                 265                 270
Lys Cys Met Arg Ser Ile Arg Arg Trp Ala Tyr Glu Met Phe Arg Asn
        275                 280                 285
Glu Arg Ala Ile Arg Phe Val Arg Met Val Thr Pro Glu Asp Leu Lys
    290                 295                 300
Ala Asn Ala Glu Tyr Ile Lys Met Ala Asp His Tyr Gly Pro Ala Pro
305                 310                 315                 320
Gly Gly Pro Asn Asn Asn Asn Tyr Ala Asn Val Glu Leu Ile Val Asp
                325                 330                 335
Ile Ala Lys Arg Ile Pro Leu Gln Ala Val Trp Ala Gly Trp Gly His
            340                 345                 350
Ala Leu Glu Asn Pro Lys Leu Pro Glu Leu Leu Cys Lys Asn Gly Val
        355                 360                 365
Ala Phe Leu Gly Pro Pro Arg Leu Arg Pro Met Val Gly Leu Gly Asp
    370                 375                 380
Lys Ile Ala Ser Thr Val Val Ala Gln Thr Leu Gln Val Pro Thr Leu
385                 390                 395                 400
Pro Arg Ser Gly Ser Ala Leu Thr Val Glu Trp Thr Glu Asp Asp Leu
                405                 410                 415
Gln Gln Gly Lys Arg Ile Ser Val Pro Glu Asp Val Tyr Asp Lys Gly
            420                 425                 430
```

-continued

```
Cys Val Lys Asp Val Asp Glu Gly Leu Glu Ala Ala Glu Arg Ile Gly
            435                 440                 445

Phe Pro Leu Met Ile Lys Ala Ser Glu Gly Gly Gly Lys Gly Ile
450                 455                 460

Arg Glu Thr Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                    485                 490                 495

His Ala Arg His Leu Glu Val Gln Ile Leu Ala Asp Gln Tyr Gly Asn
            500                 505                 510

Ala Val Ser Leu Phe Gly Arg Asp Cys Ser Ile Gln Arg Arg His Gln
            515                 520                 525

Lys Ile Val Glu Glu Ala Pro Ala Thr Ile Ala Pro Leu Ala Ile Phe
530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
                565                 570                 575

His Phe Leu Glu Leu Asn Pro Arg Leu Gln Val Glu His Pro Cys Thr
            580                 585                 590

Glu Met Ile Ala Asp Val Asn Leu Pro Ala Ala Gln Leu Gln Ile Ala
            595                 600                 605

Met Gly Ala Pro Leu His Arg Leu Lys Asp Ile Arg Leu Leu Tyr Gly
            610                 615                 620

Glu Ser Pro Trp Gly Asp Ser Pro Ile Ser Phe Glu Asn Ser Ala His
625                 630                 635                 640

Leu Pro Cys Pro Arg Gly His Val Ile Ala Thr Arg Ile Thr Ser Glu
                645                 650                 655

Asn Pro Asp Glu Gly Phe Lys Pro Ser Ser Gly Thr Val Gln Glu Leu
            660                 665                 670

Asn Phe Arg Ser Ser Lys Asn Val Trp Gly Tyr Phe Thr Val Ala Ala
            675                 680                 685

Thr Gly Gly Leu His Glu Phe Ala Ile Ser Gln Phe Gly His Cys Phe
            690                 695                 700

Ser Trp Gly Glu Asn Arg Lys Glu Ala Ile Ser Asn Met Val Val Ala
705                 710                 715                 720

Leu Lys Glu Leu Ser Leu Arg Gly Asp Phe Arg Thr Thr Val Glu Tyr
                725                 730                 735

Leu Ile Asn Leu Leu Glu Thr Glu Ser Phe Gln Asn Asn Tyr Ile Asp
            740                 745                 750

Thr Gly Trp Leu Asp Tyr Leu Ile Ala Glu Lys Val Gln Lys Lys Pro
            755                 760                 765

Asn Ile Met Leu Gly Val Val Cys Gly Ala Leu Glu Arg Gly Asp Ala
770                 775                 780

Met Phe Arg Thr Cys Met Thr Asp Phe Leu His Ser Leu Glu Arg Gly
785                 790                 795                 800

Gln Val Leu Pro Ala Asp Ser Leu Leu Asn Leu Val Asp Val Glu Leu
                805                 810                 815

Ile Tyr Glu Gly Val Lys Tyr Ile Leu Lys Val Thr Arg Gln Ser Leu
            820                 825                 830

Thr Met Phe Val Leu Ile Met Asn Gly Cys His Ile Glu Ile Asp Ala
            835                 840                 845

His Arg Leu Asn Asp Gly Gly Leu Leu Leu Ser Tyr Asn Gly Asn Ser
```

-continued

```
                850                 855                 860
Tyr Thr Thr Tyr Met Lys Glu Glu Val Asp Ser Tyr Arg Thr Ile Gly
865                 870                 875                 880

Asn Lys Thr Cys Val Phe Glu Lys Glu Asn Asp Pro Thr Val Leu Arg
                885                 890                 895

Ser Pro Ser Ala Gly Lys Leu Thr Gln Ile Thr Val Glu Asp Gly Gly
            900                 905                 910

His Val Glu Ala Gly Arg Arg Tyr Ala Glu Met Glu Val Met Lys Met
            915                 920                 925

Ile Met Thr Leu Asn Val Gln Glu Arg Gly Arg Val Lys Tyr Ile Lys
930                 935                 940

Arg Pro Gly Ala Val Leu Glu Ala Gly Cys Val Val Ala Arg Leu Glu
945                 950                 955                 960

Leu Asp Asp Pro Ser Lys Val His Pro Ala Glu Pro Phe Thr Gly Glu
                965                 970                 975

Leu Pro Ala Gln Gln Asn Thr Ala Asp Leu Gly Lys Lys Leu His Arg
            980                 985                 990

Val Phe His Ser Val Leu Gly Ser  Leu Thr Asn Val Met  Ser Gly Phe
            995                 1000                1005

Cys Leu  Pro Glu Pro Phe  Phe  Ser Ile Lys Leu Lys  Glu Trp Val
    1010                1015                1020

Gln Lys  Leu Met Met Thr Leu  Arg His Pro Ser Leu  Leu Leu Asp
    1025                1030                1035

Val Gln  Glu Ile Met Thr Ser  Arg Ala Gly Arg Ile  Pro Pro Pro
    1040                1045                1050

Val Glu  Lys Ser Val Arg Lys  Val Met Ala Gln Tyr  Ala Ser Asn
    1055                1060                1065

Ile Thr  Ser Val Leu Cys Gln  Phe Pro Ser Gln Ile  Ala Thr
    1070                1075                1080

Ile Leu  Asp Cys His Ala Ala  Thr Leu Gln Arg Lys  Ala Asp Arg
    1085                1090                1095

Glu Val  Phe Phe Ile Asn Thr  Gln Ser Met Val Gln  Leu Val Gln
    1100                1105                1110

Arg Tyr  Arg Ser Gly Ile Arg  Gly His Met Lys Thr  Val Val Ile
    1115                1120                1125

Asp Leu  Leu Arg Arg Tyr Leu  Arg Val Glu Thr Ile  Phe Gly Lys
    1130                1135                1140

Ala Arg  Asp Ala Asp Ala Asn  Ser Ser Gly Met Val  Gly Gly Val
    1145                1150                1155

Arg Ser  Leu Ser Phe Thr Ser  Val Trp Val Val Leu  Ser Pro Pro
    1160                1165                1170

Ala His  Tyr Asp Lys Cys Val  Ile Asn Leu Arg Glu  Gln Phe Lys
    1175                1180                1185

Pro Asp  Met Ser Gln Val Leu  Asp Cys Ile Phe Ser  His Ala Gln
    1190                1195                1200

Val Thr  Lys Lys Asn Gln Leu  Val Ile Met Leu Ile  Asp Glu Leu
    1205                1210                1215

Cys Gly  Pro Asp Pro Ser Leu  Ser Asp Glu Leu Ile  Ser Ile Leu
    1220                1225                1230

Asn Glu  Leu Thr Gln Leu Ser  Lys Ser Glu His Cys  Lys Val Ala
    1235                1240                1245

Leu Arg  Ala Arg Gln Ile Leu  Ile Ala Ser Pro Ser  Tyr Glu Leu
    1250                1255                1260
```

-continued

```
Arg His Asn Gln Val Glu Ser Ile Phe Leu Ser Ala Ile Asp Met
1265                1270                1275

Tyr Gly His Gln Phe Cys Pro Glu Asn Leu Gln Lys Leu Ile Leu
1280                1285                1290

Ser Glu Thr Thr Ile Phe Asp Val Leu Asn Thr Phe Phe Tyr His
1295                1300                1305

Ala Asn Lys Val Val Cys Met Ala Ser Leu Glu Val Tyr Val Gly
1310                1315                1320

Gly Ala Tyr Ile Ala Tyr Val Leu Asn Ser Leu Gln His Arg Gln
1325                1330                1335

Leu Pro Asp Gly Thr Cys Val Val Glu Phe Gln Phe Met Leu Pro
1340                1345                1350

Ser Ser His Pro Asn Arg Met Thr Val Pro Ile Ser Ile Thr Asn
1355                1360                1365

Pro Asp Leu Leu Arg His Thr Thr Glu Leu Phe Met Asp Ser Gly
1370                1375                1380

Phe Ser Pro Leu Cys Gln Arg Met Gly Ala Met Val Ala Phe Arg
1385                1390                1395

Arg Phe Glu Asp Phe Thr Arg Asn Phe Asp Glu Val Ile Ser Cys
1400                1405                1410

Phe Ala Asn Val Pro Lys Asp Pro Pro Leu Phe Ser Glu Ala Arg
1415                1420                1425

Thr Ser Leu Tyr Ser Glu Asp Asp Cys Lys Ser Leu Arg Glu Glu
1430                1435                1440

Pro Ile His Ile Leu Asn Val Ser Ile Gln Cys Ala Asp His Leu
1445                1450                1455

Glu Asp Glu Ala Leu Val Pro Ile Leu Arg Thr Phe Val Gln Ser
1460                1465                1470

Lys Lys Asn Ile Leu Val Asp Tyr Gly Leu Arg Arg Ile Pro Phe
1475                1480                1485

Leu Ile Ala Gln Glu Lys Glu Phe Pro Lys Phe Phe Thr Phe Arg
1490                1495                1500

Ala Arg Asp Glu Phe Ala Glu Asp Arg Ile Tyr Arg His Leu Glu
1505                1510                1515

Pro Ala Leu Ala Phe Gln Leu Glu Leu Asn Arg Met Arg Asn Phe
1520                1525                1530

Asp Leu Thr Ala Val Pro Cys Ala Asn His Lys Met His Leu Tyr
1535                1540                1545

Leu Gly Ala Ala Lys Val Glu Gly Arg Tyr Glu Val Thr Asp His
1550                1555                1560

Arg Phe Phe Ile Arg Ala Ile Ile Arg His Ser Asp Leu Ile Thr
1565                1570                1575

Lys Glu Ala Ser Phe Glu Tyr Leu Gln Asn Glu Gly Glu Arg Leu
1580                1585                1590

Leu Leu Glu Ala Met Asp Glu Leu Glu Val Ala Phe Asn Asn Thr
1595                1600                1605

Asn Val Arg Thr Asp Cys Asn His Ile Phe Leu Asn Phe Val Pro
1610                1615                1620

Thr Val Ile Met Asp Pro Asn Lys Ile Glu Glu Ser Val Arg Tyr
1625                1630                1635

Met Val Met Arg Tyr Gly Ser Arg Leu Trp Lys Leu Arg Val Leu
1640                1645                1650
```

-continued

```
Gln Ala Glu Val Lys Ile Asn Ile Arg Gln Thr Thr Thr Gly Ser
1655                1660                1665

Ala Val Pro Ile Arg Leu Phe Ile Thr Asn Glu Ser Gly Tyr Tyr
1670                1675                1680

Leu Asp Ile Ser Leu Tyr Lys Glu Val Thr Asp Ser Arg Ser Gly
1685                1690                1695

Asn Ile Met Phe His Ser Phe Gly Asn Lys Gln Gly Pro Gln His
1700                1705                1710

Gly Met Leu Ile Asn Thr Pro Tyr Val Thr Lys Asp Leu Leu Gln
1715                1720                1725

Ala Lys Arg Phe Gln Ala Gln Thr Leu Gly Thr Thr Tyr Ile Tyr
1730                1735                1740

Asp Phe Pro Glu Met Phe Arg Gln Ala Leu Phe Lys Leu Trp Gly
1745                1750                1755

Ser Pro Asp Lys Tyr Pro Lys Asp Ile Leu Thr Tyr Thr Glu Leu
1760                1765                1770

Val Leu Asp Ser Gln Gly Gln Leu Val Glu Met Asn Arg Leu Pro
1775                1780                1785

Gly Gly Asn Glu Val Gly Met Val Ala Phe Lys Met Arg Phe Lys
1790                1795                1800

Thr Gln Glu Tyr Pro Glu Gly Arg Asp Val Ile Val Ile Gly Asn
1805                1810                1815

Asp Ile Thr Phe Arg Ile Gly Ser Phe Gly Pro Gly Glu Asp Leu
1820                1825                1830

Leu Tyr Leu Arg Ala Ser Glu Met Ala Arg Ala Glu Ala Ile Pro
1835                1840                1845

Lys Ile Tyr Val Ala Ala Asn Ser Gly Ala Arg Ile Gly Met Ala
1850                1855                1860

Glu Glu Ile Lys His Met Phe His Val Ala Trp Val Asp Pro Glu
1865                1870                1875

Asp Pro His Lys Gly Phe Lys Tyr Leu Tyr Leu Thr Pro Gln Asp
1880                1885                1890

Tyr Thr Arg Ile Ser Ser Leu Asn Ser Val His Cys Lys His Ile
1895                1900                1905

Glu Glu Gly Gly Glu Ser Arg Tyr Met Ile Thr Asp Ile Ile Gly
1910                1915                1920

Lys Asp Asp Gly Leu Gly Val Glu Asn Leu Arg Gly Ser Gly Met
1925                1930                1935

Ile Ala Gly Glu Ser Ser Leu Ala Tyr Glu Glu Ile Val Thr Ile
1940                1945                1950

Ser Leu Val Thr Cys Arg Ala Ile Gly Ile Gly Ala Tyr Leu Val
1955                1960                1965

Arg Leu Gly Gln Arg Val Ile Gln Val Glu Asn Ser His Ile Ile
1970                1975                1980

Leu Thr Gly Ala Ser Ala Leu Asn Lys Val Leu Gly Arg Glu Val
1985                1990                1995

Tyr Thr Ser Asn Asn Gln Leu Gly Gly Val Gln Ile Met His Tyr
2000                2005                2010

Asn Gly Val Ser His Ile Thr Val Pro Asp Asp Phe Glu Gly Val
2015                2020                2025

Tyr Thr Ile Leu Glu Trp Leu Ser Tyr Met Pro Lys Asp Asn His
2030                2035                2040

Ser Pro Val Pro Ile Ile Thr Pro Thr Asp Pro Ile Asp Arg Glu
```

-continued

```
              2045                2050                2055

Ile Glu Phe Leu Pro Ser Arg Ala Pro Tyr Asp Pro Arg Trp Met
        2060                2065                2070

Leu Ala Gly Arg Pro His Pro Thr Leu Lys Gly Thr Trp Gln Ser
        2075                2080                2085

Gly Phe Phe Asp His Gly Ser Phe Lys Glu Ile Met Ala Pro Trp
        2090                2095                2100

Ala Gln Thr Val Val Thr Gly Arg Ala Arg Leu Gly Gly Ile Pro
        2105                2110                2115

Val Gly Val Ile Ala Val Glu Thr Arg Thr Val Glu Val Ala Val
        2120                2125                2130

Pro Ala Asp Pro Ala Asn Leu Asp Ser Glu Ala Lys Ile Ile Gln
        2135                2140                2145

Gln Ala Gly Gln Val Trp Phe Pro Asp Ser Ala Tyr Lys Thr Ala
        2150                2155                2160

Gln Ala Ile Lys Asp Phe Asn Arg Glu Lys Leu Pro Leu Met Ile
        2165                2170                2175

Phe Ala Asn Trp Arg Gly Phe Ser Gly Gly Met Lys Asp Met Tyr
        2180                2185                2190

Asp Gln Val Leu Lys Phe Gly Ala Tyr Ile Val Asp Gly Leu Arg
        2195                2200                2205

Gln Tyr Lys Gln Pro Ile Leu Ile Tyr Ile Arg Pro Met Arg Glu
        2210                2215                2220

Leu Arg Gly Gly Ser Trp Val Val Ile Asp Ala Thr Ile Asn Pro
        2225                2230                2235

Leu Cys Ile Glu Met Tyr Ala Asp Lys Glu Ser Arg Gly Gly Val
        2240                2245                2250

Leu Glu Pro Glu Gly Thr Val Glu Ile Lys Phe Arg Lys Glu Asp
        2255                2260                2265

Leu Ile Lys Ser Met Arg Arg Ile Asp Pro Ala Tyr Lys Lys Leu
        2270                2275                2280

Met Glu Gln Leu Gly Glu Pro Asp Leu Ser Asp Lys Asp Arg Lys
        2285                2290                2295

Asp Leu Glu Gly Arg Leu Lys Ala Arg Glu Asp Leu Leu Leu Pro
        2300                2305                2310

Ile Tyr His Gln Val Ala Val Gln Phe Ala Asp Phe His Asp Thr
        2315                2320                2325

Pro Gly Arg Met Leu Glu Lys Gly Val Ile Ser Asp Ile Leu Glu
        2330                2335                2340

Trp Lys Thr Ala Arg Thr Phe Leu Tyr Trp Arg Leu Arg Arg Leu
        2345                2350                2355

Leu Leu Glu Asp Gln Val Lys Gln Glu Ile Leu Gln Ala Ser Gly
        2360                2365                2370

Glu Leu Ser His Val His Ile Gln Ser Met Leu Arg Arg Trp Phe
        2375                2380                2385

Val Glu Thr Glu Gly Ala Val Lys Ala Tyr Leu Trp Asp Asn Asn
        2390                2395                2400

Gln Val Val Gln Trp Leu Glu Gln His Trp Gln Ala Gly Asp
        2405                2410                2415

Gly Pro Arg Ser Thr Ile Arg Glu Asn Ile Thr Tyr Leu Lys His
        2420                2425                2430

Asp Ser Val Leu Lys Thr Ile Arg Gly Leu Val Glu Glu Asn Pro
        2435                2440                2445
```

```
Glu Val Ala Val Asp Cys Val Ile Tyr Leu Ser Gln His Ile Ser
    2450            2455                2460

Pro Ala Glu Arg Ala Gln Val Val His Leu Leu Ser Thr Met Asp
    2465            2470                2475

Ser Pro Ala Ser Thr
    2480

<210> SEQ ID NO 10
<211> LENGTH: 833
<212> TYPE: PRT
<213> ORGANISM: Homo sapiens

<400> SEQUENCE: 10

Arg Val Leu Gln Ala Glu Val Lys Ile Asn Ile Arg Gln Thr Thr Thr
1               5                   10                  15

Gly Ser Ala Val Pro Ile Arg Leu Phe Ile Thr Asn Glu Ser Gly Tyr
            20                  25                  30

Tyr Leu Asp Ile Ser Leu Tyr Lys Glu Val Thr Asp Ser Arg Ser Gly
        35                  40                  45

Asn Ile Met Phe His Ser Phe Gly Asn Lys Gln Gly Pro Gln His Gly
    50                  55                  60

Met Leu Ile Asn Thr Pro Tyr Val Thr Lys Asp Leu Leu Gln Ala Lys
65                  70                  75                  80

Arg Phe Gln Ala Gln Thr Leu Gly Thr Thr Tyr Ile Tyr Asp Phe Pro
                85                  90                  95

Glu Met Phe Arg Gln Ala Leu Phe Lys Leu Trp Gly Ser Pro Asp Lys
            100                 105                 110

Tyr Pro Lys Asp Ile Leu Thr Tyr Thr Glu Leu Val Leu Asp Ser Gln
        115                 120                 125

Gly Gln Leu Val Glu Met Asn Arg Leu Pro Gly Gly Asn Glu Val Gly
    130                 135                 140

Met Val Ala Phe Lys Met Arg Phe Lys Thr Gln Glu Tyr Pro Glu Gly
145                 150                 155                 160

Arg Asp Val Ile Val Ile Gly Asn Asp Ile Thr Phe Arg Ile Gly Ser
                165                 170                 175

Phe Gly Pro Gly Glu Asp Leu Leu Tyr Leu Arg Ala Ser Glu Met Ala
            180                 185                 190

Arg Ala Glu Ala Ile Pro Lys Ile Tyr Val Ala Ala Asn Ser Gly Ala
        195                 200                 205

Arg Ile Gly Met Ala Glu Glu Ile Lys His Met Phe His Val Ala Trp
    210                 215                 220

Val Asp Pro Glu Asp Pro His Lys Gly Phe Lys Tyr Leu Tyr Leu Thr
225                 230                 235                 240

Pro Gln Asp Tyr Thr Arg Ile Ser Ser Leu Asn Ser Val His Cys Lys
                245                 250                 255

His Ile Glu Glu Gly Gly Glu Ser Arg Tyr Met Ile Thr Asp Ile Ile
            260                 265                 270

Gly Lys Asp Asp Gly Leu Gly Val Glu Asn Leu Arg Gly Ser Gly Met
        275                 280                 285

Ile Ala Gly Glu Ser Ser Leu Ala Tyr Glu Glu Ile Val Thr Ile Ser
    290                 295                 300

Leu Val Thr Cys Arg Ala Ile Gly Ile Gly Ala Tyr Leu Val Arg Leu
305                 310                 315                 320

Gly Gln Arg Val Ile Gln Val Glu Asn Ser His Ile Ile Leu Thr Gly
```

-continued

```
                325                 330                 335
Ala Ser Ala Leu Asn Lys Val Leu Gly Arg Glu Val Tyr Thr Ser Asn
                340                 345                 350
Asn Gln Leu Gly Gly Val Gln Ile Met His Tyr Asn Gly Val Ser His
                355                 360                 365
Ile Thr Val Pro Asp Asp Phe Glu Gly Val Tyr Thr Ile Leu Glu Trp
                370                 375                 380
Leu Ser Tyr Met Pro Lys Asp Asn His Ser Pro Val Pro Ile Ile Thr
385                 390                 395                 400
Pro Thr Asp Pro Ile Asp Arg Glu Ile Glu Phe Leu Pro Ser Arg Ala
                405                 410                 415
Pro Tyr Asp Pro Arg Trp Met Leu Ala Gly Arg Pro His Pro Thr Leu
                420                 425                 430
Lys Gly Thr Trp Gln Ser Gly Phe Phe Asp His Gly Ser Phe Lys Glu
                435                 440                 445
Ile Met Ala Pro Trp Ala Gln Thr Val Val Thr Gly Arg Ala Arg Leu
                450                 455                 460
Gly Gly Ile Pro Val Gly Val Ile Ala Val Glu Thr Arg Thr Val Glu
465                 470                 475                 480
Val Ala Val Pro Ala Asp Pro Ala Asn Leu Asp Ser Glu Ala Lys Ile
                485                 490                 495
Ile Gln Gln Ala Gly Gln Val Trp Phe Pro Asp Ser Ala Tyr Lys Thr
                500                 505                 510
Ala Gln Ala Ile Lys Asp Phe Asn Arg Glu Lys Leu Pro Leu Met Ile
                515                 520                 525
Phe Ala Asn Trp Arg Gly Phe Ser Gly Gly Met Lys Asp Met Tyr Asp
530                 535                 540
Gln Val Leu Lys Phe Gly Ala Tyr Ile Val Asp Gly Leu Arg Gln Tyr
545                 550                 555                 560
Lys Gln Pro Ile Leu Ile Tyr Ile Arg Pro Met Arg Glu Leu Arg Gly
                565                 570                 575
Gly Ser Trp Val Val Ile Asp Ala Thr Ile Asn Pro Leu Cys Ile Glu
                580                 585                 590
Met Tyr Ala Asp Lys Glu Ser Arg Gly Gly Val Leu Glu Pro Glu Gly
                595                 600                 605
Thr Val Glu Ile Lys Phe Arg Lys Glu Asp Leu Ile Lys Ser Met Arg
610                 615                 620
Arg Ile Asp Pro Ala Tyr Lys Lys Leu Met Glu Gln Leu Gly Glu Pro
625                 630                 635                 640
Asp Leu Ser Asp Lys Asp Arg Lys Asp Leu Glu Gly Arg Leu Lys Ala
                645                 650                 655
Arg Glu Asp Leu Leu Leu Pro Ile Tyr His Gln Val Ala Val Gln Phe
                660                 665                 670
Ala Asp Phe His Asp Thr Pro Gly Arg Met Leu Glu Lys Gly Val Ile
                675                 680                 685
Ser Asp Ile Leu Glu Trp Lys Thr Ala Arg Thr Phe Leu Tyr Trp Arg
                690                 695                 700
Leu Arg Arg Leu Leu Leu Glu Asp Gln Val Lys Gln Glu Ile Leu Gln
705                 710                 715                 720
Ala Ser Gly Glu Leu Ser His Val His Ile Gln Ser Met Leu Arg Arg
                725                 730                 735
Trp Phe Val Glu Thr Glu Gly Ala Val Lys Ala Tyr Leu Trp Asp Asn
                740                 745                 750
```

```
Asn Gln Val Val Gln Trp Leu Glu Gln His Trp Gln Ala Gly Asp
        755                 760                 765
Gly Pro Arg Ser Thr Ile Arg Glu Asn Ile Thr Tyr Leu Lys His Asp
        770                 775                 780
Ser Val Leu Lys Thr Ile Arg Gly Leu Val Glu Glu Asn Pro Glu Val
785                 790                 795                 800
Ala Val Asp Cys Val Ile Tyr Leu Ser Gln His Ile Ser Pro Ala Glu
                805                 810                 815
Arg Ala Gln Val Val His Leu Leu Ser Thr Met Asp Ser Pro Ala Ser
                820                 825                 830
Thr

<210> SEQ ID NO 11
<211> LENGTH: 1018
<212> TYPE: PRT
<213> ORGANISM: Toxoplasma gondii

<400> SEQUENCE: 11

Leu Asp Val Leu Asp Arg Cys Ala Ser Asp Pro Arg Val Ser Ala Thr
1               5                   10                  15
Ala Ser Gly Arg Leu Phe Leu His Ile Val Ser Pro Leu Asn Leu Ala
                20                  25                  30
Ser Ala Lys Ala Val Thr Glu His Phe His Lys Met Met Lys Arg Phe
            35                  40                  45
Arg Ser Glu His Asn Glu Arg Leu Leu Arg Leu Arg Val Asp Gln Ile
        50                  55                  60
Glu Val Lys Met His Leu Arg Lys Gly Gly Ser Gly Ser Asp Gly Glu
65                  70                  75                  80
Lys Arg Ser Ser Arg Glu Glu Gly Ala Glu Ala Thr Gly Ser Gln Ala
                85                  90                  95
Lys Glu Lys Glu Arg Leu Gln Val Leu Arg Leu Ser Val Ser Ser His
            100                 105                 110
Gln Gly Ser Trp Leu His Thr Lys Ala Ser Glu Asp Val Pro His Val
        115                 120                 125
Leu Thr Gly Asp Pro Ile Ala Gln Arg Ser Phe Val Phe Asp Glu Gly
    130                 135                 140
Glu Glu Thr Asp Ala Glu Gly Phe Val Ala Gln Ala Ser Pro Ala Gly
145                 150                 155                 160
Ser Gly Ala Glu Gly Ala Asp Gly Ala Lys Ser Arg Ala Thr Glu Lys
                165                 170                 175
Thr Gly Gln Arg Glu Gly Asp Ala Ala Pro Val Val Arg Arg Glu Pro
            180                 185                 190
Pro Glu Ala Glu Gly Leu Leu Gly Arg Ile Ser Val Gly Leu Lys Thr
        195                 200                 205
Leu Arg Gly Thr Gln Thr Ser Ala Thr Gly Ser Ala Gly Ala Gly Glu
    210                 215                 220
Met Pro Ala Ala Ser Ser Pro Gly Arg Trp Glu Gly Gly Asp
225                 230                 235                 240
Arg Lys Lys Gln Glu Leu Leu Ser Val Ser Arg Glu Glu Asn Glu
                245                 250                 255
Phe Phe Arg His Glu Lys Asp Ala Asp Pro Tyr Pro Glu Val Asp Arg
            260                 265                 270
Ile Ala Met Ala Arg Ser Ala Ala Arg Arg Ala Gly Ser Thr Tyr Ile
        275                 280                 285
```

-continued

```
Phe Asp Phe Leu Gly Leu Met Glu Ile Ala Leu Leu Gln Ser Trp Gln
    290                 295                 300
Thr His Leu Lys Glu Lys Gly Glu Lys Asp Gly Val Gly Gly Trp
305                 310                 315                 320
Asp Glu Ala Val Pro Arg Asp Leu Phe Lys Ala Glu Ala Phe Lys Val
                    325                 330                 335
Ser Ala Gln Gly Thr Leu Tyr Leu Asp Pro Asp Trp Arg Val Ala Asp
                340                 345                 350
Asn Lys Ile Gly Met Val Gly Phe Leu Ile Thr Leu Lys Thr Pro Glu
            355                 360                 365
Tyr Pro Ser Gly Arg Gln Val Val Leu Leu Gly Asn Asp Ile Thr Phe
    370                 375                 380
Gln Gly Gly Ser Phe Gly Val Pro Glu His Leu Phe Phe Thr Gln Val
385                 390                 395                 400
Ser Arg Phe Ser Arg Glu Gln Gly Leu Pro Arg Val Tyr Ile Ala Cys
                    405                 410                 415
Asn Ser Gly Ala Arg Ile Gly Leu Tyr Glu Asn Leu Lys Asp Lys Ile
                420                 425                 430
Lys Val Glu Trp Asn Asp Ala Ser Asn Pro Ser Leu Gly Phe Lys Asn
            435                 440                 445
Leu Tyr Leu Ser Ala Glu Asp Tyr Ala Ala Leu Pro Pro Gly Val Val
    450                 455                 460
Ser Gly His Phe Glu Glu Ala Val Asn Gly Asp Gln Arg Arg Phe Val
465                 470                 475                 480
Leu Asp Ala Ile Ile Gly Asp Pro Asp Lys Phe Ile Gly Val Glu Asn
                    485                 490                 495
Leu Arg Gly Ser Gly Thr Ile Ala Gly Glu Thr Ser Arg Ala Tyr Asp
                500                 505                 510
Glu Thr Phe Thr Leu Ser Tyr Val Thr Gly Arg Ser Val Gly Ile Gly
            515                 520                 525
Ala Tyr Ile Val Arg Leu Ala Gln Arg Thr Ile Gln Met Val Arg Gly
    530                 535                 540
Pro Leu Leu Leu Thr Gly Tyr Gln Ala Leu Asn Lys Leu Leu Gly Arg
545                 550                 555                 560
Glu Val Tyr Ala Ser Gln Asp Gln Leu Gly Gly Pro Glu Val Met Phe
                    565                 570                 575
Arg Asn Gly Val Ser His Leu Val Val Gln Asn Asp Gln Glu Gly Met
                580                 585                 590
Lys Glu Val Leu Arg Trp Leu Ala Tyr Thr Pro Lys Thr Ala Arg Asp
            595                 600                 605
Ser Val Ser Ser Ala Glu Met Phe Ser Ser Asp Pro Val Glu Arg Glu
    610                 615                 620
Val Ala Phe Thr Pro Thr Lys Ala Pro Tyr Asp Val Arg His Met Leu
625                 630                 635                 640
Ala Gly Tyr Thr Lys Glu Asp Gly Thr Phe Val Ser Gly Phe Asp
                    645                 650                 655
Lys Asn Ser Phe Lys Glu Tyr Leu Ala Gly Trp Gly Lys Ser Val Val
                660                 665                 670
Val Gly Arg Ala Arg Leu Gly Gly Ile Pro Phe Gly Ile Ala Val
            675                 680                 685
Glu Thr Arg Thr Thr Glu Ala Arg Val Pro Ala Asp Pro Ser Ser Pro
    690                 695                 700
```

```
Asp Ser Arg Glu Ser Val Ile Met His Ala Gly Gln Val Trp Phe Pro
705                 710                 715                 720

Asp Ser Ala Tyr Lys Thr Ala Gln Ala Ile Asn Asp Phe Asn Arg Gly
            725                 730                 735

Glu Asn Leu Pro Leu Ile Ile Phe Ala Asn Trp Arg Gly Phe Ser Gly
        740                 745                 750

Gly Thr Arg Asp Met Phe Glu Glu Ile Leu Lys Phe Gly Ser Gln Ile
    755                 760                 765

Val Asp Ala Leu Arg Thr Tyr Lys Gln Pro Val Phe Ile Tyr Ile Pro
770                 775                 780

Pro His Gly Glu Leu Arg Gly Gly Ser Trp Val Val Asp Pro Thr
785                 790                 795                 800

Ile Asn Leu Gln Lys Met Glu Met Tyr Ala Asp Ala Asn Ala Arg Gly
            805                 810                 815

Gly Val Leu Glu Pro Pro Gly Ile Cys Glu Ile Lys Tyr Arg Ala Ala
        820                 825                 830

Asp Gln Lys Ala Leu Met His Arg Val Asp Val Leu Lys Glu Leu
            835                 840                 845

Asp Lys Gln Leu Gln Asp Cys Gln Thr Ala Ser Asp Ala Ile Asp Leu
    850                 855                 860

Lys Glu Lys Ile Lys Arg Arg Glu Ala Ala Leu Glu Pro Leu Tyr Leu
865                 870                 875                 880

Ser Ile Ala Arg Phe Tyr Ala Asp Leu His Asp Arg Pro Glu Arg Met
                885                 890                 895

Lys Ala Arg Gly Val Ile Ser Ser Ile Val Asn Trp Lys Asn Ser Arg
            900                 905                 910

Thr Phe Phe Tyr Trp Arg Ala Lys Arg Leu Leu Gln Asp Asp Leu
            915                 920                 925

Glu Ala Arg Ile Leu Ala Ala Asp Ala Arg Leu Asp Tyr Thr Lys Ala
    930                 935                 940

Arg Ala Lys Ile Glu Asp Leu Leu Lys Ser His Gly Val Asp Ile Ala
945                 950                 955                 960

Gly Asp Lys Ala Ala Cys Glu Phe Leu Ser Ser Thr Glu Gly Lys Glu
                965                 970                 975

Ala Thr Gln Ala Ile Val Glu Arg Ser Arg Glu Gly Ala Ile Glu
            980                 985                 990

Lys Ile Arg Asp Ile Leu Ser Ser  Leu Pro Glu Ser Glu  Arg Arg Glu
            995                 1000                1005

Thr Leu  Glu Ser Ala Ala Thr  Pro Ala Cys
    1010                1015

<210> SEQ ID NO 12
<211> LENGTH: 2311
<212> TYPE: PRT
<213> ORGANISM: Triticum aestivum

<400> SEQUENCE: 12

Met Gly Ser Thr His Leu Pro Ile Val Gly Leu Asn Ala Ser Thr Thr
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Ser Arg Arg Val
        35                  40                  45

Gln Ser Leu Arg Asp Gly Asp Gly Gly Val Ser Asp Pro Asn Gln
    50                  55                  60
```

```
Ser Ile Arg Gln Gly Leu Ala Gly Ile Ile Asp Leu Pro Lys Glu Gly
 65                  70                  75                  80

Thr Ser Ala Pro Glu Val Asp Ile Ser His Gly Ser Glu Glu Pro Arg
                 85                  90                  95

Gly Ser Tyr Gln Met Asn Gly Ile Leu Asn Glu Ala His Asn Gly Arg
                100                 105                 110

His Ala Ser Leu Ser Lys Val Val Glu Phe Cys Met Ala Leu Gly Gly
            115                 120                 125

Lys Thr Pro Ile His Ser Val Leu Val Ala Asn Asn Gly Met Ala Ala
130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
                180                 185                 190

Pro Gly Gly Thr Asn Asn Asn Asn Tyr Ala Asn Val Gln Leu Ile Val
                195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Met Asn Ala Leu Gly Asp
                245                 250                 255

Lys Val Gly Ser Ala Leu Ile Ala Gln Ala Ala Gly Val Pro Thr Leu
                260                 265                 270

Pro Trp Ser Gly Ser Gln Val Glu Ile Pro Leu Glu Val Cys Leu Asp
                275                 280                 285

Ser Ile Pro Ala Glu Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
                340                 345                 350

Ser Pro Ile Phe Ile Met Arg Leu Ala Ser Gln Ser Arg His Leu Glu
                355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
                420                 425                 430

Glu Tyr Leu Tyr Ser Met Glu Thr Gly Glu Tyr Tyr Phe Leu Glu Leu
    435                 440                 445

Asn Pro Arg Leu Gln Val Glu His Pro Val Thr Glu Trp Ile Ala Glu
                450                 455                 460

Val Asn Leu Pro Ala Ala Gln Val Ala Val Gly Met Gly Ile Pro Leu
465                 470                 475                 480
```

```
Trp Gln Val Pro Glu Ile Arg Arg Phe Tyr Gly Met Asp Asn Gly Gly
            485                 490                 495
Gly Tyr Asp Ile Trp Arg Lys Thr Ala Ala Leu Ala Thr Pro Phe Asn
        500                 505                 510
Phe Asp Glu Val Asp Ser Gln Trp Pro Lys Gly His Cys Val Ala Val
    515                 520                 525
Arg Ile Thr Ser Glu Asp Pro Asp Gly Phe Lys Pro Thr Gly Gly
530                 535                 540
Lys Val Lys Glu Ile Ser Phe Lys Ser Lys Pro Asn Val Trp Ala Tyr
545                 550                 555                 560
Phe Ser Val Lys Ser Gly Gly Ile His Glu Phe Ala Asp Ser Gln
                565                 570                 575
Phe Gly His Val Phe Ala Tyr Gly Val Ser Arg Ala Ala Ala Ile Thr
            580                 585                 590
Asn Met Ser Leu Ala Leu Lys Glu Ile Gln Ile Arg Gly Glu Ile His
        595                 600                 605
Ser Asn Val Asp Tyr Thr Val Asp Leu Leu Asn Ala Ser Asp Phe Lys
    610                 615                 620
Glu Asn Arg Ile His Thr Gly Trp Leu Asp Asn Arg Ile Ala Met Arg
625                 630                 635                 640
Val Gln Ala Glu Arg Pro Pro Trp Tyr Ile Ser Val Val Gly Gly Ala
                645                 650                 655
Leu Tyr Lys Thr Ile Thr Ser Asn Thr Asp Thr Val Ser Glu Tyr Val
            660                 665                 670
Ser Tyr Leu Val Lys Gly Gln Ile Pro Pro Lys His Ile Ser Leu Val
        675                 680                 685
His Ser Thr Val Ser Leu Asn Ile Glu Glu Ser Lys Tyr Thr Ile Glu
    690                 695                 700
Thr Ile Arg Ser Gly Gln Gly Ser Tyr Arg Leu Arg Met Asn Gly Ser
705                 710                 715                 720
Val Ile Glu Ala Asn Val Gln Thr Leu Cys Asp Gly Gly Leu Leu Met
                725                 730                 735
Gln Leu Asp Gly Asn Ser His Val Ile Tyr Ala Glu Glu Ala Gly
            740                 745                 750
Gly Thr Arg Leu Leu Ile Asp Gly Lys Thr Cys Leu Leu Gln Asn Asp
        755                 760                 765
His Asp Pro Ser Arg Leu Leu Ala Glu Thr Pro Cys Lys Leu Leu Arg
    770                 775                 780
Phe Leu Val Ala Asp Gly Ala His Val Glu Ala Asp Val Pro Tyr Ala
785                 790                 795                 800
Glu Val Glu Val Met Lys Met Cys Met Pro Leu Leu Ser Pro Ala Ala
                805                 810                 815
Gly Val Ile Asn Val Leu Leu Ser Glu Gly Gln Pro Met Gln Ala Gly
            820                 825                 830
Asp Leu Ile Ala Arg Leu Asp Leu Asp Asp Pro Ser Ala Val Lys Arg
        835                 840                 845
Ala Glu Pro Phe Asn Gly Ser Phe Pro Glu Met Ser Leu Pro Ile Ala
    850                 855                 860
Ala Ser Gly Gln Val His Lys Arg Cys Ala Thr Ser Leu Asn Ala Ala
865                 870                 875                 880
Arg Met Val Leu Ala Gly Tyr Asp His Pro Ile Asn Lys Val Val Gln
                885                 890                 895
Asp Leu Val Ser Cys Leu Asp Ala Pro Glu Leu Pro Phe Leu Gln Trp
```

-continued

```
                900             905             910
Glu Glu Leu Met Ser Val Leu Ala Thr Arg Leu Pro Arg Leu Leu Lys
        915                 920                 925
Ser Glu Leu Glu Gly Lys Tyr Ser Glu Tyr Lys Leu Asn Val Gly His
    930                 935                 940
Gly Lys Ser Lys Asp Phe Pro Ser Lys Met Leu Arg Glu Ile Ile Glu
945                 950                 955                 960
Glu Asn Leu Ala His Gly Ser Glu Lys Glu Ile Ala Thr Asn Glu Arg
                965                 970                 975
Leu Val Glu Pro Leu Met Ser Leu Lys Ser Tyr Gly Gly Arg
            980                 985                 990
Glu Ser His Ala His Phe Ile Val Lys Ser Leu Phe Glu Asp Tyr Leu
        995                 1000                1005
Ser Val Glu Glu Leu Phe Ser Asp Gly Ile Gln Ser Asp Val Ile
    1010                1015                1020
Glu Arg Leu Arg Gln Gln His Ser Lys Asp Leu Gln Lys Val Val
    1025                1030                1035
Asp Ile Val Leu Ser His Gln Gly Val Arg Asn Lys Thr Lys Leu
    1040                1045                1050
Ile Leu Thr Leu Met Glu Lys Leu Val Tyr Pro Asn Pro Ala Val
    1055                1060                1065
Tyr Lys Asp Gln Leu Thr Arg Phe Ser Ser Leu Asn His Lys Arg
    1070                1075                1080
Tyr Tyr Lys Leu Ala Leu Lys Ala Ser Glu Leu Leu Glu Gln Thr
    1085                1090                1095
Lys Leu Ser Glu Leu Arg Thr Ser Ile Ala Arg Ser Leu Ser Glu
    1100                1105                1110
Leu Glu Met Phe Thr Glu Glu Arg Thr Ala Ile Ser Glu Ile Met
    1115                1120                1125
Gly Asp Leu Val Thr Ala Pro Leu Pro Val Glu Asp Ala Leu Val
    1130                1135                1140
Ser Leu Phe Asp Cys Ser Asp Gln Thr Leu Gln Gln Arg Val Ile
    1145                1150                1155
Glu Thr Tyr Ile Ser Arg Leu Tyr Gln Pro His Leu Val Lys Asp
    1160                1165                1170
Ser Ile Gln Leu Lys Tyr Gln Glu Ser Gly Val Ile Ala Leu Trp
    1175                1180                1185
Glu Phe Ala Glu Ala His Ser Glu Lys Arg Leu Gly Ala Met Val
    1190                1195                1200
Ile Val Lys Ser Leu Glu Ser Val Ser Ala Ala Ile Gly Ala Ala
    1205                1210                1215
Leu Lys Gly Thr Ser Arg Tyr Ala Ser Ser Glu Gly Asn Ile Met
    1220                1225                1230
His Ile Ala Leu Leu Gly Ala Asp Asn Gln Met His Gly Thr Glu
    1235                1240                1245
Asp Ser Gly Asp Asn Asp Gln Ala Gln Val Arg Ile Asp Lys Leu
    1250                1255                1260
Ser Ala Thr Leu Glu Gln Asn Thr Val Thr Ala Asp Leu Arg Ala
    1265                1270                1275
Ala Gly Val Lys Val Ile Ser Cys Ile Val Gln Arg Asp Gly Ala
    1280                1285                1290
Leu Met Pro Met Arg His Thr Phe Leu Leu Ser Asp Glu Lys Leu
    1295                1300                1305
```

```
Cys Tyr Glu Glu Glu Pro Val Leu Arg His Val Glu Pro Pro Leu
    1310                1315                1320

Ser Ala Leu Leu Glu Leu Gly Lys Leu Lys Val Lys Gly Tyr Asn
    1325                1330                1335

Glu Val Lys Tyr Thr Pro Ser Arg Asp Arg Gln Trp Asn Ile Tyr
    1340                1345                1350

Thr Leu Arg Asn Thr Glu Asn Pro Lys Met Leu His Arg Val Phe
    1355                1360                1365

Phe Arg Thr Leu Val Arg Gln Pro Gly Ala Ser Asn Lys Phe Thr
    1370                1375                1380

Ser Gly Asn Ile Ser Asp Val Glu Val Gly Gly Ala Glu Glu Ser
    1385                1390                1395

Leu Ser Phe Thr Ser Ser Ser Ile Leu Arg Ser Leu Met Thr Ala
    1400                1405                1410

Ile Glu Glu Leu Glu Leu His Ala Ile Arg Thr Gly His Ser His
    1415                1420                1425

Met Phe Leu Cys Ile Leu Lys Glu Gln Lys Leu Leu Asp Leu Val
    1430                1435                1440

Pro Val Ser Gly Asn Lys Val Val Asp Ile Gly Gln Asp Glu Ala
    1445                1450                1455

Thr Ala Cys Leu Leu Leu Lys Glu Met Ala Leu Gln Ile His Glu
    1460                1465                1470

Leu Val Gly Ala Arg Met His His Leu Ser Val Cys Gln Trp Glu
    1475                1480                1485

Val Lys Leu Lys Leu Asp Ser Asp Gly Pro Ala Ser Gly Thr Trp
    1490                1495                1500

Arg Val Val Thr Thr Asn Val Thr Ser His Thr Cys Thr Val Asp
    1505                1510                1515

Ile Tyr Arg Glu Val Glu Asp Thr Glu Ser Gln Lys Leu Val Tyr
    1520                1525                1530

His Ser Ala Pro Ser Ser Ser Gly Pro Leu His Gly Val Ala Leu
    1535                1540                1545

Asn Thr Pro Tyr Gln Pro Leu Ser Val Ile Asp Leu Lys Arg Cys
    1550                1555                1560

Ser Ala Arg Asn Asn Arg Thr Thr Tyr Cys Tyr Asp Phe Pro Leu
    1565                1570                1575

Ala Phe Glu Thr Ala Val Gln Lys Ser Trp Ser Asn Ile Ser Ser
    1580                1585                1590

Asp Thr Asn Arg Cys Tyr Val Lys Ala Thr Glu Leu Val Phe Ala
    1595                1600                1605

His Lys Asn Gly Ser Trp Gly Thr Pro Val Ile Pro Met Glu Arg
    1610                1615                1620

Pro Ala Gly Leu Asn Asp Ile Gly Met Val Ala Trp Ile Leu Asp
    1625                1630                1635

Met Ser Thr Pro Glu Tyr Pro Asn Gly Arg Gln Ile Val Val Ile
    1640                1645                1650

Ala Asn Asp Ile Thr Phe Arg Ala Gly Ser Phe Gly Pro Arg Glu
    1655                1660                1665

Asp Ala Phe Phe Glu Thr Val Thr Asn Leu Ala Cys Glu Arg Lys
    1670                1675                1680

Leu Pro Leu Ile Tyr Leu Ala Ala Asn Ser Gly Ala Arg Ile Gly
    1685                1690                1695
```

-continued

```
Ile Ala Asp Glu Val Lys Ser Cys Phe Arg Val Gly Trp Ser Asp
1700                1705                1710
Asp Gly Ser Pro Glu Arg Gly Phe Gln Tyr Ile Tyr Leu Thr Glu
1715                1720                1725
Glu Asp His Ala Arg Ile Ser Ala Ser Val Ile Ala His Lys Met
1730                1735                1740
Gln Leu Asp Asn Gly Glu Ile Arg Trp Val Ile Asp Ser Val Val
1745                1750                1755
Gly Lys Glu Asp Gly Leu Gly Val Glu Asn Ile His Gly Ser Ala
1760                1765                1770
Ala Ile Ala Ser Ala Tyr Ser Arg Ala Tyr Glu Glu Thr Phe Thr
1775                1780                1785
Leu Thr Phe Val Thr Gly Arg Thr Val Gly Ile Gly Ala Tyr Leu
1790                1795                1800
Ala Arg Leu Gly Ile Arg Cys Ile Gln Arg Thr Asp Gln Pro Ile
1805                1810                1815
Ile Leu Thr Gly Phe Ser Ala Leu Asn Lys Leu Leu Gly Arg Glu
1820                1825                1830
Val Tyr Ser Ser His Met Gln Leu Gly Gly Pro Lys Ile Met Ala
1835                1840                1845
Thr Asn Gly Val Val His Leu Thr Val Ser Asp Asp Leu Glu Gly
1850                1855                1860
Val Ser Asn Ile Leu Arg Trp Leu Ser Tyr Val Pro Ala Asn Ile
1865                1870                1875
Gly Gly Pro Leu Pro Ile Thr Lys Ser Leu Asp Pro Pro Asp Arg
1880                1885                1890
Pro Val Ala Tyr Ile Pro Glu Asn Thr Cys Asp Pro Arg Ala Ala
1895                1900                1905
Ile Ser Gly Ile Asp Asp Ser Gln Gly Lys Trp Leu Gly Gly Met
1910                1915                1920
Phe Asp Lys Asp Ser Phe Val Glu Thr Phe Glu Gly Trp Ala Lys
1925                1930                1935
Ser Val Val Thr Gly Arg Ala Lys Leu Gly Gly Ile Pro Val Gly
1940                1945                1950
Val Ile Ala Val Glu Thr Gln Thr Met Met Gln Leu Ile Pro Ala
1955                1960                1965
Asp Pro Gly Gln Leu Asp Ser His Glu Arg Ser Val Pro Arg Ala
1970                1975                1980
Gly Gln Val Trp Phe Pro Asp Ser Ala Thr Lys Thr Ala Gln Ala
1985                1990                1995
Met Leu Asp Phe Asn Arg Glu Gly Leu Pro Leu Phe Ile Leu Ala
2000                2005                2010
Asn Trp Arg Gly Phe Ser Gly Gly Gln Arg Asp Leu Phe Glu Gly
2015                2020                2025
Ile Leu Gln Ala Gly Ser Thr Ile Val Glu Asn Leu Arg Thr Tyr
2030                2035                2040
Asn Gln Pro Ala Phe Val Tyr Ile Pro Lys Ala Ala Glu Leu Arg
2045                2050                2055
Gly Gly Ala Trp Val Val Ile Asp Ser Lys Ile Asn Pro Asp Arg
2060                2065                2070
Ile Glu Phe Tyr Ala Glu Arg Thr Ala Lys Gly Asn Val Leu Glu
2075                2080                2085
Pro Gln Gly Leu Ile Glu Ile Lys Phe Arg Ser Glu Glu Leu Gln
```

```
                2090                2095                2100
Glu Cys Met Gly Arg Leu Asp Pro Glu Leu Ile Asn Leu Lys Ala
    2105                2110                2115

Lys Leu Gln Gly Val Lys His Glu Asn Gly Ser Leu Pro Glu Ser
    2120                2125                2130

Glu Ser Leu Gln Lys Ser Ile Glu Ala Arg Lys Gln Leu Leu
    2135                2140                2145

Pro Leu Tyr Thr Gln Ile Ala Val Arg Phe Ala Glu Leu His Asp
    2150                2155                2160

Thr Ser Leu Arg Met Ala Ala Lys Gly Val Ile Lys Lys Val Val
    2165                2170                2175

Asp Trp Glu Asp Ser Arg Ser Phe Phe Tyr Lys Arg Leu Arg Arg
    2180                2185                2190

Arg Ile Ser Glu Asp Val Leu Ala Lys Glu Ile Arg Gly Val Ser
    2195                2200                2205

Gly Lys Gln Phe Ser His Gln Ser Ala Ile Glu Leu Ile Gln Lys
    2210                2215                2220

Trp Tyr Leu Ala Ser Lys Gly Ala Glu Thr Gly Ser Thr Glu Trp
    2225                2230                2235

Asp Asp Asp Asp Ala Phe Val Ala Trp Arg Glu Asn Pro Glu Asn
    2240                2245                2250

Tyr Gln Glu Tyr Ile Lys Glu Leu Arg Ala Gln Arg Val Ser Gln
    2255                2260                2265

Leu Leu Ser Asp Val Ala Asp Ser Ser Pro Asp Leu Glu Ala Leu
    2270                2275                2280

Pro Gln Gly Leu Ser Met Leu Leu Glu Lys Met Asp Pro Ser Arg
    2285                2290                2295

Arg Ala Gln Phe Val Glu Glu Val Lys Lys Val Leu Lys
    2300                2305                2310

<210> SEQ ID NO 13
<211> LENGTH: 2110
<212> TYPE: PRT
<213> ORGANISM: Mus musculus

<400> SEQUENCE: 13

Met Trp Ala Leu Gly Asp Lys Ile Ala Ser Ser Ile Val Ala Gln Thr
1               5                   10                  15

Ala Gly Ile Pro Thr Leu Pro Trp Ser Gly Ser Gly Leu Arg Val Asp
                20                  25                  30

Trp Gln Glu Asn Asp Phe Ser Lys Arg Ile Leu Asn Val Pro Gln Asp
            35                  40                  45

Leu Tyr Glu Lys Gly Tyr Val Lys Asp Val Asp Gly Leu Lys Ala
    50                  55                  60

Ala Glu Glu Val Gly Tyr Pro Val Met Ile Lys Ala Ser Glu Gly Gly
65                  70                  75                  80

Gly Gly Lys Gly Ile Arg Lys Val Asn Asn Ala Asp Asp Phe Pro Asn
                85                  90                  95

Leu Phe Arg Gln Val Gln Ala Glu Val Pro Gly Ser Pro Ile Phe Val
            100                 105                 110

Met Arg Leu Ala Lys Gln Ser Arg His Leu Glu Val Gln Ile Leu Ala
        115                 120                 125

Asp Gln Tyr Gly Asn Ala Ile Ser Leu Phe Gly Arg Asp Cys Ser Val
    130                 135                 140
```

-continued

```
Gln Arg Arg His Gln Lys Ile Ile Glu Glu Ala Pro Ala Ala Ile Ala
145                 150                 155                 160

Thr Pro Ala Val Phe Glu His Met Glu Gln Cys Ala Val Lys Leu Ala
                165                 170                 175

Lys Met Val Gly Tyr Val Ser Ala Gly Thr Val Glu Tyr Leu Tyr Ser
            180                 185                 190

Gln Asp Gly Ser Phe Tyr Phe Leu Glu Leu Asn Pro Arg Leu Gln Val
        195                 200                 205

Glu His Pro Cys Thr Glu Met Val Ala Asp Val Asn Leu Pro Ala Ala
    210                 215                 220

Gln Leu Gln Ile Ala Met Gly Ile Pro Leu Phe Arg Ile Lys Asp Ile
225                 230                 235                 240

Arg Met Met Tyr Gly Val Ser Pro Trp Gly Asp Ala Pro Ile Asp Phe
                245                 250                 255

Glu Asn Ser Ala His Val Pro Cys Pro Arg Gly His Val Ile Ala Ala
            260                 265                 270

Arg Ile Thr Ser Glu Asn Pro Asp Glu Gly Phe Lys Pro Ser Ser Gly
        275                 280                 285

Thr Val Gln Glu Leu Asn Phe Arg Ser Asn Lys Asn Val Trp Gly Tyr
    290                 295                 300

Phe Ser Val Ala Ala Ala Gly Gly Leu His Glu Phe Ala Asp Ser Gln
305                 310                 315                 320

Phe Gly His Cys Phe Ser Trp Gly Glu Asn Arg Glu Glu Ala Ile Ser
                325                 330                 335

Asn Met Val Val Ala Leu Lys Glu Leu Ser Ile Arg Gly Asp Phe Arg
            340                 345                 350

Thr Thr Val Glu Tyr Leu Ile Lys Leu Leu Glu Thr Glu Ser Phe Gln
        355                 360                 365

Leu Asn Arg Ile Asp Thr Gly Trp Leu Asp Arg Leu Ile Ala Glu Lys
    370                 375                 380

Val Gln Ala Glu Arg Pro Asp Thr Met Leu Gly Val Val Cys Gly Ala
385                 390                 395                 400

Leu His Val Ala Asp Val Ser Leu Arg Asn Ser Ile Ser Asn Phe Leu
                405                 410                 415

His Ser Leu Glu Arg Gly Gln Val Leu Pro Ala His Thr Leu Leu Asn
            420                 425                 430

Thr Val Asp Val Glu Leu Ile Tyr Glu Gly Ile Lys Tyr Val Leu Lys
        435                 440                 445

Val Thr Arg Gln Ser Pro Asn Ser Tyr Val Val Ile Met Asn Gly Ser
    450                 455                 460

Cys Val Glu Val Asp Val His Arg Leu Ser Asp Gly Gly Leu Leu Leu
465                 470                 475                 480

Ser Tyr Asp Gly Ser Ser Tyr Thr Thr Tyr Met Lys Glu Glu Val Asp
                485                 490                 495

Arg Tyr Arg Ile Thr Ile Gly Asn Lys Thr Cys Val Phe Glu Lys Glu
            500                 505                 510

Asn Asp Pro Ser Val Met Arg Ser Pro Ser Ala Gly Lys Leu Ile Gln
        515                 520                 525

Tyr Ile Val Glu Asp Gly Gly His Val Phe Ala Gly Gln Cys Tyr Ala
    530                 535                 540

Glu Ile Glu Val Met Lys Met Val Met Thr Leu Thr Ala Val Glu Ser
545                 550                 555                 560

Gly Cys Ile His Tyr Val Lys Arg Pro Gly Ala Ala Leu Asp Pro Gly
```

-continued

```
                565                 570                 575
Cys Val Ile Ala Lys Met Gln Leu Asp Asn Pro Ser Lys Val Gln Gln
                580                 585                 590

Ala Glu Leu His Thr Gly Ser Leu Pro Gln Ile Gln Ser Thr Ala Leu
            595                 600                 605

Arg Gly Glu Lys Leu His Arg Val Phe His Tyr Val Leu Asp Asn Leu
        610                 615                 620

Val Asn Val Met Asn Gly Tyr Cys Leu Pro Asp Pro Phe Phe Ser Ser
625                 630                 635                 640

Arg Val Lys Asp Trp Val Glu Arg Leu Met Lys Thr Leu Arg Asp Pro
                645                 650                 655

Ser Leu Pro Leu Leu Glu Leu Gln Asp Ile Met Thr Ser Val Ser Gly
            660                 665                 670

Arg Ile Pro Leu Asn Val Glu Lys Ser Ile Lys Lys Glu Met Ala Gln
        675                 680                 685

Tyr Ala Ser Asn Ile Thr Ser Val Leu Cys Gln Phe Pro Ser Gln Gln
    690                 695                 700

Ile Ala Asn Ile Leu Asp Ser His Ala Ala Thr Leu Asn Arg Lys Ser
705                 710                 715                 720

Glu Arg Glu Val Phe Phe Met Asn Thr Gln Ser Ile Val Gln Leu Val
                725                 730                 735

Gln Arg Tyr Arg Ser Gly Ile Arg Gly His Met Lys Ala Val Val Met
            740                 745                 750

Asp Leu Leu Arg Gln Tyr Leu Arg Val Glu Thr Gln Phe Gln Asn Gly
        755                 760                 765

His Tyr Asp Lys Cys Val Phe Ala Leu Arg Glu Glu Asn Lys Ser Asp
    770                 775                 780

Met Asn Thr Val Leu Asn Tyr Ile Phe Ser His Ala Gln Val Thr Lys
785                 790                 795                 800

Lys Asn Leu Leu Val Thr Met Leu Ile Asp Gln Leu Cys Gly Arg Asp
                805                 810                 815

Pro Thr Leu Thr Asp Glu Leu Leu Asn Ile Leu Thr Glu Leu Thr Gln
            820                 825                 830

Leu Ser Lys Thr Thr Asn Ala Lys Val Ala Leu Arg Ala Arg Gln Val
        835                 840                 845

Leu Ile Ala Ser His Leu Pro Ser Tyr Glu Leu Arg His Asn Gln Val
    850                 855                 860

Glu Ser Ile Phe Leu Ser Ala Ile Asp Met Tyr Gly His Gln Phe Cys
865                 870                 875                 880

Ile Glu Asn Leu Gln Lys Leu Ile Leu Ser Glu Thr Ser Ile Phe Asp
                885                 890                 895

Val Leu Pro Asn Phe Phe Tyr His Ser Asn Gln Val Val Arg Met Ala
            900                 905                 910

Ala Leu Glu Val Tyr Val Arg Arg Ala Tyr Ile Ala Tyr Glu Leu Asn
        915                 920                 925

Ser Val Gln His Arg Gln Leu Lys Asp Asn Thr Cys Val Val Glu Phe
    930                 935                 940

Gln Phe Met Leu Pro Thr Ser His Pro Asn Arg Gly Asn Ile Pro Thr
945                 950                 955                 960

Leu Asn Arg Met Ser Phe Ala Ser Asn Leu Asn His Tyr Gly Met Thr
                965                 970                 975

His Val Ala Ser Val Ser Asp Val Leu Leu Asp Asn Ala Phe Thr Pro
            980                 985                 990
```

```
Pro Cys Gln Arg Met Gly Gly Met  Val Ser Phe Arg Thr  Phe Glu Asp
        995              1000              1005

Phe Val  Arg Ile Phe Asp Glu  Ile Met Gly Cys Phe  Cys Asp Ser
    1010              1015              1020

Pro Pro  Gln Ser Pro Thr Phe  Pro Glu Ser Gly His  Thr Ser Leu
    1025              1030              1035

Tyr Asp  Glu Asp Lys Val Pro  Arg Asp Glu Pro Ile  His Ile Leu
    1040              1045              1050

Asn Val  Ala Ile Lys Thr Asp  Gly Asp Ile Glu Asp  Asp Arg Leu
    1055              1060              1065

Ala Ala  Met Phe Arg Glu Phe  Thr Gln Gln Asn Lys  Ala Thr Leu
    1070              1075              1080

Val Glu  His Gly Ile Arg Arg  Leu Thr Phe Leu Val  Ala Gln Lys
    1085              1090              1095

Asp Phe  Arg Lys Gln Val Asn  Cys Glu Val Asp Gln  Arg Phe His
    1100              1105              1110

Arg Glu  Phe Pro Lys Phe Phe  Thr Phe Arg Ala Arg  Asp Lys Phe
    1115              1120              1125

Glu Glu  Asp Arg Ile Tyr Arg  His Leu Glu Pro Ala  Leu Ala Phe
    1130              1135              1140

Gln Leu  Glu Leu Asn Arg Met  Arg Asn Phe Asp Leu  Thr Ala Ile
    1145              1150              1155

Pro Cys  Ala Asn His Lys Met  His Leu Tyr Leu Gly  Ala Ala Lys
    1160              1165              1170

Val Glu  Val Gly Thr Glu Val  Thr Asp Tyr Arg Phe  Phe Val Arg
    1175              1180              1185

Ala Ile  Ile Arg His Ser Asp  Leu Val Thr Lys Glu  Ala Ser Phe
    1190              1195              1200

Glu Tyr  Leu Gln Asn Glu Gly  Glu Arg Leu Leu Leu  Glu Ala Met
    1205              1210              1215

Asp Glu  Leu Glu Val Ala Phe  Asn Asn Thr Asn Val  Arg Thr Asp
    1220              1225              1230

Cys Asn  His Ile Phe Leu Asn  Phe Val Pro Thr Val  Ile Met Asp
    1235              1240              1245

Pro Ser  Lys Ile Glu Glu Ser  Val Arg Ser Met Val  Met Arg Tyr
    1250              1255              1260

Gly Ser  Arg Leu Trp Lys Leu  Arg Val Leu Gln Ala  Glu Leu Lys
    1265              1270              1275

Ile Asn  Ile Arg Leu Thr Thr  Thr Gly Lys Ala Ile  Pro Ile Arg
    1280              1285              1290

Leu Phe  Leu Thr Asn Glu Ser  Gly Tyr Tyr Leu Asp  Ile Ser Leu
    1295              1300              1305

Tyr Lys  Glu Val Thr Asp Ser  Arg Thr Ala Gln Ile  Met Phe Gln
    1310              1315              1320

Ala Tyr  Gly Asp Lys Gln Gly  Pro Leu His Gly Met  Leu Ile Asn
    1325              1330              1335

Thr Pro  Tyr Val Thr Lys Asp  Leu Leu Gln Ser Lys  Arg Phe Gln
    1340              1345              1350

Ala Gln  Ser Leu Gly Thr Thr  Tyr Ile Tyr Asp Ile  Pro Glu Met
    1355              1360              1365

Phe Arg  Gln Ser Leu Ile Lys  Leu Trp Glu Ser Met  Ser Thr Gln
    1370              1375              1380
```

```
-continued

Ala Phe Leu Pro Ser Pro Pro Leu Pro Ser Asp Ile Leu Thr Tyr
    1385                1390                1395

Thr Glu Leu Val Leu Asp Asp Gln Gly Gln Leu Val His Met Asn
    1400                1405                1410

Arg Leu Pro Gly Gly Asn Glu Ile Gly Met Val Ala Trp Lys Met
    1415                1420                1425

Ser Leu Lys Ser Pro Glu Tyr Pro Asp Gly Arg Asp Ile Ile Val
    1430                1435                1440

Ile Gly Asn Asp Ile Thr Tyr Arg Ile Gly Ser Phe Gly Pro Gln
    1445                1450                1455

Glu Asp Leu Leu Phe Leu Arg Ala Ser Glu Leu Ala Arg Ala Glu
    1460                1465                1470

Gly Ile Pro Arg Ile Tyr Val Ala Ala Asn Ser Gly Ala Arg Ile
    1475                1480                1485

Gly Leu Ala Glu Glu Ile Arg His Met Phe His Val Ala Trp Val
    1490                1495                1500

Asp Pro Glu Asp Pro Tyr Lys Gly Tyr Lys Tyr Leu Tyr Leu Thr
    1505                1510                1515

Pro Gln Asp Tyr Lys Arg Val Ser Ala Leu Asn Ser Val His Cys
    1520                1525                1530

Glu His Val Glu Asp Glu Gly Glu Ser Arg Tyr Lys Ile Thr Asp
    1535                1540                1545

Ile Ile Gly Lys Glu Glu Gly Leu Gly Ala Glu Asn Leu Arg Gly
    1550                1555                1560

Ser Gly Met Ile Ala Gly Glu Ser Ser Leu Ala Tyr Asp Glu Val
    1565                1570                1575

Ile Thr Ile Ser Leu Val Thr Cys Arg Ala Ile Gly Ile Gly Ala
    1580                1585                1590

Tyr Leu Val Arg Leu Gly Gln Arg Thr Ile Gln Val Glu Asn Ser
    1595                1600                1605

His Leu Ile Leu Thr Gly Ala Gly Ala Leu Asn Lys Val Leu Gly
    1610                1615                1620

Arg Glu Val Tyr Thr Ser Asn Asn Gln Leu Gly Gly Ile Gln Ile
    1625                1630                1635

Met His Asn Asn Gly Val Thr His Ser Thr Val Cys Asp Asp Phe
    1640                1645                1650

Glu Gly Val Phe Thr Val Leu His Trp Leu Ser Tyr Met Pro Lys
    1655                1660                1665

Ser Val His Ser Ser Val Pro Leu Leu Asn Ser Lys Asp Pro Ile
    1670                1675                1680

Asp Arg Ile Ile Glu Phe Val Pro Thr Lys Ala Pro Tyr Asp Pro
    1685                1690                1695

Arg Trp Met Leu Ala Gly Arg Pro His Pro Thr Gln Lys Gly Gln
    1700                1705                1710

Trp Leu Ser Gly Phe Phe Asp Tyr Gly Ser Phe Ser Glu Ile Met
    1715                1720                1725

Gln Pro Trp Ala Gln Thr Val Val Val Gly Arg Ala Arg Leu Gly
    1730                1735                1740

Gly Ile Pro Val Gly Val Val Ala Val Glu Thr Arg Thr Val Glu
    1745                1750                1755

Leu Ser Ile Pro Ala Asp Pro Ala Asn Leu Asp Ser Glu Ala Lys
    1760                1765                1770

Ile Ile Gln Gln Ala Gly Gln Val Trp Phe Pro Asp Ser Ala Phe
```

-continued

```
             1775                1780                1785

Lys Thr Tyr Gln Ala Ile Lys Asp Phe Asn Arg Glu Gly Leu Pro
     1790                1795                1800

Leu Met Val Phe Ala Asn Trp Arg Gly Phe Ser Gly Gly Met Lys
     1805                1810                1815

Asp Met Tyr Asp Gln Val Leu Lys Phe Gly Ala Tyr Ile Val Asp
     1820                1825                1830

Gly Leu Arg Glu Cys Ser Gln Pro Val Met Val Tyr Ile Pro Pro
     1835                1840                1845

Gln Ala Glu Leu Arg Gly Gly Ser Trp Val Val Ile Asp Pro Thr
     1850                1855                1860

Ile Asn Pro Arg His Met Glu Met Tyr Ala Asp Arg Glu Ser Arg
     1865                1870                1875

Gly Ser Val Leu Glu Pro Glu Gly Thr Val Glu Ile Lys Phe Arg
     1880                1885                1890

Lys Lys Asp Leu Val Lys Thr Met Arg Arg Val Asp Pro Val Tyr
     1895                1900                1905

Ile Arg Leu Ala Glu Arg Leu Gly Thr Pro Glu Leu Ser Pro Thr
     1910                1915                1920

Glu Arg Lys Glu Leu Glu Ser Lys Leu Lys Glu Arg Glu Glu Phe
     1925                1930                1935

Leu Ile Pro Ile Tyr His Gln Val Ala Val Gln Phe Ala Asp Leu
     1940                1945                1950

His Asp Thr Pro Gly Arg Met Gln Glu Lys Gly Val Ile Asn Asp
     1955                1960                1965

Ile Leu Asp Trp Lys Thr Ser Arg Thr Phe Phe Tyr Trp Arg Leu
     1970                1975                1980

Arg Arg Leu Leu Leu Glu Asp Leu Val Lys Lys Ile His Asn
     1985                1990                1995

Ala Asn Pro Glu Leu Thr Asp Gly Gln Ile Gln Ala Met Leu Arg
     2000                2005                2010

Arg Trp Phe Val Glu Val Glu Gly Thr Val Lys Ala Tyr Val Trp
     2015                2020                2025

Asp Asn Asn Lys Asp Leu Val Glu Trp Leu Glu Lys Gln Leu Thr
     2030                2035                2040

Glu Glu Asp Gly Val Arg Ser Val Ile Glu Asn Ile Lys Tyr
     2045                2050                2055

Ile Ser Arg Asp Tyr Val Leu Lys Gln Ile Arg Ser Leu Val Gln
     2060                2065                2070

Ala Asn Pro Glu Val Ala Met Asp Ser Ile Val His Met Thr Gln
     2075                2080                2085

His Ile Ser Pro Thr Gln Arg Ala Glu Val Val Arg Ile Leu Ser
     2090                2095                2100

Thr Met Asp Ser Pro Ser Thr
     2105                2110

<210> SEQ ID NO 14
<211> LENGTH: 817
<212> TYPE: PRT
<213> ORGANISM: Mus musculus

<400> SEQUENCE: 14

Leu Phe Leu Thr Asn Glu Ser Gly Tyr Tyr Leu Asp Ile Ser Leu Tyr
1               5                   10                  15
```

```
Lys Glu Val Thr Asp Ser Arg Thr Ala Gln Ile Met Phe Gln Ala Tyr
            20                  25                  30

Gly Asp Lys Gln Gly Pro Leu His Gly Met Leu Ile Asn Thr Pro Tyr
        35                  40                  45

Val Thr Lys Asp Leu Leu Gln Ser Lys Arg Phe Gln Ala Gln Ser Leu
 50                  55                  60

Gly Thr Thr Tyr Ile Tyr Asp Ile Pro Glu Met Phe Arg Gln Ser Leu
 65                  70                  75                  80

Ile Lys Leu Trp Glu Ser Met Ser Thr Gln Ala Phe Leu Pro Ser Pro
                 85                  90                  95

Pro Leu Pro Ser Asp Ile Leu Thr Tyr Thr Glu Leu Val Leu Asp Asp
            100                 105                 110

Gln Gly Gln Leu Val His Met Asn Arg Leu Pro Gly Gly Asn Glu Ile
        115                 120                 125

Gly Met Val Ala Trp Lys Met Ser Leu Lys Ser Pro Glu Tyr Pro Asp
130                 135                 140

Gly Arg Asp Ile Ile Val Ile Gly Asn Asp Ile Thr Tyr Arg Ile Gly
145                 150                 155                 160

Ser Phe Gly Pro Gln Glu Asp Leu Leu Phe Leu Arg Ala Ser Glu Leu
                165                 170                 175

Ala Arg Ala Glu Gly Ile Pro Arg Ile Tyr Val Ala Ala Asn Ser Gly
            180                 185                 190

Ala Arg Ile Gly Leu Ala Glu Glu Ile Arg His Met Phe His Val Ala
        195                 200                 205

Trp Val Asp Pro Glu Asp Pro Tyr Lys Gly Tyr Lys Tyr Leu Tyr Leu
210                 215                 220

Thr Pro Gln Asp Tyr Lys Arg Val Ser Ala Leu Asn Ser Val His Cys
225                 230                 235                 240

Glu His Val Glu Asp Glu Gly Glu Ser Arg Tyr Lys Ile Thr Asp Ile
                245                 250                 255

Ile Gly Lys Glu Glu Gly Leu Gly Ala Glu Asn Leu Arg Gly Ser Gly
            260                 265                 270

Met Ile Ala Gly Glu Ser Ser Leu Ala Tyr Asp Glu Val Ile Thr Ile
        275                 280                 285

Ser Leu Val Thr Cys Arg Ala Ile Gly Ile Gly Ala Tyr Leu Val Arg
290                 295                 300

Leu Gly Gln Arg Thr Ile Gln Val Glu Asn Ser His Leu Ile Leu Thr
305                 310                 315                 320

Gly Ala Gly Ala Leu Asn Lys Val Leu Gly Arg Glu Val Tyr Thr Ser
                325                 330                 335

Asn Asn Gln Leu Gly Gly Ile Gln Ile Met His Asn Asn Gly Val Thr
            340                 345                 350

His Ser Thr Val Cys Asp Asp Phe Glu Gly Val Phe Thr Val Leu His
        355                 360                 365

Trp Leu Ser Tyr Met Pro Lys Ser Val His Ser Ser Val Pro Leu Leu
370                 375                 380

Asn Ser Lys Asp Pro Ile Asp Arg Ile Ile Glu Phe Val Pro Thr Lys
385                 390                 395                 400

Ala Pro Tyr Asp Pro Arg Trp Met Leu Ala Gly Arg Pro His Pro Thr
                405                 410                 415

Gln Lys Gly Gln Trp Leu Ser Gly Phe Phe Asp Tyr Gly Ser Phe Ser
            420                 425                 430

Glu Ile Met Gln Pro Trp Ala Gln Thr Val Val Val Gly Arg Ala Arg
```

```
                435                 440                 445
Leu Gly Gly Ile Pro Val Gly Val Ala Val Glu Thr Arg Thr Val
    450                 455                 460
Glu Leu Ser Ile Pro Ala Asp Pro Ala Asn Leu Asp Ser Glu Ala Lys
465                 470                  475                 480
Ile Ile Gln Gln Ala Gly Gln Val Trp Phe Pro Asp Ser Ala Phe Lys
                485                 490                  495
Thr Tyr Gln Ala Ile Lys Asp Phe Asn Arg Glu Gly Leu Pro Leu Met
                500                 505                 510
Val Phe Ala Asn Trp Arg Gly Phe Ser Gly Gly Met Lys Asp Met Tyr
        515                 520                 525
Asp Gln Val Leu Lys Phe Gly Ala Tyr Ile Val Asp Gly Leu Arg Glu
    530                 535                 540
Cys Ser Gln Pro Val Met Val Tyr Ile Pro Pro Gln Ala Glu Leu Arg
545                 550                 555                 560
Gly Gly Ser Trp Val Val Ile Asp Pro Thr Ile Asn Pro Arg His Met
                565                 570                 575
Glu Met Tyr Ala Asp Arg Glu Ser Arg Gly Ser Val Leu Glu Pro Glu
                580                 585                 590
Gly Thr Val Glu Ile Lys Phe Arg Lys Lys Asp Leu Val Lys Thr Met
                595                 600                 605
Arg Arg Val Asp Pro Val Tyr Ile Arg Leu Ala Glu Arg Leu Gly Thr
    610                 615                 620
Pro Glu Leu Ser Pro Thr Glu Arg Lys Glu Leu Glu Ser Lys Leu Lys
625                 630                 635                 640
Glu Arg Glu Glu Phe Leu Ile Pro Ile Tyr His Gln Val Ala Val Gln
                645                 650                 655
Phe Ala Asp Leu His Asp Thr Pro Gly Arg Met Gln Glu Lys Gly Val
                660                 665                 670
Ile Asn Asp Ile Leu Asp Trp Lys Thr Ser Arg Thr Phe Phe Tyr Trp
                675                 680                 685
Arg Leu Arg Arg Leu Leu Leu Glu Asp Leu Val Lys Lys Lys Ile His
    690                 695                 700
Asn Ala Asn Pro Glu Leu Thr Asp Gly Gln Ile Gln Ala Met Leu Arg
705                 710                 715                 720
Arg Trp Phe Val Glu Val Glu Gly Thr Val Lys Ala Tyr Val Trp Asp
                725                 730                 735
Asn Asn Lys Asp Leu Val Glu Trp Leu Glu Lys Gln Leu Thr Glu Glu
                740                 745                 750
Asp Gly Val Arg Ser Val Ile Glu Glu Asn Ile Lys Tyr Ile Ser Arg
                755                 760                 765
Asp Tyr Val Leu Lys Gln Ile Arg Ser Leu Val Gln Ala Asn Pro Glu
        770                 775                 780
Val Ala Met Asp Ser Ile Val His Met Thr Gln His Ile Ser Pro Thr
785                 790                 795                 800
Gln Arg Ala Glu Val Val Arg Ile Leu Ser Thr Met Asp Ser Pro Ser
                805                 810                 815
Thr
```